United States Patent
Chakravarty et al.

(10) Patent No.: US 9,670,172 B2
(45) Date of Patent: Jun. 6, 2017

(54) HETEROCYCLIC COMPOUNDS AND METHODS OF USE

(71) Applicant: Medivation Technologies, Inc., San Francisco, CA (US)

(72) Inventors: Sarvajit Chakravarty, San Francisco, CA (US); Roopa Rai, San Francisco, CA (US); Son Minh Pham, San Francisco, CA (US); Brahmam Pujala, Noida (IN); Ramniwas Jangir, Noida (IN); Rambabu Guguloth, Noida (IN); Vijay Kumar Sharma, Noida (IN)

(73) Assignee: MEDIVATION TECHNOLOGIES, INC., San Francisco, CA (US)

( * ) Notice: Subject to any disclaimer, the term of this patent is extended or adjusted under 35 U.S.C. 154(b) by 0 days.

(21) Appl. No.: 14/471,977

(22) Filed: Aug. 28, 2014

(65) Prior Publication Data

US 2015/0065519 A1     Mar. 5, 2015

(51) Int. Cl.

| | |
|---|---|
| *C07D 277/30* | (2006.01) |
| *C07D 417/04* | (2006.01) |
| *C07D 487/04* | (2006.01) |
| *C07D 263/34* | (2006.01) |
| *C07D 263/30* | (2006.01) |
| *C07D 277/22* | (2006.01) |
| *C07D 413/04* | (2006.01) |
| *A61K 31/421* | (2006.01) |
| *A61K 31/422* | (2006.01) |
| *A61K 31/426* | (2006.01) |
| *A61K 31/427* | (2006.01) |

(52) U.S. Cl.
CPC ......... *C07D 277/30* (2013.01); *C07D 417/04* (2013.01); *C07D 487/04* (2013.01)

(58) Field of Classification Search
CPC .. C07D 277/10; C07D 277/04; C07D 417/14; C07D 277/06; C07D 263/34; C07D 263/30; C07D 277/30; C07D 277/22; C07D 417/04; C07D 413/04; C07D 487/04; G03C 8/10; A61K 31/421; A61K 31/422; A61K 31/426; A61K 31/427
USPC .............. 548/146, 205; 514/253.1; 546/209, 546/270.4, 271.4, 274.1, 148; 544/238, 544/333, 405
See application file for complete search history.

(56) References Cited

U.S. PATENT DOCUMENTS

| | | |
|---|---|---|
| 6,444,687 B1 | 9/2002 | Stamford et al. |
| 6,924,298 B2 | 8/2005 | Tisdell et al. |
| 7,244,739 B2 | 7/2007 | Cheng et al. |
| 8,063,080 B2 | 11/2011 | Fulp et al. |
| 8,229,106 B2 | 7/2012 | Greiss et al. |
| 8,822,513 B2 | 9/2014 | Lu et al. |
| 8,907,099 B2 | 12/2014 | Learmonth et al. |
| 2001/0031781 A1 | 10/2001 | Illig et al. |
| 2013/0165472 A1 | 6/2013 | Chau et al. |
| 2014/0045854 A1 | 2/2014 | Uesugi et al. |
| 2014/0303213 A1 | 10/2014 | Uesugi et al. |

FOREIGN PATENT DOCUMENTS

| | | | | |
|---|---|---|---|---|
| JP | WO 2008097835 A2 | * | 8/2008 | ......... A61K 31/4439 |
| WO | 9940088 A1 | | 8/1999 | |
| WO | 2008097835 A2 | | 8/2008 | |
| WO | WO 2008097835 A2 | * | 8/2008 | |
| WO | 2011085269 A1 | | 7/2011 | |
| WO | 2012084678 A1 | | 6/2012 | |
| WO | 2013038136 A1 | | 3/2013 | |
| WO | 2014199164 A1 | | 12/2014 | |
| WO | 2014210389 A1 | | 12/2014 | |

OTHER PUBLICATIONS

International Search Report for PCT/US2014/053215, mailed Jan. 29, 2015.
Bellale et al., "Diarylthiazole: An Antimycobacterial Scaffold Potentially Targeting PrrB-PrrA Two-Component System," Journal of Medicinal Chemistry, 2014, vol. 57, pp. 6572-6582.
Shahlaei & Nazari, "Prediction of glucagon receptor antagonist activities of some substituted imidazoles using combined radial basis function neural network and density functional theory," Medicinal Chemistry Research, 2014, vol. 23, pp. 2744-2756.
Tani et al., "Programmed synthesis of arylthiazoles through sequential C—H couplings," Chemical Science, 2014, vol. 5, pp. 123-135.

* cited by examiner

*Primary Examiner* — Alicia L Otton
*Assistant Examiner* — Sagar Patel
(74) *Attorney, Agent, or Firm* — Banner & Witcoff, Ltd.

(57) ABSTRACT

This disclosure provides compounds and methods of using those compounds to treat metabolic disorders and hyperproliferative disorders, including administration of the compounds in conjunction with hormone receptor antagonists.

36 Claims, 6 Drawing Sheets

FIG. 4A

Compound #37 Mouse PK

| PO (10 mg/kg) | |
|---|---|
| PK Parameters | Mean |
| $C_{max}$ (µM) | 32.4 |
| $T_{max}$ (h) | 1 |
| $AUC_{last}$ (µM*h) | 294 |
| Terminal $t_{1/2}$ (h) | 4.23 |
| Bioavailability (%) | 151% |

FIG. 4B

Compound #37 Dog Oral PK

| PO Dose Level (mg/kg) | 2 (n=3) | | 10 (n=1) | |
|---|---|---|---|---|
| PO Parameters | Mean | SD | Dog 2002 | SD |
| $C_{max}$ (nM) | 27.0 | 1.21 | 182 | -- |
| $T_{max}$ (h) | 1.5 | 0 | 1.5 | -- |
| $AUC_{last}$ (µM*h) | 449 | 17.3 | 4200 | -- |
| Terminal $t_{1/2}$ (h) | 10.7 | 2.05 | 11.3 | -- |
| Bioavailability | 99.3% | 20.1% | 62.9% | -- |

HETEROCYCLIC COMPOUNDS AND METHODS OF USE

CROSS-REFERENCE TO RELATED APPLICATIONS

This application claims priority to Indian Patent Application No. 2816/MUM/2013, filed Aug. 28, 2013, and Indian Patent Application No. 3497/MUM/2013, filed Nov. 4, 2013, the disclosures of which are incorporated herein by reference in their entireties.

TECHNICAL FIELD

This disclosure relates generally to therapeutics for treatment of hyperproliferative disorders, metabolic disorders, and pancreatitis.

BACKGROUND OF THE INVENTION

Sterol regulatory element-binding proteins (SREBPs) are major transcription factors regulating the biosynthesis of cholesterol, fatty acid, and triglyceride. They control the expression of crucial genes involved in lipogenesis and uptake. Inhibition of the SREBP pathway can reduce lipid biosynthesis and thus can be a strategy to treat metabolic diseases, such as type II diabetes, insulin resistance, fatty liver and atherosclerosis [Xiao, et al. *Acta Biochim. Biophys. Sin* (2013) 45:1, pp 2-10]. In mammals, three SREBP isoforms are known, designated SREBP-1a, SREBP-1c, and SREBP-2. SREBP-1a controls a broad range of SREBP targets including production of fatty acids, triglycerides, phospholipids and cholesterol. SREBP-1c preferentially activates genes of fatty acid and triglyceride metabolism, whereas SREBP-2 preferentially activates genes of cholesterol metabolism, both of which have been studied in human and mice models [Horton, et al. *J. Clin. Invest.* (2002) 109:9, pp 1125-1131], as well as *Drosophila* [Rawson. *Nature Rev. Mol. Cell Biol.* (2003) 4:8, pp 631-640].

Recent studies have also presented a link between upregulation of lipid synthesis and prostate cancer [Suburu, et al. *Prostaglandins Other Lipid Mediat.* (2012) 98:0, pp 1-10]. The metabolic shift from catabolic to anabolic metabolism is a hallmark of cancer cells. Many cancers require synthesis of fatty acids, and other lipids such as cholesterol and androgens are implicated in prostate cancer. SREBP-1c is the major transcriptional regulator of enzymes in the fatty acid synthesis pathway, and its expression can be stimulated by androgens and epidermal growth factor (EGF) in prostate cancer cells. Overexpression of SREBP-1c is sufficient to cause tumorigenicity and invasion of prostate cancer cells. SREBP-1 can also increase expression of NOX5, a prominent producer of reactive oxygen species (ROS) and regulator of prostate cancer cell growth [Brar, et al. *Am. J. Physiol. Cell Physiol.* (2003) 285:2, pp C353-369; Huang, et al. *Mol. Cancer Res.* (2012) 10:1, pp 133-142; Huang, et al. *Cancer Research* (2012) 72:8, SUPPL. 1; Huang, et al. *Mol. Cancer Res.* (2014) 13:4, pp 855-866].

SREBP-2, a regulator of androgen synthesis, is also itself regulated by androgens, demonstrating a direct feedback circuit for regulation of androgen production. SREBP-2 expression increases during disease progression and is significantly higher after castration. This transcription factor also lacks its feedback inhibition in prostate cancer cells, implicating a role for cholesterol and androgen synthesis in prostate cancer [Eberle, et al. *Biochimie* (2004) 86:11, pp 839-848; Ettinger, et al. *Cancer Res.* (2004), 64:6, pp 2212-2221; Chen, et al. *Int. J. Cancer* (2001), 91:1, pp 41-45].

Blocking SREBP functions linked to disease states therefore represents an important therapeutic approach for limiting lipid/cholesterol synthesis in membrane production which occurs in metabolic diseases and in cancer progression, as well as in viral pathogenesis [Naar, et al. *Clin. Lipidol.* (2012) 7:1, pp 27-36]. Small molecule therapeutics affecting metabolic regulators such as mTOR, AMPK or SIRT1, including Rapamycin, Metformin, or Resveratrol, respectively, may impinge on the transcriptional activity of SREBPs. Recently, two non-sterol small molecules, fatostatin and betulin have been found to inhibit SREBP processing [Kamisuki, et al. *Chem. Biol.* (2009) 16:8, pp 882-892; Tang, et al. *Cell. Metab.* (2011) 13:1, pp 44-56]. Methods for the treatment of cancers having a p53 mutation, such as breast cancer cells, using SREBP inhibitors have been presented [Freed-Pastor, et al. PCT. Publication WO2013-110007A1].

Fatostatin analogs have recently been described as potential therapeutics for the treatment of metabolic disorders [Uesugi, et al. U.S. Pat. No. 8,207,196]. Key compounds presented therein are based around Formula X:

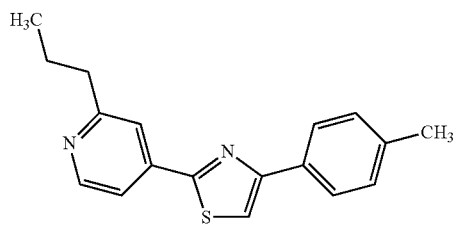

Fatostatin

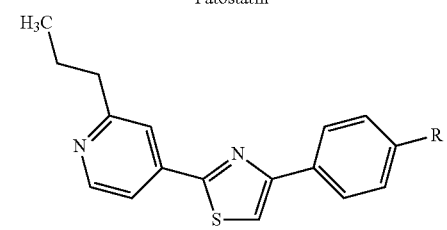

Formula X wherein R is H, F, Cl, Br, OBz, OH, OCH$_3$, OCH$_2$CO$_2$Me, OCH$_2$CO$_2$H, NH$_2$, NHiPr, NHCOCH$_3$, NHSO$_2$Me, NH[benzyl], NH[cyclopropyl], NH[tertbutyloxycarbonyl], NH[cyclohexyl], NH[tosyl], NH[quinolin-8-yl], and NH[thiophen-2-yl]. In particular, one compound (FGH10019), the methanesulfonamide derivative of fatostatin above wherein R is NHSO$_2$Me, has been described as a lead candidate [Kamisuki, et al. *J. Med. Chem.* (2011) 54:13, pp 4923-4927].

BRIEF SUMMARY OF THE INVENTION

This disclosure relates generally to therapeutics for treatment of hyperproliferative disorders, metabolic disorders, and pancreatitis. This disclosure provides compounds and methods of using those compounds to treat benign and malignant hyperproliferative disorders, as well as metabolic disorders and pancreatitis, as described below. Compounds of the invention may also find use in treating cancer.

Presented herein are novel compounds bearing a perhaloalkylsulfonamide moiety. Such compounds, in addition to being highly effective SREBP inhibitors, are also unexpectedly highly bioavailable in vivo. Heteroaromatic compounds bearing sulfonamide groups are prone to several ionic states, based on the inherent pKa values. When placed in aqueous solution, they could exist in neutral, zwitterionic or anionic forms dependent upon the pH of that solution. Each of these forms can have dramatically different solubility, and require complex pharmaceutical formulation studies to maximize in-vivo exposure. Such studies could necessitate solid dispersions, micronization, coprecipitation, salt selection, lipid emulsifiers, cosolvents, complexation carriers, solubility enhancer excipients, and the like, each of which presents its own challenges, resource requirements and unpredictability [see, for example, Julémont, et al. *J. Med. Chem.* (2004) 47:27, pp 6749-6759; Anand, et al. US Patent Publication US2014-128431A1; Patel, et al. PCT Publication WO2000-072884]. Perhaloalkylsulfonamides have, in general, a lower pKa and higher acidity relative to non-fluorinated alkylsulfonamides, with a potential to form the anion at physiological pH, depending on the remaining functionality in the molecule. This unpredictability of how perhaloalkylsulfonamide-containing compounds can be formulated as pharmaceuticals typically renders them unappealing to the skilled medicinal chemist. As presented herein, the high bioavailability of compounds of the invention is attributed to unexpectedly low pKa values found for the compounds, affording them optimal characteristics for therapeutic applications.

In some embodiments, compounds disclosed herein fall within formulae (Ia) or (Ib):

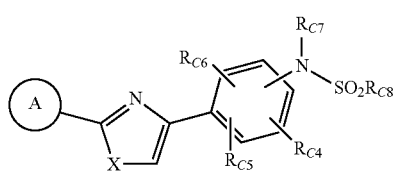

(Ia)

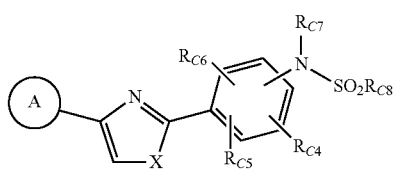

(Ib)

or a pharmaceutically acceptable salt thereof, wherein:
A is either:
  i. an aryl or heteroaryl, each having only one ring, substituted with 1, 2, or 3 substituents selected from the group consisting of halogen, CN, $CF_3$, OH, C1-C6 linear or branched alkyl, C3-C6 cycloalkyl, C3-C6 cycloalkenyl, C1-C6 linear or branched hydroxyalkyl, C1-C3 linear or branched alkoxy, C3-C6 cycloalkylmethyl, —$(CH_2)_mCF_3$, =O, —$CH_2OCH_3$, —OBn, —$CO_2H$, —$CO_2$-Alkyl, —NR10R11, and —CONR10R11; or
  ii. an aryl or heteroaryl, each having more than one ring, optionally substituted with 1, 2, or 3 substituents selected from the group consisting of halogen, CN, $CF_3$, OH, C1-C6 linear or branched alkyl, C3-C6 cycloalkyl, C3-C6 cycloalkenyl, C1-C6 linear or branched hydroxyalkyl, C1-C3 linear or branched alkoxy, C3-C6 cycloalkylmethyl, —$(CH_2)_mCF_3$, =O, —$CH_2OCH_3$, —$CH_2OH$, —OBn, —$CO_2H$, —$CO_2$-Alkyl, —NR10R11, and —CONR10R11;

Each $R_{C4}$, $R_{C5}$, and $R_{C6}$, is independently hydrogen, halogen, CN, $CF_3$, OH, C1-C3 linear or branched alkyl, C2-C3 alkenyl, C2-C3 alkynyl, C3-C6 cycloalkyl, C3-C6 cycloalkenyl, C1-C3 linear or branched alkoxy, —$CO_2H$, —CONR10R11, or —$NHCONH_2$;
or is taken with $R_{C7}$ to form the moiety

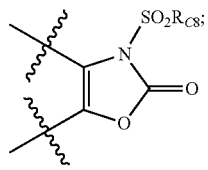

$R_{C7}$ is hydrogen, C1-C6 linear or branched alkyl, C1-C6 linear or branched hydroxyalkyl, —$(CR_{9a}R_{9b})_m$NR10R11, —$CO_2$-Alkyl, —$(CR_{9a}R_{9b})_m$O-Alkyl, —$(CR_{9a}R_{9b})_m OPO_3Na_2$, —$(CR_{9a}R_{9b})_m O(CR_{9a}R_{9b})_n$O-Alkyl, —$(CR_{9a}R_{9b})_m O(C=O)$-Alkyl, —$(CR_{9a}R_{9b})_m O(CR_{9a}R_{9b})_n O(C=O)$-Alkyl, —$(C=O)CH=CH_2$, —$SO_2R_{C8'}$; or is taken with one of $R_{C4}$, $R_{C5}$ or $R_{C6}$ to form the moiety

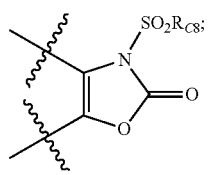

$R_{C8}$ is a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

$R_{C8'}$ is a linear or branched C1-C6 alkyl, a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

Each $R_{9a}$ and $R_{9b}$, where present, is independently hydrogen or C1-C6 linear or branched alkyl;

R10 and R11 are independently hydrogen, —$SO_2R_{C8'}$, C1-C6 linear or branched alkyl, C2-C6 linear or branched alkenyl, C3-C6 cycloalkyl, or C3-C6 cycloalkenyl; or are taken together with the N to which they are attached to form a C3-C6 heterocycle, pyrrolidinone, piperidinone, oxazolidinone, oxazinanone, imidazolidinone, tetrahydropyrimidin-2(1H)-one, a $1\lambda^6$,2-thiazolidine-1,1-dione, a $1,2\lambda^6$,3-oxathiazolidine-2,2-dione, or a $1\lambda^6$,2,5-thiadiazolidine-1,1-dione;

X is a heteroatom selected from S, O; or $NR_B$ wherein $R_B$ is hydrogen, a C1-C6 linear or branched alkyl, or a C3-C6 cycloalkyl; and Each m and n is 1, 2 or 3.

In some embodiments, compounds disclosed herein fall within formulae (IIa) or (IIb):
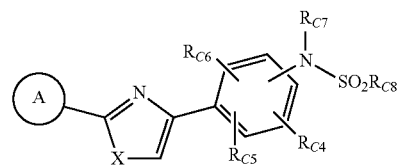
(IIa)
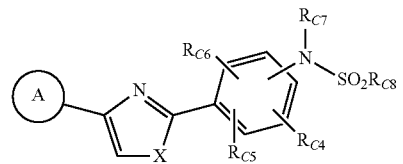
(IIb)
or a pharmaceutically acceptable salt thereof, wherein:
A is a moiety selected from the group consisting of:
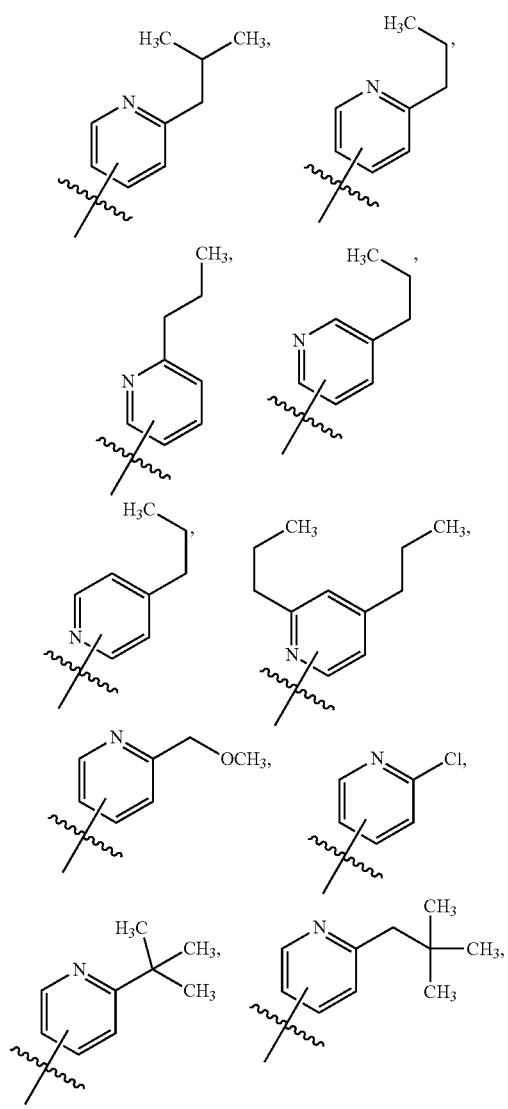
-continued
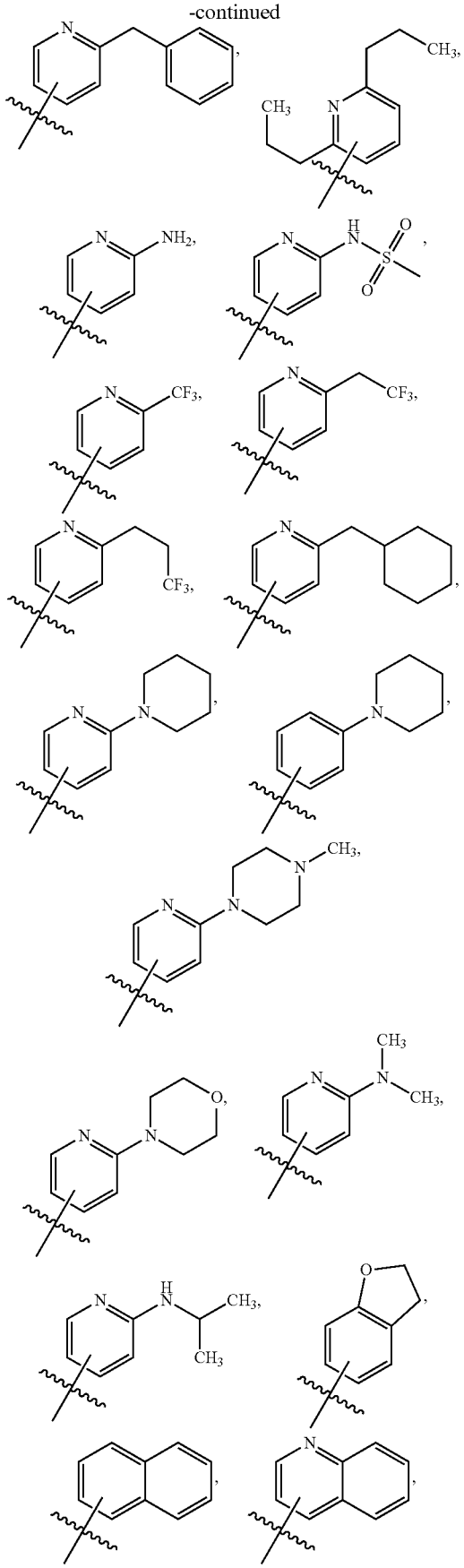

-continued
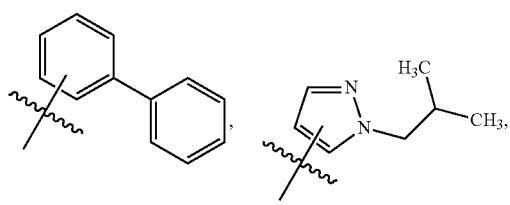
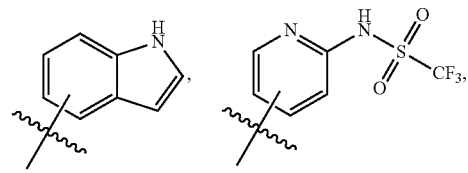
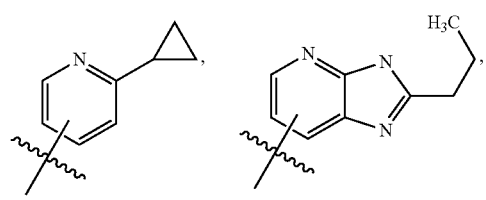
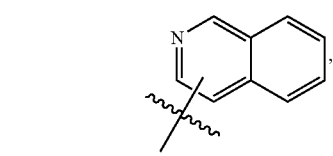
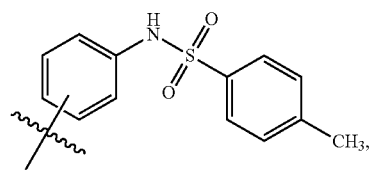
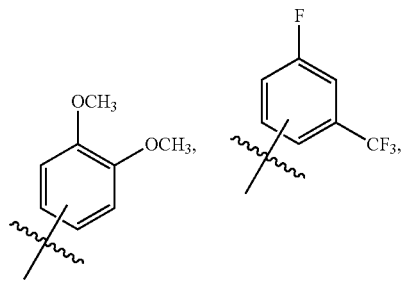
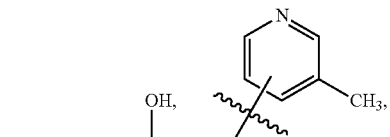
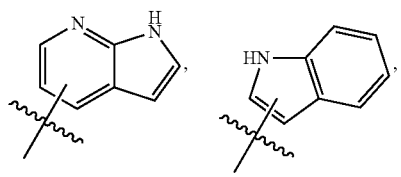
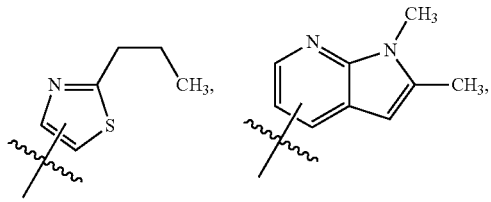
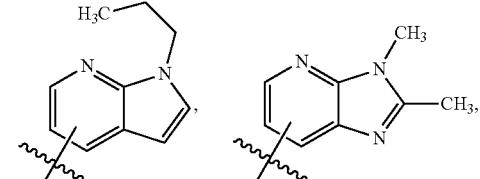
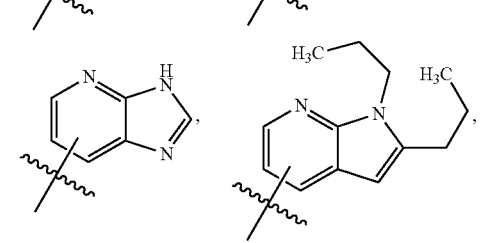
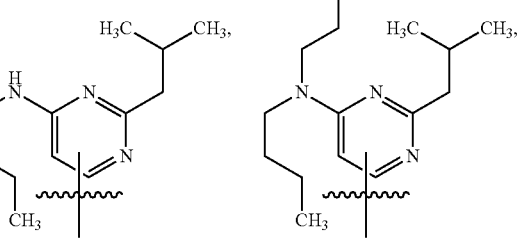
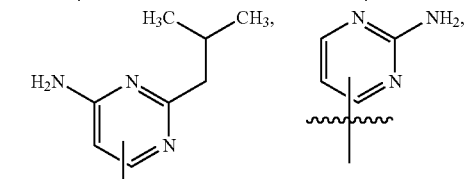
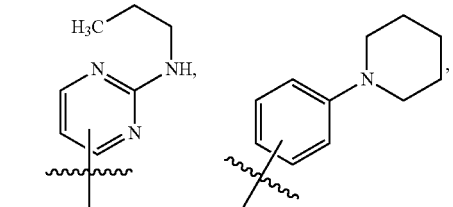
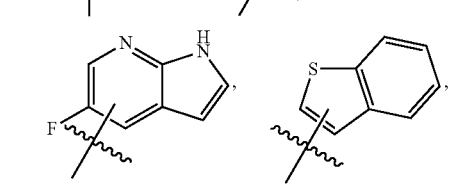
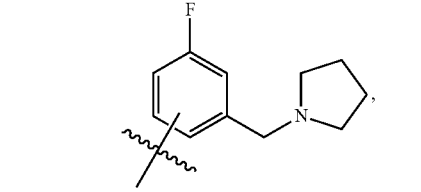

-continued

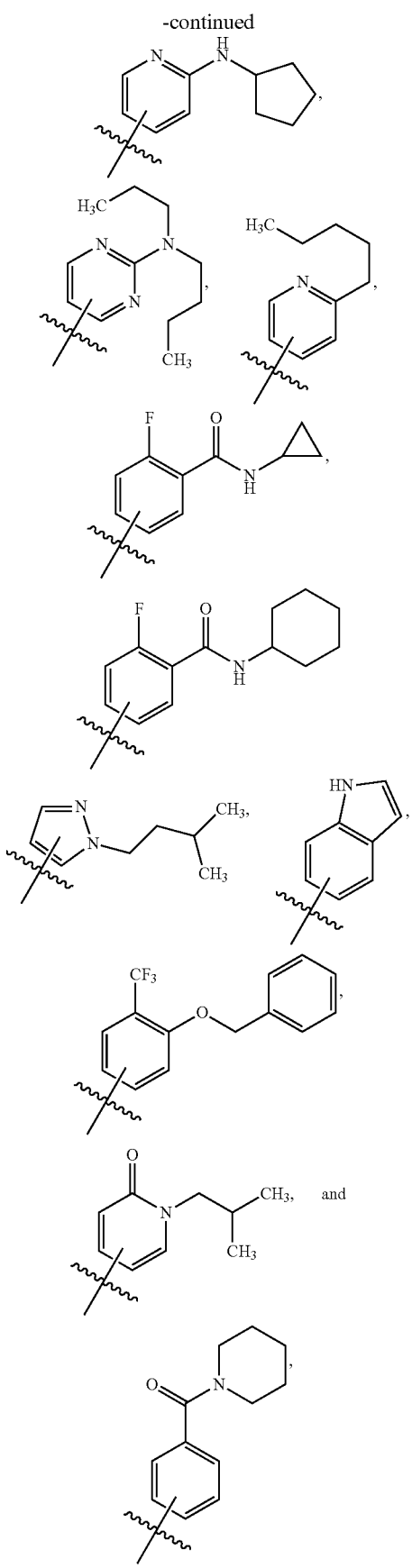

wherein the ring containing X is linked to ring A at any available position on ring A;

Each $R_{C4}$, $R_{C5}$, and $R_{C6}$, is independently hydrogen, halogen, CN, $CF_3$, OH, C1-C3 linear or branched alkyl, C2-C3 alkenyl, C2-C3 alkynyl, C3-C6 cycloalkyl, C3-C6 cycloalkenyl, C1-C3 linear or branched alkoxy, —$CO_2H$, —$CONR10R11$, or —$NHCONH_2$;

or is taken with $R_{C7}$ to form the moiety

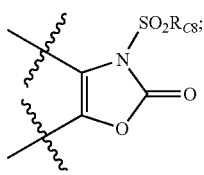

$R_{C7}$ is hydrogen, C1-C6 linear or branched alkyl, C1-C6 linear or branched hydroxyalkyl, —$(CR_{9a}R_{9b})_m NR10R11$, —$CO_2$-Alkyl, —$(CR_{9a}R_{9b})_m O$-Alkyl, —$(CR_{9a}R_{9b})_m OPO_3Na_2$, —$(CR_{9a}R_{9b})_m O(CR_{9a}R_{9b})_n O$-Alkyl, —$(CR_{9a}R_{9b})_m O(C=O)$-Alkyl, —$(CR_{9a}R_{9b})_m O(CR_{9a}R_{9b})_n O(C=O)$-Alkyl, —$(C=O)CH=CH_2$, —$SO_2R_{C8'}$; or is taken with one of $R_{C4}$, $R_{C5}$ or $R_{C6}$ to form the moiety

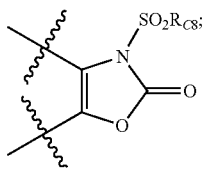

$R_{C8}$ is a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

$R_{C8'}$ is a linear or branched C1-C6 alkyl, a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

Each $R_{9a}$ and $R_{9b}$, where present, is independently hydrogen or C1-C6 linear or branched alkyl;

R10 and R11 are independently hydrogen, —$SO_2R_{C8'}$, C1-C6 linear or branched alkyl, C2-C6 linear or branched alkenyl, C3-C6 cycloalkyl, or C3-C6 cycloalkenyl; or are taken together with the N to which they are attached to form a C3-C6 heterocycle, pyrrolidinone, piperidinone, oxazolidinone, oxazinanone, imidazolidinone, tetrahydropyrimidin-2(1H)-one, a $1\lambda^6,2$-thiazolidine-1,1-dione, a $1,2\lambda^6,3$-oxathiazolidine-2,2-dione, or a $1\lambda^6,2,5$-thiadiazolidine-1,1-dione;

X is a heteroatom selected from S, O; or $NR_B$ wherein $R_B$ is hydrogen, a C1-C6 linear or branched alkyl, or a C3-C6 cycloalkyl; and Each m and n is 1, 2 or 3.

In some embodiments, compounds disclosed herein fall within formulae (IIa) or (IIb):

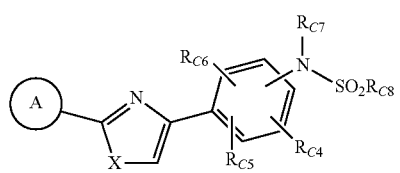  (IIa)
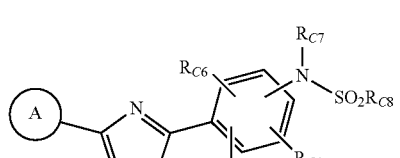  (IIb)
or a pharmaceutically acceptable salt thereof, wherein:
A is a moiety selected from the group consisting of:
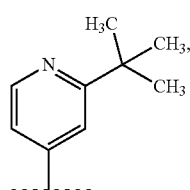 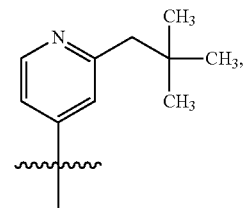
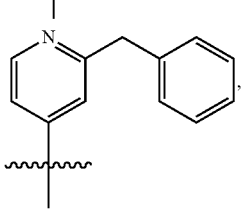
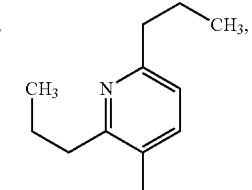
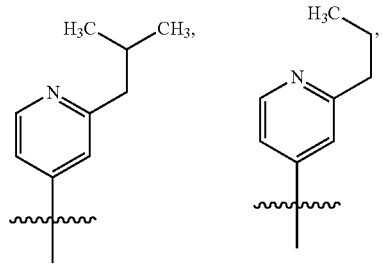
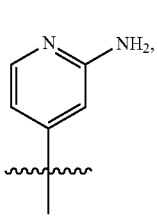 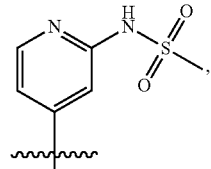
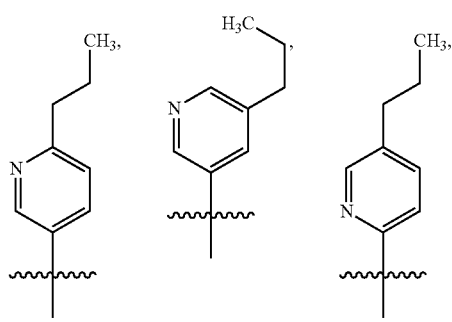
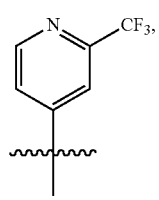 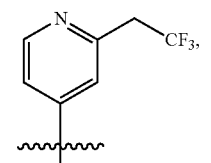
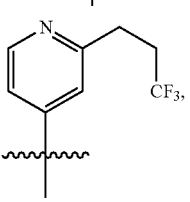 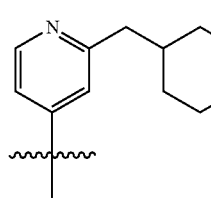
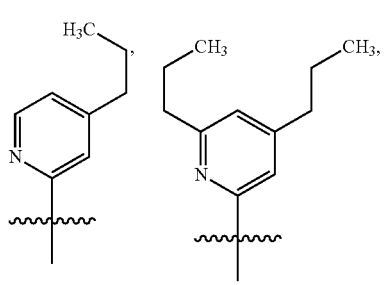
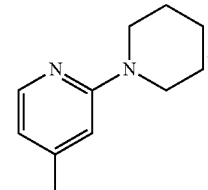 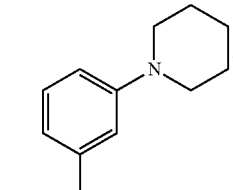
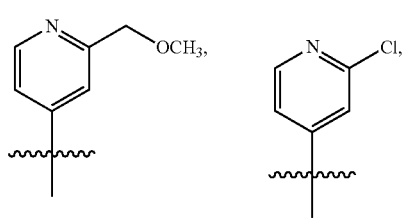
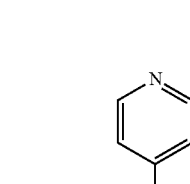 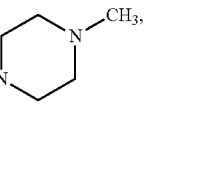
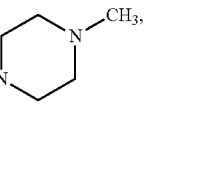

-continued
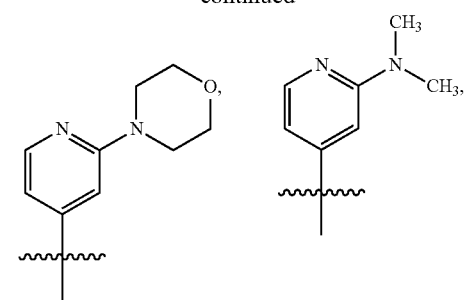
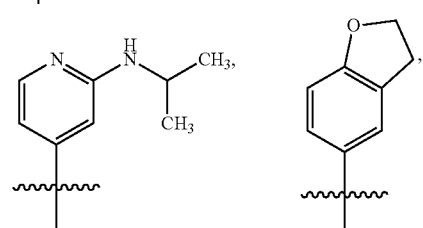
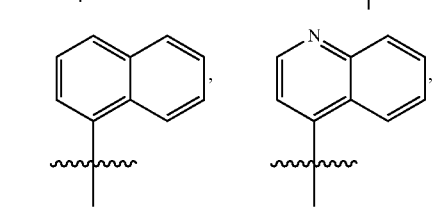
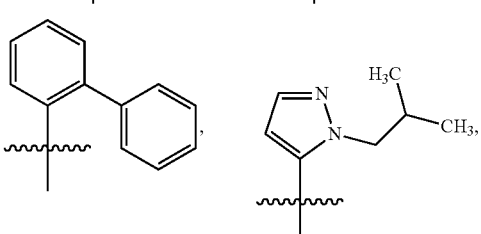
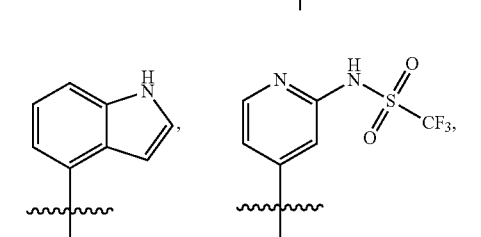
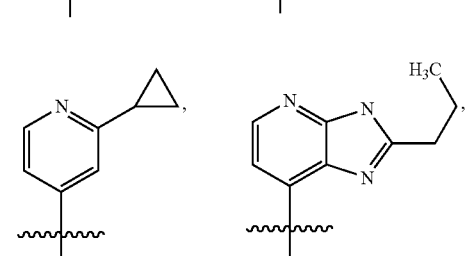
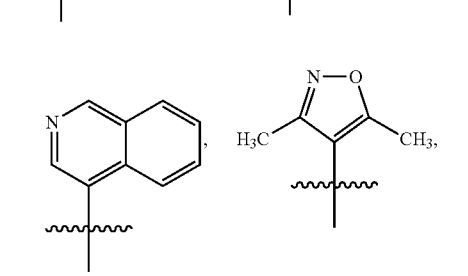
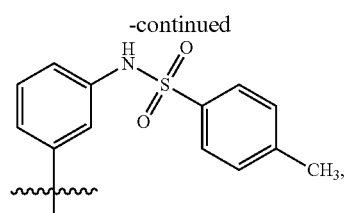
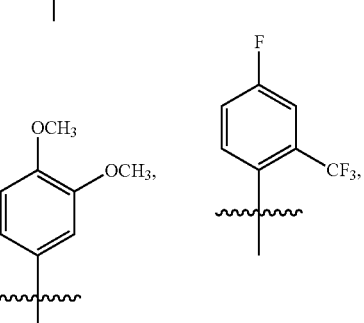
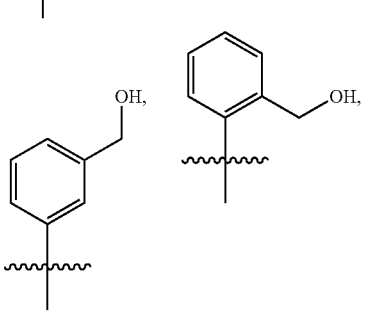
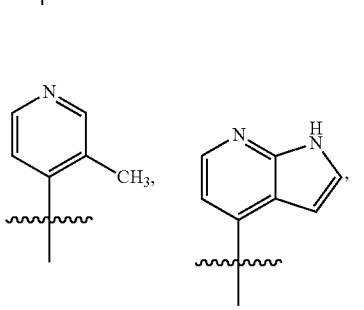
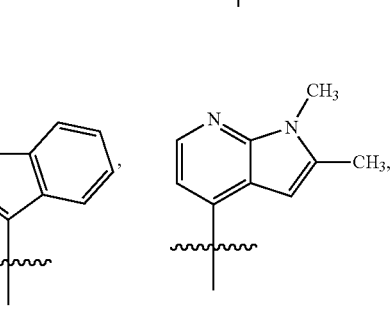
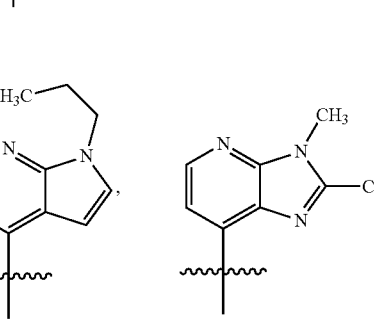

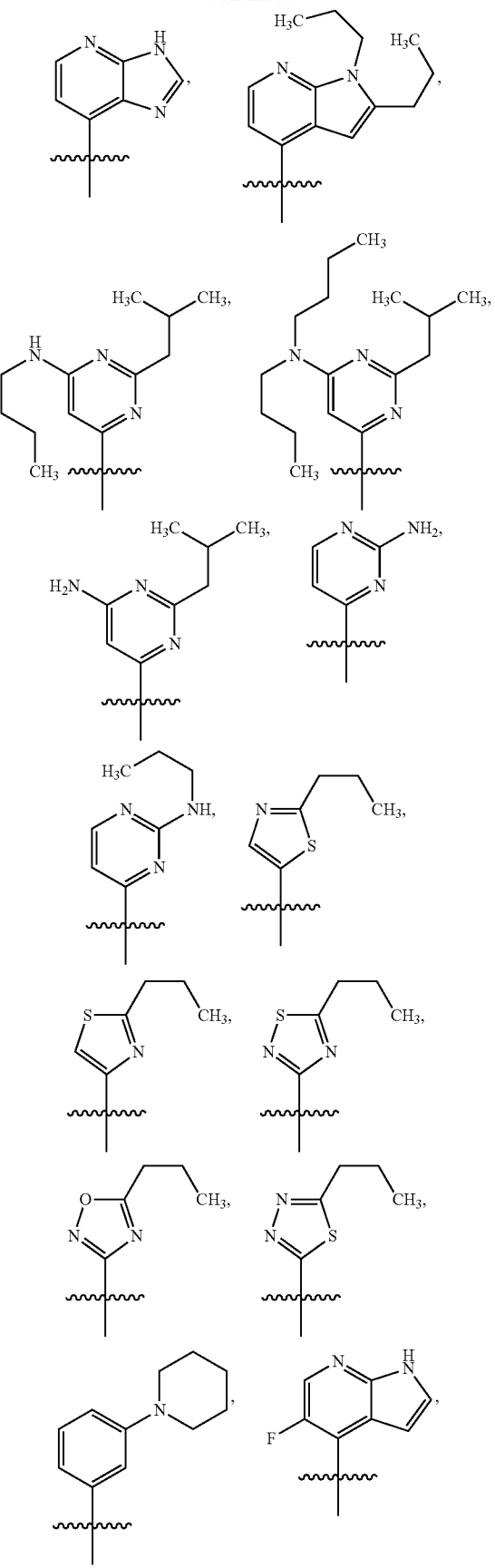
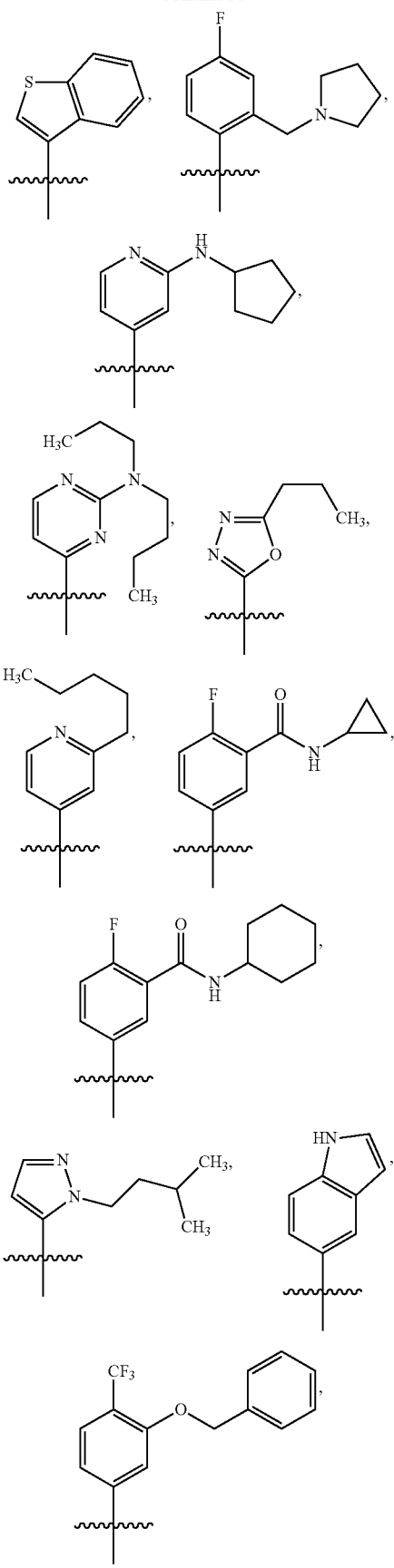

-continued

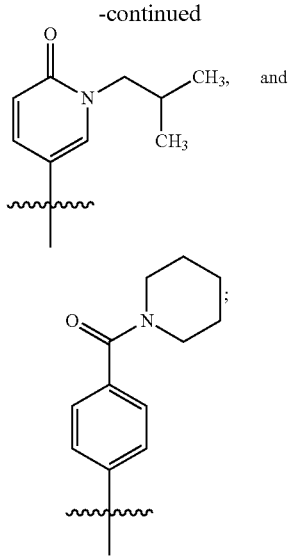

Each $R_{C4}$, $R_{C5}$, and $R_{C6}$, is independently hydrogen, halogen, CN, $CF_3$, OH, C1-C3 linear or branched alkyl, C2-C3 alkenyl, C2-C3 alkynyl, C3-C6 cycloalkyl, C3-C6 cycloalkenyl, C1-C3 linear or branched alkoxy, —$CO_2H$, —$CONR10R11$, or —$NHCONH_2$; or is taken with $R_{C7}$ to form the moiety

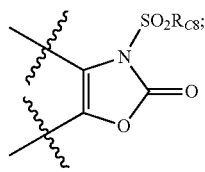

$R_{C7}$ is hydrogen, C1-C6 linear or branched alkyl, C1-C6 linear or branched hydroxyalkyl, —$(CR_{9a}R_{9b})_m NR10R11$, —$CO_2$-Alkyl, —$(CR_{9a}R_{9b})_m$O-Alkyl, —$(CR_{9a}R_{9b})_m OPO_3Na_2$, —$(CR_{9a}R_{9b})_m O(CR_{9a}R_{9b})_n$O-Alkyl, —$(CR_{9a}R_{9b})_m O(C=O)$-Alkyl, —$(CR_{9a}R_{9b})_m O(CR_{9a}R_{9b})_n O(C=O)$-Alkyl, —$(C=O)CH=CH_2$, —$SO_2R_{C8}$; or is taken with one of $R_{C4}$, $R_{C5}$ or $R_{C6}$ to form the moiety

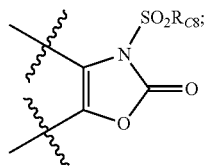

$R_{C8}$ is a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

$R_{C8'}$ is a linear or branched C1-C6 alkyl, a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

Each $R_{9a}$ and $R_{9b}$, where present, is independently hydrogen or C1-C6 linear or branched alkyl;

R10 and R11 are independently hydrogen, —$SO_2R_{C8'}$, C1-C6 linear or branched alkyl, C2-C6 linear or branched alkenyl, C3-C6 cycloalkyl, or C3-C6 cycloalkenyl; or are taken together with the N to which they are attached to form a C3-C6 heterocycle, pyrrolidinone, piperidinone, oxazolidinone, oxazinanone, imidazolidinone, tetrahydropyrimidin-2(1H)-one, a $1\lambda^6$,2-thiazolidine-1,1-dione, a $1,2\lambda^6$,3-oxathiazolidine-2,2-dione, or a $1\lambda^6$,2,5-thiadiazolidine-1,1-dione;

X is a heteroatom selected from S, O; or $NR_B$ wherein $R_B$ is hydrogen, a C1-C6 linear or branched alkyl, or a C3-C6 cycloalkyl; and Each m and n is 1, 2 or 3.

In one aspect, compounds of invention are described in Table 1, such as a compound selected from the group consisting of Compound Nos. 1 to 152; or a pharmaceutically acceptable salt, solvate, prodrug, or N-oxide thereof.

Further provided is a pharmaceutical composition, comprising a compound of Formulae (Ia), (Ib), (IIa), or (IIb), or any variations described herein, or a salt thereof, and a pharmaceutically acceptable carrier or excipient.

Further provided is a kit, comprising a compound of Formulae (Ia), (Ib), (IIa) or (IIb), or any variations described herein, or a salt thereof, and instructions for use.

Further provided are methods of treating one or more of the following: hyperproliferative disorders, metabolic disorders and/or pancreatitis in individuals in need thereof, such as humans, comprising administering to an individual in need thereof a therapeutically effective amount of a compound of Formulae (Ia), (Ib), (IIa), or (IIb), or any variations described herein, or a pharmaceutically acceptable salt thereof.

Further provided are methods of treating any diseases or conditions for which the modulation of SREBP is believed to be or is beneficial, comprising administering to an individual in need thereof a therapeutically effective amount of a compound of Formulae (Ia), (Ib), (IIa), or (IIb), or any variations described herein, or a pharmaceutically acceptable salt thereof.

BRIEF DESCRIPTION OF THE DRAWINGS

FIG. 4A. Pharmacokinetic parameters for Compound #37 (mouse).

FIG. 4B. Pharmacokinetic parameters for Compound #37 (dog).

FIG. 6A, tumor volume at three concentrations. FIG. 6B, tumor volume fold change at several doses.

DETAILED DESCRIPTION

Definitions

Figure 1:
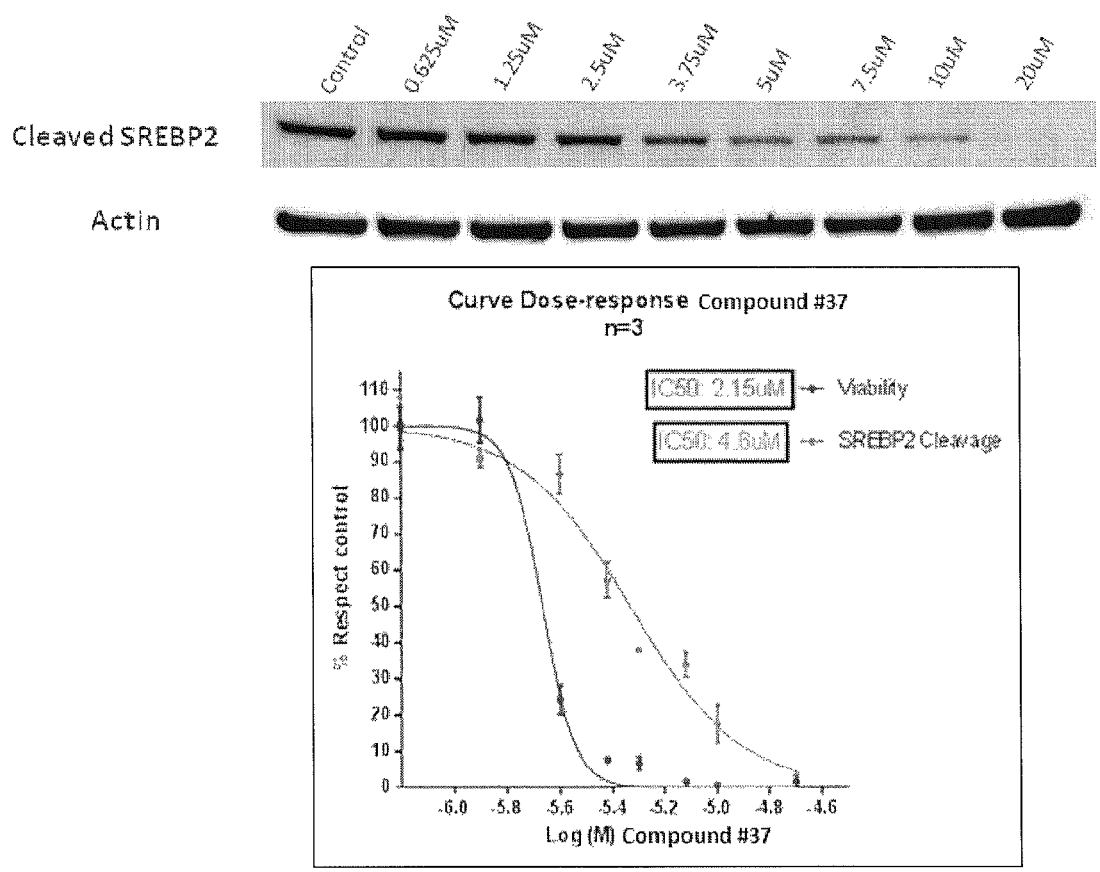
FIG. 1. Western-blots and dose response curves, with $IC_{50}$ values, of compound #37 in HepG2 cells: cell viability and SREBP-2 cleavage.

For use herein, unless clearly indicated otherwise, use of the terms "a", "an" and the like refers to one or more.

As used herein, reference to "about" a value or parameter herein includes (and describes) embodiments that are directed to that value or parameter per se. For example, description referring to "about X" includes description of "X".

"Alkyl" refers to and includes saturated linear or branched univalent hydrocarbon structures and combinations thereof. Particular alkyl groups are those having 1 to 6 carbon atoms (a "C1-C6 alkyl"). When an alkyl residue having a specific number of carbons is named, all geometric isomers having that number of carbons are intended to be encompassed and described; thus, for example, "butyl" is meant to include n-butyl, sec-butyl, iso-butyl, and tert-butyl; "propyl" includes n-propyl and iso-propyl. This term is exemplified by groups such as methyl, t-butyl, n-heptyl, octyl, and the like.

"Alkenyl" refers to an unsaturated hydrocarbon group having at least one site of olefinic unsaturation (i.e., having at least one moiety of the formula C=C) and preferably having from 2 to 10 carbon atoms and more preferably 2 to 8 carbon atoms. Examples of alkenyl include but are not limited to ethenyl "—CH=CH$_2$", —CH$_2$—CH=CH—CH$_3$ and —CH=CH—CH=CH$_2$.

"Alkynyl" refers to an unsaturated hydrocarbon group having at least one site of acetylenic unsaturation (i.e., having at least one moiety of the formula C≡C) and preferably having from 2 to 10 carbon atoms and more preferably 2 to 8 carbon atoms and the like. Examples of alkynyl include but are not limited to ethynyl "—C≡CH", —CH$_2$—C≡C—CH$_3$ and —C≡C—C≡CH.

"Cycloalkyl" refers to and includes cyclic univalent hydrocarbon structures. Cycloalkyl can consist of one ring, such as cyclohexyl, or multiple rings, such as adamantyl. A cycloalkyl comprising more than one ring may be fused, spiro or bridged, or combinations thereof. A preferred cycloalkyl is a saturated cyclic hydrocarbon having from 3 to 13 annular carbon atoms. A more preferred cycloalkyl is a saturated cyclic hydrocarbon having from 3 to 6 annular carbon atoms (a "C3-C6 cycloalkyl"). Examples of cycloalkyl groups include adamantyl, decahydronaphthalenyl, cyclopropyl, cyclobutyl, cyclopentyl, cyclohexyl, and the like.

"Cycloalkenyl" refers to an unsaturated hydrocarbon group within a cycloalkyl having at least one site of olefinic unsaturation (i.e., having at least one moiety of the formula C=C). Cycloalkenyl can consist of one ring, such as cyclohexyl, or multiple rings, such as norbornenyl. A more preferred cycloalkenyl is an unsaturated cyclic hydrocarbon having from 3 to 8 annular carbon atoms (a "C$_3$-C$_8$ cycloalkenyl"). Examples of cycloalkenyl groups include cyclopropenyl, cyclobutenyl, cyclopentenyl, cyclohexenyl, and the like.

"Heterocycle", "heterocyclic", or "heterocyclyl" refers to a saturated or an unsaturated non-aromatic group having a single ring or multiple condensed rings, and having from 1 to 10 annular carbon atoms and from 1 to 4 annular heteroatoms, such as nitrogen, sulfur or oxygen, and the like. A heterocycle comprising more than one ring may be fused, spiro or bridged, or any combination thereof. In fused ring systems, one or more of the rings can be aryl or heteroaryl. A heterocycle having more than one ring where at least one ring is aromatic may be connected to the parent structure at either a non-aromatic ring position or at an aromatic ring position. In one variation, a heterocycle having more than one ring where at least one ring is aromatic is connected to the parent structure at a non-aromatic ring position.

"Aryl" as used herein refers to an unsaturated aromatic carbocyclic group having a single ring (e.g., phenyl) or multiple condensed rings (e.g., naphthyl or anthryl) which condensed rings mayor may not be aromatic. The aryl group may be optionally substituted independently with one or more substituents described herein. Particular aryl groups are those having from 6 to 14 annular (i.e., ring) carbon atoms (a "C6-C14 aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" as used herein refers to an unsaturated aromatic cyclic group having from 1 to 14 annular (i.e., ring) carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings mayor may not be aromatic. The heteroaryl group may be optionally substituted independently with one or more substituents described herein. Particular heteroaryl groups are 5- to 14-membered rings having 1 to 12 annular (i.e., ring) carbon atoms and 1 to 6 annular (i.e., ring) heteroatoms independently selected from nitrogen, oxygen and sulfur; 5- to 10-membered rings having 1 to 8 annular carbon atoms and 1 to 4 annular heteroatoms independently selected from nitrogen, oxygen and sulfur; and 5-, 6- or 7-membered rings having 1 to 5 annular carbon atoms and 1 to 4 annular heteroatoms independently selected from nitrogen, oxygen and sulfur. In one variation, heteroaryl includes monocyclic aromatic 5-, 6- or 7-membered rings having from 1 to 6 annular carbon atoms and 1 to 4 annular heteroatoms independently selected from nitrogen, oxygen and sulfur. In another variation, heteroaryl includes polycyclic aromatic rings having from 1 to 12 annular carbon atoms and 1 to 6 annular heteroatoms independently selected from nitrogen, oxygen and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

"Alkoxy" refers to the group alkyl-O—, which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Hydroxyalkyl" refers to the group alkyl-OH, which includes, by way of example, hydroxymethyl, 1-hydroxyethyl, 2-hydroxyethyl, 1-hydroxyprop-1-yl, 2-hydroxyprop-2-yl, 3-hydroxypropyl, 4-hydroxybutyl, 5-hydroxypentyl, 6-hydroxyhexyl, and the like.

"Halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each H is replaced with a halo group is referred to as a "perhaloalkyl." An alkenyl group in which each H is replaced with a halo group is referred to as a "perhaloalkenyl." An alkynyl group in which each H is replaced with a halo group is referred to as a "perhaloalkynyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

Any and all stereoisomers, including geometric isomers (cis/trans or E/Z isomers), tautomers, salts, N-oxides, and solvates of the compounds described herein can be used in the disclosed methods. This disclosure also provides methods of making such compounds.

Compounds

In some embodiments, compounds disclosed herein fall within formulae (Ia) or (Ib):

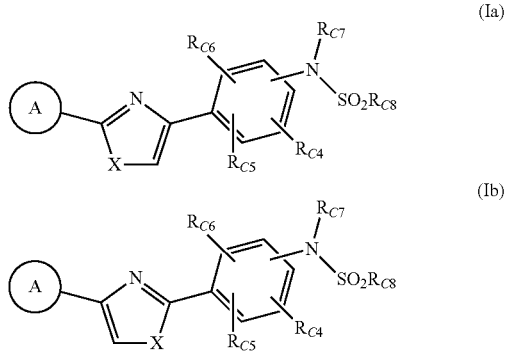

or a pharmaceutically acceptable salt thereof, wherein:
A is either:
i. an aryl or heteroaryl, each having only one ring, substituted with 1, 2, or 3 substituents selected from the group consisting of halogen, CN, $CF_3$, OH, C1-C6 linear or branched alkyl, C3-C6 cycloalkyl, C3-C6 cycloalkenyl, C1-C6 linear or branched hydroxyalkyl, C1-C3 linear or branched alkoxy, C3-C6 cycloalkylmethyl, —$(CH_2)_mCF_3$, =O, —$CH_2OCH_3$, —OBn, —$CO_2H$, —$CO_2$-Alkyl, —NR10R11, and —CONR10R11; or
ii. an aryl or heteroaryl, each having more than one ring, optionally substituted with 1, 2, or 3 substituents selected from the group consisting of halogen, CN, $CF_3$, OH, C1-C6 linear or branched alkyl, C3-C6 cycloalkyl, C3-C6 cycloalkenyl, C1-C6 linear or branched hydroxyalkyl, C1-C3 linear or branched alkoxy, C3-C6 cycloalkylmethyl, —$(CH_2)_mCF_3$, =O, —$CH_2OCH_3$, —$CH_2OH$, —OBn, —$CO_2H$, —$CO_2$-Alkyl, —NR10R11, and —CONR10R11;

Each $R_{C4}$, $R_{C5}$, and $R_{C6}$, is independently hydrogen, halogen, CN, $CF_3$, OH, C1-C3 linear or branched alkyl, C2-C3 alkenyl, C2-C3 alkynyl, C3-C6 cycloalkyl, C3-C6 cycloalkenyl, C1-C3 linear or branched alkoxy, —$CO_2H$, —CONR10R11, or —$NHCONH_2$; or is taken with $R_{C7}$ to form the moiety;

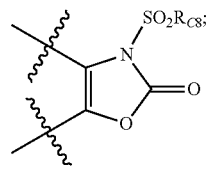

$R_{C7}$ is hydrogen, C1-C6 linear or branched alkyl, C1-C6 linear or branched hydroxyalkyl, —$(CR_{9a}R_{9b})_mNR10R11$, —$CO_2$-Alkyl, —$(CR_{9a}R_{9b})_mO$-Alkyl, —$(CR_{9a}R_{9b})_mOPO_3Na_2$, —$(CR_{9a}R_{9b})_mO(CR_{9a}R_{9b})_nO$-Alkyl, —$(CR_{9a}R_{9b})_mO(C=O)$-Alkyl, —$(CR_{9a}R_9)O(CR_{9a}R_{9b})_nO(C=O)$-Alkyl, —(C=O)CH=$CH_2$, —$SO_2R_{C8'}$; or is taken with one of $R_{C4}$, $R_{C5}$ or $R_{C6}$ to form the moiety

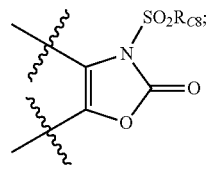

$R_{C8}$ is a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

$R_{C8'}$ is a linear or branched C1-C6 alkyl, a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

Each $R_{9a}$ and $R_{9b}$, where present, is independently hydrogen or C1-C6 linear or branched alkyl;

R10 and R11 are independently hydrogen, —$SO_2R_{C8'}$, C1-C6 linear or branched alkyl, C2-C6 linear or branched alkenyl, C3-C6 cycloalkyl, or C3-C6 cycloalkenyl; or are taken together with the N to which they are attached to form a C3-C6 heterocycle, pyrrolidinone, piperidinone, oxazolidinone, oxazinanone, imidazolidinone, tetrahydropyrimidin-2(1H)-one, a $1\lambda^6$,2-thiazolidine-1,1-dione, a $1,2\lambda^6$,3-oxathiazolidine-2,2-dione, or a $1\lambda^6$,2,5-thiadiazolidine-1,1-dione;

X is a heteroatom selected from S, O; or $NR_B$ wherein $R_B$ is hydrogen, a C1-C6 linear or branched alkyl, or a C3-C6 cycloalkyl; and Each m and n is 1, 2 or 3.

In some embodiments, compounds disclosed herein fall within formulae (IIa) or (IIb):

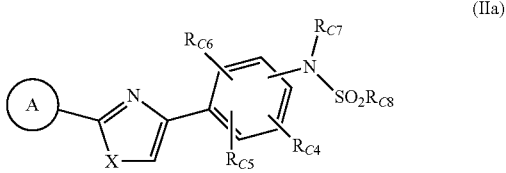

-continued
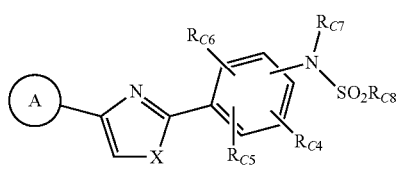
(IIb)
or a pharmaceutically acceptable salt thereof, wherein:
A is a moiety selected from the group consisting of:
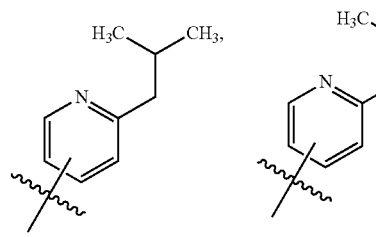
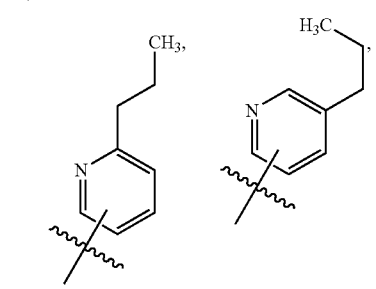
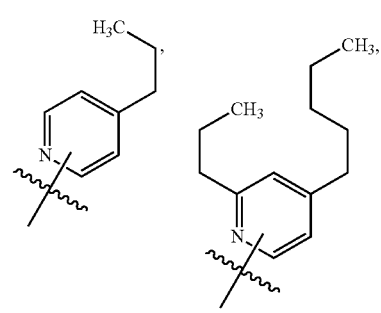
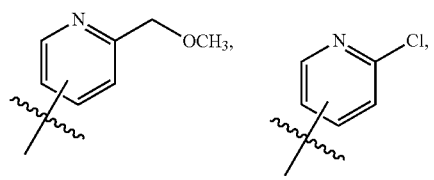
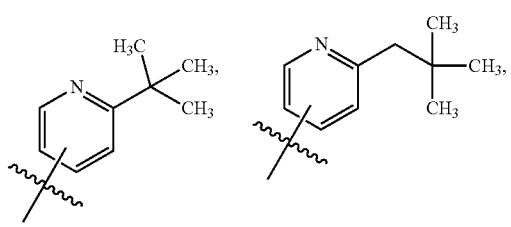
-continued
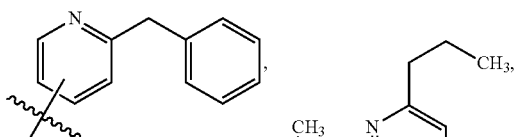
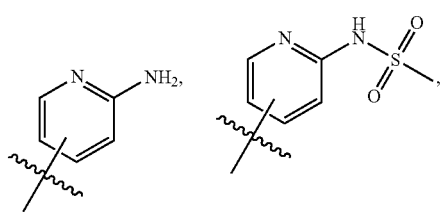
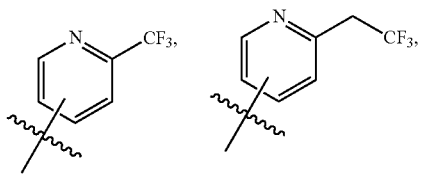
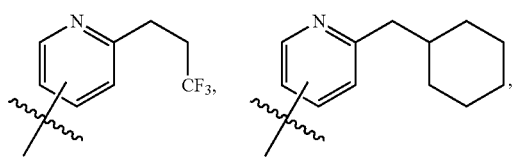
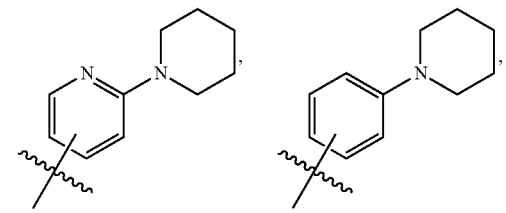
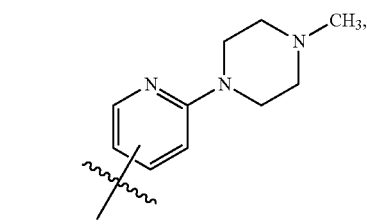
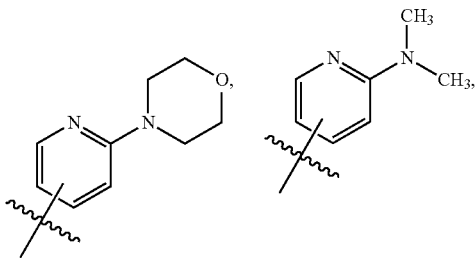
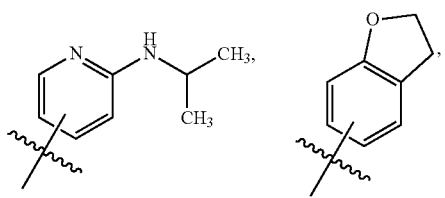

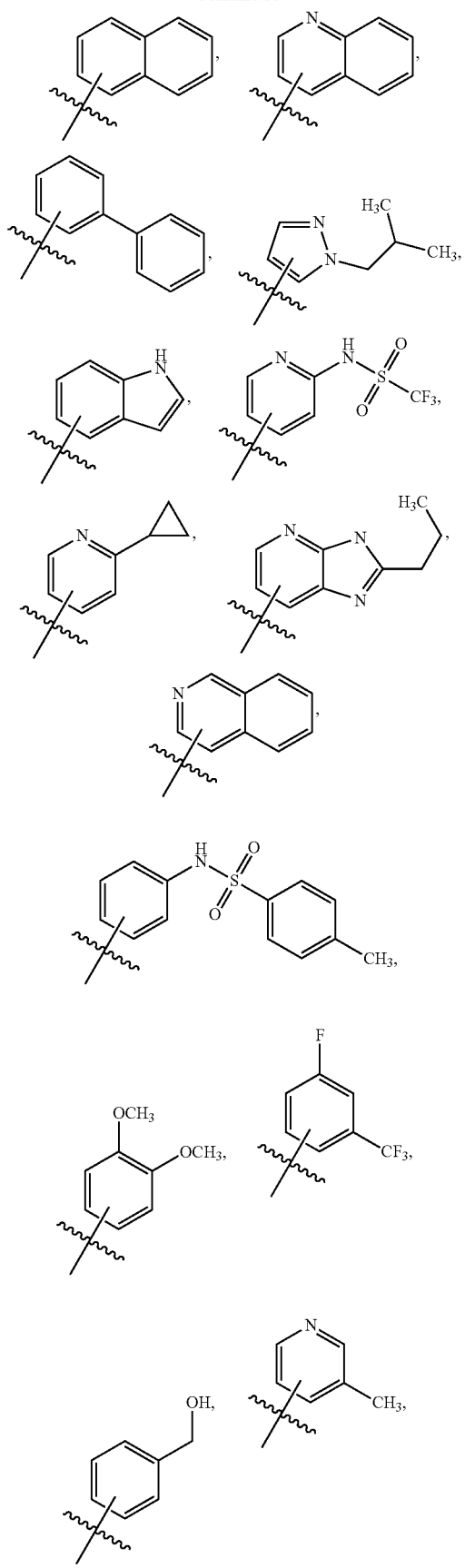
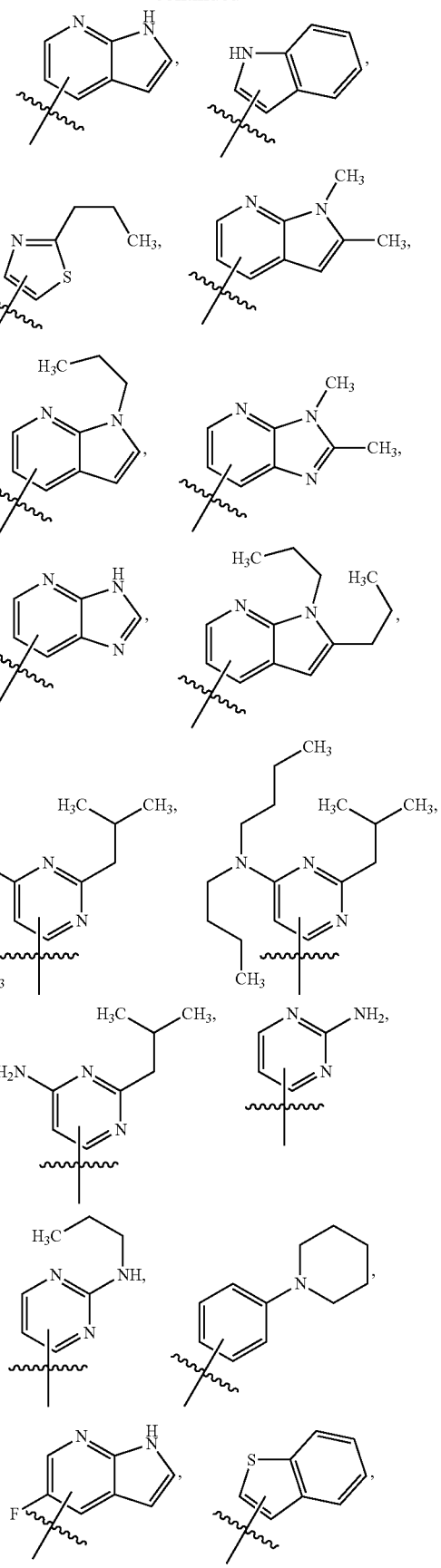

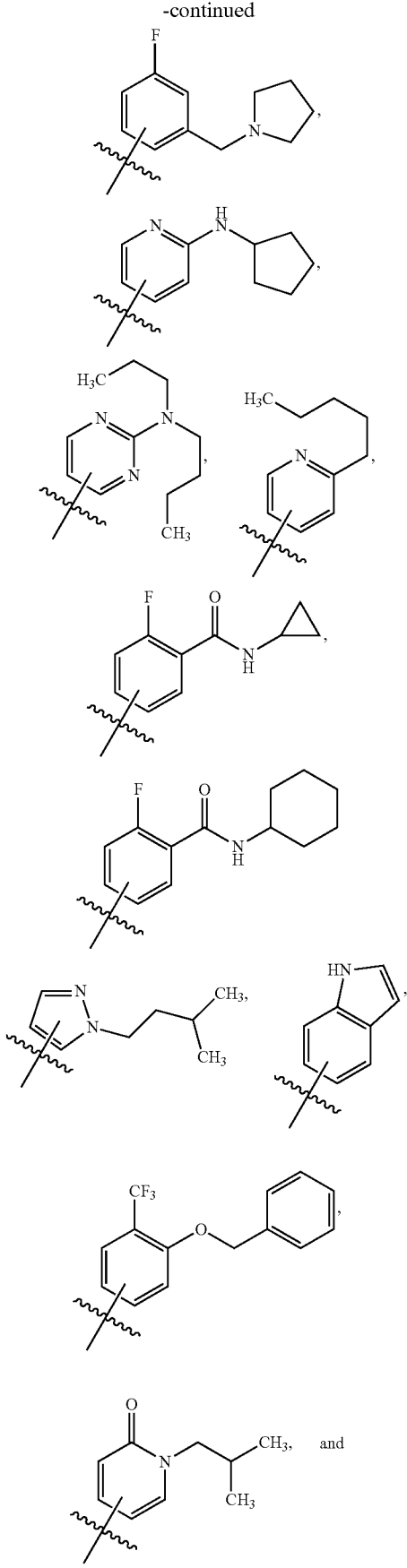

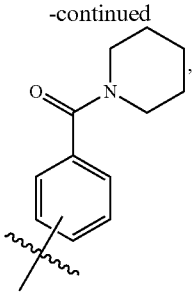

wherein the ring containing X is linked to ring A at any available position on ring A;

Each $R_{C4}$, $R_{C5}$, and $R_{C6}$, is independently hydrogen, halogen, CN, $CF_3$, OH, C1-C3 linear or branched alkyl, C2-C3 alkenyl, C2-C3 alkynyl, C3-C6 cycloalkyl, C3-C6 cycloalkenyl, C1-C3 linear or branched alkoxy, —$CO_2H$, —CONR10R11, or —$NHCONH_2$;

or is taken with $R_{C7}$ to form the moiety

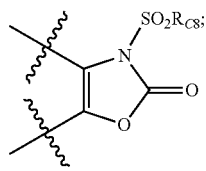

$R_{C7}$ is hydrogen, C1-C6 linear or branched alkyl, C1-C6 linear or branched hydroxyalkyl, —$(CR_{9a}R_{9b})_m$NR10R11, —$CO_2$-Alkyl, —$(CR_{9a}R_{9b})_m$O-Alkyl, —$(CR_{9a}R_{9b})_m$OPO$_3$Na$_2$, —$(CR_{9a}R_{9b})_m$O$(CR_{9a}R_{9b})_n$O-Alkyl, —$(CR_{9a}R_{9b})_m$O(C=O)-Alkyl, —$(CR_{9a}R_{9b})_m$O$(CR_{9a}R_{9b})_n$O(C=O)-Alkyl, —(C=O)CH=$CH_2$, —$SO_2R_{C8'}$; or is taken with one of $R_{C4}$, $R_{C5}$ or $R_{C6}$ to form the moiety

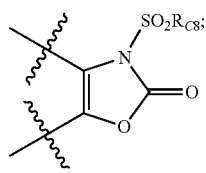

$R_{C8}$ is a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

$R_{C8'}$ is a linear or branched C1-C6 alkyl, a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

Each $R_{9a}$ and $R_{9b}$, where present, is independently hydrogen or C1-C6 linear or branched alkyl;

R10 and R11 are independently hydrogen, —$SO_2R_{C8'}$, C1-C6 linear or branched alkyl, C2-C6 linear or branched alkenyl, C3-C6 cycloalkyl, or C3-C6 cycloalkenyl; or are taken together with the N to which they are attached to form a C3-C6 heterocycle, pyrrolidinone, piperidinone, oxazolidinone, oxazinanone, imidazolidinone, tetrahydropyrimidin-2(1H)-one, a $1\lambda^6$,2-thiazolidine-1,1-dione, a $1,2\lambda^6$,3-oxathiazolidine-2,2-dione, or a $1\lambda^6$,2,5-thiadiazolidine-1,1-dione;

X is a heteroatom selected from S, O; or $NR_B$ wherein $R_B$ is hydrogen, a C1-C6 linear or branched alkyl, or a C3-C6 cycloalkyl; and Each m and n is 1, 2 or 3.

In some embodiments, compounds disclosed herein fall within formulae (IIa) or (IIb):

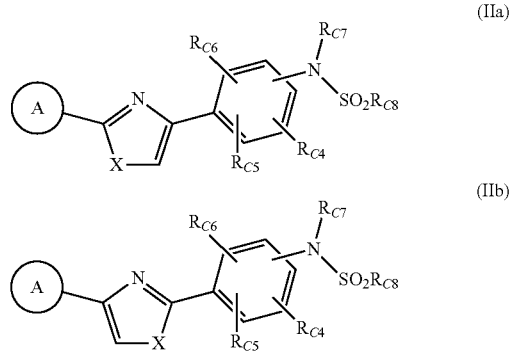

or a pharmaceutically acceptable salt thereof, wherein:

A is a moiety selected from the group consisting of:

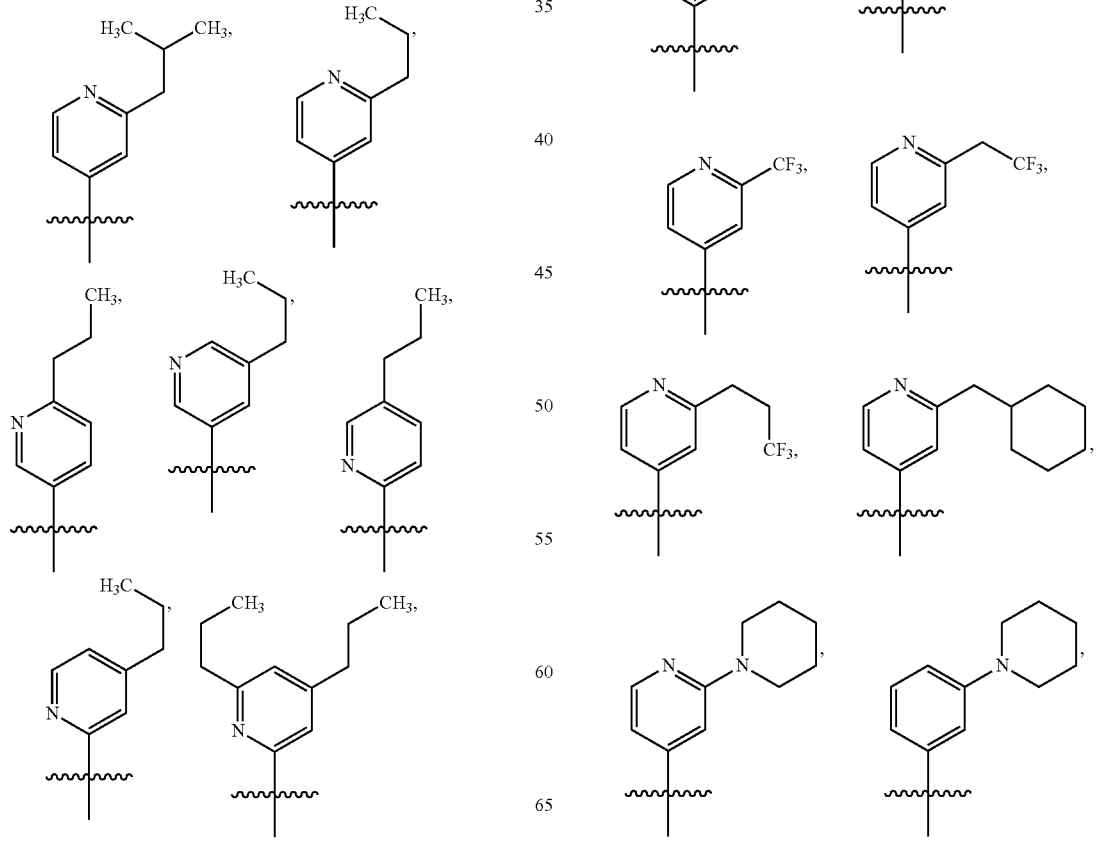

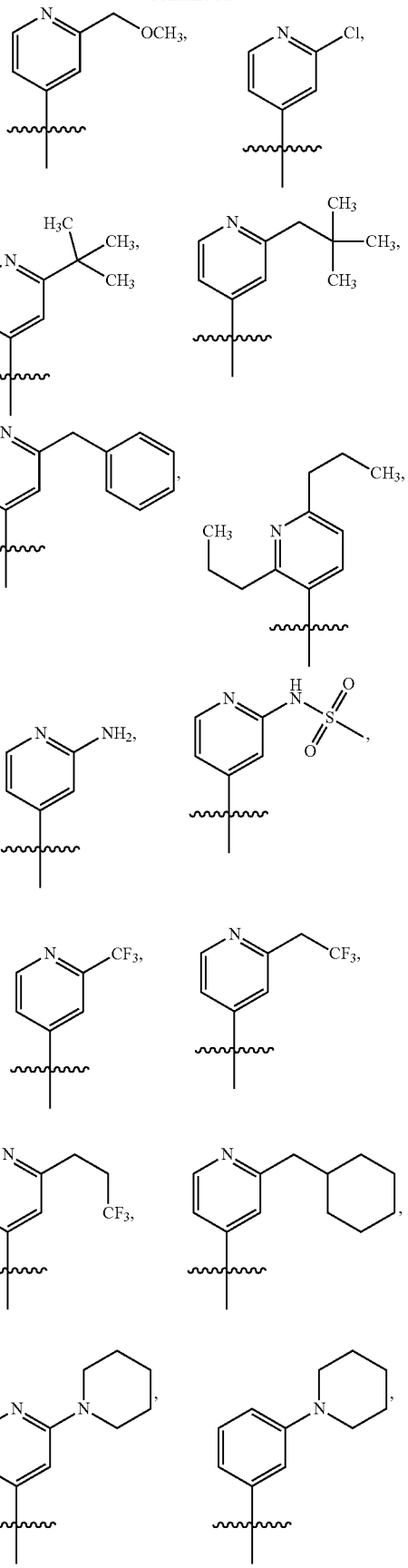

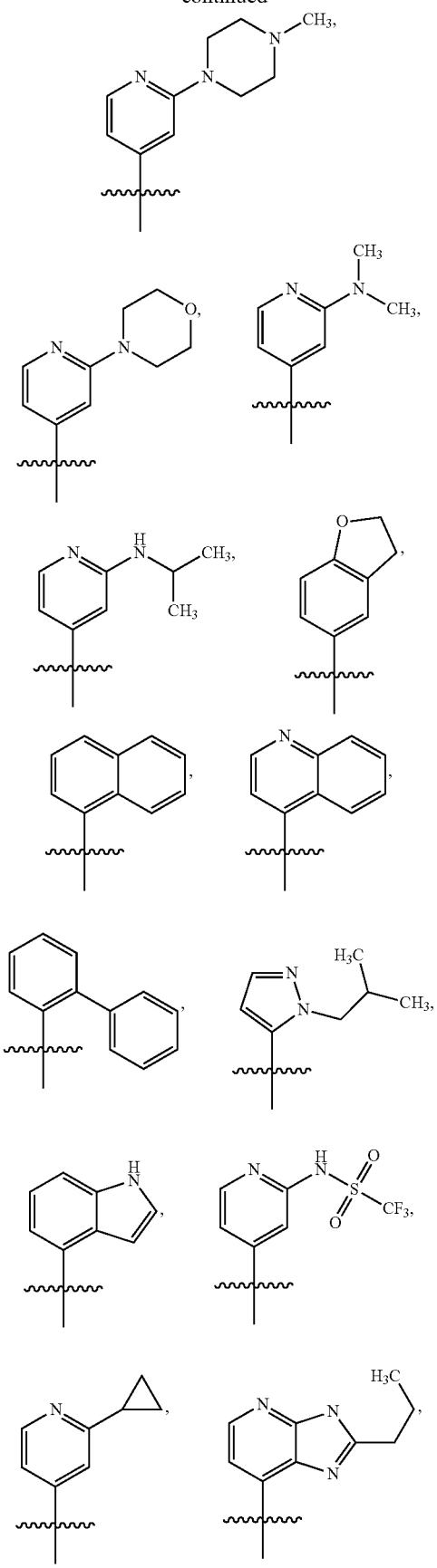
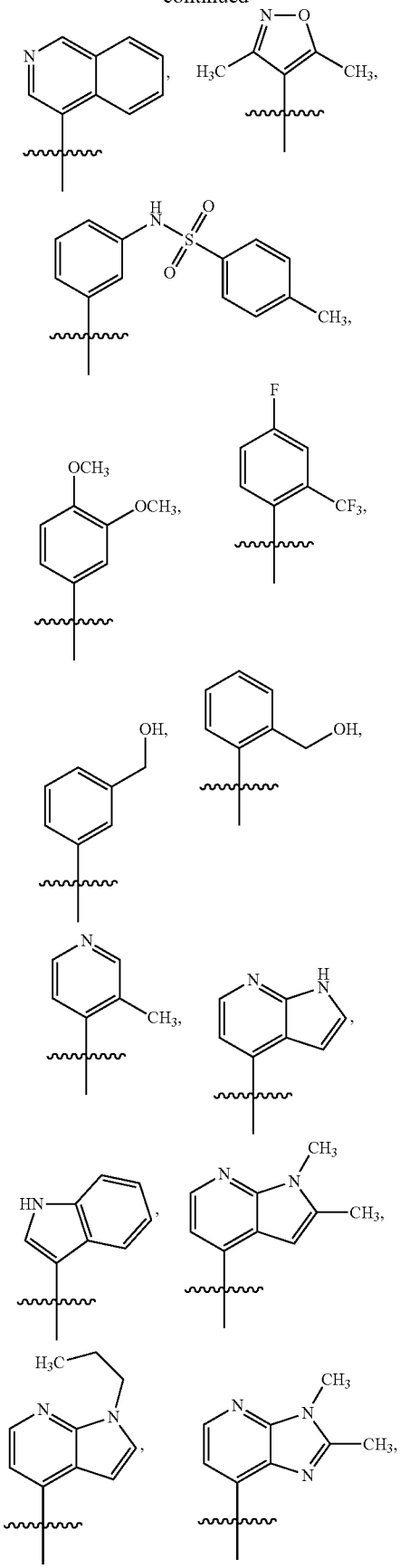

33
-continued
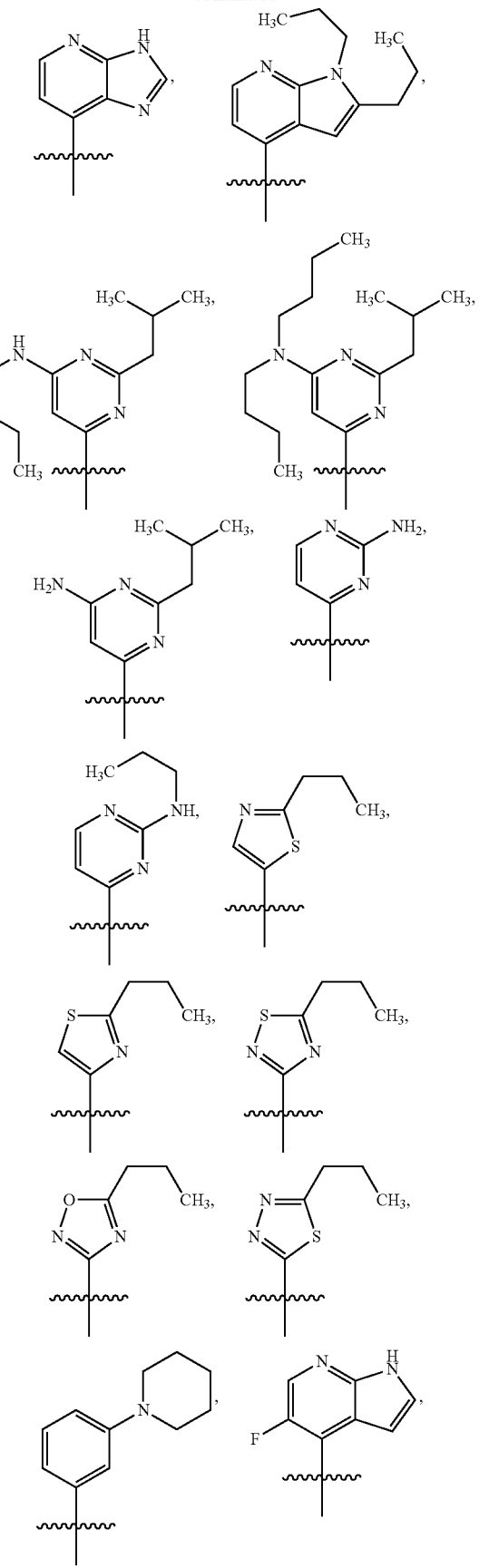
34
-continued
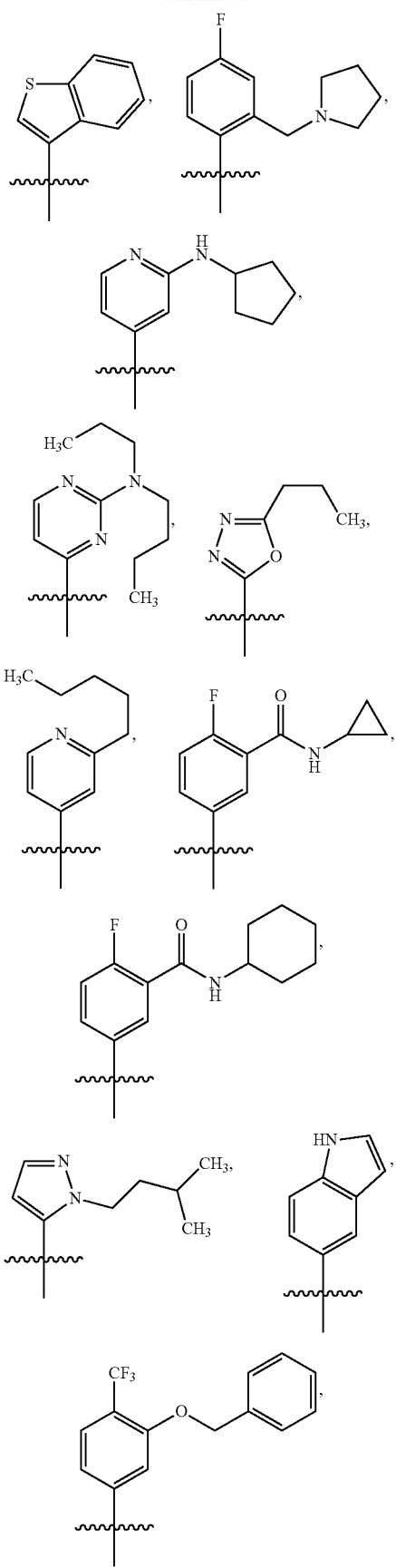

-continued

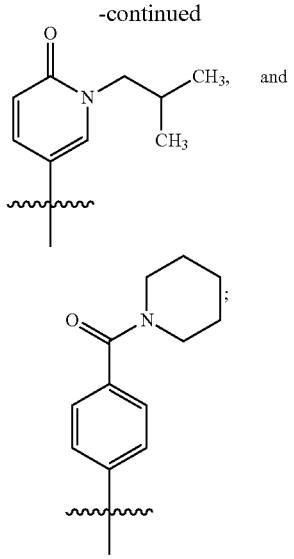

Each $R_{C4}$, $R_{C5}$, and $R_{C6}$, is independently hydrogen, halogen, CN, CF$_3$, OH, C1-C3 linear or branched alkyl, C2-C3 alkenyl, C2-C3 alkynyl, C3-C6 cycloalkyl, C3-C6 cycloalkenyl, C1-C3 linear or branched alkoxy, —CO$_2$H, —CONR10R11, or —NHCONH$_2$; or is taken with $R_{C7}$ to form the moiety

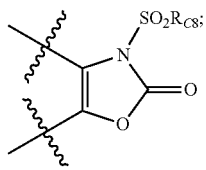

$R_{C7}$ is hydrogen, C1-C6 linear or branched alkyl, C1-C6 linear or branched hydroxyalkyl, —(CR$_{9a}$R$_{9b}$)$_m$NR10R11, —CO$_2$-Alkyl, —(CR$_{9a}$R$_{9b}$)$_m$O-Alkyl, —(CR$_{9a}$R$_{9b}$)$_m$OPO$_3$Na$_2$, —(CR$_{9a}$R$_{9b}$)$_m$O(CR$_{9a}$R$_{9b}$)$_n$O-Alkyl, —(CR$_{9a}$R$_{9b}$)$_m$O(C=O)-Alkyl, —(CR$_{9a}$R$_{9b}$)$_m$O(CR$_{9a}$R$_{9b}$)$_n$O(C=O)-Alkyl, —(C=O)CH=CH$_2$, —SO$_2$R$_{C8}$; or is taken with one of $R_{C4}$, $R_{C5}$ or $R_{C6}$ to form the moiety

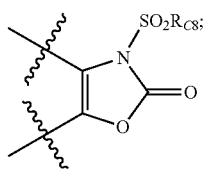

$R_{C8}$ is a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

$R_{C8'}$ is a linear or branched C1-C6 alkyl, a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

Each $R_{9a}$ and $R_{9b}$, where present, is independently hydrogen or C1-C6 linear or branched alkyl;

R10 and R11 are independently hydrogen, —SO$_2$R$_{C8'}$, C1-C6 linear or branched alkyl, C2-C6 linear or branched alkenyl, C3-C6 cycloalkyl, or C3-C6 cycloalkenyl; or are taken together with the N to which they are attached to form a C3-C6 heterocycle, pyrrolidinone, piperidinone, oxazolidinone, oxazinanone, imidazolidinone, tetrahydropyrimidin-2(1H)-one, a 1λ$^6$,2-thiazolidine-1,1-dione, a 1,2λ$^6$,3-oxathiazolidine-2,2-dione, or a 1λ$^6$,2,5-thiadiazolidine-1,1-dione;

X is a heteroatom selected from S, O; or NR$_B$ wherein R$_B$ is hydrogen, a C1-C6 linear or branched alkyl, or a C3-C6 cycloalkyl; and Each m and n is 1, 2 or 3.

In some variations of Formulae (IIa) or (IIb), A is a moiety selected from the group consisting of:

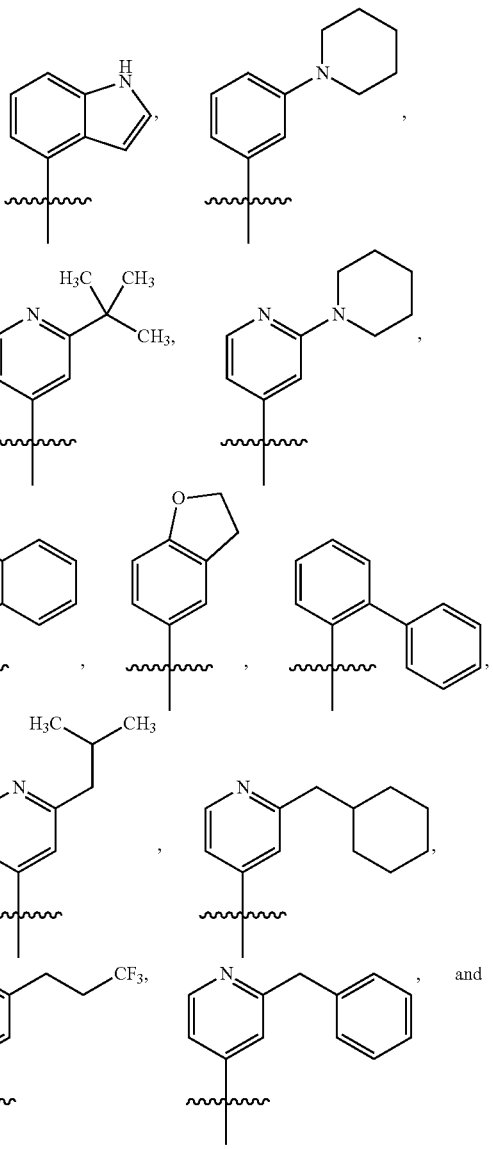

-continued

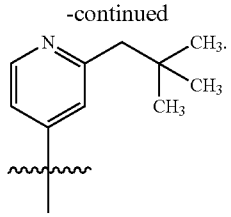

In some variations of Formulae (IIa) or (IIb), A is a moiety selected from the group consisting of:

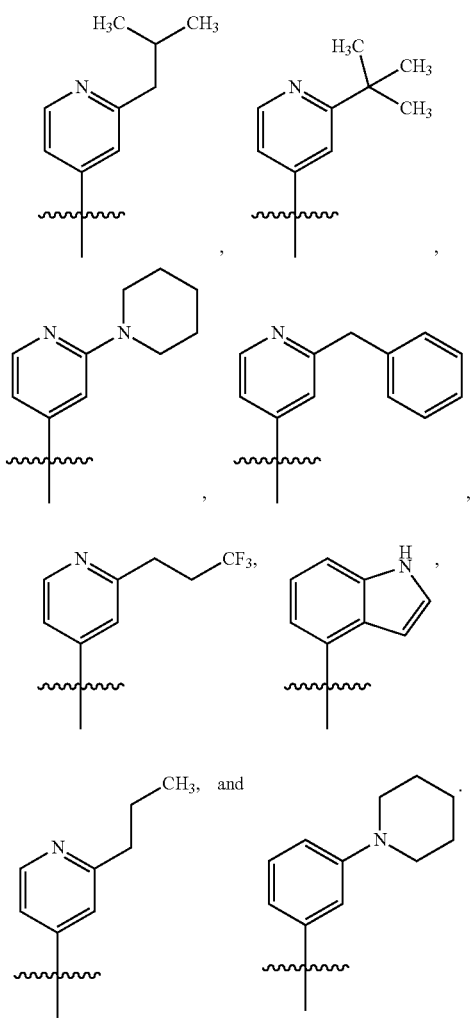

In some variations of Formulae (Ia), (Ib), (IIa) or (IIb), X is S. In some variations, X is O. In some variations, X is $NR_B$, wherein $R_B$ is hydrogen. In some variations, X is $NR_B$, wherein $R_B$ is a linear or branched C1-C6 alkyl. In these variations, $R_B$ is a linear C1-C6 alkyl selected from methyl, ethyl, n-propyl, n-butyl, n-pentyl or n-hexyl. In particular variations, $R_B$ is methyl. In some variations, $R_B$ is a branched C1-C6 alkyl selected from iso-propyl, iso-pentyl, and tert-butyl.

In some variations of Formulae (Ia), (Ib), (IIa) or (IIb), the phenyl ring containing the groups $R_{C4}$, $R_{C5}$, $R_{C6}$, and $-NR_{C7}SO_2R_{C8}$, is a moiety selected from:

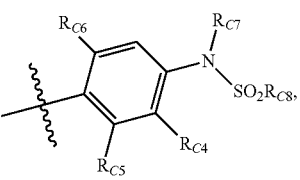

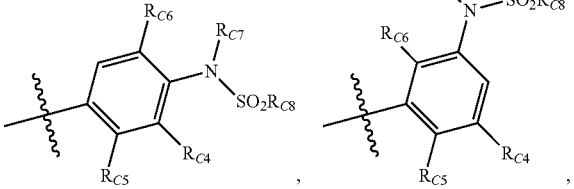

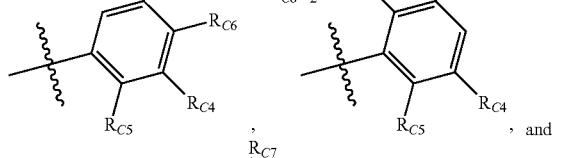

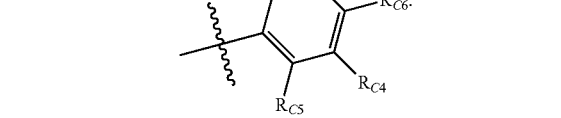
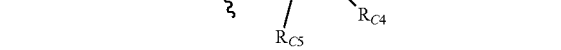
, and

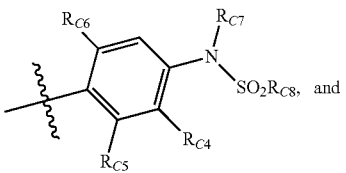

In particular variations of Formulae (Ia), (Ib), (IIa) or (IIb), the phenyl ring containing the groups $R_{C4}$, $R_{C5}$, $R_{C6}$, and $-NR_{C7}SO_2R_{C8}$, is a moiety selected from:

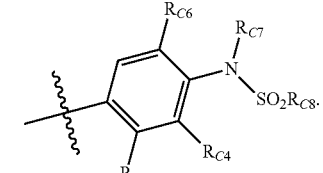
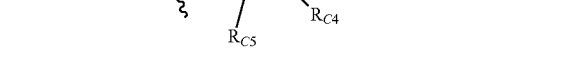

In some variations of Formulae (Ia), (Ib), (IIa) or (IIb), one or more of $R_{C4}$, $R_{C5}$ and $R_{C6}$, is hydrogen. In some variations, one or more of $R_{C4}$, $R_{C5}$ and $R_{C6}$, is halogen. In some variations, one or more of $R_{C4}$, $R_{C5}$ and $R_{C6}$, is CN. In some variations, one or more of $R_{C4}$, $R_{C5}$ and $R_{C6}$, is $CF_3$. In some variations, one or more of $R_{C4}$, $R_{C5}$ and $R_{C6}$, is OH. In some variations, one or more of $R_{C4}$, $R_{C5}$ and $R_{C6}$, is C1-C3 linear or branched alkyl. In some variations, one or more of $R_{C4}$, $R_{C5}$ and $R_{C6}$, is C2-C3 alkenyl. In some variations, one or more of $R_{C4}$, $R_{C5}$ and $R_{C6}$, is C2-C3 alkynyl. In some variations, one or more of $R_{C4}$, $R_{C5}$ and $R_{C6}$, is C3-C6 cycloalkyl. In some variations, one or more of $R_{C4}$, $R_{C5}$ and $R_{C6}$, is C3-C6 cycloalkenyl. In some variations, one or more of $R_{C4}$, $R_{C5}$ and $R_{C6}$, is C1-C3 linear or branched alkoxy. In some variations, one or more of $R_{C4}$, $R_{C5}$ and $R_{C6}$, is —CON(CH$_3$)$_2$. In some variations, one or more of $R_{C4}$, $R_{C5}$ and $R_{C6}$, is —CO$_2$H. In some variations, one or more of $R_{C4}$, $R_{C5}$ and $R_{C6}$, is —CONH$_2$. In some variations, one or more of $R_{C4}$, $R_{C5}$ and $R_{C6}$, is —NHCONH$_2$. In some variations, one or more of $R_{C4}$, $R_{C5}$ and $R_{C6}$, is —CONHCH$_3$. In some variations, one or more of $R_{C4}$, $R_{C5}$ and $R_{C6}$, is taken with $R_{C7}$ to form the moiety

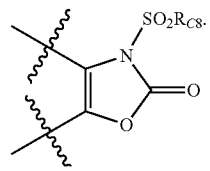

In some variations of Formulae (Ia), (Ib), (IIa) or (IIb), one of $R_{C4}$, $R_{C5}$ and $R_{C6}$ is hydrogen. In some variations, two of $R_{C4}$, $R_{C5}$ and $R_{C6}$ are hydrogen. In some variations, each $R_{C4}$, $R_{C5}$ and $R_{C6}$ is hydrogen. In some variations, one or more of $R_{C4}$, $R_{C5}$ and $R_{C6}$ is methoxy. In some variations, one or more of $R_{C4}$, $R_{C5}$ and $R_{C6}$ is OH.

In some variations of Formulae (Ia), (Ib), (IIa) or (IIb), one of $R_{C4}$, $R_{C5}$ and $R_{C6}$ is halogen. In some variations, two of $R_{C4}$, $R_{C5}$ and $R_{C6}$ are halogen. In some variations each $R_{C4}$, $R_{C5}$ and $R_{C6}$ is halogen. In some variations, one of $R_{C4}$, $R_{C5}$ and $R_{C6}$ is hydrogen, and the remaining two of $R_{C4}$, $R_{C5}$ and $R_{C6}$ are halogen. In some variations, two of $R_{C4}$, $R_{C5}$ and $R_{C6}$ are hydrogen, and the remaining one of $R_{C4}$, $R_{C5}$ and $R_{C6}$ is halogen. In some variations, $R_{C4}$, $R_{C5}$ and $R_{C6}$ are each halogen. In some embodiments, one of $R_{C4}$, $R_{C5}$ and $R_{C6}$ is fluoro, chloro or bromo. In some embodiments, two of $R_{C4}$, $R_{C5}$ and $R_{C6}$ are fluoro, chloro or bromo. In some embodiments, one of $R_{C4}$, $R_{C5}$ and $R_{C6}$ is chloro. In some embodiments, one of $R_{C4}$, $R_{C5}$ and $R_{C6}$ is chloro and one of $R_{C4}$, $R_{C5}$ and $R_{C6}$ is bromo. In some embodiments, $R_{C4}$ is chloro. In some embodiments, $R_{C5}$ is chloro. In some embodiments, $R_{C4}$ is bromo. In some embodiments, $R_{C5}$ is bromo.

In some variations of Formulae (Ia), (Ib), (IIa) or (IIb), $R_{C7}$ is hydrogen. In some variations, $R_{C7}$ is C1-C6 linear or branched alkyl. In some variations, $R_{C7}$ is C1-C6 linear or branched hydroxyalkyl. In some variations, $R_{C7}$ is —(CR$_{9a}$R$_{9b}$)$_m$NR10R11. In some variations, $R_{C7}$ is —CO$_2$-Alkyl. In some variations, $R_{C7}$ is —(CR$_{9a}$R$_{9b}$)$_m$O-Alkyl. In some variations, $R_{C7}$ is —(CR$_{9a}$R$_{9b}$)$_m$OPO$_3$Na$_2$. In some variations, $R_{C7}$ is —(CR$_{9a}$R$_{9b}$)$_m$O(CR$_{9a}$R$_{9b}$)$_n$O-Alkyl. In some variations, $R_{C7}$ is —(CR$_{9a}$R$_{9b}$)$_m$O(C=O)-Alkyl. In some variations, $R_{C7}$ is —(CR$_{9a}$R$_{9b}$)$_m$O(CR$_{9a}$R$_{9b}$)$_n$O(C=O)-Alkyl. In some variations, $R_{C7}$ is —(C=O)CH=CH$_2$. In some variations, $R_{C7}$ is —SO$_2$R$_{C8'}$. In some variations, $R_{C7}$ is taken with one of $R_{C4}$, $R_{C5}$ or $R_{C6}$ to form the moiety

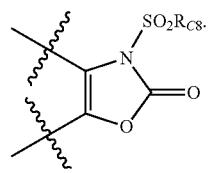

In all embodiments, $R_{C8}$ is a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom. In some embodiments, $R_{C8}$ is a linear or branched C1-C6 perhaloalkyl. In some embodiments, the C1-C6 perhaloalkyl is a C1-C6 perfluoroalkyl. In some embodiments, the C1-C6 perfluoroalkyl is selected from

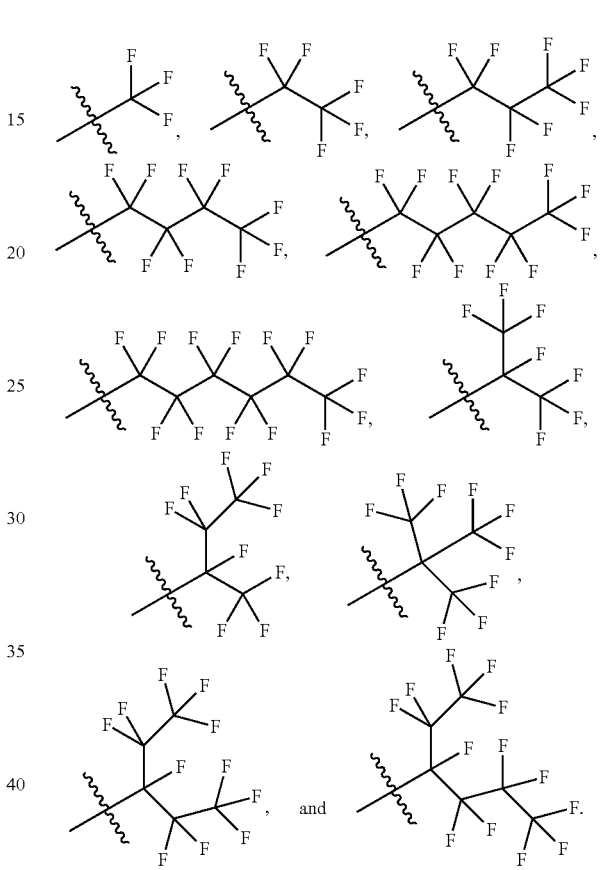

In preferred embodiments, the C1-C6 perfluoroalkyl is —CF$_3$. In some embodiments, $R_{C8}$ is a linear or branched C1-C6 alkyl having at least two halogen atoms. In some embodiments, $R_{C8}$ is selected from:

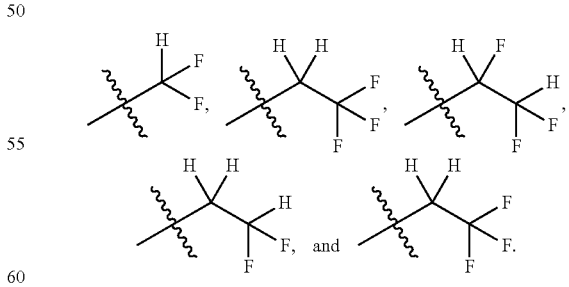

In some embodiments, $R_{C8}$ is a linear or branched C2-C6 perhaloalkenyl. In some embodiments, $R_{C8}$ is a linear or branched C2-C6 perhaloalkynyl. In some embodiments, $R_{C8}$ is a linear or branched C1-C6 alkyl having at least one halogen atom. In some embodiments, $R_{C8}$ is a linear or branched C2-C6 alkenyl having at least one halogen atom.

In some embodiments, $R_{C8}$ is or a linear or branched C2-C6 alkynyl having at least one halogen atom.

In some embodiments, $R_{C8'}$ is a linear or branched C1-C6 alkyl, a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom. In some embodiments, $R_{C8'}$ is a linear or branched C1-C6 perhaloalkyl. In some embodiments, the C1-C6 perhaloalkyl is a C1-C6 perfluoroalkyl. In some embodiments, the C1-C6 perfluoroalkyl is selected from

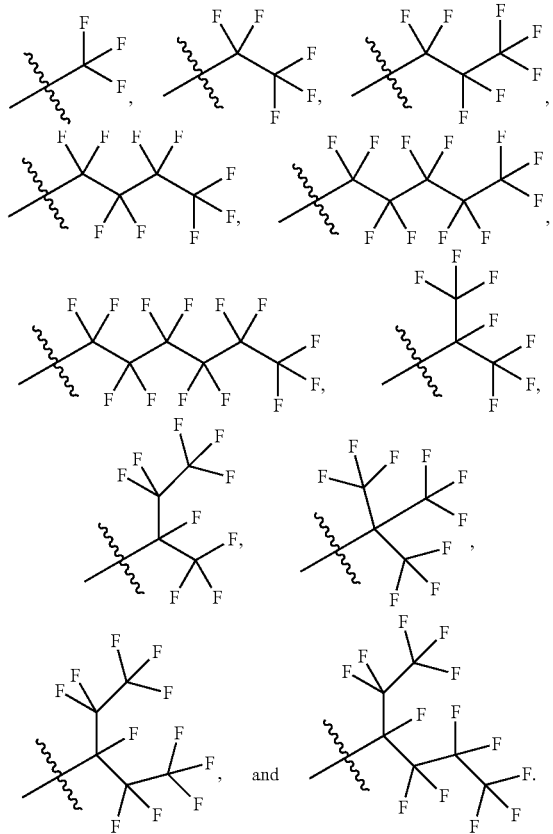

In preferred embodiments, the C1-C6 perfluoroalkyl is —CF$_3$. In some embodiments, $R_{C8'}$ is a linear or branched C1-C6 alkyl having at least two halogen atoms. In some embodiments, $R_{C8'}$ is selected from:

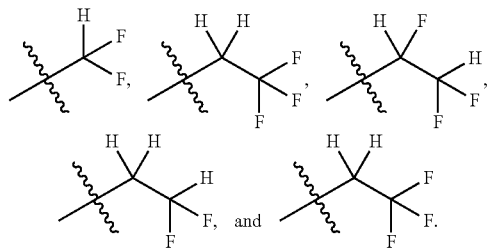

In some embodiments, $R_{C8'}$ is a linear or branched C2-C6 perhaloalkenyl. In some embodiments, $R_{C8'}$ is a linear or branched C2-C6 perhaloalkynyl. In some embodiments, $R_{C8'}$ is a linear or branched C1-C6 alkyl having at least one halogen atom. In some embodiments, $R_{C8'}$ is a linear or branched C2-C6 alkenyl having at least one halogen atom. In some embodiments, $R_{C8'}$ is or a linear or branched C2-C6 alkynyl having at least one halogen atom.

In some variations of Formulae (Ia), (Ib), (IIa) or (IIb), both $R_{9a}$ and $R_{9b}$ are hydrogen. In some embodiments, $R_{9a}$ is hydrogen, and $R_{9b}$ is C1-C6 linear or branched alkyl. In some embodiments, both $R_{9a}$ and $R_{9b}$ are C1-C6 linear or branched alkyl. In some embodiments, $R_{9a}$ is hydrogen, and $R_{9b}$ is methyl.

In some variations of Formulae (Ia), (Ib), (IIa) or (IIb), one or both of R10 and R11 are hydrogen. In some variations, one or both of R10 and R11 are —SO$_2$R$_{C8'}$. In some variations, one or both of R10 and R11 are C1-C6 linear or branched alkyl. In some variations, one or both of R10 and R11 are C2-C6 linear or branched alkenyl. In some variations, one or both of R10 and R11 are C3-C6 cycloalkyl. In some variations, one or both of R10 and R11 are C3-C6 cycloalkenyl.

In some variations of Formulae (Ia), (Ib), (IIa) or (IIb), R10 and R11 are taken together with the N to which they are attached to form a C3-C6 heterocycle. In some variations, R10 and R11 are taken together with the N to which they are attached to form a pyrrolidin-2-one or pyrrolidin-3-one. In some variations, R10 and R11 are taken together with the N to which they are attached to form a piperidin-2-one. In some variations, R10 and R11 are taken together with the N to which they are attached to form a piperidin-3-one. In some variations, R10 and R11 are taken together with the N to which they are attached to form a piperidin-4-one. In some variations, R10 and R11 are taken together with the N to which they are attached to form an oxazolidinone. In some variations, R10 and R11 are taken together with the N to which they are attached to form an oxazinanone. In some variations, R10 and R11 are taken together with the N to which they are attached to form an imidazolidinone. In some variations, R10 and R11 are taken together with the N to which they are attached to form a tetrahydropyrimidin-2(1H)-one. In some variations, R10 and R11 are taken together with the N to which they are attached to form a 1$\lambda^6$,2-thiazolidine-1,1-dione. In some variations, R10 and R11 are taken together with the N to which they are attached to form a 1,2$\lambda^6$,3-oxathiazolidine-2,2-dione. In some variations, R10 and R11 are taken together with the N to which they are attached to form a 1$\lambda^6$,2,5-thiadiazolidine-1,1-dione In some variations, the compound is of formula (Ia) or (IIa), wherein X is a heteroatom selected from S, O; or NR$_B$ wherein R$_B$ is hydrogen, a C1-C6 linear or branched alkyl, or a C3-C6 cycloalkyl. In some variations, X is S. In some variations, X is O. In some variations, X is NR$_B$ wherein R$_B$ is hydrogen, a C1-C6 linear or branched alkyl, or a C3-C6 cycloalkyl. In some variations, X is NR$_B$ wherein R$_B$ is a C1-C6 linear or branched alkyl. In some variations, X is NR$_B$ wherein R$_B$ is C3-C6 cycloalkyl.

In some variations, the compound is of formula (Ib) or (IIb), wherein X is a heteroatom selected from S, O; or NR$_B$ wherein R$_B$ is hydrogen, a C1-C6 linear or branched alkyl, or a C3-C6 cycloalkyl. In some variations, X is S. In some variations, X is O. In some variations, X is NR$_B$ wherein R$_B$ is hydrogen, a C1-C6 linear or branched alkyl, or a C3-C6 cycloalkyl. In some variations, X is NR$_B$ wherein R$_B$ is a C1-C6 linear or branched alkyl. In some variations, X is NR$_B$ wherein R$_B$ is C3-C6 cycloalkyl.

In some variations of Formulae (Ia), (Ib), (IIa) or (IIb), both m and n are 1. In some variations, m is 1 and n is 2. In some variations, m is 1 and n is 3. In some variations, m is 2 and n is 1. In some variations, both m and n are 2. In some variations, m is 2 and n is 3. In some variations, m is 3 and n is 1. In some variations, m is 3 and n is 2. In some variations, both m and n are 3.

In some variations of Formulae (Ia), (Ib), (IIa) or (IIb), A is a moiety selected from

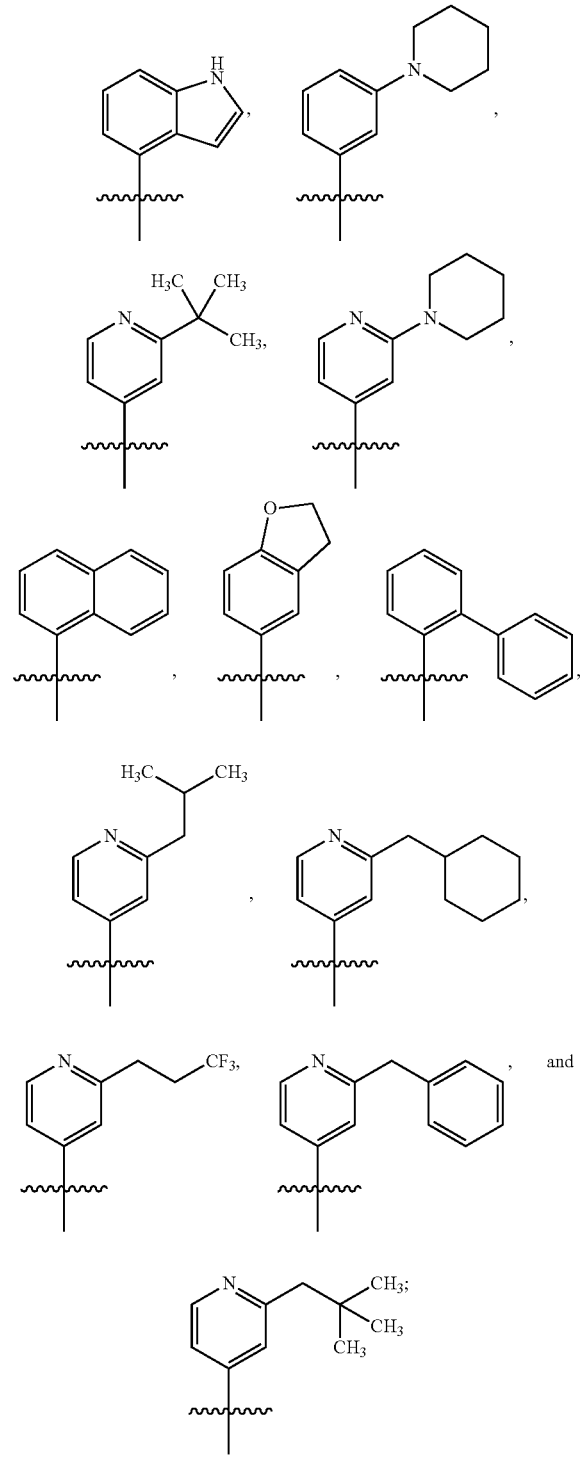

X is S, and the phenyl ring containing the groups $R_{C4}$, $R_{C5}$, $R_{C6}$, and —$NR_{C7}SO_2R_{C8}$, is a moiety selected from:

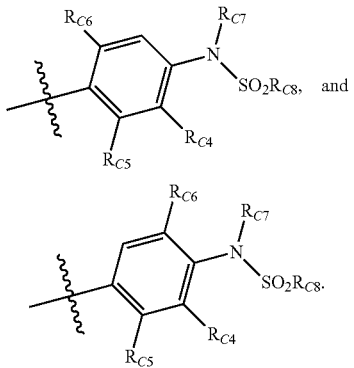

In some variations of Formulae (Ia), (Ib), (IIa) or (IIb), A is a moiety selected from

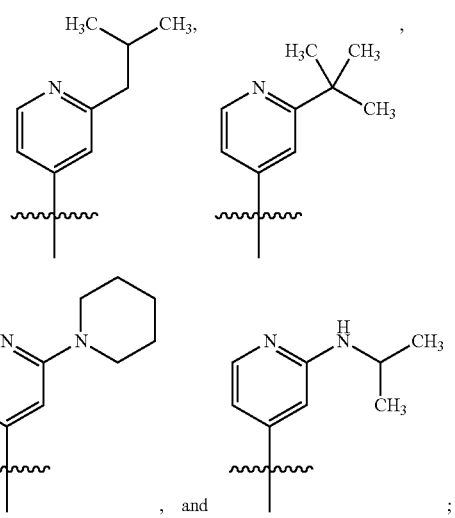

X is S, and the phenyl ring containing the groups $R_{C4}$, $R_{C5}$, $R_{C6}$, and —$NR_{C7}SO_2R_{C8}$, is a moiety selected from

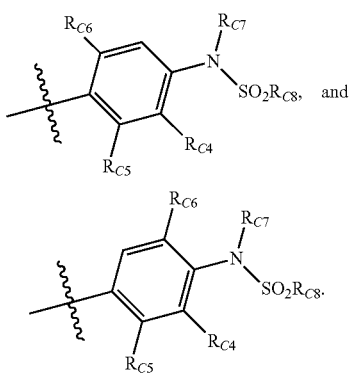

In some variations of Formulae (Ia), (Ib), (IIa) or (IIb), A is

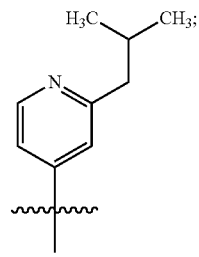

X is S; the phenyl ring containing the groups $R_{C4}$, $R_{C5}$, $R_{C6}$, and —$NR_{C7}SO_2R_{C8}$, is selected from

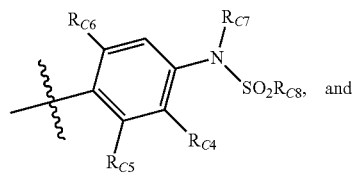

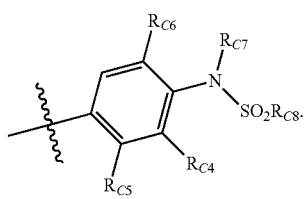

wherein $R_{C4}$, $R_{C5}$, and $R_{C6}$ are hydrogen or halogen; $R_{C7}$ is hydrogen; and $R_{C8}$ is perfluoroalkyl. In some variations $R_{C8}$ is —$CF_3$.

In some variations, the compound is of Formula (Ia), wherein A is a moiety selected from

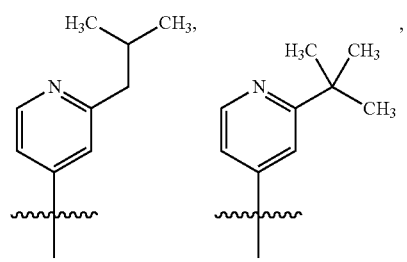

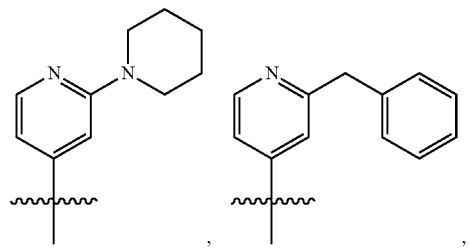

,

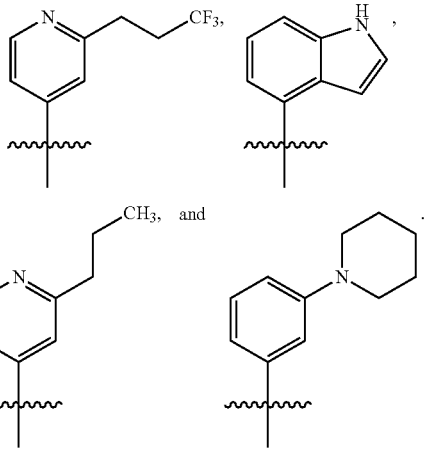

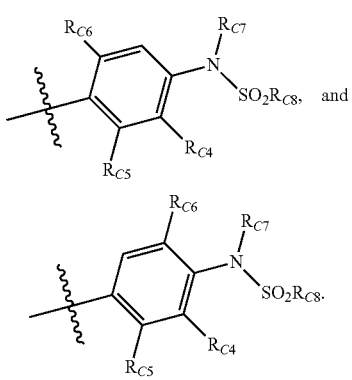

X is S, and the phenyl ring containing the groups $R_{C4}$, $R_{C5}$, $R_{C6}$, and —$NR_{C7}SO_2R_{C8}$, is a moiety selected from

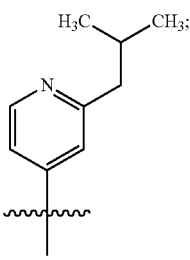 [SMILES: *c1ccnc(CC(C)C)c1]

In particular variations, the compound is of Formula (Ia), wherein A is

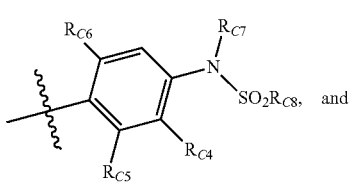

X is S; the phenyl ring containing the groups $R_{C4}$, $R_{C8}$, $R_{C6}$, and —$NR_{C7}SO_2R_{C8}$, is selected from

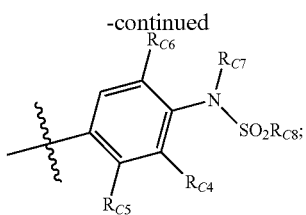

wherein $R_{C4}$, $R_{C5}$, and $R_{C6}$ are hydrogen or halogen; $R_{C7}$ is hydrogen and $R_{C8}$ is perfluoroalkyl. In some variations, $R_{C8}$ is —$CF_3$.

It is intended and understood that each and every variation of A, $R_{C4}$, $R_{C5}$, $R_{C6}$, $R_{C7}$, $R_{C8}$, $R_{C8'}$, $R_{9a}$, $R_{9b}$, R10, R11, X, m, and n, where present, described for formulae (Ia) and (Ib), may be combined with each and every variation of A, $R_{C4}$, $R_{C5}$, $R_{C6}$, $R_{C7}$, $R_{C8}$, $R_{C8'}$, $R_{9a}$, $R_{9b}$, R10, R11, X, m, and n, as if each and every combination is individually described.

In some embodiments, the compound is selected from the group consisting of:
1,1,1-trifluoro-N-(4-(2-(2-propylpyridin-4-yl)thiazol-4-yl)phenyl)methanesulfonamide;
1,1,1-trifluoro-N-(3-(2-(2-propylpyridin-4-yl)thiazol-4-yl)phenyl)methanesulfonamide;
N-(3-chloro-4-(2-(1-isobutyl-1H-pyrazol-5-yl)thiazol-4-yl)phenyl)-1,1,1-trifluoromethanesulfonamide;
N-(3-chloro-4-(2-(2-propylpyridin-4-yl)thiazol-4-yl)phenyl)-1,1,1-trifluoromethanesulfonamide;
N-(4-(2-(2-tert-butylpyridin-4-yl)thiazol-4-yl)-3-chlorophenyl)-1,1,1-trifluoromethanesulfonamide;
N-(3-chloro-4-(2-(1,2-dimethyl-1H-pyrrolo[2,3-b]pyridin-4-yl)thiazol-4-yl)phenyl)-1,1,1-trifluoromethanesulfonamide;
N-(3-chloro-4-(2-(1-propyl-1H-pyrrolo[2,3-b]pyridin-4-yl)thiazol-4-yl)phenyl)-1,1,1-trifluoromethanesulfonamide;
N-(3-chloro-4-(2-(2,3-dimethyl-3H-imidazo[4,5-b]pyridin-7-yl)thiazol-4-yl)phenyl)-1,1,1-trifluoromethanesulfonamide;
N-(3-chloro-4-(2-(3-propyl-3H-imidazo[4,5-b]pyridin-7-yl)thiazol-4-yl)phenyl)-1,1,1-trifluoromethanesulfonamide;
N-(4-(2-(3H-imidazo[4,5-b]pyridin-7-yl)thiazol-4-yl)-3-chlorophenyl)-1,1,1-trifluoromethanesulfonamide;
N-(3-chloro-4-(2-(1,2-dipropyl-1H-pyrrolo[2,3-b]pyridin-4-yl)thiazol-4-yl)phenyl)-1,1,1-trifluoromethanesulfonamide;
N-(4-(2-(6-(butylamino)-2-isobutylpyrimidin-4-yl)thiazol-4-yl)-3-chlorophenyl)-1,1,1-trifluoromethanesulfonamide;
N-(3-chloro-4-(2-(6-(dibutylamino)-2-isobutylpyrimidin-4-yl)thiazol-4-yl)phenyl)-1,1,1-trifluoromethanesulfonamide;
N-(4-(2-(6-amino-2-isobutylpyrimidin-4-yl)thiazol-4-yl)-3-chlorophenyl)-1,1,1-trifluoromethanesulfonamide;
N-(4-(2-(2-aminopyrimidin-4-yl)thiazol-4-yl)-3-chlorophenyl)-1,1,1-trifluoromethanesulfonamide;
N-(3-chloro-4-(2-(2-(propylamino)pyrimidin-4-yl)thiazol-4-yl)phenyl)-1,1,1-trifluoromethanesulfonamide;
N-(3-chloro-4-(2-(2-(dibutylamino)pyrimidin-4-yl)thiazol-4-yl)phenyl)-1,1,1-trifluoromethanesulfonamide;
N-(3-chloro-4-(2'-propyl-2,4'-bithiazol-4-yl)phenyl)-1,1,1-trifluoromethanesulfonamide;
N-(3-chloro-4-(2-(5-propyl-1,2,4-thiadiazol-3-yl)thiazol-4-yl)phenyl)-1,1,1-trifluoromethanesulfonamide;
N-(3-chloro-4-(2-(5-propyl-1,2,4-oxadiazol-3-yl)thiazol-4-yl)phenyl)-1,1,1-trifluoromethanesulfonamide;
N-(3-chloro-4-(2'-propyl-2,5'-bithiazol-4-yl)phenyl)-1,1,1-trifluoromethanesulfonamide;
N-(3-chloro-4-(2-(5-propyl-1,3,4-thiadiazol-2-yl)thiazol-4-yl)phenyl)-1,1,1-trifluoromethanesulfonamide;
N-(3-chloro-4-(2-(5-propyl-1,3,4-oxadiazol-2-yl)thiazol-4-yl)phenyl)-1,1,1-trifluoromethanesulfonamide;
N-(3-chloro-4-(2-(1-isobutyl-6-oxo-1,6-dihydropyridin-3-yl)thiazol-4-yl)phenyl)-1,1,1-trifluoromethanesulfonamide;
N-(3-chloro-4-(2-(4-fluoro-3-isobutylphenyl)thiazol-4-yl)phenyl)-1,1,1-trifluoromethanesulfonamide;
N-(2-bromo-3-chloro-4-(2-(2-isobutylpyridin-4-yl)thiazol-4-yl)phenyl)-1,1,1-trifluoromethanesulfonamide;
N-(3,5-dichloro-4-(2-(2-isobutylpyridin-4-yl)thiazol-4-yl)phenyl)-1,1,1-trifluoromethanesulfonamide;
1,1,1-trifluoro-N-(4-(2-(2-isobutylpyridin-4-yl)thiazol-4-yl)-2-(trifluoromethyl)phenyl)methanesulfonamide;
N-(2-cyclopropyl-4-(2-(2-isobutylpyridin-4-yl)thiazol-4-yl)phenyl)-1,1,1-trifluoromethanesulfonamide;
1,1,1-trifluoro-N-(4-(2-(2-isobutylpyridin-4-yl)thiazol-4-yl)-2-methylphenyl)methanesulfonamide;
1,1,1-trifluoro-N-(4-(2-(2-isobutylpyridin-4-yl)thiazol-4-yl)-2-isopropylphenyl)methanesulfonamide;
N-(2-ethynyl-4-(2-(2-isobutylpyridin-4-yl)thiazol-4-yl)phenyl)-1,1,1-trifluoromethanesulfonamide;
N-(2-bromo-3-ethynyl-4-(2-(2-isobutylpyridin-4-yl)thiazol-4-yl)phenyl)-1,1,1-trifluoromethanesulfonamide;
N-(2-bromo-6-chloro-4-(2-(2-isobutylpyridin-4-yl)thiazol-4-yl)phenyl)-1,1,1-trifluoromethanesulfonamide;
N-(2-chloro-4-(2-(2-isobutylpyridin-4-yl)thiazol-4-yl)-6-methylphenyl)-1,1,1-trifluoromethanesulfonamide;
N-(4-(4-(2-tert-butylpyridin-4-yl)-1-methyl-1H-imidazol-2-yl)-3-chlorophenyl)-1,1,1-trifluoromethanesulfonamide;
N-(3-chloro-4-(2-(2-isobutylpyridin-4-yl)thiazol-4-yl)phenyl)-1,1,1-trifluoromethanesulfonamide;
N-(2-bromo-4-(1-methyl-2-(2-propylpyridin-4-yl)-1H-imidazol-4-yl)phenyl)-1,1,1-trifluoromethanesulfonamide;
N-(2-bromo-3-chloro-4-(2-(2-propylpyridin-4-yl)-1H-imidazol-4-yl)phenyl)-1,1,1-trifluoromethanesulfonamide;
N-(2-bromo-5-chloro-4-(1-methyl-2-(2-propylpyridin-4-yl)-1H-imidazol-4-yl)phenyl)-1,1,1-trifluoromethanesulfonamide;
N-(4-(4-(2-tert-butylpyridin-4-yl)oxazol-2-yl)-3-chlorophenyl)-1,1,1-trifluoromethanesulfonamide;
N-(4-(2-(2-tert-butylpyridin-4-yl)oxazol-4-yl)-3-chlorophenyl)-1,1,1-trifluoromethanesulfonamide;
N-(3-chloro-4-(2-(2-(dimethylamino)pyridin-4-yl)thiazol-4-yl)phenyl)-1,1,1-trifluoromethanesulfonamide;
N-(3-chloro-4-(2-(2-propylpyridin-4-yl)thiazol-4-yl)phenyl)-N-(trifluoromethylsulfonyl)acrylamide;
N-(3-chloro-4-(2-(2-(methylsulfonamido)pyridin-4-yl)thiazol-4-yl)phenyl)-1,1,1-trifluoromethanesulfonamide;
N-(3-chloro-4-(2-(2-(3,3,3-trifluoropropyl)pyridin-4-yl)thiazol-4-yl)phenyl)-1,1,1-trifluoromethanesulfonamide;
1,1,1-trifluoro-N-(2-hydroxy-4-(2-(2-isobutylpyridin-4-yl)thiazol-4-yl)phenyl)methanesulfonamide;
1,1,1-trifluoro-N-(2-hydroxy-4-(2-(2-propylpyridin-4-yl)thiazol-4-yl)phenyl)methanesulfonamide;
N-(4-(2-(2-tert-butylpyridin-4-yl)thiazol-4-yl)-2-hydroxyphenyl)-1,1,1-trifluoromethanesulfonamide;
1,1,1-trifluoro-N-(2-methoxy-4-(2-(2-propylpyridin-4-yl)thiazol-4-yl)phenyl)methanesulfonamide;
1,1,1-trifluoro-N-(4-(2-(2-isobutylpyridin-4-yl)thiazol-4-yl)-2-methoxyphenyl)methanesulfonamide;
N-(4-(2-(2-tert-butylpyridin-4-yl)thiazol-4-yl)-2-methoxyphenyl)-1,1,1-trifluoromethanesulfonamide;

1,1,1-trifluoro-N-(4-(2-(2-isobutylpyridin-4-yl)thiazol-4-yl)-3-(trifluoromethyl)phenyl)methanesulfonamide;
N-(3-chloro-4-(2-(2-neopentylpyridin-4-yl)thiazol-4-yl)phenyl)-1,1,1-trifluoromethanesulfonamide;
6-(2-(2-isobutylpyridin-4-yl)thiazol-4-yl)-3-(trifluoromethylsulfonyl)benzo[d]oxazol-2(3H)-one;
N-(3-chloro-4-(2-(2-isobutylpyridin-4-yl)thiazol-4-yl)phenyl)-1,1,2,2,2-pentafluoroethanesulfonamide;
1,1,1-trifluoro-N-(2-methoxy-4-{2-[2-(2-methylpropyl)pyridin-4-yl]-1,3-thiazol-4-yl}phenyl)methanesulfonamide;
1,1,1-trifluoro-N-{2-methoxy-4-[2-(2-propylpyridin-4-yl)-1,3-thiazol-4-yl]phenyl}methanesulfonamide;
N-{4-[2-(2-tert-butylpyridin-4-yl)-1,3-thiazol-4-yl]-2-methoxyphenyl}-1,1,1-trifluoromethanesulfonamide;
N-{4-[2-(2-benzylpyridin-4-yl)-1,3-thiazol-4-yl]-3-chlorophenyl}-1,1,1-trifluoromethanesulfonamide;
N-{4-[2-(2-aminopyridin-4-yl)-1,3-thiazol-4-yl]-3-chlorophenyl}-1,1,1-trifluoromethanesulfonamide;
N-{3-chloro-4-[2-(2-methanesulfonamidopyridin-4-yl)-1,3-thiazol-4-yl]phenyl}-1,1,1-trifluoromethanesulfonamide;
1,1,1-trifluoro-N-{2-hydroxy-4-[2-(2-propylpyridin-4-yl)-1,3-thiazol-4-yl]phenyl}methanesulfonamide;
N-(3-chloro-4-{2-[2-(3,3,3-trifluoropropyl)pyridin-4-yl]-1,3-thiazol-4-yl}phenyl)-1,1,1-trifluoromethanesulfonamide;
N-(4-{2-[2-(2,2-dimethylpropyl)pyridin-4-yl]-1,3-thiazol-4-yl}-2-methoxyphenyl)-1,1,1-trifluoromethanesulfonamide;
N-{3-chloro-4-[2-(2-trifluoromethanesulfonamidopyridin-4-yl)-1,3-thiazol-4-yl]phenyl}-1,1,1-trifluoromethanesulfonamide;
N-(3-chloro-4-(2-(4-(piperidine-1-carbonyl)phenyl)thiazol-4-yl)phenyl)-1,1,1-trifluoromethanesulfonamide;
N-(3-chloro-4-{2-[1-(3-methylbutyl)-1H-pyrazol-5-yl]-1,3-thiazol-4-yl}phenyl)-1,1,1-trifluoromethanesulfonamide;
N-{4-[5-(2-tert-butylpyridin-4-yl)thiophen-3-yl]-3-chlorophenyl}methanesulfonamide;
N-(3-chloro-4-{2-[2-(cyclohexylmethyl)pyridin-4-yl]-1,3-thiazol-4-yl}phenyl)-1,1,1-trifluoromethanesulfonamide;
N-{3-chloro-4-[2-(naphthalen-1-yl)-1,3-thiazol-4-yl]phenyl}-1,1,1-trifluoromethanesulfonamide;
N-{3-chloro-4-[2-(1H-indol-6-yl)-1,3-thiazol-4-yl]phenyl}-1,1,1-trifluoromethanesulfonamide;
N-(4-{2-[3-(benzyloxy)-4-(trifluoromethyl)phenyl]-1,3-thiazol-4-yl}-3-chlorophenyl)-1,1,1-trifluoromethane sulfonamide;
N-{3-chloro-4-[2-(2-phenylphenyl)-1,3-thiazol-4-yl]phenyl}-1,1,1-trifluoromethanesulfonamide;
N-{3-chloro-4-[2-(isoquinolin-4-yl)-1,3-thiazol-4-yl]phenyl}-1,1,1-trifluoromethanesulfonamide;
N-(3-chloro-4-{2-[2-(4-methylpiperazin-1-yl)pyridin-4-yl]-1,3-thiazol-4-yl}phenyl)-1,1,1-trifluoromethanesulfonamide;
N-{3-chloro-4-[2-(dimethyl-1,2-oxazol-4-yl)-1,3-thiazol-4-yl]phenyl}-1,1,1-trifluoromethanesulfonamide;
N-{3-[4-(2-chloro-4-trifluoromethanesulfonamidophenyl)-1,3-thiazol-2-yl]phenyl}-4-methylbenzene-1-sulfonamide;
N-{3-chloro-4-[2-(3,4-dimethoxyphenyl)-1,3-thiazol-4-yl]phenyl}-1,1,1-trifluoromethanesulfonamide;
N-{3-chloro-4-[2-(1H-indol-4-yl)-1,3-thiazol-4-yl]phenyl}-1,1,1-trifluoromethanesulfonamide;
N-(3-chloro-4-{2-[4-fluoro-2-(trifluoromethyl)phenyl]-1,3-thiazol-4-yl}phenyl)-1,1,1-trifluoromethanesulfonamide;
N-{3-chloro-4-[2-(2,3-dihydro-1-benzofuran-5-yl)-1,3-thiazol-4-yl]phenyl}-1,1,1-trifluoromethanesulfonamide;
N-(3-chloro-4-{2-[3-(hydroxymethyl)phenyl]-1,3-thiazol-4-yl}phenyl)-1,1,1-trifluoromethanesulfonamide;
N-(3-chloro-4-{2-[2-(hydroxymethyl)phenyl]-1,3-thiazol-4-yl}phenyl)-1,1,1-trifluoromethanesulfonamide;
N-(3-chloro-4-{2-[2-(piperidin-1-yl)pyridin-4-yl]-1,3-thiazol-4-yl}phenyl)-1,1,1-phenyl-trifluoromethanesulfonamide;
N-{3-chloro-4-[2-(3-methylpyridin-4-yl)-1,3-thiazol-4-yl]phenyl}-1,1,1-trifluoromethanesulfonamide;
N-[3-chloro-4-(2-{1H-pyrrolo[2,3-b]pyridin-4-yl}-1,3-thiazol-4-yl)phenyl]-1,1,1-trifluoromethanesulfonamide;
N-(3-chloro-4-{2-[3-(piperidin-1-yl)phenyl]-1,3-thiazol-4-yl}phenyl)-1,1,1-trifluoromethanesulfonamide;
N-[3-chloro-4-(2-{5-fluoro-1H-pyrrolo[2,3-b]pyridin-4-yl}-1,3-thiazol-4-yl)phenyl]-1,1,1-trifluoromethanesulfonamide;
N-{4-[2-(1-benzothiophen-3-yl)-1,3-thiazol-4-yl]-3-chlorophenyl}-1,1,1-trifluoromethanesulfonamide;
N-(3-chloro-4-{2-[4-fluoro-2-(pyrrolidin-1-ylmethyl)phenyl]-1,3-thiazol-4-yl}phenyl)-1,1,1-trifluoromethanesulfonamide;
N-(3-chloro-4-{2-[2-(cyclopentylamino)pyridin-4-yl]-1,3-thiazol-4-yl}phenyl)-1,1,1-trifluoromethanesulfonamide;
N-{3-chloro-4-[2-(1H-indol-3-yl)-1,3-thiazol-4-yl]phenyl}-1,1,1-trifluoromethanesulfonamide;
N-(3-chloro-4-(2-(quinolin-4-yl)thiazol-4-yl)phenyl)-1,1,1-trifluoromethanesulfonamide;
N-(3-chloro-4-(2-(2-chloropyridin-4-yl)thiazol-4-yl)phenyl)-1,1,1-trifluoromethanesulfonamide;
N-(2-bromo-4-(2-(2-tert-butylpyridin-4-yl)thiazol-4-yl)-3-chlorophenyl)-1,1,1-trifluoromethanesulfonamide;
N-(2-bromo-4-(2-(2-propylpyridin-4-yl)-1H-imidazol-4-yl)phenyl)-1,1,1-trifluoromethanesulfonamide;
N-(2-bromo-4-(2-(2-tert-butylpyridin-4-yl)thiazol-4-yl)-3-chlorophenyl)-1,1,1-trifluoro-N-(2-hydroxyethyl)methanesulfonamide;
N-(4-(2-(2-tert-butylpyridin-4-yl)thiazol-4-yl)-3-chlorophenyl)-1,1,1-trifluoro-N-(2-(2-oxopyrrolidin-1-yl)ethyl)methanesulfonamide;
N-(4-(2-(2-tert-butylpyridin-4-yl)thiazol-4-yl)-3-chlorophenyl)-1,1,1-trifluoro-N-(2-(2-oxooxazolidin-3-yl)ethyl)methanesulfonamide;
N-(4-(2-(2-tert-butylpyridin-4-yl)thiazol-4-yl)-3-chlorophenyl)-1,1,1-trifluoro-N-(2-(2-oxoimidazolidin-1-yl)ethyl)methanesulfonamide;
N-(2-bromo-4-(2-(2-(piperidin-1-yl)pyridin-4-yl)-1H-imidazol-4-yl)phenyl)-1,1,1-trifluoromethanesulfonamide;
2-(N-(4-(2-(2-tert-butylpyridin-4-yl)thiazol-4-yl)-3-chlorophenyl)-1,1,1-trifluoromethylsulfonamido)ethyl acetate;
(2-(N-(4-(2-(2-tert-butylpyridin-4-yl)thiazol-4-yl)-3-chlorophenyl)-1,1,1-trifluoromethylsulfonamido)ethoxy)methyl acetate;
N-{4-[2-(2-tert-butylpyridin-4-yl)-1,3-thiazol-4-yl]-3-chlorophenyl}-N-(2-{[4-(3-chlorophenyl)-2-oxo-1,3,2$\lambda^5$-dioxaphosphinan-2-yl]oxy}ethyl)-1,1,1-trifluoromethanesulfonamide;
(N-(4-(2-(2-tert-butylpyridin-4-yl)thiazol-4-yl)-3-chlorophenyl)-1,1,1-trifluoromethylsulfonamido)methyl acetate;
N-(4-(2-(2-tert-butylpyridin-4-yl)thiazol-4-yl)-3-chlorophenyl)-1,1,1-trifluoro-N-(methoxymethyl)methanesulfonamide;
N-{4-[2-(2-tert-butylpyridin-4-yl)-1,3-thiazol-4-yl]-3-chlorophenyl}-N-({[4-(3-chlorophenyl)-2-oxo-1,3,2$\lambda^5$-dioxaphosphinan-2-yl]oxy}methyl)-1,1,1-trifluoromethanesulfonamide;

methyl 4-(2-(2-tert-butylpyridin-4-yl)thiazol-4-yl)-3-chlorophenyl(trifluoromethylsulfonyl)carbamate;
sodium (N-(4-(2-(2-tert-butylpyridin-4-yl)thiazol-4-yl)-3-chlorophenyl)-1,1,1-trifluoromethylsulfonamido)methyl phosphate;
1-(N-(3-chloro-4-(2-(2-isobutylpyridin-4-yl)thiazol-4-yl)phenyl)-1,1,1-trifluoromethylsulfonamido)ethyl isobutyrate;
N-(3-chloro-4-(2-(2-isobutylpyridin-4-yl)thiazol-4-yl)phenyl)-1,1,1-trifluoro-N-(2-(2-oxooxazolidin-3-yl)ethyl)methanesulfonamide;
N-(4-(2-(2-tert-butylpyridin-4-yl)thiazol-4-yl)-3-chlorophenyl)-1,1,1-trifluoro-N-(2-hydroxyethyl)methanesulfonamide;
N-(3-chloro-4-(2-(2-isobutylpyridin-4-yl)thiazol-4-yl)phenyl)-1,1,1-trifluoro-N-(2-(pyrrolidin-1-yl)ethyl)methanesulfonamide;
N-(3-chloro-4-(2-(2-isobutylpyridin-4-yl)thiazol-4-yl)phenyl)-N-(2-(diethylamino)ethyl)-1,1,1-trifluoromethanesulfonamide;
N-(3-chloro-4-(2-(2-isobutylpyridin-4-yl)thiazol-4-yl)phenyl)-N-(2-(dimethylamino)ethyl)-1,1,1-trifluoromethanesulfonamide;
1,1,1-trifluoro-N-(3-fluoro-4-(2-(2-propylpyridin-4-yl)thiazol-4-yl)phenyl)methanesulfonamide;
N-(3-chloro-4-(2-(2-isobutylpyridin-4-yl)-1H-imidazol-4-yl)phenyl)-1,1,1-trifluoromethanesulfonamide;
N-(3-chloro-4-(2-(2-isobutylpyridin-4-yl)thiazol-4-yl)phenyl)-1,1,1-trifluoro-N-(2-hydroxyethyl)methanesulfonamide;
N-(3-chloro-4-(2-(2-propylpyridin-4-yl)thiazol-4-yl)phenyl)-1,1,1-trifluoro-N-methylmethanesulfonamide;
1,1,1-trifluoro-N-(3-(2-(2-isobutylpyridin-4-yl)thiazol-4-yl)phenyl)methanesulfonamide;
N-(2-bromo-4-(2-(2-isobutylpyridin-4-yl)thiazol-4-yl)phenyl)-1,1,1-trifluoromethanesulfonamide;
1,1,1-trifluoro-N-methyl-N-(4-(2-(2-propylpyridin-4-yl)thiazol-4-yl)phenyl)methanesulfonamide;
N-(4-(2-(2-butylpyridin-4-yl)thiazol-4-yl)phenyl)-1,1,1-trifluoromethanesulfonamide
1,1,1-trifluoro-N-(4-(2-(2-(methoxymethyl)pyridin-4-yl)thiazol-4-yl)phenyl)methanesulfonamide;
N-(4-(2-(4,6-dipropylpyridin-2-yl)thiazol-4-yl)phenyl)-1,1,1-trifluoromethanesulfonamide;
1,1,1-trifluoro-N-(4-(2-(4-propylpyridin-2-yl)thiazol-4-yl)phenyl)methanesulfonamide;
N-(4-(2-(2,6-dipropylpyridin-3-yl)thiazol-4-yl)phenyl)-1,1,1-trifluoromethanesulfonamide;
N-(4-(2-(2-(cyclohexylmethyl)pyridin-4-yl)thiazol-4-yl)phenyl)-1,1,1-trifluoromethanesulfonamide;
1,1,1-trifluoro-N-(4-(2-(2-isobutylpyridin-4-yl)thiazol-4-yl)-3-methoxyphenyl)methanesulfonamide;
N-(3-chloro-4-(2-(2-((trifluoromethylsulfonyl)methyl)pyridin-4-yl)thiazol-4-yl)phenyl)-1,1,1-trifluoromethanesulfonamide;
N-(4-(2-(1H-pyrrolo[2,3-b]pyridin-4-yl)thiazol-4-yl)-3-chlorophenyl)-1,1,1-trifluoromethanesulfonamide;
N-(3-chloro-4-(2-(2-propyl-3H-imidazo[4,5-b]pyridin-7-yl)thiazol-4-yl)phenyl)-1,1,1-trifluoromethanesulfonamide;
5-(4-(2-chloro-4-(trifluoromethylsulfonamido)phenyl)thiazol-2-yl)-N-cyclopropyl-2-fluorobenzamide;
5-(4-(2-chloro-4-(trifluoromethylsulfonamido)phenyl)thiazol-2-yl)-N-cyclohexyl-2-fluorobenzamide;
N-(4-(2-(1H-indol-4-yl)thiazol-4-yl)-3-chlorophenyl)-1,1,1-trifluoromethanesulfonamide;
N-(3-chloro-4-(2-(3-(piperidin-1-yl)phenyl)thiazol-4-yl)phenyl)-1,1,1-trifluoromethanesulfonamide;
N-(3-chloro-4-(2-(2-(piperidin-1-yl)pyridin-4-yl)thiazol-4-yl)phenyl)-1,1,1-trifluoromethanesulfonamide;
N-(2-bromo-4-(2-(2-tert-butylpyridin-4-yl)-1H-imidazol-4-yl)phenyl)-1,1,1-trifluoromethanesulfonamide;
N-(2-chloro-4-(2-(2-propylpyridin-4-yl)-1H-imidazol-4-yl)phenyl)-1,1,1-trifluoromethanesulfonamide;
N-(2-bromo-5-chloro-4-(2-(2-propylpyridin-4-yl)-1H-imidazol-4-yl)phenyl)-1,1,1-trifluoromethanesulfonamide; and
N-(2-bromo-4-(2-(2-propylpyridin-4-yl)thiazol-4-yl)phenyl)-1,1,1-trifluoromethanesulfonamide.

In some embodiments, the compound is selected from the group consisting of:
1,1,1-trifluoro-N-(4-(2-(2-propylpyridin-4-yl)thiazol-4-yl)phenyl)methanesulfonamide;
1,1,1-trifluoro-N-(3-(2-(2-propylpyridin-4-yl)thiazol-4-yl)phenyl)methanesulfonamide;
N-(3-chloro-4-(2-(1-isobutyl-1H-pyrazol-5-yl)thiazol-4-yl)phenyl)-1,1,1-trifluoromethanesulfonamide;
N-(3-chloro-4-(2-(2-propylpyridin-4-yl)thiazol-4-yl)phenyl)-1,1,1-trifluoromethanesulfonamide;
N-(4-(2-(2-tert-butylpyridin-4-yl)thiazol-4-yl)-3-chlorophenyl)-1,1,1-trifluoromethanesulfonamide;
N-(3-chloro-4-(2-(2-isobutylpyridin-4-yl)thiazol-4-yl)phenyl)-1,1,1-trifluoromethanesulfonamide;
1,1,1-trifluoro-N-(2-methoxy-4-{2-[2-(2-methylpropyl)pyridin-4-yl]-1,3-thiazol-4-yl}phenyl)methanesulfonamide;
1,1,1-trifluoro-N-{2-methoxy-4-[2-(2-propylpyridin-4-yl)-1,3-thiazol-4-yl]phenyl}methanesulfonamide;
N-{4-[2-(2-tert-butylpyridin-4-yl)-1,3-thiazol-4-yl]-2-methoxyphenyl}-1,1,1-trifluoromethanesulfonamide;
N-{4-[2-(2-benzylpyridin-4-yl)-1,3-thiazol-4-yl]-3-chlorophenyl}-1,1,1-trifluoromethanesulfonamide;
N-{4-[2-(2-aminopyridin-4-yl)-1,3-thiazol-4-yl]-3-chlorophenyl}-1,1,1-trifluoromethanesulfonamide;
N-{3-chloro-4-[2-(2-methanesulfonamidopyridin-4-yl)-1,3-thiazol-4-yl]phenyl}-1,1,1-trifluoromethanesulfonamide;
1,1,1-trifluoro-N-{2-hydroxy-4-[2-(2-propylpyridin-4-yl)-1,3-thiazol-4-yl]phenyl}methanesulfonamide;
N-(3-chloro-4-{2-[2-(3,3,3-trifluoropropyl)pyridin-4-yl]-1,3-thiazol-4-yl}phenyl)-1,1,1-trifluoromethanesulfonamide;
N-(4-{2-[2-(2,2-dimethylpropyl)pyridin-4-yl]-1,3-thiazol-4-yl}-2-methoxyphenyl)-1,1,1-trifluoromethanesulfonamide;
N-{3-chloro-4-[2-(2-trifluoromethanesulfonamidopyridin-4-yl)-1,3-thiazol-4-yl]phenyl}-1,1,1-trifluoromethanesulfonamide;
N-(3-chloro-4-(2-(4-(piperidine-1-carbonyl)phenyl)thiazol-4-yl)phenyl)-1,1,1,1-trifluoromethanesulfonamide;
N-(3-chloro-4-{2-[1-(3-methylbutyl)-1H-pyrazol-5-yl]-1,3-thiazol-4-yl}phenyl)-1,1,1-trifluoromethanesulfonamide;
N-{4-[5-(2-tert-butylpyridin-4-yl)thiophen-3-yl]-3-chlorophenyl}methanesulfonamide;
N-(3-chloro-4-{2-[2-(cyclohexylmethyl)pyridin-4-yl]-1,3-thiazol-4-yl}phenyl)-1,1,1-trifluoromethanesulfonamide;
N-{3-chloro-4-[2-(naphthalen-1-yl)-1,3-thiazol-4-yl]phenyl}-1,1,1-trifluoromethanesulfonamide;
N-{3-chloro-4-[2-(1H-indol-6-yl)-1,3-thiazol-4-yl]phenyl}-1,1,1-trifluoromethanesulfonamide;
N-(4-{2-[3-(benzyloxy)-4-(trifluoromethyl)phenyl]-1,3-thiazol-4-yl}-3-chlorophenyl)-1,1,1-trifluoromethane sulfonamide;
N-{3-chloro-4-[2-(2-phenylphenyl)-1,3-thiazol-4-yl]phenyl}-1,1,1-trifluoromethanesulfonamide;

N-{3-chloro-4-[2-(isoquinolin-4-yl)-1,3-thiazol-4-yl]phenyl}-1,1,1-trifluoromethanesulfonamide;
N-(3-chloro-4-{2-[2-(4-methylpiperazin-1-yl)pyridin-4-yl]-1,3-thiazol-4-yl}phenyl)-1,1,1-trifluoromethanesulfonamide;
N-{3-chloro-4-[2-(dimethyl-1,2-oxazol-4-yl)-1,3-thiazol-4-yl]phenyl}-1,1,1-trifluoromethanesulfonamide;
N-{3-[4-(2-chloro-4-trifluoromethanesulfonamidophenyl)-1,3-thiazol-2-yl]phenyl}-4-methylbenzene-1-sulfonamide;
N-{3-chloro-4-[2-(3,4-dimethoxyphenyl)-1,3-thiazol-4-yl]phenyl}-1,1,1-trifluoromethanesulfonamide;
N-{3-chloro-4-[2-(1H-indol-4-yl)-1,3-thiazol-4-yl]phenyl}-1,1,1-trifluoromethanesulfonamide;
N-(3-chloro-4-{2-[4-fluoro-2-(trifluoromethyl)phenyl]-1,3-thiazol-4-yl}phenyl)-1,1,1-trifluoromethanesulfonamide;
N-{3-chloro-4-[2-(2,3-dihydro-1-benzofuran-5-yl)-1,3-thiazol-4-yl]phenyl}-1,1,1-trifluoromethanesulfonamide;
N-(3-chloro-4-{2-[3-(hydroxymethyl)phenyl]-1,3-thiazol-4-yl}phenyl)-1,1,1-trifluoromethanesulfonamide;
N-(3-chloro-4-{2-[2-(hydroxymethyl)phenyl]-1,3-thiazol-4-yl}phenyl)-1,1,1-trifluoromethanesulfonamide;
N-(3-chloro-4-{2-[2-(piperidin-1-yl)pyridin-4-yl]-1,3-thiazol-4-yl}phenyl)-1,1,1-trifluoromethanesulfonamide;
N-{3-chloro-4-[2-(3-methylpyridin-4-yl)-1,3-thiazol-4-yl]phenyl}-1,1,1-trifluoromethanesulfonamide;
N-[3-chloro-4-(2-{1H-pyrrolo[2,3-b]pyridin-4-yl}-1,3-thiazol-4-yl)phenyl]-1,1,1-trifluoromethanesulfonamide;
N-(3-chloro-4-{2-[3-(piperidin-1-yl)phenyl]-1,3-thiazol-4-yl}phenyl)-1,1,1-trifluoromethanesulfonamide;
N-[3-chloro-4-(2-{5-fluoro-1H-pyrrolo[2,3-b]pyridin-4-yl}-1,3-thiazol-4-yl)phenyl]-1,1,1-trifluoromethanesulfonamide;
N-{4-[2-(1-benzothiophen-3-yl)-1,3-thiazol-4-yl]-3-chlorophenyl}-1,1,1-trifluoromethanesulfonamide;
N-(3-chloro-4-{2-[4-fluoro-2-(pyrrolidin-1-ylmethyl)phenyl]-1,3-thiazol-4-yl}phenyl)-1,1,1-trifluoromethanesulfonamide;
N-(3-chloro-4-{2-[2-(cyclopentylamino)pyridin-4-yl]-1,3-thiazol-4-yl}phenyl)-1,1,1-trifluoromethanesulfonamide;
N-{3-chloro-4-[2-(1H-indol-3-yl)-1,3-thiazol-4-yl]phenyl}-1,1,1-trifluoromethanesulfonamide; and
N-(3-chloro-4-(2-(quinolin-4-yl)thiazol-4-yl)phenyl)-1,1,1-trifluoromethanesulfonamide.

In some embodiments, the compound is selected from the group consisting of:
N-(3-chloro-4-(2-(2-propylpyridin-4-yl)thiazol-4-yl)phenyl)-1,1,1-trifluoromethanesulfonamide;
N-(4-(2-(2-tert-butylpyridin-4-yl)thiazol-4-yl)-3-chlorophenyl)-1,1,1-trifluoromethanesulfonamide;
N-(3-chloro-4-(2-(2-isobutylpyridin-4-yl)thiazol-4-yl)phenyl)-1,1,1-trifluoromethanesulfonamide;
N-{4-[2-(2-benzylpyridin-4-yl)-1,3-thiazol-4-yl]-3-chlorophenyl}-1,1,1-trifluoromethanesulfonamide;
N-(3-chloro-4-{2-[2-(3,3,3-trifluoropropyl)pyridin-4-yl]-1,3-thiazol-4-yl}phenyl)-1,1,1-trifluoromethanesulfonamide;
N-{3-chloro-4-[2-(1H-indol-4-yl)-1,3-thiazol-4-yl]phenyl}-1,1,1-trifluoromethanesulfonamide;
N-(3-chloro-4-{2-[2-(piperidin-1-yl)pyridin-4-yl]-1,3-thiazol-4-yl}phenyl)-1,1,1-trifluoromethanesulfonamide; and
N-(3-chloro-4-{2-[3-(piperidin-1-yl)phenyl]-1,3-thiazol-4-yl}phenyl)-1,1,1-trifluoromethanesulfonamide.

In some embodiments, the compound is compound #37: N-(3-chloro-4-(2-(2-isobutylpyridin-4-yl)thiazol-4-yl)phenyl)-1,1,1-trifluoromethanesulfonamide.

The compounds described below are not intended to be limiting; rather, these embodiments and variations are intended to provide examples of compounds within the scope of Formulae (Ia), (Ib), (IIa) or (IIb).

Representative compounds are presented in Table 1.

TABLE 1

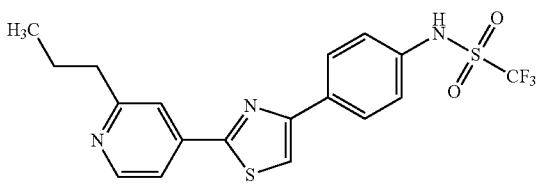 [SMILES: CCCc1cc(-c2nc(-c3ccc(NS(=O)(=O)C(F)(F)F)cc3)cs2)ccn1]

1

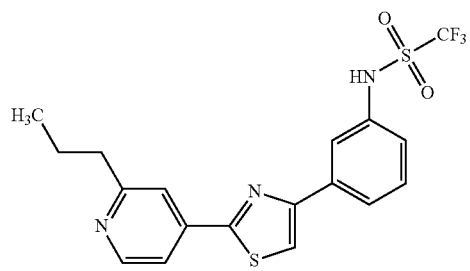 [SMILES: CCCc1cc(-c2nc(-c3cccc(NS(=O)(=O)C(F)(F)F)c3)cs2)ccn1]

2

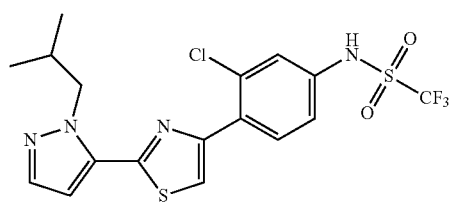 [SMILES: CC(C)Cn1nccc1-c1nc(-c2ccc(NS(=O)(=O)C(F)(F)F)cc2Cl)cs1]

3

TABLE 1-continued

| Structure | # |
|---|---|
| (chemical structure) | 4 |
| (chemical structure) | 5 |
| (chemical structure) | 6 |
| (chemical structure) | 7 |
| (chemical structure) | 8 |
| (chemical structure) | 9 |
| (chemical structure) | 10 |
| (chemical structure) | 11 |

TABLE 1-continued

| | |
|---|---|
| (structure) | 12 |
| (structure) | 13 |
| (structure) | 14 |
| (structure) | 15 |
| (structure) | 16 |
| (structure) | 17 |
| (structure) | 18 |

TABLE 1-continued
| | |
|---|---|
| 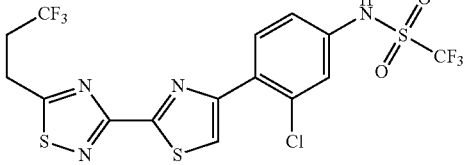 | 19 |
| 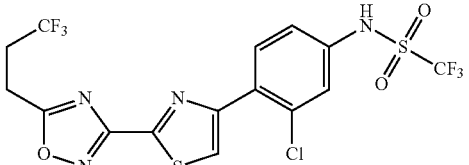 | 20 |
| 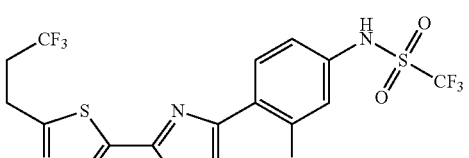 | 21 |
| 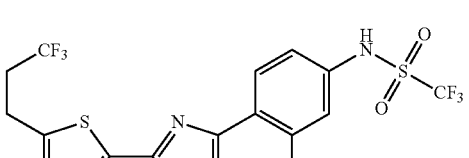 | 22 |
| 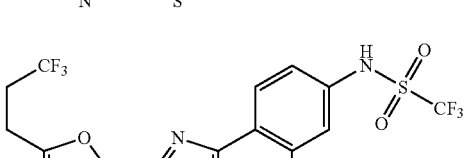 | 23 |
| 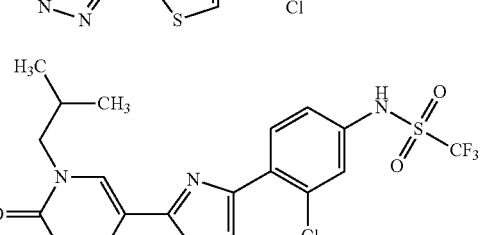 | 24 |
| 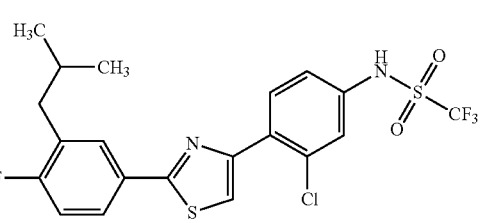 | 25 |
| 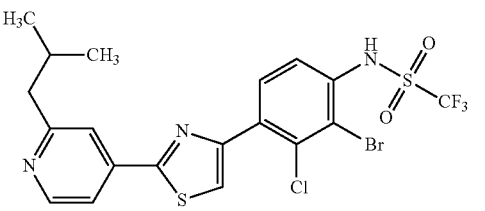 [SMILES: CC(C)Cc1cc(-c2nc(-c3ccc(NS(=O)(=O)C(F)(F)F)c(Br)c3Cl)cs2)ccn1] | 26 |

TABLE 1-continued
| | |
|---|---|
| 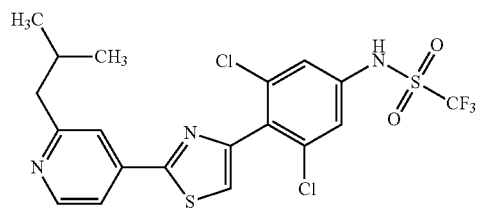 [SMILES: CC(C)Cc1cc(-c2nc(-c3c(Cl)cc(NS(=O)(=O)C(F)(F)F)cc3Cl)cs2)ccn1] | 27 |
| 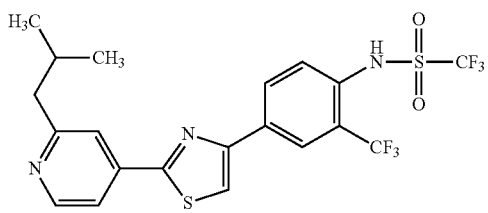 | 28 |
| 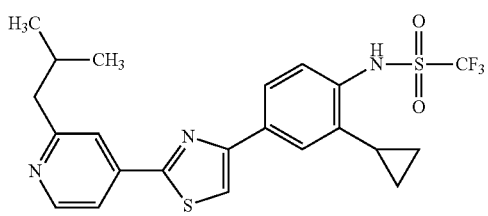 | 29 |
| 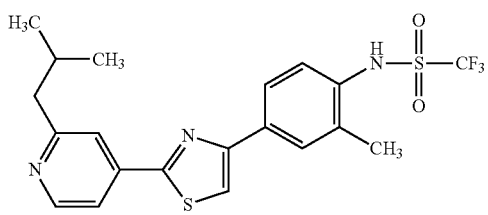 [SMILES: CC(C)Cc1cc(-c2nc(-c3ccc(NS(=O)(=O)C(F)(F)F)c(C(F)(F)F)c3)cs2)ccn1] | 30 |
| 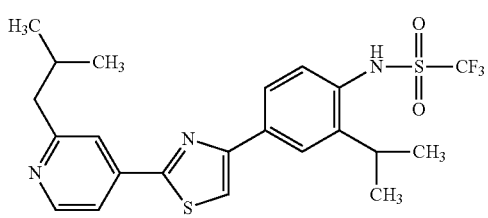 [SMILES: CC(C)Cc1cc(-c2nc(-c3ccc(NS(=O)(=O)C(F)(F)F)c(C(C)C)c3)cs2)ccn1] | 31 |
| 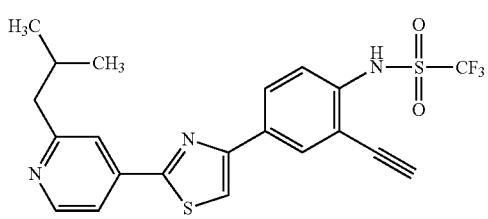 [SMILES: C#Cc1cc(-c2csc(-c3ccnc(CC(C)C)c3)n2)ccc1NS(=O)(=O)C(F)(F)F] | 32 |
| 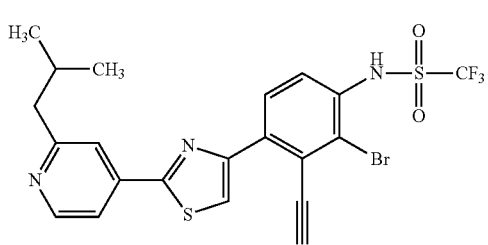 [SMILES: C#Cc1c(-c2csc(-c3ccnc(CC(C)C)c3)n2)ccc(NS(=O)(=O)C(F)(F)F)c1Br] | 33 |

TABLE 1-continued
| | |
|---|---|
|  | 34 |
|  | 35 |
| 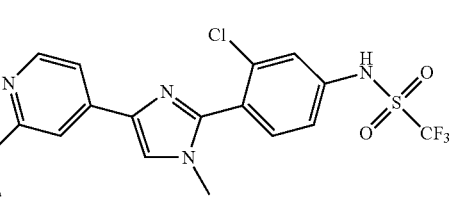 | 36 |
|  | 37 |
| 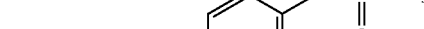 | 38 |
|  | 39 |
|  | 40 |

TABLE 1-continued
| | |
|---|---|
| 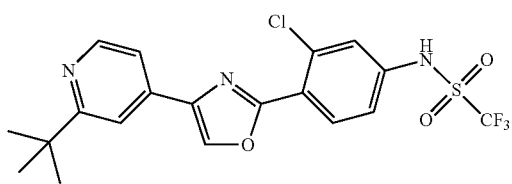 [SMILES: CC(C)(C)c1cc(-c2coc(-c3ccc(NS(=O)(=O)C(F)(F)F)cc3Cl)n2)ccn1] | 41 |
| 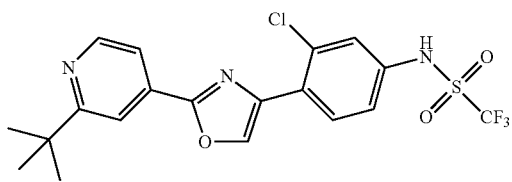 [SMILES: CC(C)(C)c1cc(-c2nc(-c3ccc(NS(=O)(=O)C(F)(F)F)cc3Cl)co2)ccn1] | 42 |
| 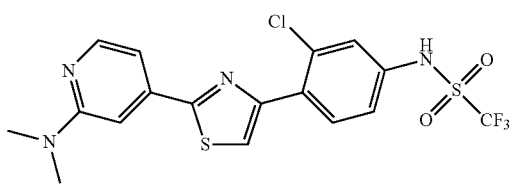 [SMILES: CN(C)c1cc(-c2nc(-c3ccc(NS(=O)(=O)C(F)(F)F)cc3Cl)cs2)ccn1] | 43 |
| 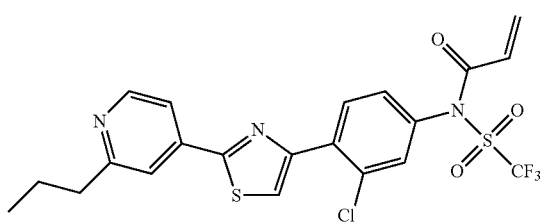 [SMILES: C=CC(=O)N(c1ccc(-c2csc(-c3ccnc(CCC)c3)n2)c(Cl)c1)S(=O)(=O)C(F)(F)F] | 44 |
| 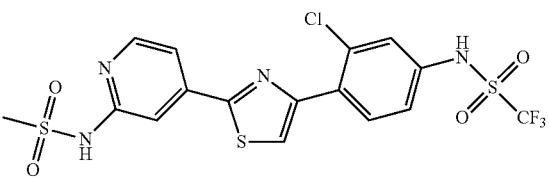 [SMILES: CS(=O)(=O)Nc1cc(-c2nc(-c3ccc(NS(=O)(=O)C(F)(F)F)cc3Cl)cs2)ccn1] | 45 |
| 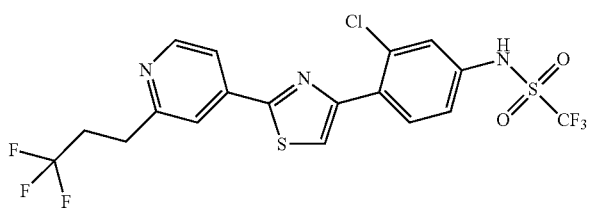 [SMILES: O=S(=O)(Nc1ccc(-c2csc(-c3ccnc(CCC(F)(F)F)c3)n2)c(Cl)c1)C(F)(F)F] | 46 |
| 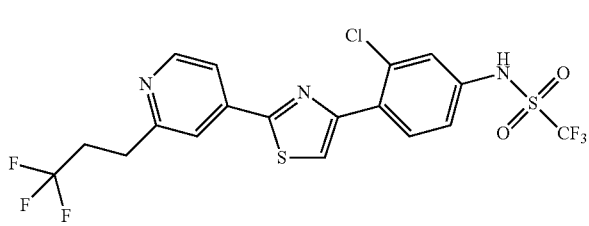 [SMILES: O=S(=O)(Nc1ccc(-c2csc(-c3ccnc(CCC(F)(F)F)c3)n2)c(Cl)c1)C(F)(F)F] | 47 |

TABLE 1-continued
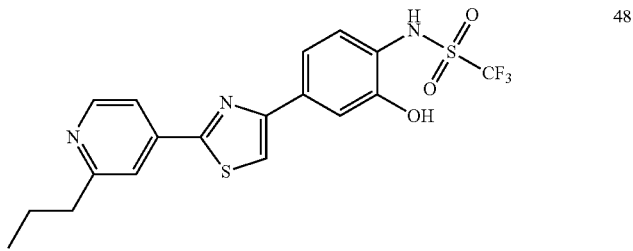
48
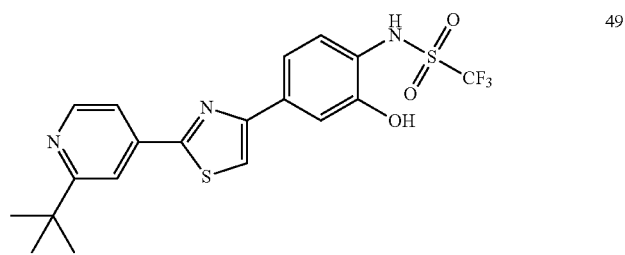
49
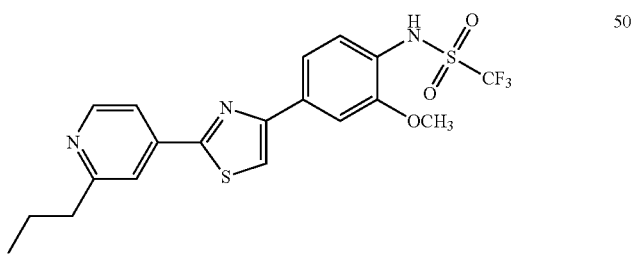
50
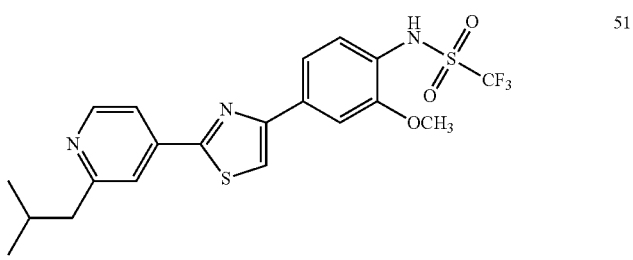
51
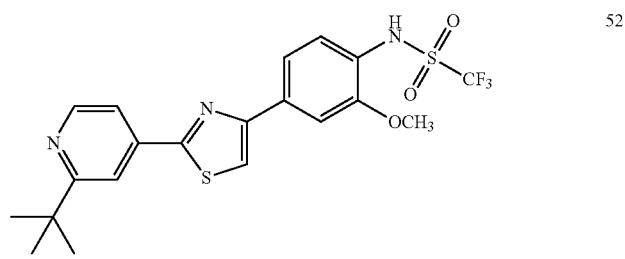
52
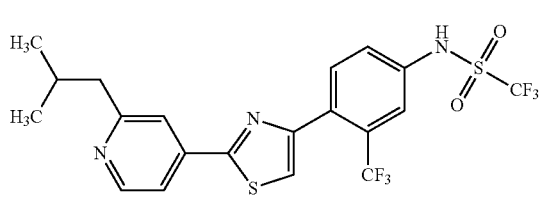
53

TABLE 1-continued
| | |
|---|---|
| 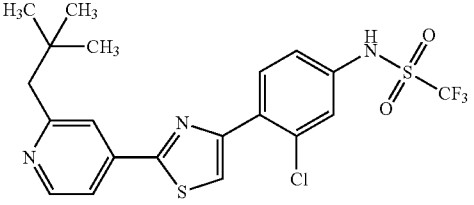 [SMILES: CC(C)(C)Cc1cc(-c2nc(-c3ccc(NS(=O)(=O)C(F)(F)F)cc3Cl)cs2)ccn1] | 54 |
| 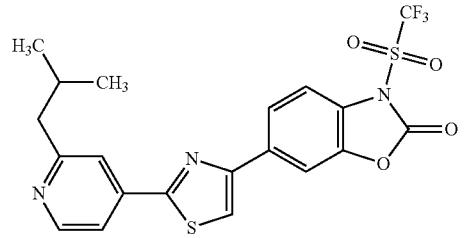 [SMILES: CC(C)Cc1cc(-c2nc(-c3ccc4c(c3)oc(=O)n4S(=O)(=O)C(F)(F)F)cs2)ccn1] | 55 |
| 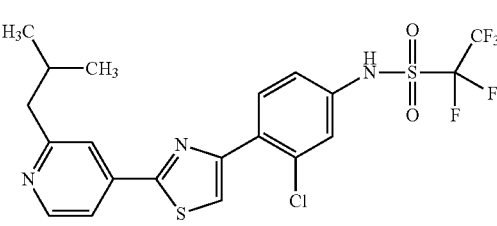 [SMILES: CC(C)Cc1cc(-c2nc(-c3ccc(NS(=O)(=O)C(F)(F)C(F)(F)F)cc3Cl)cs2)ccn1] | 56 |
| 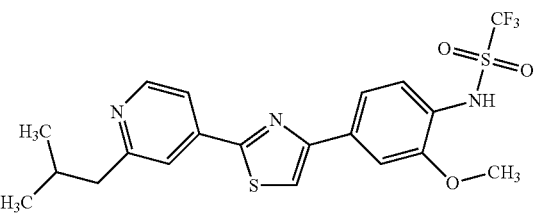 [SMILES: COc1cc(-c2csc(-c3ccnc(CC(C)C)c3)n2)ccc1NS(=O)(=O)C(F)(F)F] | 57 |
| 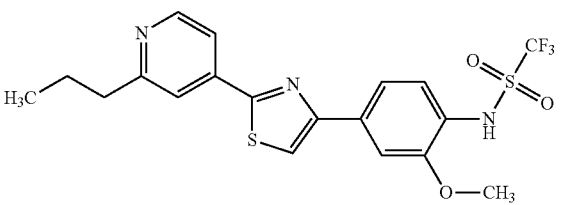 [SMILES: CCCc1cc(-c2nc(-c3ccc(NS(=O)(=O)C(F)(F)F)c(OC)c3)cs2)ccn1] | 58 |
| 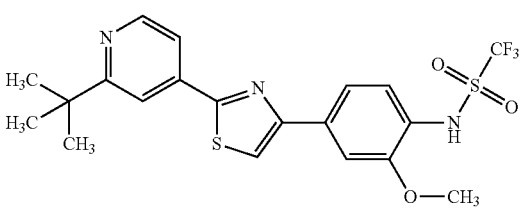 [SMILES: COc1cc(-c2csc(-c3ccnc(C(C)(C)C)c3)n2)ccc1NS(=O)(=O)C(F)(F)F] | 59 |
| 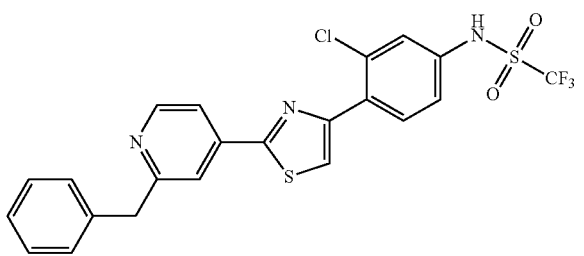 [SMILES: O=S(=O)(Nc1ccc(-c2csc(-c3ccnc(Cc4ccccc4)c3)n2)c(Cl)c1)C(F)(F)F] | 60 |

TABLE 1-continued
| | |
|---|---|
| 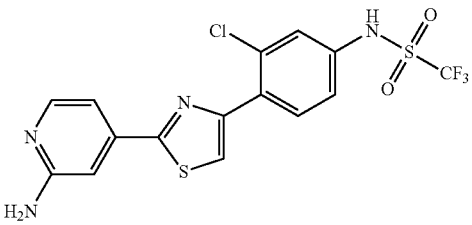 [SMILES: Nc1cc(-c2nc(-c3ccc(NS(=O)(=O)C(F)(F)F)cc3Cl)cs2)ccn1] | 61 |
| 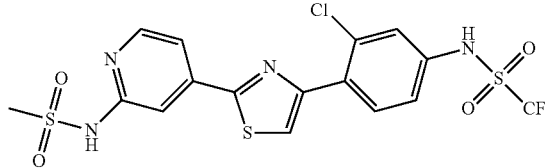 | 62 |
| 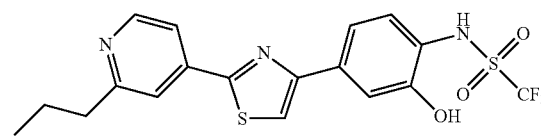 | 63 |
| 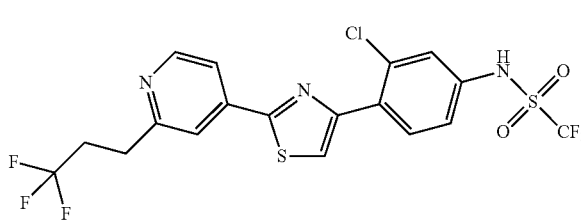 | 64 |
| 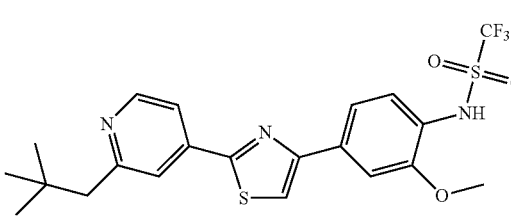 | 65 |
| 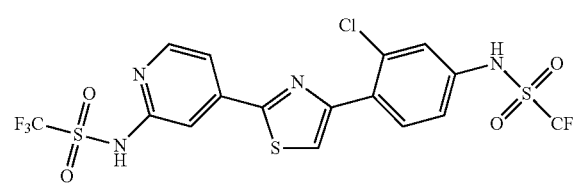 | 66 |
| 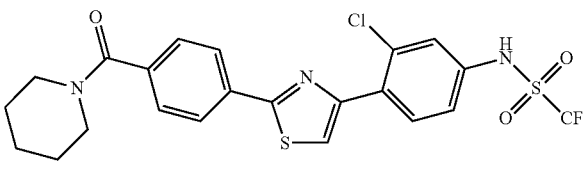 | 67 |
| 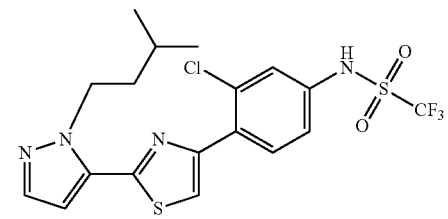 [SMILES: CC(C)CCn1nccc1-c1nc(-c2ccc(NS(=O)(=O)C(F)(F)F)cc2Cl)cs1] | 68 |

TABLE 1-continued
| | |
|---|---|
| 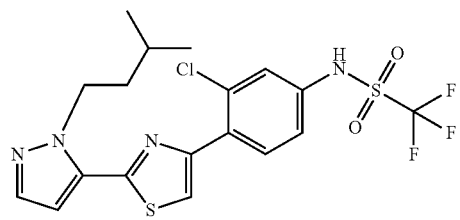 [SMILES: CC(C)CCn1nccc1-c1nc(-c2ccc(NS(=O)(=O)C(F)(F)F)cc2Cl)cs1] | 69 |
| 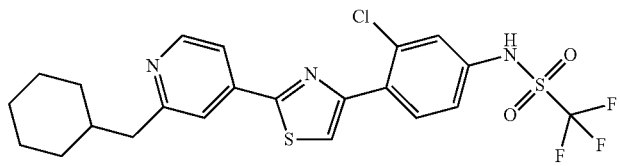 [SMILES: O=S(=O)(Nc1ccc(-c2csc(-c3ccnc(CC4CCCCC4)c3)n2)c(Cl)c1)C(F)(F)F] | 70 |
| 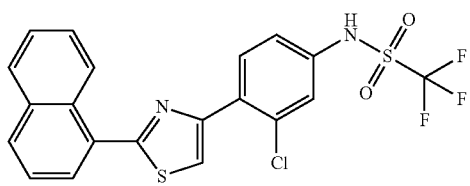 [SMILES: O=S(=O)(Nc1ccc(-c2csc(-c3cccc4ccccc34)n2)c(Cl)c1)C(F)(F)F] | 71 |
| 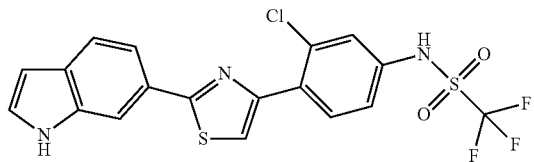 [SMILES: O=S(=O)(Nc1ccc(-c2csc(-c3ccc4cc[nH]c4c3)n2)c(Cl)c1)C(F)(F)F] | 72 |
| 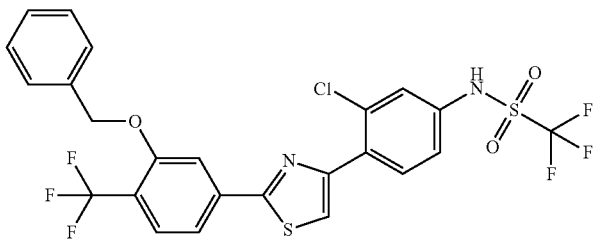 [SMILES: O=S(=O)(Nc1ccc(-c2csc(-c3ccc(C(F)(F)F)c(OCc4ccccc4)c3)n2)c(Cl)c1)C(F)(F)F] | 73 |
| 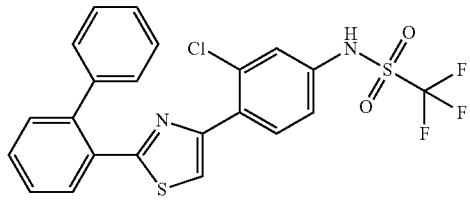 [SMILES: O=S(=O)(Nc1ccc(-c2csc(-c3ccccc3-c3ccccc3)n2)c(Cl)c1)C(F)(F)F] | 74 |
| 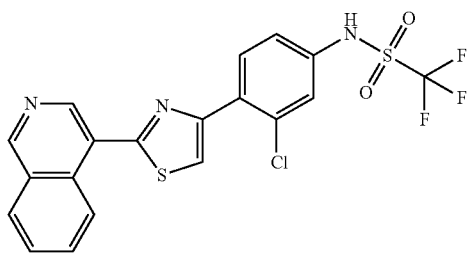 [SMILES: O=S(=O)(Nc1ccc(-c2csc(-c3cncc4ccccc34)n2)c(Cl)c1)C(F)(F)F] | 75 |

TABLE 1-continued
| | |
|---|---|
| 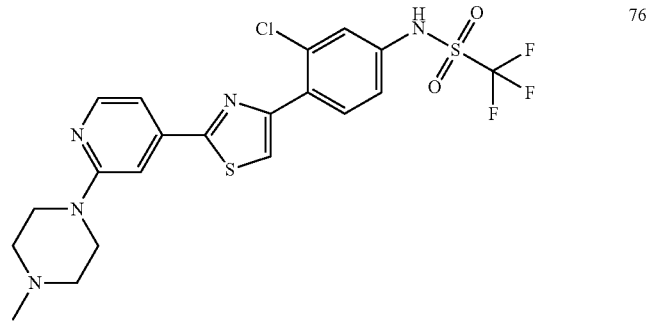 | 76 |
| 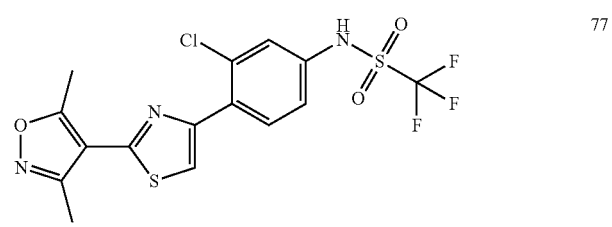 | 77 |
| 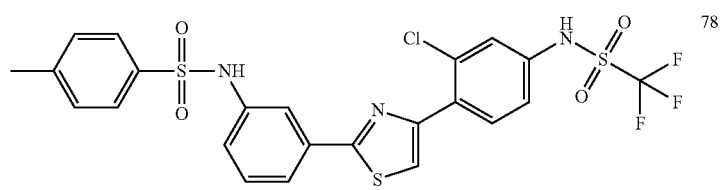 | 78 |
| 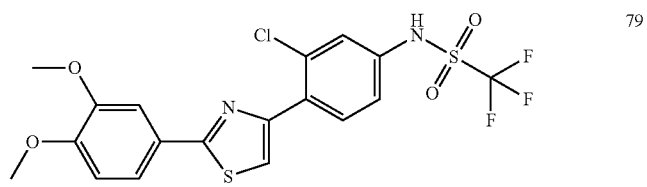 | 79 |
| 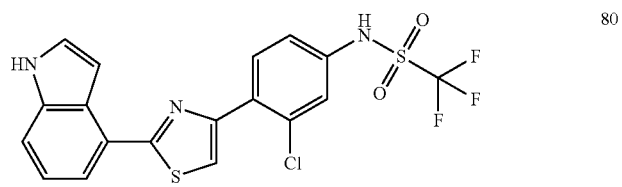 | 80 |
| 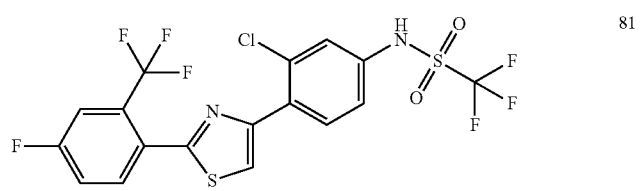 | 81 |
| 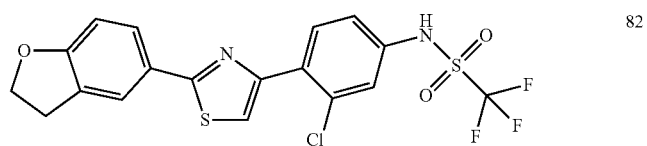 | 82 |

TABLE 1-continued

| | |
|---|---|
| [structure] | 83 |
| [structure] | 84 |
| [structure] | 85 |
| [structure] | 86 |
| [structure] | 87 |
| [structure] | 88 |
| [structure] | 89 |

TABLE 1-continued
| | |
|---|---|
| 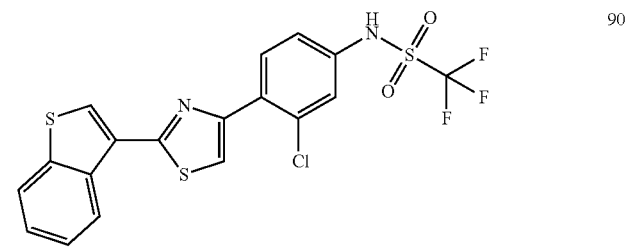 | 90 |
| 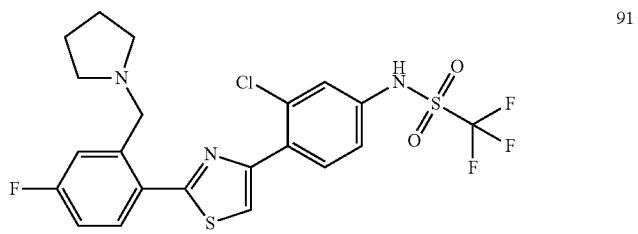 | 91 |
| 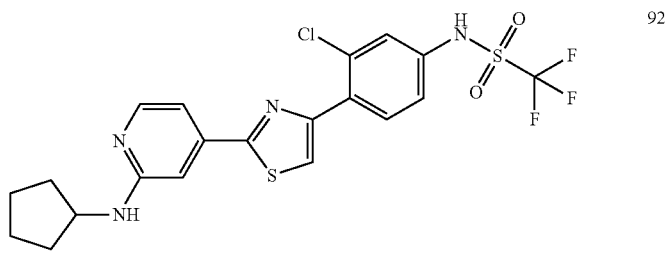 | 92 |
| 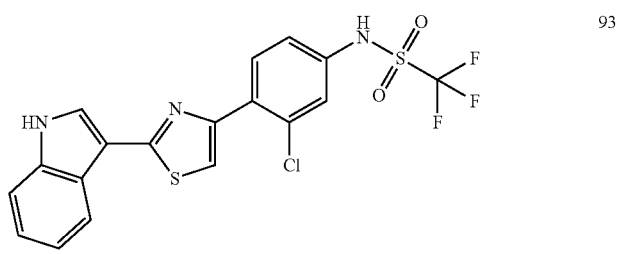 | 93 |
| 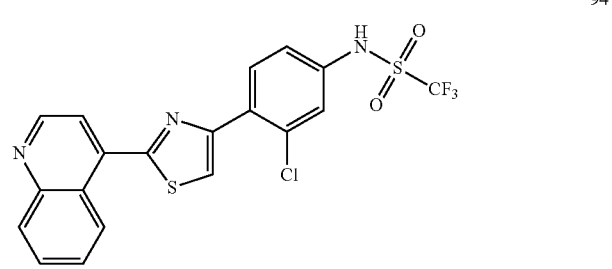 | 94 |
| 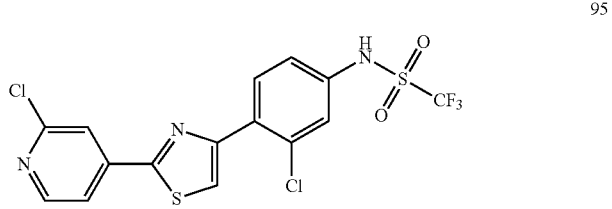 | 95 |

TABLE 1-continued
| | |
|---|---|
| 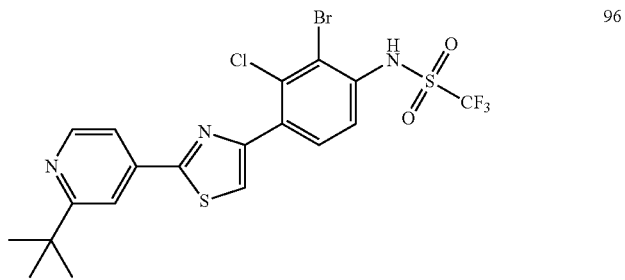 | 96 |
| 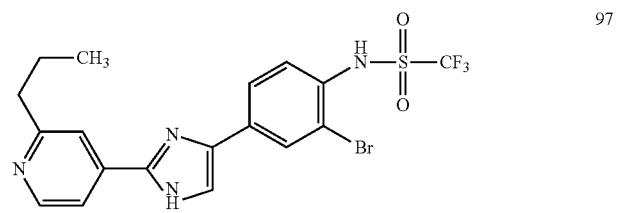 | 97 |
| 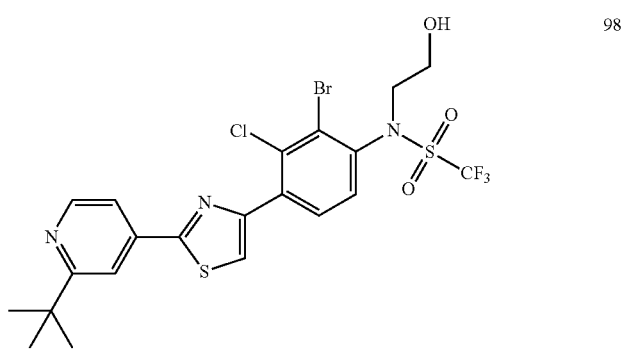 | 98 |
| 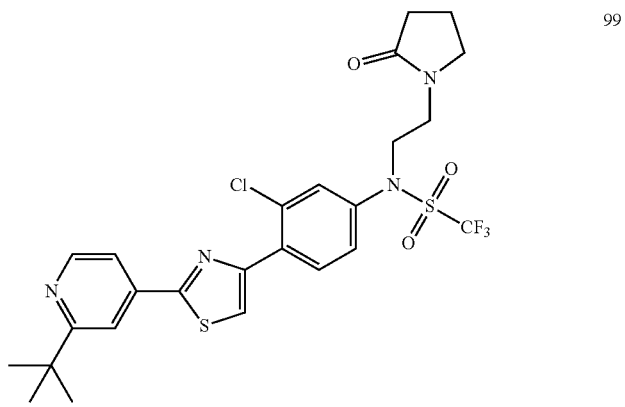 | 99 |
| 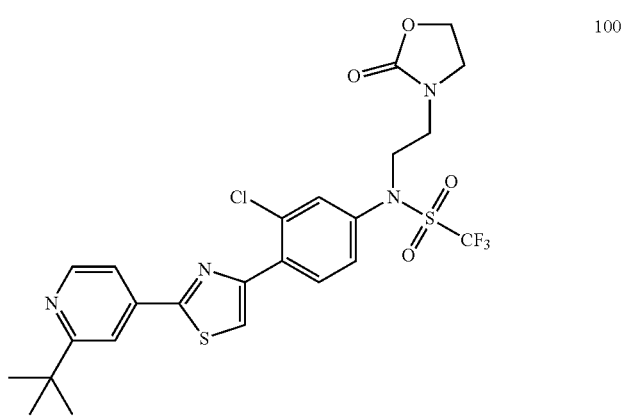 | 100 |

TABLE 1-continued
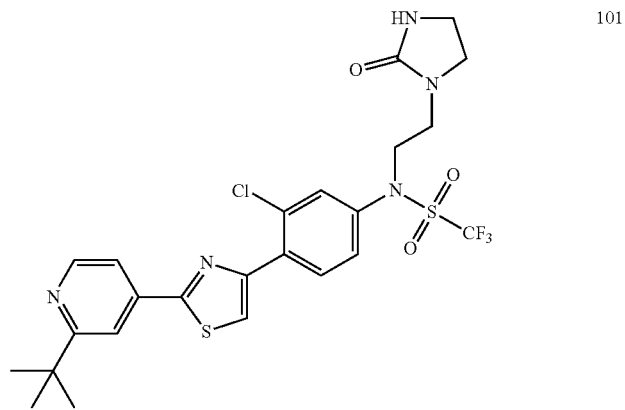
101
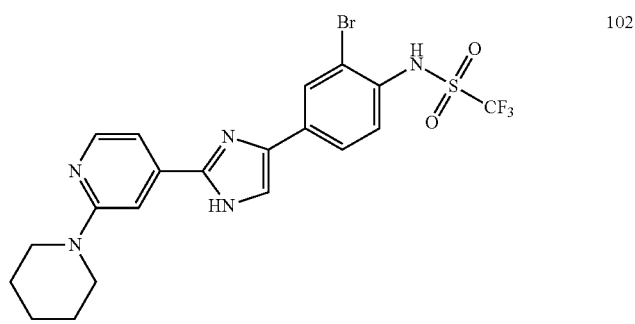
102
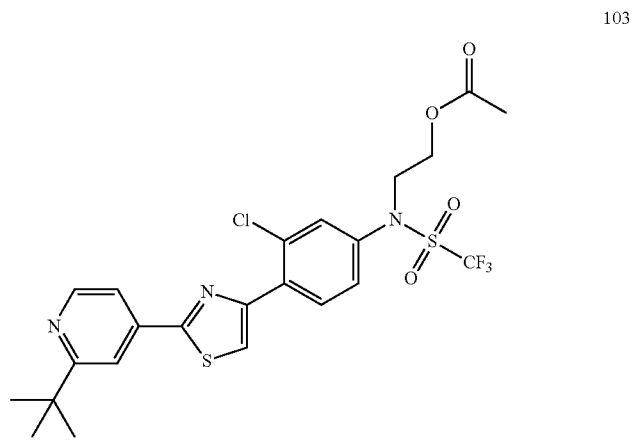
103
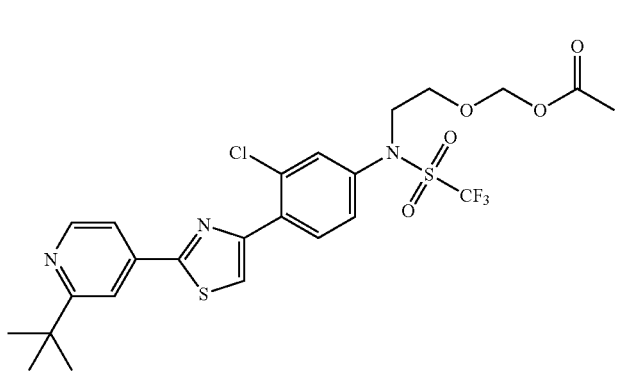 [SMILES: CC(=O)OCOCCN(c1ccc(-c2csc(-c3ccnc(C(C)(C)C)c3)n2)c(Cl)c1)S(=O)(=O)C(F)(F)F]
104

TABLE 1-continued
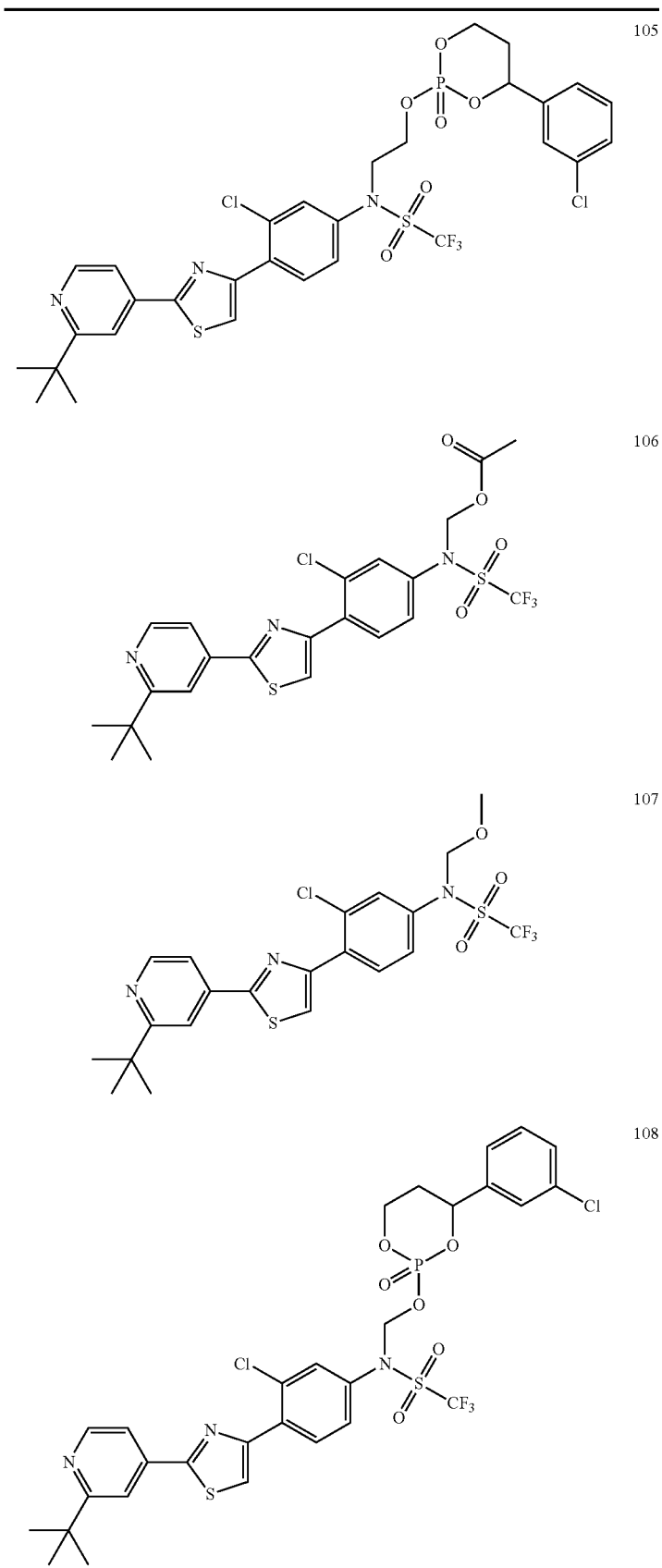

TABLE 1-continued
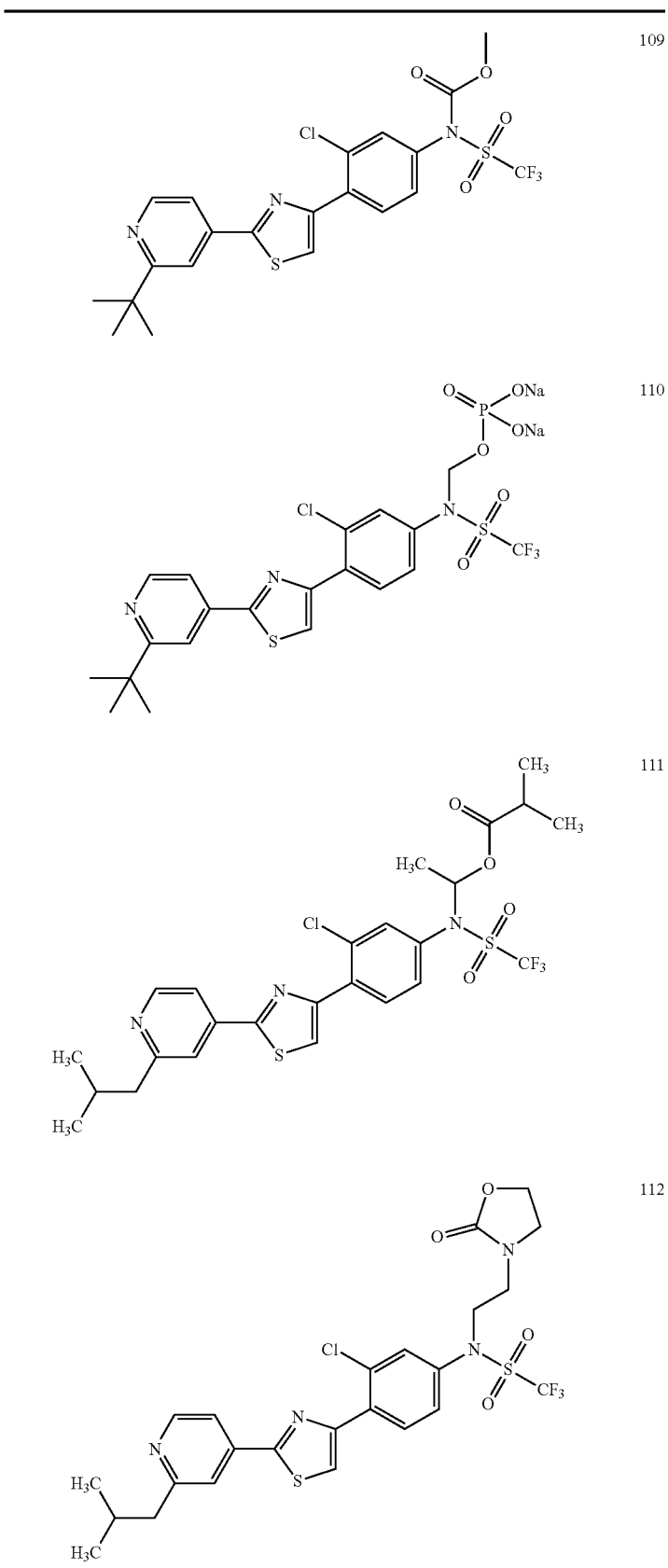

TABLE 1-continued
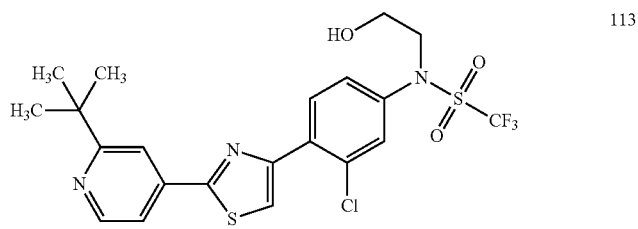
113
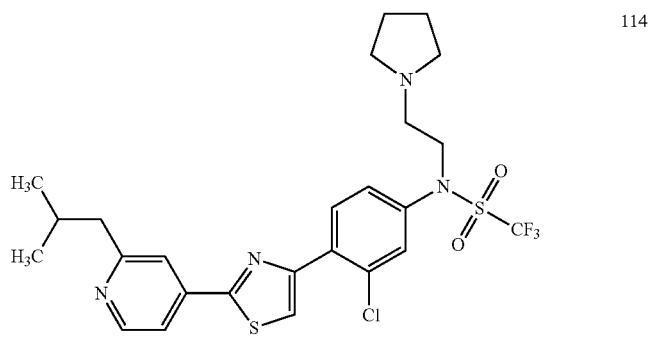
114
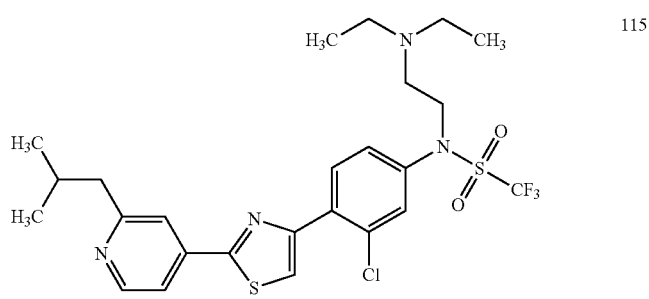
115
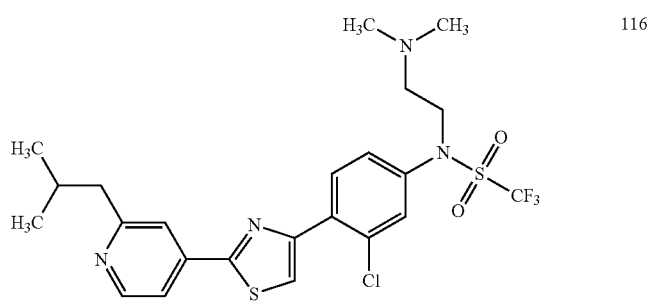
116
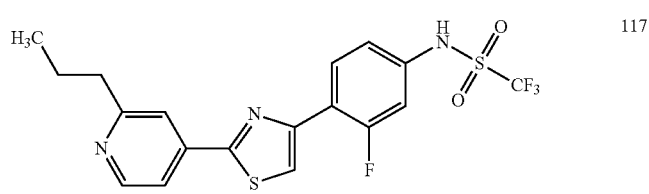
117
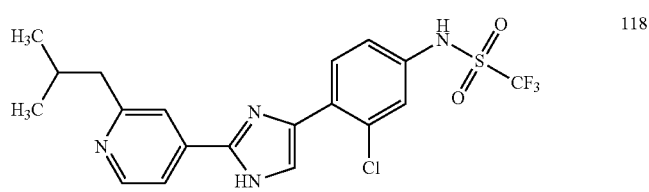
118

TABLE 1-continued
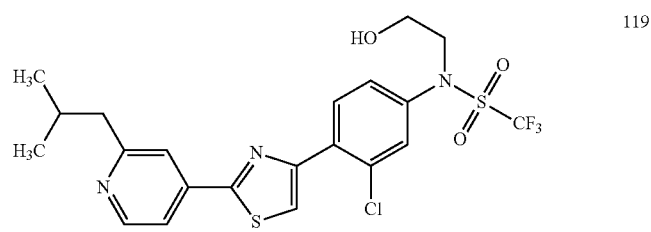 119
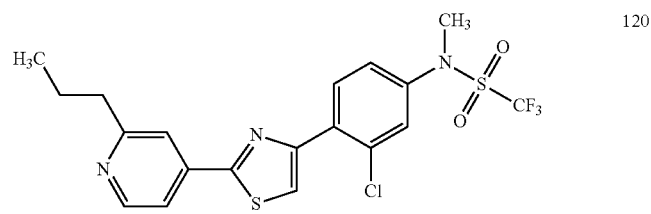 120
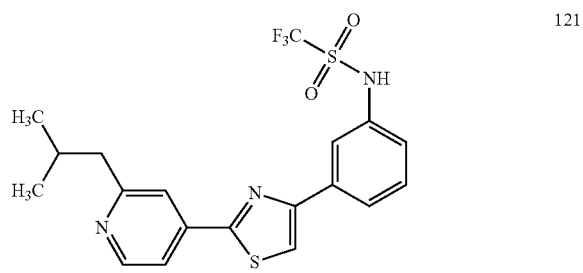 121
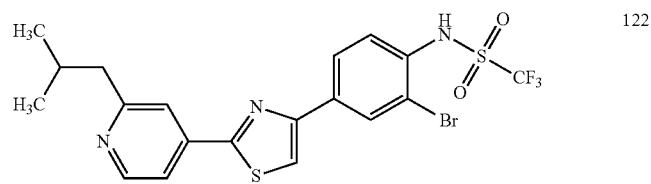 122
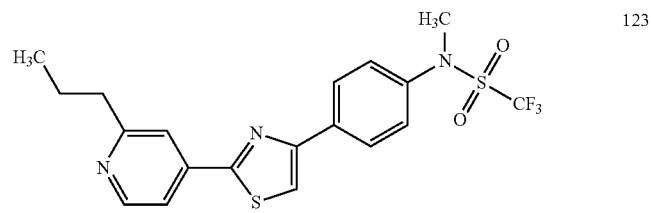 123
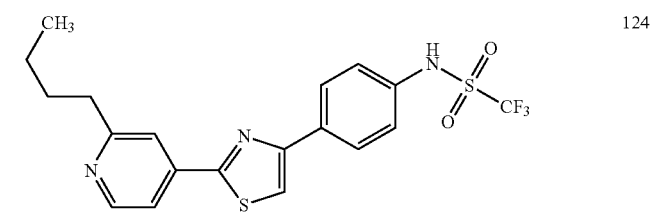 124
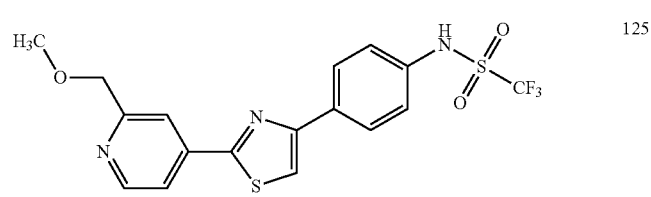 125

TABLE 1-continued
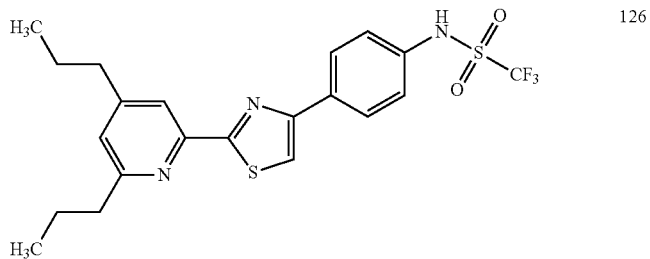 126
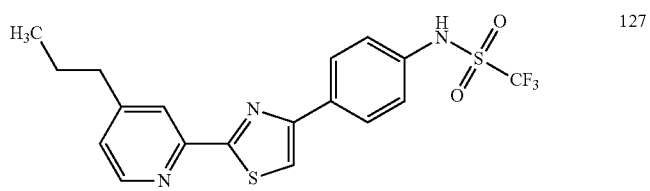 127
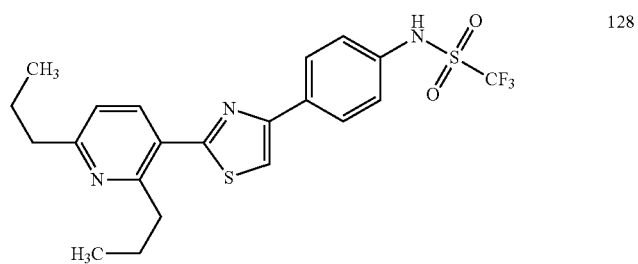 128
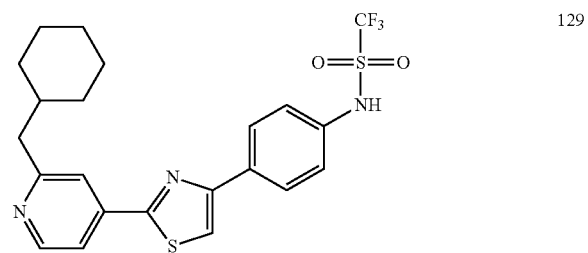 129
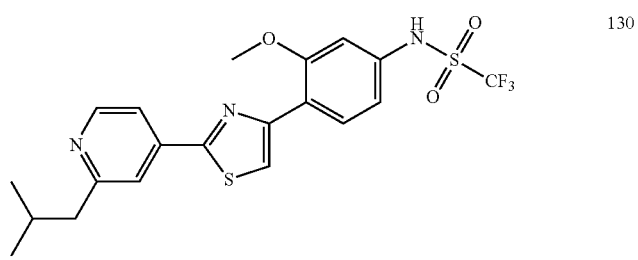 130
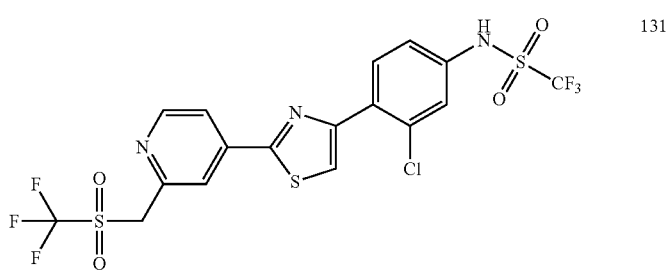 131

TABLE 1-continued
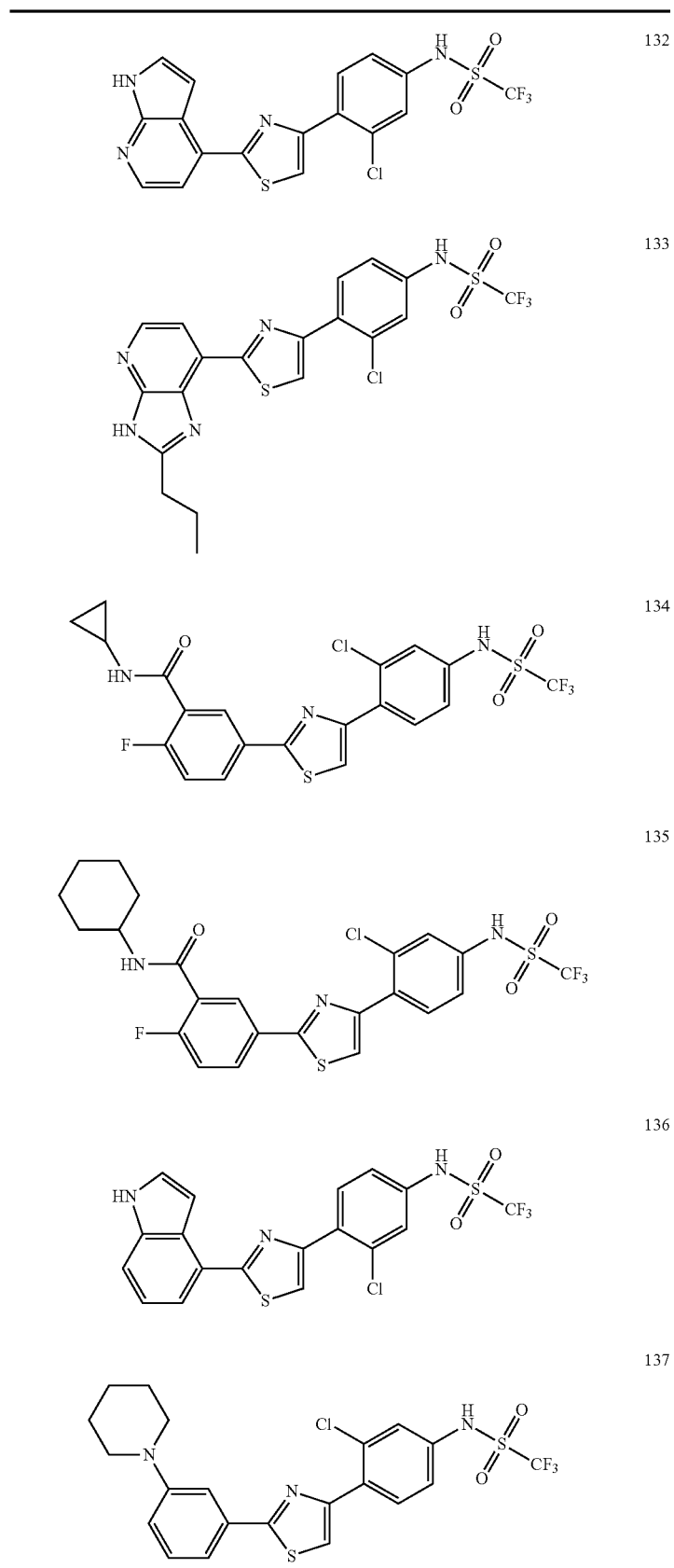

TABLE 1-continued
| | |
|---|---|
| 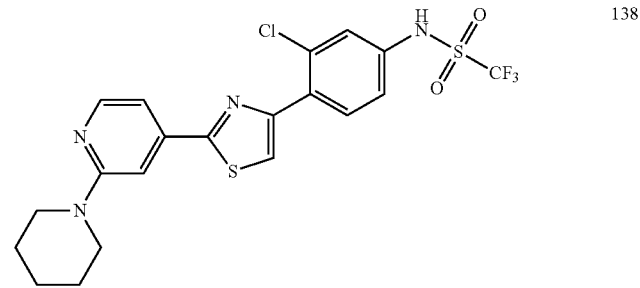 | 138 |
| 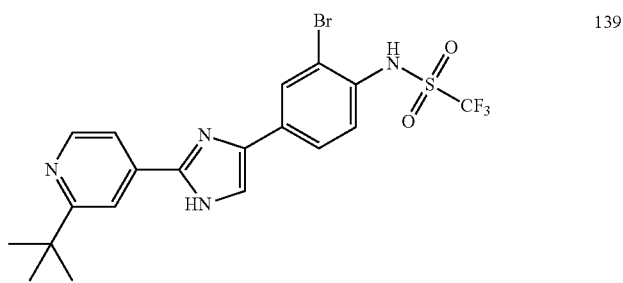 | 139 |
| 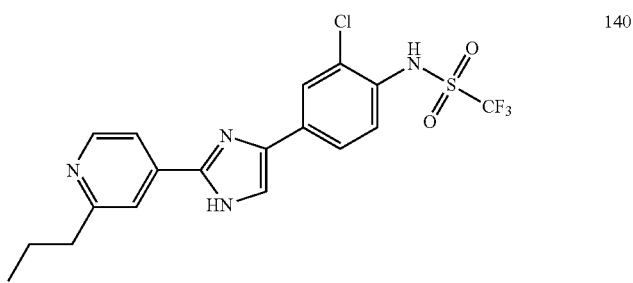 | 140 |
| 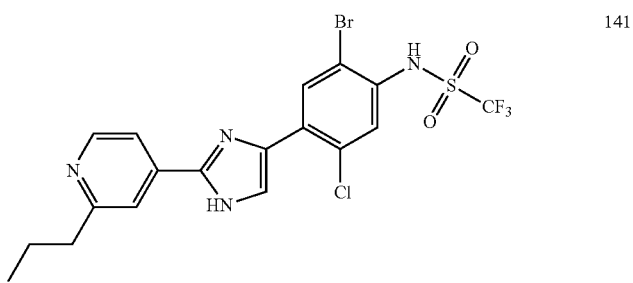 | 141 |
| 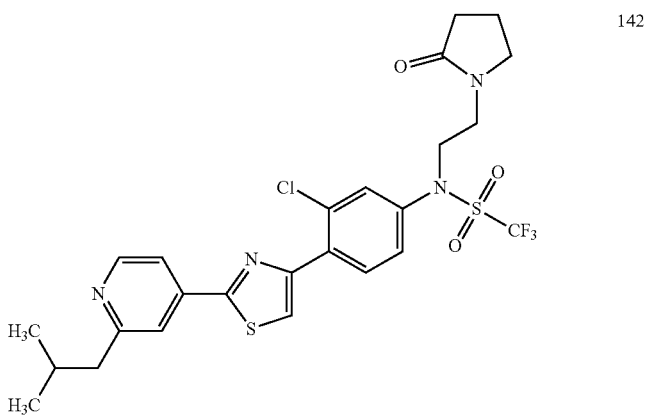 | 142 |

TABLE 1-continued

TABLE 1-continued

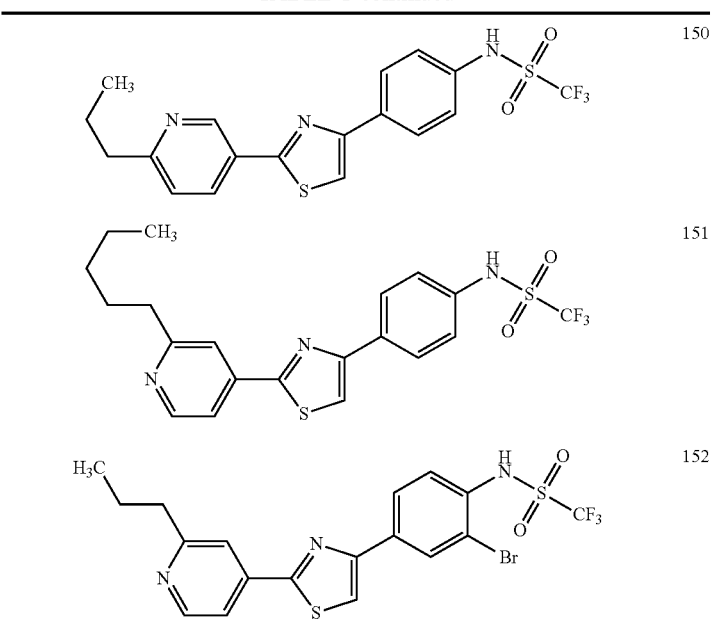

In some embodiments, the compound is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, or 152.

In some embodiments, the compound is 1, 2, 3, 4, 5, 37, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, or 94.

Representative examples of compounds detailed herein, including intermediates and final compounds, are depicted in Table 1 and elsewhere herein. It is understood that in one aspect, any of the compounds may be used in the methods detailed herein, including, where applicable, intermediate compounds that may be isolated and administered to an individual.

The compounds depicted herein may be present as salts even if salts are not depicted, and it is understood that the compositions and methods provided herein embrace all salts and solvates of the compounds depicted here, as well as the non-salt and non-solvate form of the compound, as is well understood by the skilled artisan. In some embodiments, the salts of the compounds provided herein are pharmaceutically acceptable salts.

In one embodiment, the compound is a pharmaceutically acceptable salt of a compound of Formulae (Ia), (Ib), (IIa) or (IIb), or any variation presented herein, or a pharmaceutically acceptable salt thereof.

In some embodiments, certain compounds presented herein are considered to be "prodrug" forms of other compounds herein. Prodrugs are precursor derivatives that, upon administration to a patient, undergo metabolism in-vivo such as, for example, hydrolysis to release the active form of the compound—the 'parent' compound. The prodrug form itself is either inactive or less active than the parent. Prodrugs are designed to improve bioavailability or to improve selective administration to particular organs, such as the liver [see, for example, Erion, et al. PNAS (2007) 104:39, pp 15490-15495; Erion, et al. J. Pharmacol. Exp. Ther. (2005) 312:2, pp 554-560; Meyer, et al. Patent Publication US 2006-0281695A1]. Compounds provided herein such as, for example, compound nos. 106-111 can be considered prodrug forms of the 'parent' compound no. 5. In some embodiments, prodrug forms of compounds presented herein are provided. Conventional procedures for the selection and preparation of suitable prodrug derivatives are described, for example, in "Design of Prodrugs", ed. H. Bundgaard, Elsevier, 1985; Beaumont; K. et al. Curr. Drug Metab. (2003) 4, pp 461-485; Mizen, L, et al. Pharm. Biotechnol. (1998) 11, pp 345-365. In addition to prodrugs, the invention provides the salts, esters, amides, and other protected or derivatized forms of the described compounds.

As has been described above, the inherent pKa(s) of molecules can be assessed by potentiometric methods known to the skilled artisan, typically UV spectrophotometry [see, for example, Julémont, et al. J. Med. Chem. (2002), 45, pp 5182-5185]. In-silico methods can be used as a predictive tool, and software is commercially available from, for example, ACD/Labs, Molecular Discovery, ChemAxon, and other vendors. Without being bound by theory, it is presented that compounds provided herein possess unexpected physicochemical properties presumed to arise from the presence of the trifluoromethylsulfonamide moiety and its effect on the acidity of the remaining structure of the provided compounds as a whole. The compounds provided herein contain several ionizable centers including, for example, the trifluoromethylsulfonamide nitrogen atom; the thiazole ring nitrogen atom; the "ring A" pyridine nitrogen atom, etc.

As one example to describe the theory, compound #37 could exist in the following forms:

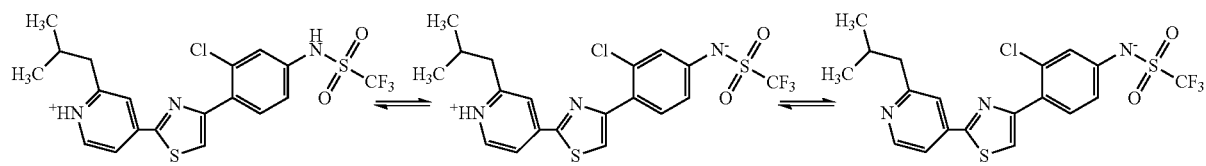 [SMILES: CC(C)Cc1cc(-c2nc(-c3ccc(NS(=O)(=O)C(F)(F)F)cc3Cl)cs2)cc[nH+]1 ; CC(C)Cc1cc(-c2nc(-c3ccc([N-]S(=O)(=O)C(F)(F)F)cc3Cl)cs2)cc[nH+]1 ; CC(C)Cc1cc(-c2nc(-c3ccc([N-]S(=O)(=O)C(F)(F)F)cc3Cl)cs2)ccn1]

Other ionized forms are conceivable, but those presented here are a protonated form; a neutral or internal zwitterionic form; and an anionic form. Which form would exist is dependent upon the pH of the aqueous or physiological solution in which the compound is placed. Calculated pKa values of compound #37 [provided by I-Lab 2.0 (ACD/Labs, Inc.)] give two values of 3.4 and 5.4. These values are similar to those experimentally obtained under potentiometric and spectrophotometric methods [courtesy of Pion, Inc.], found to be 3.09 and 5.27. When the $CF_3$ group is replaced by a $CH_3$ group, the calculated pKa values become 5.1 and 7.5—both notably higher. It is postulated that the more electronegative nature of the $CF_3$ group results in a more highly acidic nature of the compound. Based on the calculated/measured pKa values of the trifluoromethylsulfonamide containing compounds claimed herein, it is likely that at a pH of 6-8, these compounds will predominantly exist in the anionic form, with the above equilibrium lying to the right at higher pH values. The anionic form renders the compound more aqueous soluble and therefore better absorbed. A solubility study [courtesy of Pion, Inc.] showed average solubilities of 13 µg/mL @pH 6.0, 104 µg/mL @pH 7.0, and >130 µg/mL @pH 8.0. When a compound is dosed orally, most of the absorption occurs in the intestines where the pH ranges from 6-8. Therefore it is likely that the trifluoromethylsulfonamide containing compounds claimed herein will have significantly better solubility and absorption when dose orally relative to the methylsulfonamides which the anionic form would be present to a significantly lower extent at pH 6-8, compared to its neutral/zwitterionic form).

Examples of perhaloalkylsulfonamide groups are presented hereinabove. In some embodiments, also provided are compounds bearing perhaloalkenylsulfonamide groups, perhaloalkynylsulfonamide groups, or alkylsulfonamide groups bearing 1 or more halogen atoms. Such compounds can include, for example, the following:

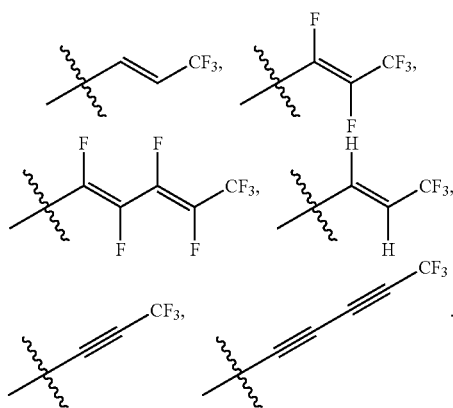

Without being bound by theory, it is expected that each of these particular groups, and variations therein, has varying degrees of electronegativity, affording subtle changes in pKa, and allowing a tuning of the acidity to compounds of the invention, where required by the skilled artisan.

Pharmaceutically Acceptable Salts

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth metal ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, *J. Pharm. Sci.* 1977 January; 66(1):1-19. Pharmaceutically acceptable salts can be prepared in situ in the manufacturing process, or by separately reacting a purified compound disclosed herein in its free acid or base form with a suitable organic or inorganic base or acid, respectively, and isolating the salt thus formed during subsequent purification. In one embodiment, a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Pharmaceutical Compositions

A compound of Formulae (Ia), (Ib), (IIa) or (IIb), or any variation presented herein, typically is provided in a pharmaceutical composition comprising a pharmaceutically acceptable carrier and/or excipient. A "pharmaceutically acceptable" carrier or excipient is a material that is not biologically or otherwise undesirable, e.g., the material may be incorporated into a pharmaceutical composition administered to an individual without causing significant undesirable biological effects or interacting in a deleterious manner with any of the other components of the composition, wherein it is contained. Pharmaceutically acceptable carriers or excipients meet the required standards of toxicological and manufacturing testing and/or are included on the Inactive Ingredient Guide prepared by the U.S. Food and Drug administration.

A pharmaceutical composition can comprise one or more compounds of Formulae (Ia), (Ib), (IIa) or (IIb), or any variation presented herein. In some embodiments, a pharmaceutical composition further comprises chemotherapeutic agent, as described below.

Preferably a compound of Formulae (Ia), (Ib), (IIa) or (IIb), or any variation presented herein, is bioavailable orally. However, the compounds may also be formulated for parenteral (e.g., intravenous) administration.

A compound of Formulae (Ia), (Ib), (IIa) or (IIb), or any variation presented herein, can be used in the preparation of a medicament by combining the compound or compounds as an active ingredient with a pharmacologically acceptable carrier, which is known in the art. Depending on the therapeutic form of the medication, the carrier may be in various forms. In one variation, the manufacture of a medicament is for use in any of the methods disclosed herein.

Methods as provided herein may comprise administering to an individual a pharmacological composition that contains an effective amount of a compound of Formulae (Ia), (Ib), (IIa) or (IIb), or any variation presented herein, and a pharmaceutically acceptable carrier. The effective amount of the compound may in one aspect be a dose of between about 0.01 and about 100 mg.

The compound may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

A compound of Formulae (Ia), (Ib), (IIa) or (IIb), or any variation presented herein, can be used in the preparation of a formulation, such as a pharmaceutical formulation, by combining the compound or compounds as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., 20$^{th}$ ed. (2000), which is incorporated herein by reference.

A compound of Formulae (Ia), (Ib), (IIa) or (IIb), or any variation presented herein, may be administered to individuals in a form of generally accepted oral compositions, such as tablets, coated tablets, gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, salts for the adjustment of osmotic pressure, buffers, coating agents or antioxidants.

A compound of Formulae (Ia), (Ib), (IIa) or (IIb), or any variation presented herein, can be formulated in a tablet in any dosage form described, for example, a compound as described herein or a pharmaceutically acceptable salt thereof can be formulated as a 10 mg tablet.

A compound of Formulae (Ia), (Ib), (IIa) or (IIb), or any variation presented herein, may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, a compound of Formulae (Ia), (Ib), (IIa) or (IIb), or any variation presented herein, is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

In some embodiments, a pharmaceutical composition is provided as a unit dosage form, such as a tablet, capsule, or individually packaged container (e.g., an ampoule, syringe, or vial).

In some embodiments, the unit dosage form contains a daily dose of a compound of Formulae (Ia), (Ib), (IIa) or (IIb), or any variation presented herein. In some embodiments, the unit dosage form contains a daily sub-dose of the compound.

In some embodiments, the unit dosage form contains a daily dose of each of two or more compounds of Formulae (Ia), (Ib), (IIa) or (IIb), or any variation presented herein. In some embodiments, the unit dosage form contains a daily sub-dose of each of two or more compounds.

In some embodiments, the unit dosage form contains a daily dose of compound of Formulae (Ia), (Ib), (IIa) or (IIb), or any variation presented herein, and a daily dose of each of one or more chemotherapeutic agents. In some embodiments, the unit dosage form contains a daily sub-dose of the compound and a daily sub-dose of each of one or more chemotherapeutic agents.

In some embodiments, the unit dosage form contains a daily dose of each of two or more compounds of Formulae (Ia), (Ib), (IIa) or (IIb), or any variation presented herein, and a daily dose of each of one or more chemotherapeutic agents. In some embodiments, the unit dosage form contains a daily sub-dose of each of two or more compounds and a daily dose of each of one or more chemotherapeutic agents.

Kits and Articles of Manufacture

This disclosure also provides kits and articles of manufacture comprising one or more compounds of Formulae (Ia), (Ib), (IIa) or (IIb), or any variation presented herein, or a pharmacological composition comprising a compound of Formulae (Ia), (Ib), (IIa) or (IIb), or any variation presented herein. The kits may employ any of the compounds disclosed herein. In one variation, the kit employs a compound described herein or a pharmaceutically acceptable salt thereof.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or a second pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the disclosed methods. The instructions included with the kit generally include information as to the components and their administration to an individual.

Therapeutic Uses

Compounds of Formulae (Ia), (Ib), (IIa) or (IIb), or any variation presented herein, can be used to treat hyperproliferative disorders. A "hyperproliferative disorder" is a disorder associated with some degree of abnormal cell proliferation. A hyperproliferative disorder can be benign (including pre-cancerous disorders) or malignant.

In some embodiments, the hyperproliferative disorder is benign, such as benign prostatic hyperplasia, neurofibromatosis, actinic keratosis, hypertrophic actinic keratosis, Bowenoid actinic keratosis, arsenical keratosis, hydrocarbon keratosis, thermal keratosis, radiation keratosis, chronic scar keratosis, viral keratosis, actinic cheilitis, Bowen's disease, erythroplaquia of queyrat, oral erythroplaquia, leukoplakia, intraepidermal epithelioma, psoriasis, polyps, Barrett's esophagus, atrophic gastritis, cervical dysplasia, benign meningioma, and benign ovarian epithelial tumors (e.g., serous adenomas, mucinous adenomas, Brenner tumors).

In some embodiments, the hyperproliferative disorder is malignant, e.g., adenocarcinoma, bladder cancer, breast cancer, cervical cancer, cholangiocarcinoma, CNS cancer (e.g., astrocytoma, dendroma, ependymoma, glioma, malignant meningioma, medulloblastoma, neuroblastoma, neuroglioma, oligodendroglioma), gastrointestinal cancer (e.g., gastrointestinal stromal carcinoma, colorectal cancer), kidney cancer, leukemia (e.g., acute lymphocytic leukemia; acute myelogenous leukemia; chronic lymphocytic leukemia; chronic myelogenous leukemia), liver cancer (e.g., hepatic cancer, hepatocellular carcinoma), lung cancer (e.g., lung squamous carcinoma, small-cell lung carcinoma, non-small-cell lung carcinoma, mesothelioma), lymphoma (e.g., Hodgkin lymphoma and non-Hodgkin lymphoma), melanoma, myeloma (e.g., multiple myeloma, plasmacytoma), ovarian cancer, pancreatic cancer, prostate cancer, renal cancer, thyroid cancer, and uterine cancer.

In some embodiments, the breast cancer is AR+, ER+, and Her2+. In some embodiments, the breast cancer is AR+, ER+, and PR+. In some embodiments, the breast cancer is AR+, ER+, Her2+, and PR+. In some embodiments, the breast cancer is AR−, ER+, and Her2+. In some embodiments, the breast cancer is AR−, ER+, and PR+. In some embodiments, the breast cancer is AR−, ER+, Her2+, and PR+.

In some embodiments, the breast cancer is ductal carcinoma in situ. In some embodiments, the breast cancer is invasive ductal carcinoma. In some embodiments, the breast cancer is triple negative breast cancer (e.g., basal-like type 1 (BL1), basal-like type 2 (BL2), immunomodulatory (IM), mesenchymal (M), mesenchymal stem-like (MSL), and luminal androgen receptor (LAR) subtypes). In some embodiments, the breast cancer is inflammatory breast cancer. In some embodiments, the breast cancer is BRCA1-related breast cancer. In some embodiments, the breast cancer is medullary breast cancer, metaplastic breast cancer. In some embodiments, the breast cancer is special histologic type of breast cancer. In some embodiments, the breast cancer is resistant to endocrine therapy.

In some embodiments, the prostate cancer is hormone-sensitive prostate cancer. In some embodiments, the prostate cancer is castration-resistant prostate cancer.

In some embodiments, the ovarian cancer is an epithelial carcinoma. In some embodiments, the ovarian cancer is a germ cell tumor. In some embodiments, the ovarian cancer is an ovarian stromal tumor (e.g., granulosa-theca tumors and Sertoli-Leydig cell tumors).

Compounds disclosed herein also can be used to treat a variety of metabolic disorders, including metabolic disorders that are mediated by genetic factors (e.g., Niemann-Pick disease, Fabry disease, Gaucher disease, Forbe's disease, Tangier disease) and environmental factors (e.g., diets rich in fat and/or sugar). Compounds also may be useful in the treatment of complications of metabolic diseases, such as cardiovascular disease, non-alcoholic hepatic steatosis, hyperlipemia, and obesity.

Compounds disclosed herein also can be used to treat pancreatitis.

Treatment Regimens

Compounds can be administered alone or in conjunction with other therapeutic interventions. The disclosed compounds decrease the synthesis of cholesterol and fatty acids, which are essential components of cell membranes and cell division; accordingly, administration of a compound should decrease the rate of cell division. These effects, coupled with alterations in lipid-mediated cell signaling pathways, induce cell death.

Administration of a compound of Formulae (Ia), (Ib), (IIa) or (IIb), or any variation presented herein, "in conjunction with" another therapeutic intervention may include any of the following regimens.

Dosing and Method of Administration

The dose of a compound administered to an individual (such as a human) may vary with the particular compound or salt thereof, the method of administration, and the particular stage of hyperproliferative or metabolic disorder being treated. For therapeutic purposes, "effective dose" or "effective amount" refers to that amount of each active compound or pharmaceutical agent, alone or in combination, that elicits the biological or medicinal response in a tissue system, animal, or human that is being sought by a researcher, veterinarian, medical doctor, or other clinician, which includes alleviation of the symptoms of the disease or disorder being treated. For prophylactic purposes (i.e., preventing or inhibiting the onset or progression of a disorder), the term "effective dose" or "effective amount" refers to that amount of each active compound or pharmaceutical agent, alone or in combination, that inhibits in a subject the onset or progression of a disorder as being sought by a researcher, veterinarian, medical doctor, or other clinician, the delaying of which disorder is mediated, at least in part, by blocking of SREBP function. The amount should be sufficient to produce a desirable response, such as a therapeutic or prophylactic response against the disorder. In some embodiments, the amount of the compound or salt thereof is a therapeutically effective amount. In some embodiments, the amount of the compound or salt thereof is a prophylactically effective amount. In some embodiments, the amount of compound or salt thereof is below the level that induces a toxicological effect (e.g., an effect above a clinically acceptable level of toxicity) or is at a level where a potential side effect can be controlled or tolerated when the composition is administered to the individual.

In some embodiments, the amount of compound or salt thereof is an amount sufficient to inhibit cancer cell growth and/or proliferation or increase apoptosis of cancer cells.

The effective amount of the compound may in one aspect be a dose of between about 0.01 and about 100 mg/kg.

Any of the methods provided herein may in one aspect comprise administering to an individual a pharmaceutical composition that contains an effective amount of a compound provided herein or a salt thereof and a pharmaceutically acceptable excipient.

A compound or composition provided herein may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

The compounds provided herein or a salt thereof may be administered to an individual via various routes, including, e.g., intravenous, intramuscular, subcutaneous, oral and transdermal.

In one aspect, provided is a method of treating cancer in an individual by parenterally administering to the individual (e.g., a human) an effective amount of a compound or salt thereof. In some embodiments, the route of administration is intravenous, intra-arterial, intramuscular, or subcutaneous. In some embodiments, the route of administration is oral. In still other embodiments, the route of administration is transdermal. In one aspect are provided compositions (including pharmaceutical compositions) as described herein for the use in treating a hyperproliferative or metabolic disorder, such as cancer (e.g., prostate cancer).

Also provided are compositions (including pharmaceutical compositions) as described herein for the use in treating, preventing, and/or delaying the onset and/or development of cancer and other methods described herein. In certain embodiments, the composition comprises a pharmaceutical formulation which is present in a unit dosage form.

Also provided are articles of manufacture, comprising a compound provided herein or a salt thereof, composition, and unit dosages described herein in suitable packaging for use in the methods described herein. Suitable packaging is known in the art and includes, for example, vials, vessels, ampules, bottles, jars, flexible packaging and the like. An article of manufacture may further be sterilized and/or sealed.

Anti-Proliferative Agents

An "anti-proliferative agent" is an intervention that increases apoptosis of hyperproliferating cells. In some embodiments, a compound of Formulae (Ia), (Ib), (IIa) or (IIb), or any variation presented herein, is used in conjunction with an anti-proliferative agent which is a chemotherapeutic agent. Chemotherapeutic agents include any pharmacological agent which is currently approved by the FDA in the U.S. (or elsewhere by any other regulatory body) for use as pharmacological treatment for hyperproliferative disorders, including cancer, or which is currently being used experimentally as part of a clinical trial program.

General Synthetic Methods

The compounds may be prepared by a number of processes as generally described below in the General Synthetic Schemes and more specifically in the Examples hereinafter. In the following process descriptions, the symbols when used in the formulae depicted are to be understood to represent those groups described above in relation to the formulae herein.

Chromatography, recrystallization and other conventional separation procedures may also be used with intermediates or final products where it is desired to obtain a particular isomer of a compound or to otherwise purify a product of a reaction.

The following abbreviations are used herein: thin layer chromatography (TLC); hour (h); minute (min); second (sec); ethanol (EtOH); dimethylsulfoxide (DMSO); N,N-dimethylformamide (DMF); trifluoroacetic acid (TFA); tetrahydrofuran (THF); Normal(N); aqueous (aq.); methanol (MeOH); dichloromethane (DCM); ethyl acetate (EtOAc); Retention factor (Rf); room temperature (RT).

The following General Synthetic Schemes and Examples are provided to illustrate but not to limit the invention. Those skilled in the art will be familiar with many of the reaction steps described. Particular publications are presented to assist with certain steps of the synthetic route.

General Synthetic Scheme 1

General Synthetic Scheme 1 provides methods to prepare compounds with a thiazole or imidazole B-ring as presented herein. Substituents $R_1$-$R_6$ are as exemplified in the Examples below. Syntheses of tricyclic substituted thiazoles, oxazoles and imidazoles, such as those presented herein, will be familiar to those skilled in the art. An example to illustrate a synthesis of a substituted thiazole is presented below. Complete details for syntheses of the compounds presented herein are provided in the Examples.

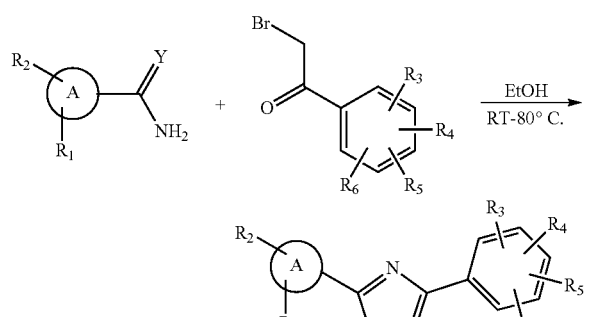

A = aromatic or heteroaromatic ring
Y = O, S, NH

General Procedure:

The corresponding substituted pyridine-4-carbothioamide or isonicotinamide and the corresponding substituted 2-bromoacetylbenzene are dissolved in EtOH. The resultant reaction mixture is stirred at between RT and 70° C. for between 30 min and 2 h. The progress of the reaction is monitored by TLC and LCMS. The reaction mixture is cooled to RT, basified with aq. sodium bicarbonate solution and the mixture extracted with EtOAc. The organic layer is dried over sodium sulfate and concentrated to obtain the crude product, which is purified by silica gel (100-200 mesh) column chromatography/by HPLC to obtain the desired product.

EXAMPLES

Example 1

Preparation of Compound No. 1

Pyridine (0.02 mL, 0.248 mmol) was added to a solution of triflic anhydride (0.05 mL, 0.297 mmol) at 0° C. under nitrogen in DCM (2 mL). After 15 min, 4-(2-(2-propylpyridin-4-yl)thiazol-4-yl)aniline (70 mg, 0.236 mmol) was added dropwise at 0° C. in DCM (3 mL). The reaction was allowed to stir at RT for additional 30 min, monitored by TLC. After completion, the reaction mixture was diluted with water (10 mL) and the mixture extracted with EtOAc (2×20 mL). The combined organic layer was dried over anhydrous sodium sulfate and concentrated under reduced pressure to afford the crude product, which was purified by reverse phase preparative HPLC to obtain 17 mg of 1,1,1-trifluoro-N-(4-(2-(2-propylpyridin-4-yl)thiazol-4-yl)phenyl)methanesulfonamide (yellow solid). This was treated with 2N aq. HCl for salt formation. $^1$H NMR (400 MHz, CD$_3$OD) δ (ppm): 8.77 (d, J=6.2 Hz, 1H), 8.54 (s, 1H), 8.48 (d, J=6.2 Hz, 1H), 8.36 (s, 1H), 8.13 (d, J=8.2 Hz, 2H), 7.42 (d, J=8.4 Hz, 2H), 3.18-2.98 (m, 2H), 1.91 (p, J=7.7 Hz, 2H), 1.10 (t, J=7.4 Hz, 3H).

Example 2

Preparation of Compound No. 2

2-Propylpyridine-4-carbothioamide (50 mg, 0.118 mmol) and N-(3-(2,2-dibromoacetyl)phenyl)-1,1,1-trifluoromethanesulfonamide (16.9 mg, 0.09 mmol) were charged in acetic acid (1 mL) and the reaction mixture was stirred at 80° C. for 30 min. The reaction was monitored by LCMS and acetic acid was evaporated under vacuum. The crude reaction mixture was purified using reverse phase chromatography to get 2.4 mg of 1,1,1-trifluoro-N-(3-(2-(2-propylpyridin-4-yl)thiazol-4-yl)phenyl)methanesulfonamide. $^1$H NMR (CD$_3$OD) δ (ppm): 8.59 (d, J=5.3 Hz, 1H), 8.08 (s, 1H), 8.00 (s, 1H), 7.94 (m, 2H), 7.49 (m, 1H), 7.33 (d, J=8.1 Hz, 1H), 2.99-2.77 (m, 3H), 1.83 (m, 2H), 1.03 (t, J=7.3 Hz, 3H).

Example 4

Preparation of Compound No. 4

N-(4-(2-Bromoacetyl)-3-chlorophenyl)-1,1,1-trifluoromethanesulfonamide (50 mg, 0.132 mmol) and 2-propylpyridine-4-carbothioamide (23.8 mg, 0.132 mmol) were charged in EtOH (10 mL) and the reaction mixture was heated at 80° C. for 1 h. The reaction mixture was concentrated and purified through reverse phase HPLC. Yield: 17 mg TFA salt. $^1$H NMR (TFA salt, CD$_3$OD) δ (ppm): 8.72 (d, J=6.0 Hz, 1H), 8.38 (d, J=7.6 Hz, 1H), 8.31 (d, J=6.0 Hz, 2H), 8.07 (d, J=8.5 Hz, 1H), 7.49 (s, 1H), 3.04 (t, J=7.8 Hz, 3H), 1.88 (m, 2H), 1.07 (s, J=7.3 Hz, 3H).

Example 5

Preparation of Compound No. 5

2-tert-Butylpyridine-4-carbothioamide (100 mg, 0.26 mmol) and N-(4-(2-bromoacetyl)-3-chlorophenyl)-1,1,1-trifluoromethanesulfonamide (51 mg, 0.26 mmol) were charged in EtOH (5 mL) and the reaction mixture was stirred at 80° C. for 30 min. The reaction was monitored by LCMS, and then the EtOH was evaporated under vacuum. The reaction mixture was purified using reverse phase chromatography to get 43 mg of N-(4-(2-(2-tert-butylpyridin-4-yl)thiazol-4-yl)-3-chlorophenyl)-1,1,1-trifluoromethanesulfonamide. $^1$H NMR (HCl salt, CD$_3$OD) δ (ppm): 8.76 (d, J=6.1 Hz, 1H), 8.50 (s, 1H), 8.43 (m, 2H), 8.06 (d, J=8.5 Hz, 1H), 7.50 (d, J=2.2 Hz, 1H), 7.4 (m, 1H), 1.58 (s, 9H).

Example 6

Preparation of Compound No. 57

Synthesis of 1,1,1-trifluoro-N-(2-methoxy-4-{2-[2-(2-methylpropyl)pyridin-4-yl]-1,3-thiazol-4-yl}phenyl)methanesulfonamide Step-1: Synthesis of 3-methoxy-4-nitrobenzoyl chloride 3-Methoxy-4-nitrobenzoicacid (5) (3 g) and thionyl chloride (10 mL) were added dropwise at 0° C. The reaction mixture was allowed to come to RT and heated to reflux overnight. Thionyl chloride was evaporated and ice was added to the reaction mixture. The organic layer was extracted in ethyl acetate (2×50 mL). The combined organic layer was dried over anhydrous sodium sulfate and concentrated to get 6 g of 3-methoxy-4-nitrobenzoyl chloride.

Step-2: Synthesis of 1-(3-methoxy-4-nitrophenyl)ethanone

A suspension of anhydrous magnesium chloride (932 mg, 9.8 mmol) in toluene (13 mL) was treated with triethylamine (4.7 mL, 33.4 mmol) and diethylmalonate (2.7 mL, 16.74 mmol). The reaction mixture was stirred at RT for 1.5 h. Finally, 3-methoxy-4-nitrobenzoyl chloride (6) (3 g, 13.9 mmol) was added and the reaction mixture was stirred at RT for 18 h. Concentrated hydrochloric acid (10 mL) was added and the organic layer was separated. DMSO (11.5 mL) and water (0.5 mL) were added and the mixture was heated to reflux for 2 h. The reaction mixture was allowed to come to RT and partitioned between water and EtOAc. The organic phase was washed subsequently with saturated sodium bicarbonate solution and brine and concentrated to get 2.5 g of 1-(3-methoxy-4-nitrophenyl)ethanone.

Step-3: Synthesis of 1-(4-amino-3-methoxyphenyl)ethanone 1-(3-Methoxy-4-nitrophenyl)ethanone (2 g, 10.25 mmol) was charged in MeOH (30 mL). Iron powder (1.72 g, 30.76 mmol) was added and concentrated HCl (10 mL) was added dropwise with constant stirring. The reaction mixture was heated at 60° C. for 1 h. The iron powder was filtered off and MeOH was concentrated. Water (10 mL) was added and the organic layer was extracted in EtOAc (3×50 mL). The combined organic layer was dried over anhydrous sodium sulfate and concentrated to get 1.2 g of 1-(4-amino-3-methoxyphenyl)ethanone.

Step-4: Synthesis of N-(4-acetyl-2-methoxyphenyl)-1,1,1-trifluoromethanesulfonamide Triflic anhydride (0.6 ml 3.6 mmol) was charged in DCM (20 mL). The reaction mixture was cooled to 0° C. and pyridine was added dropwise with constant stirring. After 15 min, 1-(4-amino-3-methoxyphenyl)ethanone (500 mg, 3.03 mmol) was dissolved in DCM (10 mL) and added slowly to the reaction mixture. The reaction mixture was allowed to come to RT and the reaction mixture was stirred at RT for 1 h. The reaction was monitored by TLC. Water (15 mL) was added and the organic layer was extracted in DCM (3×100 mL). The combined organic layer was dried over anhydrous sodium sulfate and concentrated to get 700 mg of N-(4-acetyl-2-methoxyphenyl)-1,1,1-trifluoromethanesulfonamide.

Step-5: Synthesis of N-(4-(2-bromoacetyl)-2-methoxyphenyl)-1,1,1-trifluoromethanesulfonamide N-(4-Acetyl-2-methoxyphenyl)-1,1,1-trifluoromethanesulfonamide (700 mg, 2.35 mmol) was charged in chloroform (50 mL) and the reaction mixture was cooled to 0° C. Liquid bromine (0.125 mL, 2.35 mmol) was added dropwise and the reaction mixture was stirred at RT for 18 h. A saturated solution of sodium thiosulfate (20 mL) was added and the chloroform layer was isolated and concentrated under reduced pressure to get 525 mg of N-(4-(2-bromoacetyl)-2-methoxyphenyl)-1,1,1-trifluoromethanesulfonamide.

Step-6: Synthesis of 1,1,1-trifluoro-N-(4-(2-(2-isobutylpyridin-4-yl)thiazol-4-yl)-2-methoxyphenyl) methanesulfonamide N-(4-(2-Bromoacetyl)-3-chlorophenyl)methanesulfonamide (50 mg, 0.133 mmol) and 2-isobutylpyridine-4-carbothioamide compound (20.6 mg, 0.10 mmol) were charged in ethanol (5 mL) and the reaction mixture was heated at 80° C. for 1 h. The reaction mixture was concentrated under reduced pressure and purified through reverse phase HPLC to get 16 mg of 1,1,1-trifluoro-N-(2-methoxy-4-{2-[2-(2-methylpropyl)pyridin-4-yl]-1,3-thiazol-4-yl}phenyl)methanesulfonamide. $^1$H NMR (400 MHz, Methanol-d4): δ (ppm): 8.56 (d, J=5.2 Hz, 1H), 7.96-7.70 (m, 3H), 7.58 (d, J=1.9 Hz, 1H), 7.48 (dd, J=8.3, 1.9 Hz, 1H), 7.33 (dd, J=8.3, 2.1 Hz, 2H), 3.92 (s, 3H), 2.76 (d, J=7.3 Hz, 2H), 2.12 (td, J=14.0, 7.2 Hz, 1H), 0.98 (d, J=6.6 Hz, 6H). LCMS: 473.2 (M+1).

Example 7

Preparation of Compound No. 58

Steps 1-5: Synthesis of N-(4-(2-bromoacetyl)-2-methoxyphenyl)-1,1,1-trifluoromethanesulfonamide See Example 6.

Step-6: Synthesis of N-(2-methoxy-4-(2-(2-propylpyridin-4-yl)thiazol-4-yl)phenyl)methanesulfonamide N-(4-(2-Bromoacetyl)-3-chlorophenyl)methanesulfonamide (50 mg, 0.133 mmol) and 2-propylpyridine-4-carbothioamide (18 mg, 0.1 mmol) were charged in ethanol (10 mL) and the reaction mixture was heated at 80° C. for 1 h. The reaction mixture was concentrated under reduced pressure and purified through reverse phase HPLC to get 17 mg of N-(2-methoxy-4-(2-(2-propylpyridin-4-yl)thiazol-4 yl)phenyl)methanesulfonamide. $^1$H NMR (400 MHz, Methanol-d4): δ (ppm): 8.68 (d, J=5.8 Hz, 1H), 8.28 (d, J=5.9 Hz, 1H), 8.22 (d, J=5.6 Hz, 1H), 7.77 (d, J=1.8 Hz, 1H), 7.68 (dd, J=8.4, 1.8 Hz, 1H), 7.47 (d, J=8.2 Hz, 2H), 4.02 (s, 3H), 3.01 (m, 2H), 1.87 (m, 2H), 1.07 (t, J=7.4 Hz, 3H). LCMS: (M+1) 458.3.

Example 8

Preparation of Compound No. 59

Steps 1-5: Synthesis of N-(4-(2-bromoacetyl)-2-methoxyphenyl)-1,1,1-trifluoromethanesulfonamide See Example 6.

Step-6: Synthesis of N-(4-(2-(2-tert-butylpyridin-4-yl)thiazol-4-yl)-2-methoxyphenyl)-1,1,1-trifluoromethanesulfonamide N-(4-(2-Bromoacetyl)-3-chlorophenyl)methanesulfonamide (50 mg, 0.133 mmol) and 2-tert-butylpyridine-4-carbothioamide (20.6 mg, 0.10 mmol) were charged in ethanol (5 mL) and the reaction mixture was heated at 80° C. for 1 h. The reaction mixture was concentrated under reduced pressure and purified through reverse phase HPLC to get 15 mg of N-(4-(2-(2-tert-butylpyridin-4-yl)thiazol-4-yl)-2-methoxyphenyl)-1,1,1-trifluoromethanesulfonamide. $^1$H NMR (400 MHz, Methanol-d4): δ (ppm): 8.61 (d, J=5.1 Hz, 1H), 8.03 (d, J=3.3 Hz, 2H), 7.82 (dd, J=5.2, 1.6 Hz, 1H), 7.70 (d, J=1.8 Hz, 1H), 7.60 (dd, J=8.3, 1.9 Hz, 1H), 7.41 (d, J=8.2 Hz, 1H), 3.98 (s, 3H), 1.45 (s, 9H). LCMS: (M+1) 472.5.

Example 9

Preparation of Compound No. 60

N-(4-(2-Bromoacetyl)-3-chlorophenyl)-1,1,1,trifluoromethane sulfonamide (100 mg, 0.263 mol) and 2-benzylpyridine-4-carbothioamide (54.1 mg, 0.237 mol) were charged in ethanol (5 mL) and the reaction mixture was heated at 80° C. for 1 h. A yellow solid reaction mixture was obtained, which was filtered and the residue was washed with diethyl ether (15 mL) to get N-{4-[2-(2-benzylpyridin-4-yl)-1,3-thiazol-4-yl]-3-chlorophenyl}-1,1,1-trifluoromethanesulfonamide (33 mg) as a brown solid. $^1$H NMR (400 MHz, Methanol-d4) δ (ppm): 8.85-8.68 (d, J=6.2 Hz, 1H), 8.55-8.39 (m, 2H), 8.03 (d, J=8.5 Hz, 1H), 7.49 (d, J=2.3 Hz, 1H), 7.48-7.31 (m, 7H), 4.51 (s, 2H). LCMS (M+1): 510.1.

Example 10

Preparation of Compound No. 61

Step-1: Synthesis of
2-aminopyridine-4-carbothioamide

To a solution of 2-aminoisonicotinamide (100 mg, 0.0729 mol, 1 eq.) in pyridine (3 mL), phosphorus pentasulfide (83 mg, 0.0365 mol, 0.5 eq.) was added. The reaction was heated at 100° C. for 3 h. The reaction was monitored by LCMS. After completion, pyridine was concentrated under reduced pressure and residue was dissolved in water (5 mL) and the mixture extracted with EtOAc (3×15 mL). The EtOAc extracts were combined, dried over anhydrous sodium sulfate and concentrated under reduced pressure to get 33 mg of 2-aminopyridine-4-carbothioamide as a yellow solid.

Step-2: Synthesis of 2-chloro-4-nitrobenzoyl chloride

To a two neck RBF (1 liter) placed in ice bath, 2-chloro-4-nitrobenzoic acid (50 g, 0.248 mol, 1 eq.) was charged. Thionyl chloride (110 mL, 1.51 mol, 6.1 eq.) was added dropwise at 0° C. The reaction mixture was allowed to come to RT and then heated to reflux. The reflux was continued overnight. Thionyl chloride was evaporated and ice (approx. 150 g) was added into the reaction mixture. The aqueous reaction mass was extracted with DCM (2×200 mL). The DCM extracts were combined dried over anhydrous sodium sulfate and concentrated under vacuum to get 50 g (91.7%) of 2-chloro-4-nitrobenzoyl chloride as a light yellow liquid.

Step-3: Synthesis of
1-(2-chloro-4-nitrophenyl)ethanone

A suspension of anhydrous magnesium chloride (47 g, 0.214 mol, 0.7 eq.) in toluene (300 mL) was treated with triethylamine (75.04 mL, 0.535 mol, 2.5 eq.) and diethylmalonate (41.09 g, 0.257 mol, 1.2 eq.). The reaction mixture was stirred at RT for 1.5 h. To this was added 2-chloro-4-nitrobenzoyl chloride (4) (47 g, 0.214 mol, 1 eq.) was added dropwise (an exothermic reaction up to 50° C. was observed during addition). Toluene (50 mL) was used for complete transfer of 2-chloro-4-nitrobenzoyl chloride to the reaction mixture. The reaction mixture was stirred at RT for 18 h. The reaction was monitored by TLC and NMR. After complete consumption of starting material, concentrated hydrochloric acid (35% solution) (300 mL) was added and the upper toluene layer was separated. Toluene was evaporated under reduced pressure below 50° C. To the residue after concentration, DMSO (200 mL) and water (10 mL) were added and the mixture was heated at 160° C. for 12 h. The reaction was monitored by TLC and NMR. The reaction mixture was allowed to come to RT and water (40 mL) was added to the reaction mixture. The reaction mixture was extracted with EtOAc (3×200 mL). The EtOAc extracts were combined was washed brine solution (3×300 mL) and dried over anhydrous sodium sulfate. The EtOAc layer was concentrated to get 43 g (100%) of 1-(2-chloro-4-nitrophenyl)ethanone as a yellow liquid which solidified upon refrigeration.

Step-4: Synthesis of
1-(4-amino-2-chlorophenyl)ethanone 1-(2-Chloro-4-nitrophenyl)ethanone (126 g, 0.63 mole 1 eq.) was dissolved in MeOH (600 mL). Iron powder (105.8 g, 1.89 mol, 3 eq.) was added to the solution. Concentrated HCl (130 mL, 1.89 mol, 3 eq.) was added dropwise with constant stirring. The reaction mixture was then heated at 70° C. for 12 h. The reaction was monitored by TLC and NMR. The reaction mixture showed presence of starting material. The same quantity of iron powder and concentrated HCl were added again at 70° C. and the heating was continued at 70° C. for 4 h. The reaction mixture was again monitored by TLC and NMR. After completion of reaction, Iron powder was filtered through a celite bed and the MeOH filtrate was concentrated. Water (100 mL) was added and the reaction mixture was extracted in EtOAc (5×300 mL). The EtOAc extracts were combined, dried over anhydrous sodium sulfate and concentrated to get 100 g of crude product. 71 g of the crude product was purified through silica column (#100-200) using 0-20% EtOAc: hexane as eluant to get 38.6 g (52.5%) of 1-(4-amino-3-methoxyphenyl)ethanone (6) as pink solid. $^1$H NMR (400 MHz, Chloroform-d): δ (ppm): 7.62 (d, J=8.5 Hz, 1H), 6.66 (d, J=2.3 Hz, 1H), 6.54 (dd, J=8.5, 2.3 Hz, 1H), 4.07 (s, 2H), 2.61 (s, 3H).

Step-5: Synthesis of N-(4-acetyl-3-chlorophenyl)-1,1,1-trifluoromethanesulfonamide A solution of triflic anhydride (75.1 g, 0.266 mol, 1.5 eq.) in DCM (600 mL) was cooled to 0° C. Pyridine (21.4 mL, 0.266 mol, 1.5 eq.) was added dropwise with constant stirring over 30 min. The reaction mixture was stirred at same temperature for 1 h. A solution of 1-(4-amino-2-chlorophenyl)ethanone (30 g, 0.177 mol, 1 eq.) in DCM (400 mL) was added dropwise maintaining the temperature 0° C. with constant stirring over a period of 45 min. The reaction mixture was then allowed to come to RT and stirred for 1 h at RT. The reaction was monitored by TLC and NMR. Upon completion, ice water (500 mL) was added and the DCM layer was separated. The aqueous layer was again extracted with DCM (2×100 mL). The DCM extracts were combined washed with ice water (2×500 mL). The DCM layer was dried over anhydrous sodium sulfate and concentrated under reduced pressure below 40° C. to obtain the crude product. Diethyl ether (200 mL) and pentane (600 mL) were added into the reaction mixture and stirred for 30 min. The reaction mixture was filtered and the mother liquor was concentrated and triturated in pentane to get 28 g (52.8%) of N-(4-acetyl-3-chlorophenyl)-1,1,1-trifluoromethanesulfonamide as a light pink solid.

Step-6: Synthesis of N-(4-(2-bromoacetyl)-3-chlorophenyl)-1,1,1-trifluoromethanesulfonamide A solution of N-(4-acetyl-3-chlorophenyl)-1,1,1-trifluoromethanesulfonamide (21 g, 0.07 mol, 1 eq.) in chloroform (600 mL) was cooled to 0° C. Liquid bromine (2.9 mL, 0.004 mol, 0.8 eq.) dissolved in chloroform (400 mL) was added dropwise over a period of 40 min, maintaining the temperature between 0-10° C. The reaction mixture was allowed to come to RT and was stirred at RT for 18 h. The reaction was monitored by TLC and NMR, which indicated the presence of starting material and desired compound along with some amount of N-(3-chloro-4-(2,2-dibromoacetyl)phenyl)-1,1,1-trifluoromethanesulfonamide (dibromo impurity). A saturated solution of sodium thiosulfate (200 mL) was added and the chloroform layer was separated. The aqueous layer was extracted with chloroform (2×100 mL). The main chloroform layer and the chloroform extracts were combined, dried over anhydrous sodium sulfate and concentrated under reduced pressure. A clear liquid was obtained as a residue. To this were added diethylether (50 mL) and pentane (250 mL) and the mixture stirred for 10 min. The reaction mixture was filtered off and mother liquor was concentrated. The crude product obtained was triturated with pentane (~50 mL) to obtain a white solid. The white solid obtained was filtered off and dried under vacuum to get 20 g of N-(4-(2-bromoacetyl)-3-chlorophenyl)-1,1,1-trifluoromethanesulfonamide with contained approximately 35% of starting material i.e. N-(4-acetyl-3-chlorophenyl)-1,1,1-trifluoromethanesulfonamide by NMR. The mixture of both was directly used in the next step.

Step-7: Synthesis of N-(4-(2-(2-aminopyridin-4-yl)thiazol-5-yl)-3-chlorophenyl)-1,1,1-trifluoromethanesulfonamide N-(4-(2-Bromoacetyl)-3-chlorophenyl)-1,1,1-trifluoromethanesulfonamide (50 mg, 0.132 mmol, 1 eq.) and 2-aminopyridine-4-carbothioamide (32.8 mg, 0.132 mmol, 1 eq.) were charged in ethanol (5 mL) and the reaction mixture was heated at 80° C. for 12 h. The reaction mixture was concentrated and purified by reverse phase chromatography to get 6.8 mg of N-(4-(2-(2-aminopyridin-4-yl)thiazol-5-yl)-3-chlorophenyl)-1,1,1-trifluoromethanesulfonamide. $^1$H NMR (400 MHz, Methanol-d4): δ (ppm): 8.25 (s, 1H), 8.01-7.89 (m, 2H), 7.55 (d, J=1.6 Hz, 1H), 7.46-7.40 (m, 1H), 7.33 (dd, J=8.5, 2.2 Hz, 1H). LCMS: (M+1) 435.1.

Example 11

Preparation of Compound No. 62

Steps 1-7: Synthesis of N-{3-chloro-4-[2-(2-methanesulfonamidopyridin-4-yl)-1,3-thiazol-4-yl]phenyl}-1,1,1-trifluoromethanesulfonamide See Example 10.

Step-8: Synthesis of N-(3-chloro-4-(2-(2-(methylsulfonamido)pyridin-4-yl)thiazol-5-yl)phenyl)-1,1,1-trifluoromethanesulfonamide N-(4-(2-(2-Aminopyridin-4-yl)thiazol-5-yl)-3-chlorophenyl)-1,1,1-trifluoro methane sulfonamide (50 mg, 0.115 mmol, 1 eq.) was charged in pyridine (3 mL). The reaction mixture was cooled to 0° C. and methane sulfonyl chloride (0.01 mL, 0.115 mol, 1 eq.) was added dropwise with constant stirring. The reaction mixture was allowed to come to RT and the reaction mixture was stirred at RT for 1 h. Pyridine was evaporated and water was added and the mixture extracted in EtOAc (3×100 mL). The combined organic layer was concentrated and purified using reverse phase chromatography to get 1.3 mg of N-(3-chloro-4-(2-(2-(methylsulfonamido)pyridin-4-yl)thiazol-5-yl)phenyl)-1,1,1-trifluoromethanesulfonamide. $^1$H NMR (400 MHz, Methanol-d4): δ (ppm): 8.32 (d, J=5.6 Hz, 1H), 8.17 (s, 1H), 8.02 (d, J=8.5 Hz, 1H), 7.66 (s, 1H), 7.59 (dd, J=5.6, 1.6 Hz, 1H), 7.47 (d, J=2.3 Hz, 1H), 7.35 (dd, J=8.6, 2.3 Hz, 1H), 3.2 (s, 1H). LCMS: 513 (M+1).

Example 12

Preparation of Compound No. 63

Steps 1-6: Synthesis of N-(2-methoxy-4-(2-(2-propylpyridin-4-yl)thiazol-4-yl)phenyl)methanesulfonamide See Example 7.

Step-7: Synthesis of 1,1,1-trifluoro-N-(2-hydroxy-4-(2-(2-propylpyridin-4-yl)thiazol-4-yl)phenyl)methanesulfonamide 1,1,1-Trifluoro-N-(2-methoxy-4-(2-(2-propylpyridin-4-yl)thiazol-4-yl)phenyl)methanesulfonamide (17 mg, 0.037 mmol, 1 eq.) charged in DCM (5 mL) and the reaction mixture was cooled at 0° C. A 1M solution of boron tribromide (0.12 mL, 0.11 mmol) was added dropwise. The reaction mixture was allowed to come to RT and stirred at RT for 12 h. The reaction was monitored by LCMS. A saturated sodium bicarbonate was added and the mixture extracted in EtOAc (3×25 mL). The combined organic layer was dried over anhydrous sodium sulfate and concentrated under reduced pressure and the crude reaction mixture was purified using reverse phase HPLC to get (1.5 mg) of 1,1,1-trifluoro-N-(2-hydroxy-4-(2-(2-propylpyridin-4-yl)thiazol-4-yl)phenyl)methanesulfonamide as the TFA salt. $^1$H NMR (400 MHz, Methanol-d4): δ (ppm): 8.63 (d, J=5.6 Hz, 1H), 8.13-8.00 (m, 2H), 7.63 (d, J=1.9 Hz, 1H), 7.53-7.38 (m, 2H), 2.94 (t, J=7.7 Hz, 2H), 1.84 (p, J=7.5 Hz, 2H), 1.05 (t, J=7.4 Hz, 3H) LCMS (M+1): 444.4.

Example 13

Preparation of Compound No. 64

N-(4-(2-Bromoacetyl)-3-chlorophenyl) 1,1,1-trifluoro methane sulfonamide (100 mg, 0.263 mol) and 2-(3,3,3-trifluoropropyl)pyridine-4-carbothioamide (55.5 mg, 0.237 mol) were charged in ethanol (5 mL) and the reaction mixture was heated at 80° C. for 1 h. The resultant reaction mixture was concentrated under reduced pressure and purified by reverse phase HPLC to afford N-(3-chloro-4-{2-[2-(3,3,3-trifluoropropyl)pyridin-4-yl]-1,3-thiazol-4-yl}phenyl)-1,1,1-trifluoromethanesulfonamide (27 mg) as a yellow solid. $^1$H NMR (400 MHz, Methanol-d4) δ (ppm): 8.84 (d, J=6.2 Hz, 1H), 8.63 (d, J=2.0 Hz, 1H), 8.52 (d, J=6.1 Hz, 1H), 8.42 (s, 1H), 8.09 (d, J=8.5 Hz, 1H), 7.50 (d, J=2.3 Hz, 1H), 7.40 (d, J=8.5 Hz, 1H), 3.42 (m 2H), 2.87 (m, 2H). LCMS (M+1): 516.1.

Example 14

Preparation of Compound No. 65

Steps 1-5: Synthesis of N-(4-(2-bromoacetyl)-2-methoxyphenyl)-1,1,1-trifluoromethanesulfonamide See Example 6

Step-6: Synthesis of 1,1,1-trifluoro-N-(2-methoxy-4-(2-(2-neopentylpyridin-4-yl)thiazol-4-yl)phenyl)methanesulfonamide N-(4-(2-Bromoacetyl)-3-chlorophenyl)methanesulfonamide (50 mg, 0.133 mmol) and 2-neopentylpyridine-4-carbothioamide (50 mg, 0.10 mmol) was charged in ethanol (5 mL) and the reaction mixture was heated at 80° C. for 1 h. The reaction mixture was concentrated under reduced pressure and purified through reverse phase HPLC to get 14 mg of 1,1,1-trifluoro-N-(2-methoxy-4-(2-(2-neopentylpyridin-4-yl)thiazol-4-yl)phenyl)methanesulfonamide. $^1$H NMR (400 MHz, Methanol-d4): δ (ppm): 8.71 (d, J=5.8 Hz, 1H), 8.33-8.14 (m, 2H), 7.76 (d, J=1.9 Hz, 1H), 7.68 (dd, J=8.4, 1.9 Hz, 1H), 7.47 (d, J=8.3 Hz, 1H), 4.01 (s, 3H), 2.95 (s, 2H), 1.06 (s, 9H). LCMS: 486 (M+1).

Example 15

Preparation of Compound No. 66

A solution of triflic anhydride (0.03 ml, 0.17 mmol, 1.5 eq.) in DCM (8 mL) was cooled to 0° C. Pyridine (0.01 mL, 0.17 mmol, 1.5 eq.) was added dropwise with constant stirring over 30 min. A solution of N-(4-(2-(2-aminopyridin-4-yl)thiazol-4-yl)-3-chlorophenyl)-1,1,1-trifluoromethanesulfonamide (50 mg, 0.115 mmol, 1 eq.) in DCM (2 mL) was added dropwise maintaining the temperature at 0° C. with constant stirring over a period of 5 min. The reaction mixture was then allowed to come to RT and stirred for 1 h at RT. The reaction was monitored by LCMS and NMR. Upon completion, ice water (10 mL) was added and the DCM layer was separated. The aqueous layer was again extracted with DCM (2×20 mL). The DCM layer was dried over anhydrous sodium sulfate and concentrated under reduced pressure and purified using reverse phase chromatography to get 9.26 mg of N-{3-chloro-4-[2-(2-trifluoromethanesulfonamidopyridin-4-yl)-1,3-thiazol-4-yl]phenyl}-1,1,1-trifluoromethanesulfonamide. $^1$H NMR (400 MHz, Methanol-d4): δ (ppm): 8.40-8.22 (m, 2H), 8.06 (dd, J=7.6, 3.6 Hz, 2H), 7.72 (dd, J=6.6, 1.7 Hz, 1H), 7.49 (d, J=2.3 Hz, 1H), 7.37 (dd, J=8.6, 2.3 Hz, 1H). LCMS (M+1): 566.8.

Example 16

Preparation of Compound No. 67

N-[4-(2-Bromothiazol-4-yl)-3-chloro-phenyl]-1,1,1-trifluoro-methanesulfonamide (300 mg, 0.71 mmol, 1 eq.), [4-(piperidine-1-carbonyl)phenyl]boronic acid (233 mg, 1.4 eq.) and sodium carbonate (189 mg, 2.5 eq. in 1 mL water) were charged in 5 mL of DMF in a 25 mL glass bottle and aerated with nitrogen gas for 7 min. After adding Pd(PPh$_3$)$_4$ (82.5 mg, 0.1 mmol) the mixture was further purged for 3 min and was heated to 100° C. overnight. The reaction was monitored by LCMS. The reaction mixture was allowed to cool to RT; water (10 mL) was added and the mixture extracted with EtOAc (3×50 mL). The combined organic layer was washed with water (4×50 mL), dried over anhydrous sodium sulfate and concentrated under reduced pressure to obtain a crude product, which was purified by reverse phase HPLC to afford N-(3-chloro-4-{2-[4-(piperidine-1-carbonyl)phenyl]-1,3-thiazol-4-yl}phenyl)-1,1,1-trifluoromethanesulfonamide (207 mg) as a white solid as the free base. $^1$H NMR (400 MHz, Chloroform-d) δ (ppm): 7.98 (d, J=8.5 Hz, 1H), 7.89 (d, J=7.9 Hz, 2H), 7.82 (s, 1H), 7.36 (d, J=7.9 Hz, 2H), 7.18 (d, J=2.2 Hz, 1H), 6.98 (dd, J=8.5, 2.3 Hz, 1H), 3.78 (s, 2H), 3.37 (s, 2H), 1.72 (s, 4H), 1.55 (s, 2H). LCMS (M+1): 530.1.

Example 17

Preparation of Compound No. 68

N-(4-(2-Bromothiazol-4-yl)-3-chlorophenyl)-1,1,1-trifluoromethane sulfonamide (200 mg, 0.4761 mmol) and 1-isopentyl-5-(4,4,5,5-tetramethyl-1,3,2-dioxaborolan-2-yl)pyrazole (150.9 mg, 0.5714 mmol), sodium carbonate (100 mg, 0.952 mmol), dimethyl formamide (5 mL), water (0.5 mL) were charged in a 2 neck round bottom flask and aerated with nitrogen gas for 5 min. After adding Pd(PPh$_3$)$_4$ (55 mg, 0.0476 mmol), the mixture was heated to 100° C. for 18 h. The reaction was monitored by LCMS. The reaction mixture was allowed to cool to RT; water (10 mL) was added and the mixture extracted with EtOAc (3×25 mL). The combined organic layer was washed with water (30 mL), dried over anhydrous sodium sulfate and concentrated under reduced pressure to obtain a crude product, which was purified by reverse phase HPLC to afford N-(3-chloro-4-{2-[1-(3-methylbutyl)-1H-pyrazol-5-yl]-1,3-thiazol-4-yl}phenyl)-1,1,1-trifluoromethanesulfonamide (135 mg) as a white solid. $^1$H NMR (400 MHz, Methanol-d4) δ (ppm): 8.05 (s, 1H), 7.96 (d, J=8.6 Hz, 1H), 7.55 (d, J=2.1 Hz, 1H), 7.47 (d, J=2.2 Hz, 1H), 7.33 (d, J=8.5 Hz, 1H), 6.82 (d, J=2.1 Hz, 1H), 4.75 (m, 2H), 1.77 (m, J=9.4 Hz, 2H), 1.60 (m, 1H), 0.91 (d, J=6.6 Hz, 6H). LCMS (M+1): 479.1.

Example 18

Preparation of Compound No. 69

Step-1: Synthesis of N-[3-chloro-4-(4,4,5,5-tetramethyl-1,3,2-dioxaborolan-2-yl)phenyl]methanesulfonamide 3-Chloro-4-(4,4,5,5-tetramethyl-1,3,2-dioxaborolan-2-yl)aniline (506 mg, 1 mmol, 1 eq.) was suspended in DCM (18 mL) then TEA (808 mg, 4 eq.) added and stirred for 5 min at RT. The mixture was maintained at ice-bath condition and mesyl chloride (458 mg, 2 eq.) was added dropwise and stirred for 2 h at the same temperature. The reaction was monitored by 1H-NMR. After completion of the reaction, the solvent was evaporated to get the desired product as a solid which was used for next step without any further purification.

Step-2: Synthesis of 4-(4-bromo-2-thienyl)-2-tert-butyl-pyridine 2,4-Dibromothiophene (150 mg, 0.62 mmol), 2-tert-butyl-4-(4,4,5,5-tetramethyl-1,3,2-dioxaborolan-2-yl)pyridine (242 mg, 1.5 equiv) and sodium carbonate (164 mg, 1.54 mmol, 2.5 eq. in 1.0 mL water) in dimethyl formamide (5 mL) were charged in a 25 mL glass bottle and aerated with nitrogen gas for 8 min. After adding Pd(PPh$_3$)$_4$ (35 mg, 0.05 mmol) and Xantphos (35.8 mg, 0.1 eq.), the mixture was further purged for 3 min, and was heated to 100° C. overnight. The reaction was monitored by LCMS. The reaction mixture was allowed to cool to RT; water (10 mL) was added and the mixture extracted with EtOAc (3×25 mL). The combined organic layer was washed with water (4×30 mL), dried over anhydrous sodium sulfate and concentrated under reduced pressure to obtain crude 4-(4-bromo-2-thienyl)-2-tert-butyl-pyridine, which was used as such for the next step of synthesis without any further purification.

Step-3: Synthesis of N-[4-[5-(2-tert-butyl-4-pyridyl)-3-thienyl]-3-chloro-phenyl]methanesulfonamide 4-(4-Bromo-2-thienyl)-2-tert-butyl-pyridine (170 mg, 0.576 mmol, 1 eq.), N-[3-chloro-4-(4,4,5,5-tetramethyl-1,3,2-dioxaborolan-2-yl)phenyl]methanesulfonamide (286 mg, 1.5 eq.) and sodium carbonate (152 mg, 2.5 equiv) were charged in DMF (5 mL) in a 25 mL glass bottle and aerated with nitrogen gas for 7 min. After adding $Pd(PPh_3)_4$ (66 mg, 0.1 mmol) the mixture was further purged for 3 min and was heated to 100° C. overnight. The reaction was monitored by LCMS. The reaction mixture was allowed to come to RT, water (10 mL) was added and the mixture extracted with EtOAc (3×25 mL). The combined organic layer was washed with water (4×30 mL), dried over anhydrous sodium sulfate and concentrated under reduced pressure to obtain a crude product, which was purified by reverse phase HPLC to afford N-{4-[5-(2-tert-butylpyridin-4-yl)thiophen-3-yl]-3-chlorophenyl}methanesulfonamide (64 mg) as a light yellow solid as the formate salt. $^1$H NMR (400 MHz, DMSO-d6) δ (ppm): 8.53 (d, J=5.2 Hz, 1H), 7.99 (s, 1H), 7.82 (s, 1H), 7.65 (s, 1H), 7.57 (d, J=8.4 Hz, 1H), 7.47 (d, J=5.2 Hz, 1H), 7.36 (d, J=2.2 Hz, 1H), 7.24 (dd, J=8.2, 2.1 Hz, 1H), 3.07 (s, 3H), 1.36 (s, 9H). LCMS (M+1): 421.1.

Example 19

Preparation of Compound No. 70

N-(4-(2-Bromoacetyl)-3-chlorophenyl) 1,1,1-trifluoro methane sulfonamide (200 mg, 0.527 mol) and 2-(cyclohexylmethyl)pyridine-4-carbothioamide (111.2 mg, 0.475 mol) were charged in ethanol (10 mL) and the reaction mixture was heated at 80° C. for 1 h. The resultant reaction mixture was concentrated under reduced pressure and purified by reverse phase HPLC to afford N-(3-chloro-4-{2-[2-(cyclohexylmethyl)pyridin-4-yl]-1,3-thiazol-4-yl}phenyl)-1,1,1-trifluoromethanesulfonamide (45 mg) as a white solid. $^1$H NMR (400 MHz, Methanol-d4) δ (ppm): 8.75 (d, J=6.2 Hz, 1H), 8.46-8.36 (m, 3H), 8.07 (d, j=8.5 Hz, 1H), 7.49 (d, J=2.3 Hz, 1H), 7.40 (d, J=8.5 Hz, 1H), 2.98 (d, J=7.3 Hz, 2H), 1.88 (m, J=10.9 Hz, 1H), 1.76 (m 5H), 1.35 (m, 5H). LCMS (M+1): 516.1.

Example 20

Preparation of Compound No. 71

N-(4-(2-Bromothiazol-4-yl)-3-chlorophenyl)-1,1,1-trifluoromethane sulfonamide (100 mg, 0.2380 mmol) and naphthalene-1-yl-boronic acid (61.3 mg, 0.3571 mmol), cesium carbonate (155 mg, 0.476 mmol), dimethyl formamide (5 mL), water (0.5 mL) were charged in a 2 neck round bottom flask and aerated with nitrogen gas for 5 min. After adding $Pd(PPh_3)_4$ (27.4 mg, 0.0238 mmol), the mixture was heated to 100° C. for 18 h. The reaction was monitored by LCMS. The reaction mixture was allowed to cool to RT, water (10 mL) was added and the mixture extracted with EtOAc (3×25 mL). The combined organic layer was washed with water (30 mL), dried over anhydrous sodium sulfate and concentrated under reduced pressure to obtain a crude product, which was purified by reverse phase HPLC to afford N-{3-chloro-4-[2-(naphthalen-1-yl)-1,3-thiazol-4-yl]phenyl}-1,1,1-trifluoromethanesulfonamide (40 mg) as a yellow solid. $^1$H NMR (400 MHz, Methanol-d4) δ (ppm): 8.69-8.60 (d, J=6.2 Hz, 1H), 8.18 (s, 1H), 8.10 (d, J=8.1 Hz, 1H), 8.04-7.96 (m, 2H), 7.92 (d, J=7.2 Hz, 1H), 7.6 (m, 3H), 7.53 (d, J=2.2 Hz, 1H), 7.39 (d, J=8.4 Hz, 1H). LCMS (M+1): 469.0.

Example 21

Preparation of Compound No. 72

N-(4-(2-Bromothiazol-4-yl)-3-chlorophenyl)-1,1,1-trifluoromethane sulfonamide (100 mg, 0.2380 mmol) and 1H-indole-6-yl-boronic acid (57.4 mg, 0.357 mmol), potassium carbonate (65 mg, 0.476 mmol), dimethyl formamide (5 mL), water (0.5 mL) were charged in a 2 neck round bottom flask and aerated with nitrogen gas for 5 min. After adding $Pd(PPh_3)_4$ (27.4 mg, 0.0238 mmol) the reaction mixture was heated to 100° C. for 18 h. The reaction was monitored by LCMS. The reaction mixture was cooled to RT, water (10 mL) was added and the mixture extracted with EtOAc (3×25 mL). The combined organic layer was washed with water (30 mL), dried over sodium sulfate and concentrated under reduced pressure to obtain the crude product, which was purified by reverse phase HPLC to afford N-{3-chloro-4-[2-(1H-indol-6-yl)-1,3-thiazol-4-yl]phenyl}-1,1,1-trifluoromethanesulfonamide (43 mg) as a yellow solid. $^1$H NMR (400 MHz, Methanol-d4) δ (ppm): 8.10 (d, J=6.2 Hz, 1H), 8.04 (d, J=1.9 Hz, 1H), 7.88 (s, 1H), 7.65 (m, 2H), 7.48 (d, J=2.2 Hz, 1H), 7.39 (m, 2H), 6.52 (d, J=7.2 Hz, 1H). LCMS (M+1): 457.9.

Example 22

Preparation of Compound No. 73

N-(4-(2-Bromothiazol-4-yl)-3-chlorophenyl)-1,1,1-trifluoromethane sulfonamide (100 mg, 0.2380 mmol) and 3-(benzyloxy)-4-(trifluoromethyl)phenylboronic acid (105.7 mg, 0.357 mmol), potassium carbonate (65 mg, 0.476 mmol), dimethyl formamide (5 mL), water (0.5 mL) were charged in a 2 neck round bottom flask and aerated with nitrogen gas for 5 min. After adding $Pd(PPh_3)_4$ (27.4 mg, 0.0238 mmol), the mixture was heated to 100° C. for 18 h. The reaction was monitored by LCMS. The reaction mixture was cooled to RT, water (10 mL) was added and the mixture extracted with EtOAc (3×25 mL). The combined organic layer was washed with water (30 mL), dried over sodium sulfate and concentrated under reduced pressure to obtain the crude product, which was purified by reverse phase HPLC to afford N-(4-{2-[3-(benzyloxy)-4-(trifluoromethyl)phenyl]-1,3-thiazol-4-yl}-3-chlorophenyl)-1,1,1-trifluoromethanesulfonamide (10 mg) as a yellow solid. $^1$H NMR (400 MHz, Methanol-d4) δ (ppm): 8.06-7.94 (m, 2H), 7.91-7.80 (d, J=1.9 Hz, 1H), 7.71-7.67 (d, J=1.9 Hz, 1H), 7.65-7.60 (m, 1H), 7.48-7.40 (m, 3H), 7.38-7.27 (m, 4H), 3.33 (d, J=15.4 Hz, 2H). LCMS (M+1): 593.2.

Example 23

Preparation of Compound No. 74

N-(4-(2-Bromothiazol-4-yl)-3-chlorophenyl)-1,1,1-trifluoromethane sulfonamide (100 mg, 0.2380 mmol) and biphenyl-2-ylboronic acid (70 mg, 0.357 mmol), potassium carbonate (65 mg, 0.476 mmol), dimethyl formamide (5 mL), water (0.5 mL) were charged in a 2 neck round bottom flask and aerated with nitrogen gas for 5 min. After adding Pd(PPh$_3$)$_4$ (27.4 mg, 0.238 mol), the mixture was heated to 100° C. for 18 h. The reaction was monitored by LCMS. The reaction mixture was cooled to RT, water (10 mL) was added and the mixture extracted with EtOAc (3×25 mL). The combined organic layer was washed with water (30 mL), dried over sodium sulfate and concentrated under reduced pressure to obtain the crude product, which was purified by reverse phase HPLC to afford N-{3-chloro-4-[2-(2-phenylphenyl)-1,3-thiazol-4-yl]phenyl}-1,1,1-trifluoromethanesulfonamide (18 mg) as a yellow solid. $^1$H NMR (400 MHz, Methanol-d4) δ (ppm): 7.92 (d, J=7.8 Hz, 2H), 7.72-7.59 (m, 2H), 7.57-7.47 (m, 2H), 7.43 (d, J=2.2 Hz 1H), 7.43-7.35 (m, 3H), 7.28 (m, 3H). LCMS (M+1): 495.

Example 24

Preparation of Compound No. 75

N-(4-(2-Bromothiazol-4-yl)-3-chlorophenyl)-1,1,1-trifluoromethane sulfonamide (100 mg, 0.2380 mmol) and isoquinolin-4-ylboronic acid (61.7 mg, 0.357 mmol), potassium carbonate (65 mg, 0.476 mmol), dimethyl formamide (5 mL), water (0.5 mL) were charged in a 2 neck round bottom flask and aerated with nitrogen gas for 5 min. After adding Pd(PPh$_3$)$_4$ (27.4 mg, 0.0238 mmol), the mixture was heated to 100° C. for 18 h. The reaction was monitored by LCMS. The reaction mixture was cooled to RT, water (10 mL) was added and the mixture extracted with EtOAc (3×25 mL). The combined organic layer was washed with water (30 mL), dried over sodium sulfate and concentrated under reduced pressure to obtain the crude product, which was purified by reverse phase HPLC to afford N-{3-chloro-4-[2-(isoquinolin-4-yl)-1,3-thiazol-4-yl]phenyl}-1,1,1-trifluoromethanesulfonamide (18 mg) as a yellow solid. $^1$H NMR (400 MHz, Methanol-d4) δ (ppm): 9.41 (s, 1H), 9.08 (d, J=8.5 Hz, 1H) 8.95 (s, 1H), 8.38 (d, J=2.3 Hz, 1H), 8.28 (s, 1H), 7.98-8.12 (m, 2H), 7.88 (m, 1H)), 7.58 (s, 1H), 7.39 (d, J=5.5 Hz, 1H). LCMS (M+1): 469.9.

Example 25

Preparation of Compound No. 76

N-(4-(2-Bromothiazol-4-yl)-3-chlorophenyl)-1,1,1-trifluoromethane sulfonamide (100 mg, 0.2380 mmol) and 1-methyl-4-(4-(4,4,5,5-tetramethyl-1,3,2-dioxaborolan-2-yl)pyridine-2-yl)piperazine (108 mg, 0.357 mmol), potassium carbonate (65 mg, 0.476 mmol), dimethyl formamide (5 mL), water (0.5 mL) were charged in a 2 neck round bottom flask and aerated with nitrogen gas for 5 min. After adding Pd(PPh$_3$)$_4$ (27.4 mg, 0.0238 mmol), the mixture was heated to 100° C. for 18 h. The reaction was monitored by LCMS. The reaction mixture was cooled to RT, water (10 mL) was added and the mixture extracted with EtOAc (3×25 mL). The combined organic layer was washed with water (30 mL), dried over sodium sulfate and concentrated under reduced pressure to obtain the crude product, which was purified by reverse phase HPLC to afford N-(3-chloro-4-{2-[2-(4-methylpiperazin-1-yl)pyridin-4-yl]-1,3-thiazol-4-yl}phenyl)-1,1,1-trifluoromethanesulfonamide (54.2 mg) as a yellow solid. $^1$H NMR (400 MHz, Methanol-d4) δ (ppm): 8.28 (d, J=5.6 Hz, 1H), 8.19 (s, 1H), 8.02 (d, J=8.6 Hz, 1H), 7.67 (s, 1H), 7.52-7.43 (m, 2H), 7.38 (d, J=8.4, Hz, 1H), 4.60 (d, J=14.5 Hz, 2H), 3.67 (d, J=12.5 Hz, 2H), 3.42 (s, 2H), 3.22 (d, J=10.5 Hz, 2H), 2.99 (s, 3H). LCMS (M+1): 518.06.

Example 26

Preparation of Compound No. 77

N-(4-(2-Bromothiazol-4-yl)-3-chlorophenyl)-1,1,1-trifluoromethane sulfonamide (100 mg, 0.2380 mmol) and 3,5-dimethyl-4-(4,4,5,5-tetramethyl-1,3,2-dioxaborolan-2-yl)isoxazole (79.6 mg, 0.357 mmol), potassium carbonate (65 mg, 0.476 mmol), dimethyl formamide (5 mL), water (0.5 mL) were charged in a 2 neck round bottom flask and aerated with nitrogen gas for 5 min. After adding Pd(PPh$_3$)$_4$ (27.4 mg, 0.0238 mmol), the mixture was heated to 100° C. for 18 h. The reaction was monitored by LCMS. The reaction mixture was cooled to RT, water (10 mL) was added and the mixture extracted with EtOAc (3×25 mL). The combined organic layer was washed with water (30 mL), dried over sodium sulfate and concentrated under reduced pressure to obtain the crude product, which was purified by reverse phase HPLC to afford N-{3-chloro-4-[2-(dimethyl-1,2-oxazol-4-yl)-1,3-thiazol-4-yl]phenyl}-1,1,1-trifluoromethanesulfonamide (3.2 mg) as a yellow solid. $^1$H NMR (400 MHz, DMSO-d6) δ (ppm): 8.20 (s, 1H), 7.97 (d, J=8.5 Hz, 1H), 7.41 (d, J=2.2 Hz, 1H), 7.32 (d, J=8.5 Hz, 1H), 2.73 (s, 3H), 2.52 (s, 3H). LCMS (M+1): 437.9.

Example 27

Preparation of Compound No. 78

N-(4-(2-Bromothiazol-4-yl)-3-chlorophenyl)-1,1,1-trifluoromethane sulfonamide (100 mg, 0.2380 mmol) and 4-methyl-N-(3-(4,4,5,5-tetramethyl-1,3,2-dioxaborolan-2-yl)phenyl)benzenesulfonamide (133 mg, 0.357 mmol), potassium carbonate (65 mg, 0.476 mmol), dimethyl formamide (5 mL), water (0.5 mL) were charged in a 2 neck round bottom flask and aerated with nitrogen gas for 5 min. After adding Pd(PPh$_3$)$_4$ (27.4 mg, 0.0238 mmol), the mixture was heated to 100° C. for 18 h. The reaction was monitored by LCMS. The reaction mixture was cooled to RT, water (10 mL) was added and the mixture extracted with EtOAc (3×25 mL). The combined organic layer was washed with water (30 mL), dried over sodium sulfate and concentrated under reduced pressure to obtain the crude product, which was purified by reverse phase HPLC to afford N-{3-[4-(2-chloro-4-trifluoromethanesulfonamidophenyl)-1,3-thiazol-2-yl]phenyl}-4-methylbenzene-1-sulfonamide (35.2 mg) as a white solid. $^1$H NMR (400 MHz, DMSO-d6) δ (ppm): 10.48 (s, 1H), 8.11 (s, 1H), 7.91 (d, J=8.5 Hz, 1H), 7.78-7.66 (m, 3H), 7.62 (d, J=7.8 Hz, 1H), 7.43-7.34 (m, 2H), 7.37-7.27 (m, 2H), 7.23 (d, J=8.0 Hz, 1H), 2.32 (s, 3H). LCMS (M+1): 588.

Example 28

Preparation of Compound No. 79

N-(4-(2-Bromothiazol-4-yl)-3-chlorophenyl)-1,1,1-trifluoromethane sulfonamide (100 mg, 0.2380 mmol) and (3,4-dimethoxy phenyl)boronic acid (64.9 mg, 0.3571 mmol), cesium carbonate (155 mg, 0.476 mmol), dimethyl formamide (5 mL), water (0.5 mL) were charged in a 2 neck round bottom flask and aerated with nitrogen gas for 5 min. After adding Pd(PPh$_3$)$_4$ (27.4 mg, 0.0238 mmol), the mixture was heated to 100° C. for 18 h. The reaction was monitored by LCMS. The reaction mixture was allowed to cool to RT, water (10 mL) was added and the mixture extracted with EtOAc (3×25 mL). The combined organic layer was washed with water (30 mL), dried over anhydrous sodium sulfate and concentrated under reduced pressure to obtain a crude product, which was purified by reverse phase HPLC to afford N-{3-chloro-4-[2-(3,4-dimethoxyphenyl)-1,3-thiazol-4-yl]phenyl}-1,1,1-trifluoromethanesulfonamide (11 mg) as a white solid. $^1$H NMR (400 MHz, Methanol-d4) δ (ppm): 7.70 (d, J=8.6 Hz, 2H), 7.63 (d, J=2.1 Hz, 1H), 7.54 (d, J=8.4 Hz, 1H), 7.31 (d, J=2.1 Hz, 1H), 7.16 (d, J=8.4 Hz, 1H), 7.05 (d, J=8.4 Hz, 1H), 3.93 (s, 3H), 3.90 (s, 3H). LCMS (M+1): 479.0.

Example 29

Preparation of Compound No. 80

N-(4-(2-Bromothiazol-4-yl)-3-chlorophenyl)-1,1,1-trifluoromethane sulfonamide (100 mg, 0.2380 mmol) and 1H-indole-4-yl-boronic acid (57.5 mg, 0.3571 mmol), potassium carbonate (65 mg, 0.476 mmol), dimethyl formamide (5 mL), water (0.5 mL) were charged in a 2 neck round bottom flask and aerated with nitrogen gas for 5 min. After adding Pd(PPh$_3$)$_4$ (27.4 mg, 0.0238 mmol), the mixture was heated to 100° C. for 18 h. The reaction was monitored by LCMS. The reaction mixture was allowed to cool to RT, water (10 mL) was added and the mixture extracted with EtOAc (3×25 mL). The combined organic layer was washed with water (30 mL), dried over anhydrous sodium sulfate and concentrated under reduced pressure to obtain a crude product, which was purified by reverse phase HPLC to afford N-{3-chloro-4-[2-(1H-indol-4-yl)-1,3-thiazol-4-yl]phenyl}-1,1,1-trifluoromethanesulfonamide (30 mg) as a white solid. $^1$H NMR (400 MHz, Methanol-d4) δ (ppm): 8.10 (d, J=8.5 Hz, 1H), 7.98 (s, 1H), 7.72 (d, J=7.4 Hz, 1H), 7.55 (d, J=8.1 Hz, 1H), 7.48 (d, J=2.3 Hz, 1H), 7.43 (t, J=2.8 Hz, 1H), 7.37 (d, J=8.6 Hz, 1H), 7.25 (d, J=5.4 Hz, 1H), 7.22 (d, J=7.8 Hz, 1H). LCMS (M+1): 457.7.

Example 30

Preparation of Compound No. 81

Step-1: Synthesis of 4-fluoro-2-(trifluoromethyl)benzamide

A solution of 4-fluoro-2-(trifluoromethyl)benzonitrile (100 mg, 0.528 mmol) in conc. sulfuric acid (1.2 mL) and glacial acetic acid (0.8 mL) was heated at 120° C. for 0.5 h, monitored by TLC. The reaction was diluted with water and the mixture extracted with EtOAc (2×30 mL). The organic layer was dried over anhydrous sodium sulfate and concentrated under reduced pressure to afford 80 mg of 4-fluoro-2-(trifluoromethyl)benzamide as an off-white solid.

Step-2: Synthesis of 4-fluoro-2-(trifluoromethyl)benzenecarbothioamide

A solution of 4-fluoro-2-(trifluoromethyl)benzamide (500 mg, 2.414 mmol) and Lawesson's Reagent (1.95 g, 4.821 mmol) in toluene (30 mL) was heated at 80° C. for 1 h. The progress of the reaction was monitored by TLC. The reaction was diluted with water (30 mL) and the mixture extracted with EtOAc (2×50 mL). The organic layer was dried over anhydrous sodium sulfate and concentrated under reduced pressure to afford a crude product, which was purified by column chromatography (silica-gel, 230-400 mesh) using 10% EtOAc in hexane as eluent to obtain 100 mg of 4-fluoro-2-(trifluoromethyl)benzenecarbothioamide as a yellow sticky compound.

Step-3: Synthesis of N-[3-chloro-4-[2-[4-fluoro-2-(trifluoromethyl)phenyl]thiazol-4-yl]phenyl]-1,1,1-trifluoro-methanesulfonamide A solution of 4-fluoro-2-(trifluoromethyl)benzenecarbothioamide (50 mg, 0224 mmol) and N-[4-(2-bromoacetyl)-3-chloro-phenyl]-1,1,1-trifluoro-methanesulfonamide (170 mg, 0.446 mmol) in ethanol (10 mL) was heated at 70° C. for 40 min, monitored by TLC. The reaction was diluted with aqueous saturated NaHCO$_3$ solution (25 mL) and the mixture extracted with EtOAc (2×50 mL). The combined organic layer was dried over anhydrous sodium sulfate and concentrated under reduced pressure to afford a crude product, which was purified by reverse phase preparative HPLC to obtain N-[3-chloro-4-[2-[4-fluoro-2-(trifluoromethyl)phenyl]thiazol-4-yl]phenyl]-1,1,1-trifluoro-methanesulfonamide (22 mg) as an off-white solid. $^1$H NMR (400 MHz, Methanol-d4): δ (ppm): 7.98 (s, 1H), 7.81 (dd, J=8.6, 5.4 Hz, 1H), 7.68 (dd, J=8.9, 3.0 Hz, 2H), 7.53 (td, J=8.4, 2.6 Hz 1H), 7.30 (d, J=2.2 Hz, 1H), 7.11 (dd, J=8.4, 2.1 Hz, 1H).

Example 31

Preparation of Compound No. 82

N-(4-(2-Bromothiazol-4-yl)-3-chlorophenyl)-1,1,1-trifluoromethane sulfonamide (100 mg, 0.2380 mmol) and 2,3-dihydrobenzofuran-5-boronic acid (58.5 mg, 0.3571 mmol), potassium carbonate (65 mg, 0.476 mmol), dimethyl formamide (5 mL), water (0.5 mL) were charged in a 2 neck round bottom flask and aerated with nitrogen gas for 5 min. After adding Pd(PPh$_3$)$_4$ (27.4 mg, 0.0238 mmol), the mixture was heated to 100° C. for 18 h. The reaction was monitored by LCMS. The reaction mixture was allowed to cool to RT; water (10 mL) was added and the mixture extracted with EtOAc (3×25 mL). The combined organic layer was washed with water (30 mL), dried over anhydrous sodium sulfate and concentrated under reduced pressure to obtain a crude product, which was purified by reverse phase HPLC to afford N-{3-chloro-4-[2-(2,3-dihydro-1-benzofuran-5-yl)-1,3-thiazol-4-yl]phenyl}-1,1,1-trifluoromethanesulfonamide (15 mg) as a white solid. $^1$H NMR (400 MHz, Methanol-d4) δ (ppm): 7.97 (d, J=8.5 Hz, 1H), 7.88 (s, 1H), 7.82 (s, 1H), 7.77 (d, J=8.3 Hz, 1H), 7.44 (s, 1H), 7.32 (d, J=8.5 Hz, 1H), 6.83 (d, J=8.3 Hz, 1H), 4.63 (t, J=8.7 Hz, 2H), 2.17 (t, J=9.3 Hz, 2H). LCMS (M+1): 460.6.

Example 32

Preparation of Compound No. 83

N-(4-(2-Bromothiazol-4-yl)-3-chlorophenyl)-1,1,1-trifluoromethane sulfonamide (100 mg, 0.2380 mmol) and [3-(bromomethyl)phenyl]boronic acid (61.3 mg, 0.261 mmol), sodium carbonate (63 mg, 0.595 mmol), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol), the mixture was further purged for 2 min and was heated to 100° C. for 18 h. The reaction was monitored by LCMS. The reaction mixture was allowed to cool to RT, water (10 mL) was added and the mixture extracted with EtOAc (3×25 mL). The combined organic layer was washed with water (4×30 mL), dried over anhydrous sodium sulfate and concentrated under reduced pressure to obtain a crude product, which was purified by reverse phase HPLC to afford N-(3-chloro-4-{2-[3-(hydroxymethyl)phenyl]-1,3-thiazol-4-yl}phenyl)-1,1,1-trifluoromethanesulfonamide (9 mg) as a white solid. $^1$H NMR (400 MHz, DMSO-d6) δ (ppm): 8.13 (s, 1H), 8.00 (d, J=8.5 Hz, 2H), 7.97-7.79 (m, 1H), 7.51-7.43 (m, 2H), 7.41 (d, J=2.2 Hz, 1H), 7.33 (dd, J=8.6, 2.2 Hz, 1H), 4.59 (s, 2H). LCMS (M+1): 448.9.

Example 33

Preparation of Compound No. 84

N-(4-(2-Bromothiazol-4-yl)-3-chlorophenyl)-1,1,1-trifluoromethane sulfonamide (100 mg, 0.2380 mmol) and [2-(bromomethyl)phenyl]boronic acid (56 mg, 0.261 mmol), sodium carbonate (63 mg, 0.595 mmol), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol) the mixture was further purged for 2 min and heated to 100° C. for 18 h. The reaction was monitored by LCMS. The reaction mixture was cooled to RT, water (10 mL) was added and the mixture extracted with EtOAc (3×25 mL). The combined organic layer was washed with water (4×30 mL), dried over sodium sulfate and concentrated under reduced pressure to obtain the crude product, which was purified by reverse phase HPLC to afford N-(3-chloro-4-{2-[2-(hydroxymethyl)phenyl]-1,3-thiazol-4-yl}phenyl)-1,1,1-trifluoromethanesulfonamide (25 mg) as a white solid. $^1$H NMR (400 MHz, DMSO-d6) δ (ppm): 8.20 (s, 1H), 7.95 (d, J=8.5 Hz, 1H), 7.81-7.79 (m, 1H), 7.79-7.71 (m, 1H), 7.54 (dd, J=7.5, 1.3 Hz, 1H), 7.43 (dt, J=3.7, 1.9 Hz, 2H), 7.35 (dd, J=8.5, 2.3 Hz, 1H), 4.87 (s, 2H). LCMS (M+1): 449.1.

Example 34

Preparation of Compound No. 85

N-(4-(2-Bromothiazol-4-yl)-3-chlorophenyl)-1,1,1-trifluoromethane sulfonamide (100 mg, 0.2380 mmol) and [2-(1-piperidyl)-4-pyridyl]boronic acid (53 mg, 0.261 mmol), sodium carbonate (63 mg, 0.595 mmol), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol) the mixture was further purged for 2 min and was heated to 100° C. for 18 h. The reaction was monitored by LCMS. The reaction mixture was cooled to RT, water (10 mL) was added and the mixture extracted with EtOAc (3×25 mL). The combined organic layer was washed with water (4×30 mL), dried over sodium sulfate and concentrated under reduced pressure to obtain the crude product, which was purified by reverse phase HPLC to afford N-(3-chloro-4-{2-[2-(piperidin-1-yl)pyridin-4-yl]-1,3-thiazol-4-yl}phenyl)-1,1,1-trifluoromethanesulfonamide (56 mg) as a yellow solid. $^1$H NMR (400 MHz, DMSO-d6) δ (ppm): 8.23-8.07 (m, 2H), 7.38 (s, 1H) 7.83 (d, J=8.5 Hz, 1H), 7.35 (s, 1H), 7.19-7.09 (m, 2H), 3.62 (t, J=5.1 Hz, 4H), 3.17 (s, 2H), 1.60 (dt, J=9.7, 5.7 Hz, 4H). LCMS (M+1): 504.0.

Example 35

Preparation of Compound No. 86

N-(4-(2-Bromothiazol-4-yl)-3-chlorophenyl)-1,1,1-trifluoromethane sulfonamide (100 mg, 0.2380 mmol) and (3-methyl-4-pyridyl)boronic acid (35 mg, 0. 0.261 mmol), sodium carbonate (63 mg, 0. 0.595 mmol), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol) the mixture was further purged for 2 min and was heated to 100° C. for 18 h. The reaction was monitored by LCMS. The reaction mixture was cooled to RT, water (10 mL) was added and the mixture extracted with EtOAc (3×25 mL). The combined organic layer was washed with water (4×30 mL), dried over sodium sulfate and concentrated under reduced pressure to obtain the crude product, which was purified by reverse phase HPLC to afford N-{3-chloro-4-[2-(3-methylpyridin-4-yl)-1,3-thiazol-4-yl]phenyl}-1,1,1-trifluoromethanesulfonamide (13 mg) as a white solid. $^1$H NMR (400 MHz, Methanol-d4) δ (ppm): 8.80 (s, 1H), 8.70 (s, 1H), 8.41 (s, 2H), 8.04 (d, J=8.5 Hz, 1H), 7.49 (d, J=2.3 Hz, 1H), 7.38 (dd, J=8.5, 2.3 Hz, 1H), 2.86 (s, 3H). LCMS (M+1): 434.4.

Example 36

Preparation of Compound No. 87

N-(4-(2-Bromothiazol-4-yl)-3-chlorophenyl)-1,1,1-trifluoromethane sulfonamide (100 mg, 0.2380 mmol) and 4-(4,4,5,5-tetramethyl-1,3,2-dioxaborolan-2-yl)-1H-pyrrolo[2,3-b]pyridine (63 mg, 0. 0.261 mmol), sodium carbonate (63 mg, 0.595 mmol), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol) the mixture was further purged for 2 min and was heated to 100° C. for 18 h. The reaction was monitored by LCMS. The reaction mixture was cooled to RT, water (10 mL) was added and the mixture extracted with EtOAc (3×25 mL). The combined organic layer was washed with water (4×30 mL), dried over sodium sulfate and concentrated under reduced pressure to obtain the crude product, which was purified by reverse phase HPLC to afford N-[3-chloro-4-(2-{1H-pyrrolo[2,3-b]pyridin-4-yl}-1,3-thiazol-4-yl)phenyl]-1,1,1-trifluoromethanesulfonamide (37 mg) as a white solid. $^1$H NMR (400 MHz, Methanol-d4) δ (ppm): 8.39 (d, J=5.6 Hz, 1H), 8.29 (s, 1H), 8.11 (d, J=8.5 Hz, 1H), 7.92 (d, J=5.6 Hz, 1H), 7.69 (d, J=3.5 Hz, 1H), 7.50 (d, J=2.3 Hz, 1H), 7.43-7.33 (m, 2H). LCMS (M+1): 459.5.

Example 37

Preparation of Compound No. 37

N-(4-(2-Bromoacetyl)-3-chlorophenyl)-1,1,1-trifluoromethanesulfonamide (50 mg, 0.132 mmol) and 2-isobutylpyridine-4-carbothioamide (25.34 mg, 0.132 mmol) were charged in EtOH (10 mL) and the reaction mixture was heated at 80° C. for 1 h. The reaction mixture was concentrated and purified through reverse phase HPLC. (Yield: 17 mg TFA salt). $^1$H NMR (TFA salt, CD$_3$OD) δ (ppm): 8.73 (d, J=5.9 Hz, 1H), 8.38 (d, J=2.9 Hz, 1H), 8.31 (d, J=6.2 Hz, 1H), 8.07 (d, J=8.5 Hz, 1H), 7.49 (s, 1H), 7.39 (d, J=8.2 Hz, 1H), 2.94 (d, J=7.3 Hz, 2H), 2.19 (m, 2H), 1.07 (d, J=6.6 Hz, 6H).
Complete Synthesis of Compound No. 37
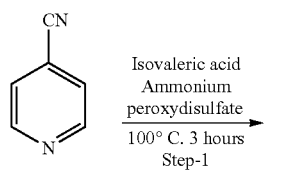
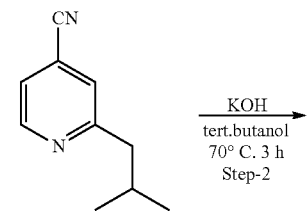
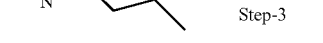
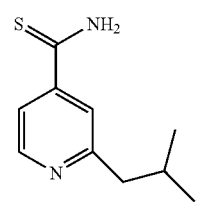
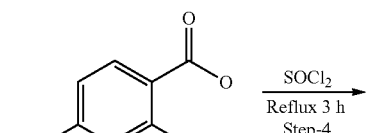
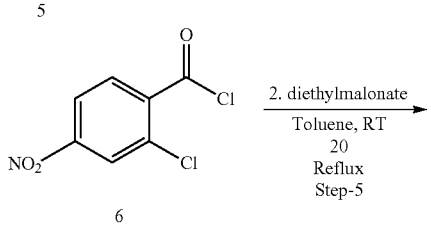
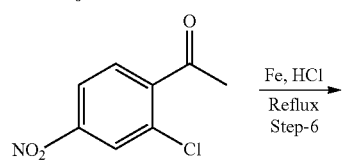
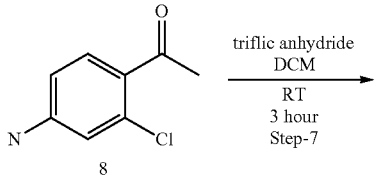
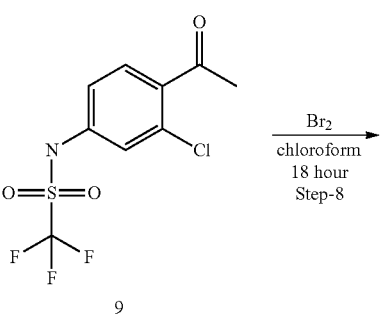
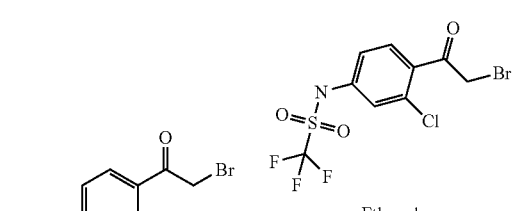
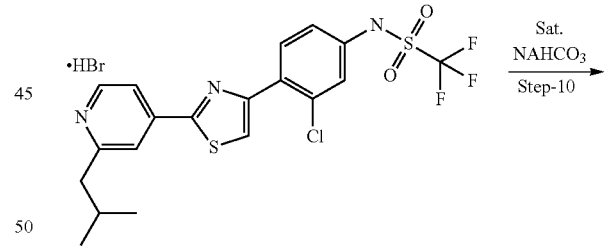
11
Compound No. 37 HBr salt
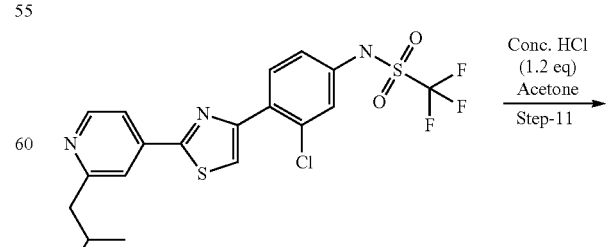
Compound No. 37- freebase -continued

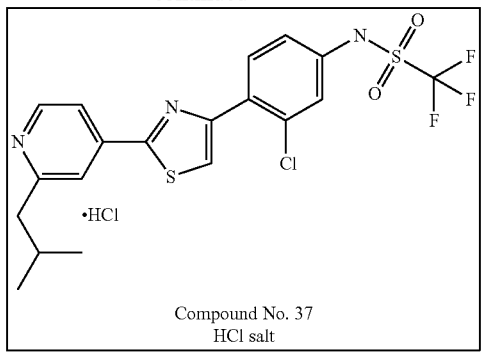 [SMILES: CC(C)Cc1cc(-c2nc(-c3ccc(NS(=O)(=O)C(F)(F)F)cc3Cl)cs2)ccn1 ; Cl]

Compound No. 37
HCl salt

Step 1: Synthesis of 2-isobutylpyridine-4-carbonitrile (2)

To a suspension of 4-cyano pyridine (1) (30 g, 0.288 mol, 1 equiv.) in water (210 mL), concentrated sulfuric acid (15.3 mL, 0.288 mol, 1 equiv.) was added dropwise maintaining the temperature at 20-25° C. After formation of a clear solution, AgNO$_3$ (4.9 g, 0.028 mmol, 0.0001 equiv.) followed by isovaleric acid (160 mL, 1.47 mol, 5 equiv.) were added in to the reaction mixture. A white hazy solution formed. Ammonium peroxydisulfate (66 g, 0.288 mol, 1 equiv.) dissolved in water (90 mL) was then added. A black clear solution formed. The reaction mixture was then heated to reflux at 100° C. for 3 h. The reaction was monitored by TLC. After completion, the reaction mixture was basified (pH=7-8) using a saturated solution of sodium bicarbonate, and extracted with EtOAc (3×750 mL). The extracts were combined and were washed with brine (3×300 mL) and dried over anhydrous sodium sulfate. The solution was concentrated under reduced pressure and the crude product was purified by column chromatography (silica gel: #100-200) using 0-6% EtOAc in hexane as eluant to afford 2-isobutylpyridine-4-carbonitrile (2) (15 g (32.5% yield)) as a pale yellow liquid. $^1$H NMR (400 MHz, Chloroform-d): δ (ppm): 8.78-8.63 (m, 1H), 7.41-7.27 (m, 2H), 2.72 (d, J=7.2 Hz, 2H), 1.35-1.23 (m, 1H), 0.94 (d, J=6.6 Hz, 6H).

Step 2: Synthesis of 2-isobutylpyridine-4-carboxamide (3)

2-Isobutylpyridine-4-carbonitrile (2) (15 g, 0.093 mol, 1 equiv.) and KOH (15.7 g, 0.281 mol, 3 equiv.) was dissolved in tert-butanol (160 mL). The reaction mixture was stirred at 70° C. for 90 min. The reaction was monitored by TLC. After completion, the tert-butanol was removed under reduced pressure; the residue was dissolved in water and extracted with EtOAc (3×275 mL). The extracts were combined, dried over anhydrous sodium sulfate and concentrated under reduced pressure. The crude product was triturated with n-hexane (3×200 mL). To the residue was added diethyl ether (50 mL) and then concentrated under reduced pressure to afford 2-isobutylpyridine-4-carboxamide (3) (13.5 g (81.3% yield)) as a white solid. $^1$H NMR (400 MHz, Chloroform-d): δ (ppm): 8.68 (d, J=5.1 Hz, 1H), 7.49 (s, 1H), 7.42 (d, J=5.1 Hz, 1H), 6.14 (s, 1H), 5.81 (s, 1H), 2.73 (d, J=7.3 Hz, 2H), 2.13 (m, 1H), 0.94 (d, J=6.7 Hz, 6H).

Step 3: Synthesis of 2-isobutylpyridine-4-carbothioamide (4)

To a solution of 2-isobutylpyridine-4-carboxamide (3) (13.5 g, 0.075 mol, 1 equiv.) in pyridine (135 ml), was added P$_2$S$_5$ (8.45 g, 0.037 mol, 0.5 equiv.). The reaction was heated at 100° C. for 3 h. The progress of the reaction was monitored by TLC. After completion, the pyridine was evaporated under reduced pressure; the residue was dissolved in water (100 mL) and extracted with EtOAc (3×250 mL). The EtOAc extracts were combined, dried over anhydrous sodium sulfate and concentrated under reduced pressure. The crude product obtained was triturated with n-hexane (3×200 mL) to afford 2-isobutylpyridine-4-carbothioamide (4) (8 g (54.4% yield)) as a yellow solid. $^1$H NMR (400 MHz, Chloroform-d): δ (ppm): 8.62 (d, J=5.1 Hz, 1H), 7.73-7.64 (broad, 1H), 7.52-7.40 (m, 2H), 7.32-7.25 (m, 1H), 2.72 (d, J=7.2 Hz, 2H), 2.13 (m, 1H), 0.95 (d, J=6.6 Hz, 6H).

Step 4: Synthesis of 2-chloro-4-nitrobenzoyl chloride (6)

To a two neck flask (1 L) placed in ice bath was placed 2-chloro-4-nitrobenzoic acid (5) (50 g, 0.248 mol, 1 equiv.). Thionyl chloride (110 ml, 1.51 mol, 6.1 equiv.) was added dropwise at 0° C. The reaction mixture was allowed to come to RT and then heated to reflux. The heating was continued overnight. The thionyl chloride was evaporated and ice (approx. 150 g) was added to the reaction mixture. The aqueous reaction mixture was extracted with DCM (2×200 mL).

The DCM extracts were combined dried over anhydrous sodium sulfate and concentrated under vacuum to get 2-chloro-4-nitrobenzoyl chloride (6) (50 g (91.7% yield)) as a light yellow liquid. $^1$H NMR (400 MHz, Chloroform-d): δ (ppm): 8.37 (d, J=2.2 Hz, 1H), 8.25 (dd, J=8.6, 2.2 Hz, 1H), 8.15 (d, J=8.7 Hz, 1H).

Step 5: Synthesis of 1-(2-chloro-4-nitrophenyl)ethanone (7)

A suspension of anhydrous magnesium chloride (47 g, 0.214 mol, 0.7 equiv.) in toluene (300 mL) was treated with triethylamine (75.04 mL, 0.535 mol, 2.5 equiv.) and diethylmalonate (41.09 g, 0.257 mol, 1.2 equiv.). The reaction mixture was stirred at RT for 1.5 h. To this was added 2-chloro-4-nitrobenzoyl chloride (6) (47 g, 0.214 mol, 1 equiv.) dropwise (an exothermic reaction up to 50° C. was observed during addition). Toluene (50 mL) was used for complete transfer of 2-chloro-4-nitrobenzoyl chloride to the reaction mixture. The reaction mixture was stirred at RT for 18 h. The reaction was monitored by TLC and NMR. After complete consumption of starting material, concentrated hydrochloric acid (35% solution) (300 mL) was added and the upper toluene layer was separated. The toluene was evaporated under reduced pressure below 50° C. To the residue were added DMSO (200 mL) and water (10 mL), and the mixture heated at 160° C. for 12 h. The reaction was monitored by TLC and NMR. The reaction mixture was allowed to come to RT and water (40 mL) was added. The reaction mixture was extracted with EtOAc (3×200 mL). The EtOAc extracts were combined and washed with brine solution (3×300 mL) and dried over anhydrous sodium sulfate. The EtOAc layer was concentrated to get 1-(2-chloro-4-nitrophenyl)ethanone (7) (43 g (84% yield)) as a yellow liquid which solidified upon refrigeration. $^1$H NMR (400 MHz, Chloroform-d): δ (ppm): 8.29 (d, J=2.2 Hz, 1H), 8.17 (dd, J=8.5, 2.1 Hz, 1H), 7.65 (d, J=8.4 Hz, 1H), 2.66 (s, 3H).

Step 6: Synthesis of 1-(4-amino-2-chlorophenyl)ethanone (8)

1-(2-Chloro-4-nitrophenyl)ethanone (87.8 g, 0.43 mol, 1 equiv.) was charged in methanol (600 mL). The reaction mixture was heated to 70° C. and concentrated HCl (131 mL, 1.29 mol, 3 equiv.) was added dropwise with constant stirring. After the completion of addition, iron powder (98.2 g, 1.75 mol, 4 equiv.) was added in four parts at 5 minute intervals. The reaction mixture was heated at 70° C. for 7 h and the reaction monitored by TLC and NMR. After completion of reaction, the mixture was allowed to come to RT and then filtered through a celite bed. The filtrate was concentrated under reduced pressure and celite bed was washed with EtOAc to obtain further crude product. Both portions were combined and water (200 mL) was added. The EtOAc layer was separated and aqueous layer was extracted with EtOAc (2×500 mL). The combined organic layer was dried over anhydrous sodium sulfate and concentrated to get crude product (57 g). This crude product was precipitated in pentane to get 1-(4-amino-3-methoxyphenyl)ethanone (8) (50 g (67% yield)) as a pink solid. $^1$H NMR (400 MHz, Chloroform-d): δ (ppm): 7.62 (d, J=8.5 Hz, 1H), 6.66 (d, J=2.3 Hz, 1H), 6.54 (dd, J=8.5, 2.3 Hz, 1H), 4.07 (s, 2H), 2.61 (s, 3H).

Step 7: Synthesis of N-(4-acetyl-3-chlorophenyl)-1,1,1-trifluoromethanesulfonamide (9)

A solution of triflic anhydride (75.1 g, 0.266 mol, 1.5 equiv.) in DCM (600 mL) was cooled to 0° C. Pyridine (23.4 mL, 0.266 mol, 1.5 equiv.) was added dropwise with constant stirring over 30 min. The reaction mixture was stirred at the same temperature for 1 h. A solution of 1-(4-amino-2-chlorophenyl)ethanone (8) (30 g, 0.177 mol, 1 equiv.) in DCM (400 mL) was added dropwise maintaining the temperature at 0° C. with constant stirring over a period of 45 min. The reaction mixture was then allowed to come to RT and stirred for 1 h at RT. The reaction was monitored by TLC and NMR. Upon completion, ice cold water (500 mL) was added and the DCM layer was separated. The aqueous layer was again extracted with DCM (2×100 mL). The DCM extracts were combined washed with ice cold water (2×500 mL). The DCM layer was dried over anhydrous sodium sulfate and concentrated under reduced pressure below 40° C. to obtain the crude product. Diethyl ether (200 mL) and pentane (600 mL) were added to the mixture which was then stirred for 30 min. The mixture was filtered and the filtrate concentrated and triturated in pentane to get N-(4-acetyl-3-chlorophenyl)-1,1,1-trifluoromethanesulfonamide (9) (28 g (52.8% yield)) as a light pink solid. $^1$H NMR (400 MHz, Chloroform-d): δ (ppm): 7.63 (d, J=8.4 Hz, 1H), 7.36 (d, J=2.2 Hz, 1H), 7.28-7.21 (m, 1H), 2.66 (s, 3H).

Step 8: Synthesis of N-(4-(2-bromoacetyl)-3-chlorophenyl)-1,1,1-trifluoromethanesulfonamide (10)

A solution of N-(4-acetyl-3-chlorophenyl)-1,1,1-trifluoromethanesulfonamide (9) (21 g, 0.07 mol, 1 equiv.) in chloroform (600 mL) was cooled to 0° C. Liquid bromine (2.9 mL, 0.004 mol, 0.8 equiv.) dissolved in chloroform (400 mL) was added dropwise over a period of 40 min, maintaining the reaction temperature between 0-10° C. The mixture was allowed to come to RT and then stirred at RT for 18 h. The reaction was monitored by TLC and NMR. There was an indication of the presence of starting material and desired compound along with some amount of N-(3-chloro-4-(2,2-dibromoacetyl)phenyl)-1,1,1-trifluoromethanesulfonamide (dibromo impurity). A saturated solution of sodium thiosulfate (200 mL) was added and the chloroform layer was separated. The aqueous layer was extracted with chloroform (2×100 mL). The main chloroform layer and the chloroform extracts were combined, dried over anhydrous sodium sulfate and concentrated under reduced pressure. A clear liquid was obtained as the residue. To this were added diethylether (50 mL) and pentane (250 mL) and the mixture stirred for 10 min. The reaction mixture was filtered and the filtrate concentrated. The crude product obtained was triturated with pentane (~50 mL) to obtain a white solid. This white solid was filtered and dried under vacuum to get N-(4-(2-bromoacetyl)-3-chlorophenyl)-1,1,1-trifluoromethanesulfonamide (10) (20 g) which contained approximately 35% of starting material i.e. N-(4-acetyl-3-chlorophenyl)-1,1,1-trifluoromethanesulfonamide (9) by NMR. The mixture of products was directly used for the next step without any further purification. $^1$H NMR (400 MHz, Chloroform-d): δ (ppm): 7.64 (d, J=8.4 Hz, 1H), 7.38 (d, J=2.2 Hz, 1H), 7.30-7.27 (m, 1H), 4.51 (s, 2H).

Step 9: Synthesis of N-(3-chloro-4-(2-(2-isobutylpyridin-4-yl)thiazol-4-yl)phenyl)-1,1,1-trifluoromethanesulfonamide (11)

N-(4-(2-Bromoacetyl)-3-chlorophenyl)-1,1,1-trifluoromethanesulfonamide (10) (15.5 g, 0.041 mol, 1 equiv.) and 2-isobutylpyridine-4-carbothioamide (5.2 g, 0.027 mol, 0.65 equiv.) were charged in ethanol (40 mL) and the reaction mixture was heated at 80° C. for 30 min. The reaction mixture was cooled in an ice bath and stirred at 0° C. for 30 min. The solid obtained was isolated by filtration and washed with cold ethanol (2×5 mL). The solid obtained was dried under vacuum to get N-(3-chloro-4-(2-(2-isobutylpyridin-4-yl)thiazol-4-yl)phenyl)-1,1,1-trifluoromethanesulfonamide (11) (10.2 g (53.6% yield)) as the hydrobromide salt. $^1$H NMR (400 MHz, Methanol-d4): δ (ppm): 8.80 (d, J=6.3 Hz, 1H), 8.57-8.45 (m, 3H), 8.08 (d, J=8.5 Hz, 1H), 7.50 (d, J=2.2 Hz, 1H), 7.40 (dd, J=8.6, 2.3 Hz, 1H), 3.01 (d, J=7.4 Hz, 2H), 2.21 (m, 1H), 1.06 (d, J=6.6 Hz, 6H). UPLC: In method, Column Type: ACQUITY BEH SHIELD C18, Column ID: 2.1*50 mm, 1.7µ; Flow Rate—0.35 mL/min, Mobile Phase A: 0.05% TFA;

Mobile Phase B: acetonitrile. Gradient: 10% B To 50% B in 1 min., hold for 0.5 min, 50% B to 90% B in 0.1 min, hold for 1 min, 90% B to 10% B in 0.4 min compound eluted at a retention time of 2.66 min.

Step 10: Synthesis of N-(3-chloro-4-(2-(2-isobutylpyridin-4-yl)thiazol-4-yl)phenyl)-1,1,1-trifluoromethanesulfonamide-free base (12)

N-(3-Chloro-4-(2-(2-isobutylpyridin-4-yl)thiazol-4-yl)phenyl)-1,1,1-trifluoromethanesulfonamide hydrobromide salt (11) (88.5. g) was charged in a flask and a saturated solution of sodium bicarbonate (300 mL) was added so that the pH became slightly basic (pH=7-8). EtOAc (3×500 mL) was added and the reaction mixture was stirred at RT until the mixture became clear. The organic layer was separated and washed with water (50 mL). The EtOAc layer was dried over anhydrous sodium sulfate and concentrated to get N-(3-chloro-4-(2-(2-isobutylpyridin-4-yl)thiazol-4-yl)phenyl)-1,1,1-trifluoromethanesulfonamide (12) (46.3 g (61% yield)) as the free base. $^1$H NMR (400 MHz, Methanol-d): δ (ppm): 8.56 (d, J=5.3 Hz, 1H), 8.10 (s, 1H), 7.99 (d, J=8.6 Hz, 1H), 7.92-7.80 (m, 2H), 7.44 (d, J=2.2 Hz, 1H), 7.31

(dd, J=8.5, 2.3 Hz, 1H), 3.06 (s, 3H), 2.86 (dd, J=8.6, 6.7 Hz, 2H), 1.88-1.74 (m, 2H), 1.01 (t, J=7.4 Hz, 3H).

Step 11: Synthesis of N-(3-chloro-4-(2-(2-isobutylpyridin-4-yl)thiazol-4-yl)phenyl)-1,1,1-trifluoromethanesulfonamide Hydrochloride (13)

N-(3-chloro-4-(2-(2-isobutylpyridin-4-yl)thiazol-4-yl)phenyl)-1,1,1-trifluoromethanesulfonamide—free base (12) (46.4 g, 0.097 mol, 1 equiv.) was charged in acetone (1.5 L) and stirred at RT for 5-10 min until a clear solution was obtained. A solution of concentrated hydrochloric acid [~35% v/v](13.3 mL, 0.126 mol, 1.3 equiv.) in acetone (85 mL) was added dropwise with constant stirring. After addition, the pH of the reaction mixture was 1-2. The reaction mixture was stirred for 30 min at RT. The solid obtained was filtered under vacuum and washed with acetone (3×100 mL) (the washing was performed without vacuum and once acetone was absorbed by the solid, the solvent was removed by vacuum filtration). The washing was repeated until the filtrate was colorless. The light yellow solid obtained was dried at 50° C. under reduced pressure for 2 h to get N-(3-chloro-4-(2-(2-isobutylpyridin-4-yl)thiazol-4-yl)phenyl)-1,1,1-trifluoromethanesulfonamide—hydrochloride salt (13) (44 g (88% yield)). $^1$H NMR (400 MHz, Methanol-d4): δ (ppm): 8.81 (d, J=6.3 Hz, 1H), 8.58-8.45 (m, 3H), 8.08 (d, J=8.5 Hz, 1H), 7.49 (t, J=2.8 Hz, 1H), 7.40 (dd, J=8.5, 2.4 Hz, 1H), 3.02 (d, J=7.3 Hz, 2H), 2.22 (m, 1H), 1.06 (d, J=6.6 Hz, 6H). Melting point: 165° C.-173° C. (FB). LCMS—(M+1): 475.9 (99.5%). In method, Column type: HYPERSILGOLD, C18, Column_ID: 4.6*50 mm, 5μ; Mobile Phase A: 0.05% formic acid in H$_2$O; Mobile Phase B: 0.01% formic acid in acetonitrile. Gradient: 10% B to 90% B From 0.2 to 2 min, hold for 2.5 min, 10% B in 0.1 min. Flow: 0.7 mL/min. The desired compound has RT of 4.514 min. UPLC—In method, Column Type: ACQUITY BEH C18; Column ID: 2.1*50 mm, 1.7μ; Flow Rate: 0.35 mL/min. Mobile phase A: 0.05% TFA Mobile phase B: Acetonitrile, Gradient: 10% B to 90% B in 2.5 min, hold for 1 min, 90% B to 10% B in 0.3 min. The desired compound had RT of 2.793 min. Melting point: 220° C.-227° C. (Hydrochloride salt).

Example 38

Preparation of Compound No. 88

N-(4-(2-Bromothiazol-4-yl)-3-chlorophenyl)-1,1,1-trifluoromethane sulfonamide (100 mg, 0.2380 mmol) and [3-(1-piperidyl)phenyl]boronic acid (53 mg, 0. 0.261 mmol), sodium carbonate (63 mg, 0.595 mmol), dimethyl formamide (4 mL), water (1.0 mL) were charged in a 25 mL glass bottle and aerated with nitrogen gas for 5 min. After adding Pd-acetate (8 mg, 0.035 mmol) and xantphos (27.5 mg, 0.0476 mmol), the mixture was further purged for 2 min and was heated to 100° C. for 18 h. The reaction was monitored by LCMS. The reaction mixture was cooled to RT, water (10 mL) was added and the mixture extracted with EtOAc (3×25 mL). The combined organic layer was washed with water (4×30 mL), dried over sodium sulfate and concentrated under reduced pressure to obtain the crude product, which was purified by reverse phase HPLC to afford N-(3-chloro-4-{2-[3-(piperidin-1-yl)phenyl]-1,3-thiazol-4-yl}phenyl)-1,1,1-trifluoromethanesulfonamide (25 mg) as a yellow solid. $^1$H NMR (400 MHz, Methanol-d4) δ (ppm): 8.23 (s, 1H), 8.11-7.94 (m, 3H), 7.71-7.59 (m, 2H), 7.47 (d, J=2.2 Hz, 1H), 7.37 (dd, J=8.6, 2.2 Hz, 1H), 3.63 (t, J=5.5 Hz, 4H), 2.01 (q, J=6.2 Hz, 4H), 1.80 (q, J=6.0 Hz, 2H). LCMS (M+1): 502.5.

Example 39

Preparation of Compound No. 89

N-(4-(2-Bromothiazol-4-yl)-3-chlorophenyl)-1,1,1-trifluoromethane sulfonamide (100 mg, 0.2380 mmol) and [5-fluoro-4-(4,4,5,5-tetramethyl-1,3,2-dioxaborolan-2-yl)pyrrolo[2,3-b]pyridin-1-yl]-triisopropyl-silane (109 mg, 0. 0.261 mmol), sodium carbonate (63 mg, 0.595 mmol), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol) the mixture was further purged for 2 min and was heated to 100° C. for 18 h. The reaction was monitored by LCMS. The reaction mixture was cooled to RT, water (10 mL) was added and the mixture extracted with EtOAc (3×25 mL). The combined organic layer was washed with water (4×30 mL), dried over sodium sulfate and concentrated under reduced pressure to obtain the crude product, which was purified by reverse phase HPLC to afford N-[3-chloro-4-(2-{5-fluoro-1H-pyrrolo[2,3-b]pyridin-4-yl}-1,3-thiazol-4-yl)phenyl]-1,1,1-trifluoromethanesulfonamide (35 mg) as a white color solid. $^1$H NMR (400 MHz, DMSO-d6) δ (ppm): 12.10 (s, 1H), 8.43 (d, J=2.2 Hz, 2H), 8.08 (d, J=8.5 Hz, 1H), 7.74 (t, J=3.0 Hz, 1H), 7.47 (d, J=2.2 Hz, 1H), 7.45-7.36 (m, 2H). LCMS (M+1): 477.1.

Example 40

Preparation of Compound No. 90

N-(4-(2-Bromothiazol-4-yl)-3-chlorophenyl)-1,1,1-trifluoromethane sulfonamide (100 mg, 0.2380 mmol) and benzothiophen-3-ylboronic acid (47 mg, 0.261 mmol), sodium carbonate (63 mg, 0.595 mmol), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol) the mixture was further purged for 2 min and heated to 100° C. for 18 h. The reaction was monitored by LCMS. The reaction mixture was cooled to RT, water (10 mL) was added and the mixture extracted with EtOAc (3×25 mL). The combined organic layer was washed with water (4×30 mL), dried over sodium sulfate and concentrated under reduced pressure to obtain the crude product, which was purified by reverse phase HPLC to afford N-{4-[2-(1-benzothiophen-3-yl)-1,3-thiazol-4-yl]-3-chlorophenyl}-1,1,1-trifluoromethanesulfonamide (59 mg) as a white solid. $^1$H NMR (400 MHz, Methanol-d4) δ (ppm): 8.80 (d, J=8.0 Hz, 1H), 8.26 (s, 1H), 8.08 (d, J=8.5 Hz, 1H), 7.99 (s, 1H), 7.98 (d, J=8.1 Hz, 1H), 7.57-7.51 (m, 1H), 7.51-7.43 (m, 2H), 7.38 (dd, J=8.6, 2.3 Hz, 1H). LCMS (M+1): 475.

Example 41

Preparation of Compound No. 91

N-(4-(2-Bromothiazol-4-yl)-3-chlorophenyl)-1,1,1-trifluoromethane sulfonamide (100 mg, 0.2380 mmol) and 1-[[5-fluoro-2-(4,4,5,5-tetramethyl-1,3,2-dioxaborolan-2-yl)phenyl]methyl]pyrrolidine (80 mg, 0.261 mmol), sodium carbonate (63 mg, 0.595 mmol), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol) the mixture was further purged for 2 min and was heated to 100° C. for 18 h. The reaction was monitored by LCMS. The reaction mixture was cooled to RT, water (10 mL) was added and the mixture extracted with EtOAc (3×25 mL). The combined organic layer was washed with water (4×30 mL), dried over sodium sulfate and concentrated under reduced pressure to obtain the crude product, which was purified by reverse phase HPLC to afford N-(3-chloro-4-{2-[4-fluoro-2-(pyrrolidin-1-ylmethyl)phenyl]-1,3-thiazol-4-yl}phenyl)-1,1,1-trifluoromethanesulfonamide (80 mg) as a pale red solid. $^1$H NMR (400 MHz, Methanol-d4) δ (ppm): 8.11 (dd, J=8.7, 5.4 Hz, 1H), 7.98 (s, 1H), 7.72 (d, J=8.4 Hz, 1H), 7.56 (dd, J=9.0, 2.7 Hz, 1H), 7.51-7.43 (m, 2H), 7.33 (dd, J=8.4, 2.2 Hz, 1H), 4.61 (s, 2H), 3.43 (t, 2H), 3.25 (t, 2H), 2.17 (m, 2H), 1.97 (m, 2H). LCMS (M+1): 521.4.

Example 42

Preparation of Compound No. 92

N-(4-(2-Bromothiazol-4-yl)-3-chlorophenyl)-1,1,1-trifluoromethane sulfonamide (100 mg, 0.2380 mmol) and N-cyclopentyl-4-(4,4,5,5-tetramethyl-1,3,2-dioxaborolan-2-yl)pyridin-3-amine (76 mg, 0. 0.261 mmol), sodium carbonate (63 mg, 0.595 mmol), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol) the mixture was further purged for 2 min and was heated to 100° C. for 18 h. The reaction was monitored by LCMS. The reaction mixture was cooled to RT; water (10 mL) was added and the mixture extracted with EtOAc (3×25 mL). The combined organic layer was washed with water (4×30 mL), dried over sodium sulfate and concentrated under reduced pressure to obtain the crude product, which was purified by reverse phase HPLC to afford N-(3-chloro-4-{2-[2-(cyclopentylamino)pyridin-4-yl]-1,3-thiazol-4-yl}phenyl)-1,1,1-trifluoromethanesulfonamide (96 mg) as a yellow solid. $^1$H NMR (400 MHz, Methanol-d4) δ (ppm): 8.25 (s, 1H), 7.94 (dd, J=14.6, 7.6 Hz, 2H), 7.57 (d, J=1.6 Hz, 1H), 7.44 (d, J=2.3 Hz, 1H), 7.40 (d, J=1.7 Hz, 1H), 7.38-7.29 (m, 1H), 4.11 (q, J=6.1 Hz, 1H), 2.14 (dt, J=13.2, 6.4 Hz, 2H), 1.84 (dt, J=6.6 Hz, 2H), 1.71 (tt, J=24.6, 11.7, 6.0 Hz, 4H). LCMS (M+1): 503.8.

Example 43

Preparation of Compound No. 93

N-(4-(2-Bromothiazol-4-yl)-3-chlorophenyl)-1,1,1-trifluoromethane sulfonamide (100 mg, 0.2380 mmol) and 3-(4,4,5,5-tetramethyl-1,3,2-dioxaborolan-2-yl)-1H-indole (64 mg, 0.261 mmol), sodium carbonate (63 mg, 0.595), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol) the mixture was further purged for 2 min and was heated to 100° C. for 18 h. The reaction was monitored by LCMS. The reaction mixture was cooled to RT, water (10 mL) was added and the mixture extracted with EtOAc (3×25 mL). The combined organic layer was washed with water (4×30 mL), dried over sodium sulfate and concentrated under reduced pressure to obtain the crude product, which was purified by reverse phase HPLC to afford N-{3-chloro-4-[2-(1H-indol-3-yl)-1,3-thiazol-4-yl]phenyl}-1,1,1-trifluoromethanesulfonamide (42 mg) as a white solid. $^1$H NMR (400 MHz, Methanol-d4) δ (ppm): 8.24-8.19 (m, 1H), 8.03 (d, J=8.5 Hz, 1H), 7.98 (s, 1H), 7.77 (s, 1H), 7.50-7.45 (m, 2H), 7.36 (dd, J=8.5, 2.3 Hz, 1H), 7.26-7.20 (m, 2H). LCMS (M+1): 458.3.

Example 44

Preparation of Compound No. 94

N-(4-(2-Bromothiazol-4-yl)-3-chlorophenyl)-1,1,1-trifluoromethane sulfonamide (100 mg, 0.2380 mmol) and 4-quinolyl boronic acid (61.7 mg, 0.3571 mol), sodium carbonate (63 mg, 0.595 mmol), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol) re-purged the mixture for 2 min and was heated to 100° C. for 18 h. The reaction was monitored by LCMS. The reaction mixture was allowed to cool to RT, water (10 mL) was added and the mixture extracted with EtOAc (3×25 mL). The combined organic layer was washed with water (4×30 mL), dried over anhydrous sodium sulfate and concentrated under reduced pressure to obtain a crude product, which was purified by reverse phase HPLC to afford N-[3-chloro-4-[2-(4-quinolyl)thiazol-4-yl]phenyl]-1,1,1-trifluoro-methanesulfonamide (37 mg) as a white solid. $^1$H NMR (400 MHz, Methanol-d4) δ (ppm): 7.94 (s, 1H), 7.89 (d, J=8.5 Hz, 1H), 7.57-7.48 (m, 1H), 7.46-7.38 (m, 4H), 7.31 (dd, J=8.5, 2.3 Hz, 2H), 6.16 (s, 1H), 5.64 (s, 1H). LCMS (M+1): 445.3.

Example 45

Preparation of Compound Nos. 6-36, 38-56, and 95-152

Compound nos. 6-36, 38-56, and 95-152 can be prepared using conditions analogous to those in both the General Methods and Examples provided above.

Example B1

Effect of Compounds on SREBP2 Cleavage and Cell Viability in HEPG2 Cells

Average SREBP2 cleavage in HEPG2 cells was measured in the presence of compounds disclosed in Table 1. HepG2 cells were seeded at 500,000 cells per well in 6-well plates in DMEM supplemented with 10% FBS. After 2 days, cells were treated with compounds (20 μM) for 1 day in DMEM without FBS. Western blots were normalized with respect to actin.

For viability measurements, HepG2 cells were seeded at 5,000 cells per well in 96-well plates in DMEM supplemented with 10% FBS. After 1 day in culture, cells were treated with compounds (20 μM & 5 μM) for 3 days in DMEM without FBS. Viability was measured by MTS. Treatment with compounds (20 μM & 5 μM) was carried out in medium without FBS, and viability was measured by MTS.

The results are shown in Table 3 as percent inhibition@20 μM, and in Table 4 as percent inhibition@5 μM.

TABLE 3

(20 μM)

| Compound No. | Average SREBP2 cleavage (% Inhibition, n = 3) | Average Viability (% Inhibition, n = 3) |
|---|---|---|
| 1 | 73.7 | 92.07 |
| 2 | 73 | 80.5 |
| 4 | 96.07 | 94.38 |
| 5 | 81.7 | 99.2 |
| 37 | 94.59 | 95.03 |
| 57 | 46.9 | 56.4 |
| 58 | 29.4 | 67.9 |
| 59 | 60.6 | 99.8 |
| 60 | 99.0 | 100.0 |
| 61 | 2.0 | 43.0 |
| 62 | 0.0 | 0.0 |
| 63 | 39.0 | 47.0 |
| 64 | 97.0 | 100.0 |
| 66 | 0.0 | 11.0 |
| 67 | 3.0 | 20.0 |

TABLE 4

(5 μM)

| Compound No. | Average SREBP2 cleavage (% Inhibition, n = 3) | Average Viability (% Inhibition, n = 3) |
|---|---|---|
| 37 | 75 | 94 |
| 70 | 73 | 100 |
| 71 | 77 | 97 |
| 72 | 61 | 94 |
| 73 | 64 | 99 |
| 74 | 76 | 97 |
| 75 | 55 | 88 |
| 76 | 7 | 3 |
| 77 | 56 | 41 |
| 78 | 38 | 87 |
| 79 | 65 | 74 |
| 80 | 90 | 86 |
| 81 | 44 | 88 |
| 82 | 77 | 82 |
| 83 | 2 | 0 |
| 84 | 20 | 18 |
| 85 | 82 | 93 |
| 86 | 54 | 27 |
| 87 | 50 | 9 |
| 88 | 90 | 19 |
| 89 | 53 | 5100 |
| 90 | 64 | 99 |
| 91 | 16 | 4 |
| 92 | 59 | 94 |
| 93 | 28 | 82 |
| 94 | 35 | 84 |
| 95 | 39 | 86 |

Compound #37 was further tested at several concentrations to obtain an $IC_{50}$ for SREBP2 cleavage of 4.6 μM and Viability of 2.15 μM, as shown in FIG. 1.

Example B2

Effect of Compounds on a Human LnCap Xenograft

Figure 2:
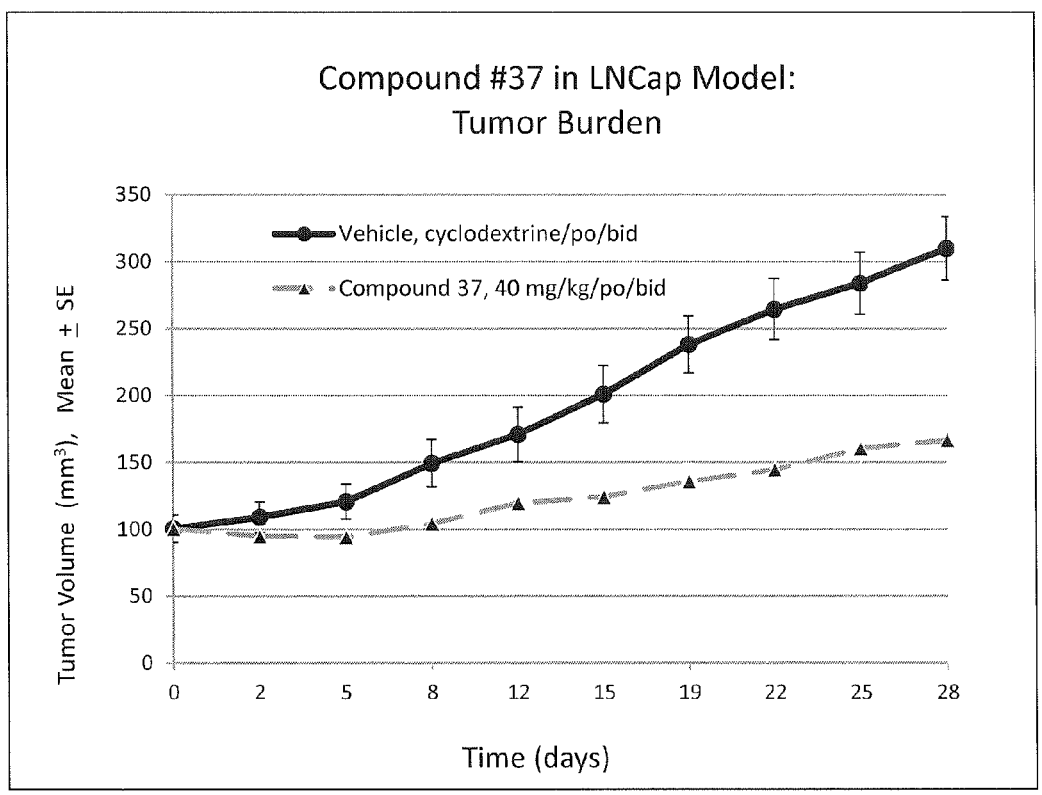
FIG. 2. Graph showing effect of compound #37 on a human LnCap xenograft.

LnCap cells were inoculated in male nude mice. Animals were randomized into 3 treatment groups (n=10 per group) when tumor size reached 100 mm³. One group was treated by oral gavage with the vehicle solution twice a day; and another group was treated at 40 mg/kg/po/bid compound #37. Tumor volume was measured by caliper measurements twice a week during the course of the experiment (4 weeks). The results are shown in FIG. 2.

Example B3

Effect of Compounds in Various Cell Lines

Cytotoxicity and $IC_{50}$ Determination

Cell plating: Cells were cultured in medium with 10% regular FBS. Cells were harvested respectively during the logarithmic growth period and counted using Countstar. Cells were split to two sets: one set was cultured in medium+ 5% regular FBS and the other set was cultured in medium+ 5% LDFBS (lipid reduced FBS). Cell concentrations were adjusted to 2.22×104 cells/mL with respective culture medium for 3-day CTG assay. (The cell density was optimized before actual study; cell density used in the test may vary for different cell lines). For each serum condition, 90 μl cell suspensions were added to two 96-well plates (plate A and B) with the final cell density of 2×103 cells/well for 3-day CTG assay (The cell density was optimized before actual study; cell density used in the test may vary for different cell lines). 10 μl of culture medium was added to each well of plate A group for T0 reading. All plates were incubated (A and B groups) overnight in humidified incubator at 37° C. with 5% CO2.

Day 0: T0 reading: For plate A group, CellTiter-Glo® Reagent was added at equal volume of cell culture medium present in each well (e.g., add 100 μl of reagent to 100 μl of medium containing cells for a 96-well plate). Contents were mixed for 2 min on an orbital shaker to facilitate cell lysis. The plate was allowed to incubate at RT for 10 min to stabilize luminescent signal. Note: Uneven luminescent signal within standard plates can be caused by temperature gradients, uneven seeding of cells or edge effects in multi-wall plates. A Backseal black sticker was affixed to the bottom of each plate. Luminescence was recorded (T0) using EnVision Multi Label Reader.

Day 0: compound treatment: Test compounds and positive controls were dissolved with PBS as stock solution at the concentration indicated at Test Article Dilution map. A 500× solution was prepared in DMSO, then diluted with appropriate culture media (1:50) into 10× working solutions. 10 μl (10×) drug solutions were dispensed in each well (triplicate for each drug concentration) of the plate B group according to plate inoculation map. The test plates were incubated for 3 days in the humidified incubator at 37° C. with 5% CO2.

Figure 3:
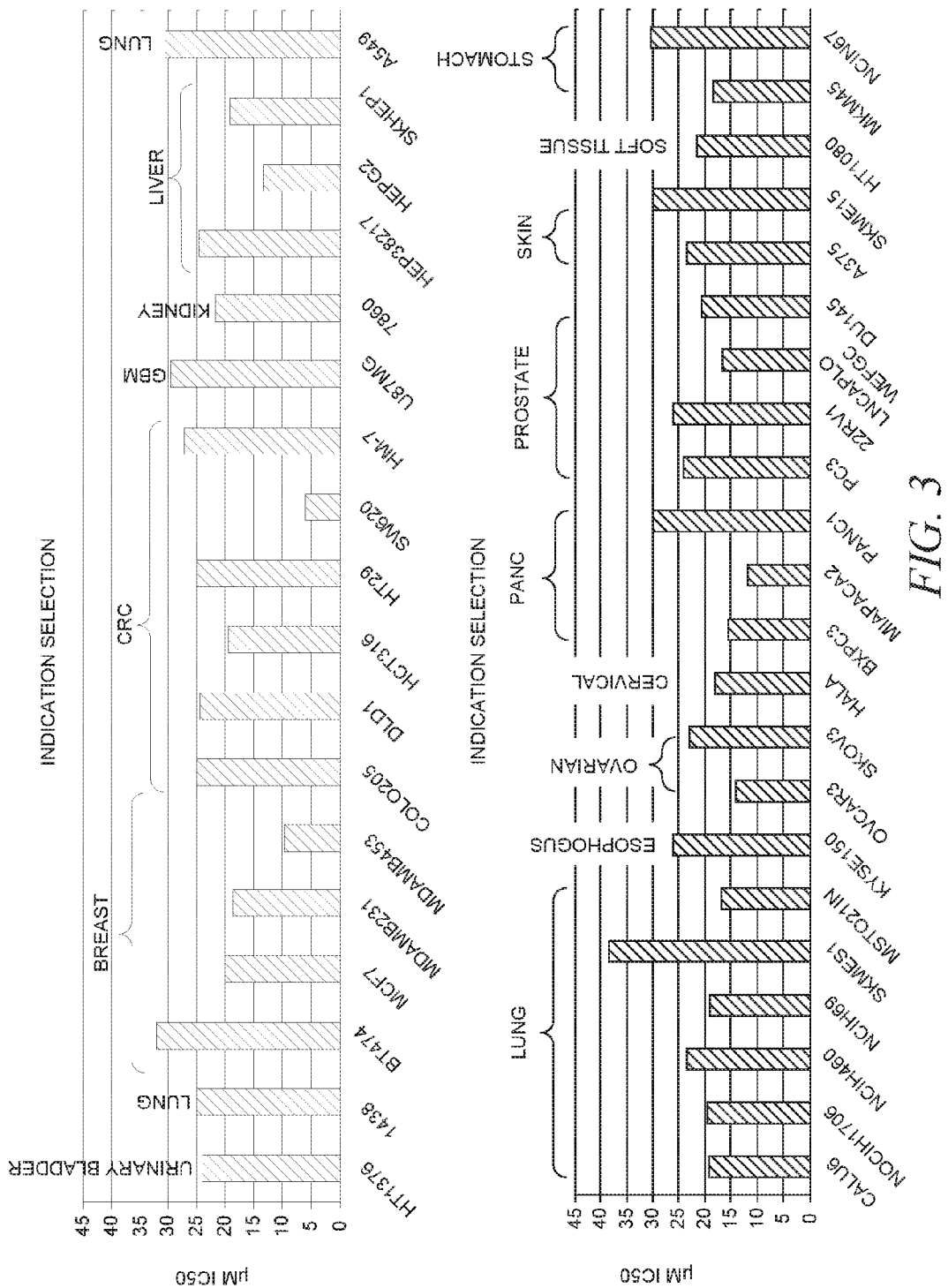
FIG. 3. Cell line panel $IC_{50}$ data for Compound #37.

Day 3: Plate B group reading. CellTiter-Glo® Reagent was added at equal volume of cell culture medium present in each well (e.g., add 100 μl of reagent to 100 μl of medium containing cells for a 96-well plate). Contents were mixed for 2 min on an orbital shaker to induce cell lysis. The plate was allowed to incubate at RT for 10 min to stabilize luminescent signal. Note: Uneven luminescent signal within standard plates can be caused by temperature gradients, uneven seeding of cells or edge effects in multiwall plates. A Backseal black sticker was affixed to the bottom of each plate. Record luminescence using EnVision Multi Label Reader. $IC_{50}$ values were calculated for each Compound for each cell line. The results are shown in FIG. 3 for Compound #37.

Example B4

PK Data for Representative Compounds

Standard PK parameters were collected in Mouse and Dog for Compound #37 in mouse (FIG. 4A) and dog (FIG. 4B). Data for additional compounds was collected and is presented in Table B4:

TABLE B4

PK parameters for representative compounds

| | i.v. @ 2 mg/kg | | | | | p.o. @ 10 mg/kg | | | | |
|---|---|---|---|---|---|---|---|---|---|---|
| Cpd No. | $C_{max}$ (µM) | $AUC_{last}$ (µM * h) | Terminal $t_{1/2}$ (h) | CL (L/h/kg) | $V_d$ (L/kg) | $C_{max}$ (µM) | $T_{max}$ (h) | $AUC_{last}$ (µM * h) | Terminal $t_{1/2}$ (h) | Bioavailability |
| 5 | 10.2 | 41 | 2.51 | 0.095 | 0.345 | 20.3 | 1 | 302 | 6.96 | 149.0% |
| 60 | 3.38 | 12.6 | 3.08 | 0.288 | 1.28 | 6.58 | 4 | 57.1 | >8 hrs | 90.20% |
| 64 | 7.13 | 38.5 | | 0.055 | 1.95 | 32.1 | 24 | 526 | >8 hrs | 273% |
| 70 | 4 | 2.2 | 1.1 | 3.28 | 5.22 | 2.2 | 0.5 | 5.19 | 1.04 | 46.4% |
| 71 | 3.57 | 13.6 | 3.5 | 0.251 | 1.27 | 7.57 | 4 | 51.5 | >8 hrs | 75.9% |
| 80 | 3.63 | 8.94 | 2.8 | 4.25 | 1.72 | 20.6 | 4 | 130 | >8 hrs | 291.0% |
| 82 | 12.6 | 25.4 | 3.64 | 0.137 | 0.719 | 25.8 | 4 | 175 | >8 hrs | 138.0% |
| 85 | 0.241 | 0.655 | 4.08 | 4.63 | 27.3 | 0.45 | 2 | 2.27 | >8 hrs | 69.3% |
| 88 | 3.44 | 10.6 | 3.35 | 0.3 | 1.45 | 8.41 | 2 | 51.5 | >8 hrs | 96.8% |

Example B5

Effect of Compounds on a Human In-Vivo MDA-MB-453 Xenograft

Cell line: Human breast cancer cell line MD-MB-453 was purchased from ATCC (Manassas, Va.). Cells were grown at atmospheric $CO_2$ in L-15 media containing 10% fetal bovine serum, penicillin streptomycin, L-glutamine, and sodium pyruvate. Cells were spun down and resuspended at a concentration of 6.0E07 cells/mL in serum-free medium without additives, then combined 1:1 with Matrigel™ (Trevigen, Gaithersburg, Md.).

Surgical implantation of DHT pellets: One week after castration, the animals were anesthetized with a mixture of isoflurane and oxygen and the surgical area was sterilized using iodine and alcohol. Each animal was implanted with 12.5 mg 5α-DHT 60-day slow release pellets (Innovative Research of America, Sarasota, Fla.) on the lateral side of the neck between the ear and the shoulder. The skin was closed with a 6-0 silk suture.

Injection of orthotopic cells: Two days after pellet implantation, the mice were inoculated by injection underneath the nipple of the number 4 mammary fat pad with 200 µL (6.0E06 cells) per mouse of the freshly prepared MD-MB-453: Matrigel mixture. All procedures were carried out in HEPA-filtered laminar-flow hoods.

Study design: When the tumors reached a mean volume of approximately 100 $mm^3$, sixty animals with established tumors and moderate body weights were randomized into 6 treatment groups (Group 1-6, n=10 mice each). Group 1 was treated once daily with vehicle (20% HPBCD). Groups 2 to 5 were treated once daily with Compound #37 with (respectively) 1, 3, 10, or 30 mg/kg. Group 6 was treated twice daily (at intervals of ~8-10 h) with Compound #37 at 10 mg/kg. All treatments were administered as oral gavage (PO) at a dose volume of 5 mL/kg. Doses were administered starting on the staging day and continued for 42 days (Days 0-41).

Figure 5:
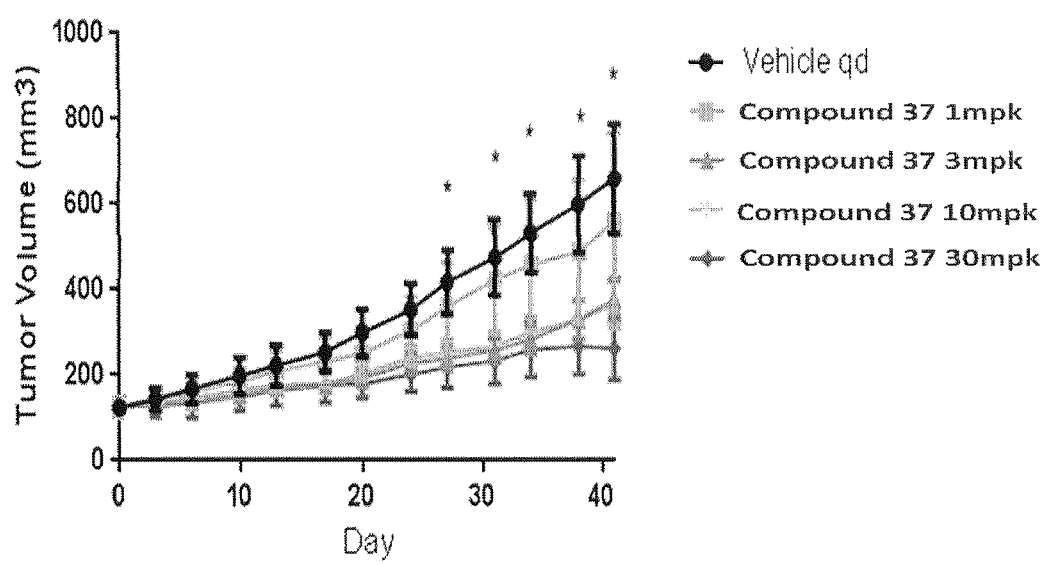
FIG. 5. Graph showing the effect of Compound #37 on a human in vivo MDA-MB-453 xenograft.

Tumor volume was measured by caliper measurements twice a week during the course of the experiment (4 weeks). The results are shown in FIG. 5.

Example B6

Effect of Compounds on an In-Vivo LnCAP Human Prostate Adenocarcinoma Xenograft

An efficacy study of Compound #37 on LnCap Cancer Xenograft in SCID Mice was performed by MuriGenics, Inc.

Experimental Animals:

Ninety-five male Beige Severe Combined Immune Deficiency (SCID) mice were purchased from Charles River (Hollister, Calif.) as 6- to 7-week-old mice.

Following arrival, animals were weighed using an electronic balance (Ohaus SCOUT® PRO, Parsippany, N.J.), given a clinical examination to ensure that the animals were in good condition, and housed 5 per cage. The animals were maintained in a HEPA-filtered environment in a Modular Animal Caging System (MACS) full-ventilation rodent housing system (Alternative Design, Arkansas). Animal room controls were set to maintain temperature and relative humidity at 22° C.±4° C. and 50%±20%, respectively. Housing rooms were on a 12:12 light/dark cycle. Cages were autoclaved. Water was autoclaved and supplied ad libitum to each cage via water bottles. Irradiated 2016 Teklad Global 16% Protein Rodent Diet and SaniChip irradiated bedding 7090A were obtained from Harlan Teklad (Hayward, Calif.).

Compound Formulation:

Dose suspensions of Compound #37 were formulated in 20% HPCD at 5.0, 15.0, 50.0, and 150 mg/mL (for administration at 1, 3, 10, and 30 mg/kg (mg/kg), respectively). Specifically, vehicle was dispensed into a vial containing a measured amount of test article powder and the vial was vortexed and sonicated until the test article was suspended completely, approximately 5-15 minutes. The vial contents then were brought to the required volume with additional vehicle, and the solution was vortexed and sonicated for an additional 2-5 minutes. The dosing suspensions (test article in 20% HPCD) were prepared freshly and used within one hour of formulation.

Cell Line:

Human prostate adenoma cancer cell line LnCaP was purchased from ATCC (Manassas, Va.). Cells were grown in 1640 RPMI containing 10% fetal bovine serum. Cells were spun down and resuspended at a concentration of 5.0E07 cells/mL in serum-free medium without additives, then combined 1:1 with Matrigel™ (Trevigen, Gaithersburg, Md.).

Injection of Cells:

At approximately 5 weeks before the projected initiation of dosing, each mouse was implanted, under isoflurane anesthesia, by injection into the left flank with 200 µL (5.0E06 cells) per mouse of the freshly prepared LnCaP: Matrigel mixture (50:50). All procedures were carried out in HEPA-filtered laminar-flow hoods.

Study Design:
Study design and treatments of all groups are shown in B6.

TABLE B6

Study Design

Treatment Phase (Days 0-39)

| Group | Agent | Dose (mg/kg, PO) | Frequency | n |
|---|---|---|---|---|
| 1 | Vehicle | 0 | QD | 10 |
| 2 | Compound #37 | 1 | QD | 10 |
| 3 | Compound #37 | 3 | QD | 10 |
| 4 | Compound #37 | 10 | QD | 10 |
| 5 | Compound #37 | 30 | QD | 10 |
| 6 | Compound #37 | 10 | BID | 10 |

When the tumors reached a mean volume of approximately 100 mm³, sixty animals with established tumors and moderate body weights were randomized into 6 treatment groups (Group 1-6, n=10 mice each). Group 1 was treated once daily with vehicle. Groups 2 to 5 were treated once daily with Compound #37 with (respectively) 1, 3, 10, or 30 mg/kg. Group 6 was treated twice daily (at intervals of ~8-10 hr) with Compound #37 at 10 mg/kg. All treatments were administered as oral gavage (PO) at a dose volume of 5 mL/kg. Doses were administered starting on the staging day and continued for 40 days (Days 0-39).

Body weights were measured twice per week using an electronic balance (Ohaus SCOUT® PRO). Tumor sizes were measured twice per week using microcalipers (Mitutoyo, Aurora, Ill.) to measure the perpendicular minor dimension (W) and major dimension (L). Tumor volume (mm³) was calculated using the formula L×W×H/2.

At 1 hr after the final dose administration on Day 39, animals were subjected to terminal cardiocentesis and euthanized. For each animal, blood was collected as $K_2$EDTA plasma, split into 2 aliquots (minimum 50 μL each), and frozen at -80° C. One aliquot from each animal was submitted to Integrated Analytical Solutions, Inc. (Berkeley, Calif.), for assessment of test article exposure; the remaining aliquot was retained at -80° C. at MuriGenics pending further instructions from the client. At necropsy, terminal body weights were recorded, and tumors were excised, weighed, and split in two. Separate halves of each specimen were flash-frozen on dry ice and stored at -80° C. or drop-fixed in 10% neutral buffered formalin (NBF) pending further analyses.

Figure 6A:
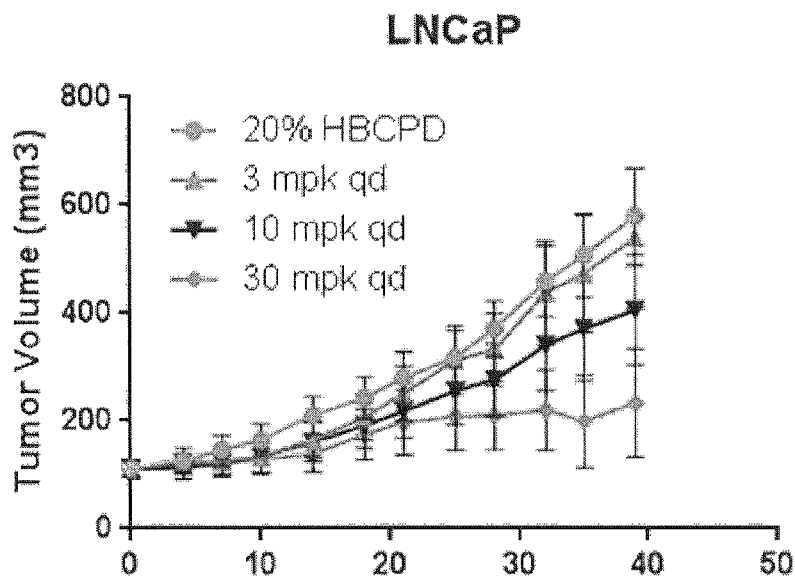
FIGS. 6A-B. Graph showing the effect of Compound #37 on a human in vivo LNCaP xenograft.
Figure 6B:
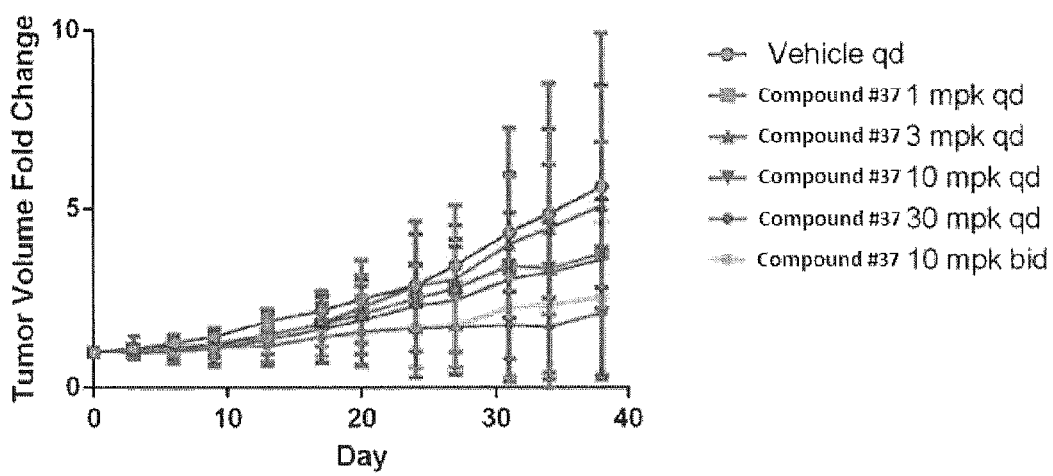

Statistical Analysis:
Descriptive and inferential analyses were performed using the corresponding functions of Excel 2010 (Microsoft, Redmond, Wash.). Inferential analysis consisted of t-test comparisons (two-tailed, heteroscedasticity assumed) to data from the vehicle-dosed (Group-1) animals. Values of p≤0.05 were considered statistically significant. The results on the effect of Compound #37 on tumor volumes are presented in FIGS. 6A and 6B.

Example B7

Effect of Compounds in a Mouse Liver Steatosis Model

The effects of Compounds of the invention in a non-alcoholic steatohepatitis (NASH) mouse screening model will be determined, provided by Physiogenex. Male C57BL/6J mice (n=40), 8 weeks old, are fed a high fat/cholesterol/cholic acid diet ("Paigen" diet) for up to 21 days, and compounds of the invention are dosed once daily at both 5 mg/kg and 20 mg/kg. Parameters to be determined include plasma biochemistry (ALT, AST, triglycerides, total cholesterol, fatty acids, IL-6), liver biochemistry (triglycerides, total cholesterol, fatty acids, 15 gene expression by RT-qPCR to assess lipid metabolism, cholesterol metabolism, SREBP proteolysis, ER stress, oxidative stress, inflammation, and fibrosis), and liver histology (H/E, Red Oil with quantification). Changes in liver weight, cholesterol, triglycerides, fatty acids, and enzymes will be assessed.

The invention claimed is:
1. A compound of Formulae (Ia):

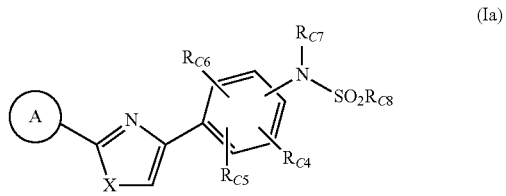

(Ia)

or a pharmaceutically acceptable salt thereof, wherein:
A is either:
  i. an aryl or heteroaryl, each having only one ring, substituted with 1, 2, or 3 substituents selected from the group consisting of halogen, CN, $CF_3$, OH, C1-C6 linear or branched alkyl, C3-C6 cycloalkyl, C3-C6 cycloalkenyl, C1-C6 linear or branched hydroxyalkyl, C1-C3 linear or branched alkoxy, C3-C6 cycloalkylmethyl, —$(CH_2)_mCF_3$, =O, —$CH_2OCH_3$, —OBn, —$CO_2H$, —$CO_2$-Alkyl, —NR10R11, and —CONR10R11; or
  ii. an aryl or heteroaryl, each having more than one ring, optionally substituted with 1, 2, or 3 substituents selected from the group consisting of halogen, CN, $CF_3$, OH, C1-C6 linear or branched alkyl, C3-C6 cycloalkyl, C3-C6 cycloalkenyl, C1-C6 linear or branched hydroxyalkyl, C1-C3 linear or branched alkoxy, C3-C6 cycloalkylmethyl, —$(CH_2)_mCF_3$, =O, —$CH_2OCH_3$, —$CH_2OH$, —OBn, —$CO_2H$, —$CO_2$-Alkyl, —NR10R11, and —CONR10R11;

Each $R_{C4}$, $R_{C5}$, and $R_{C6}$, is independently hydrogen, halogen, CN, $CF_3$, OH, C1-C3 linear or branched alkyl, C2-C3 alkenyl, C2-C3 alkynyl, C3-C6 cycloalkyl, C3-C6 cycloalkenyl, C1-C3 linear or branched alkoxy, —$CO_2H$, —CONR10R11, or —$NHCONH_2$;
or is taken with $R_{C7}$ to form the moiety

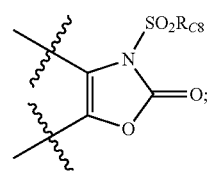

$R_{C7}$ is hydrogen, C1-C6 linear or branched alkyl, C1-C6 linear or branched hydroxyalkyl, —$(CR_{9a}R_{9b})_m$NR10R11, —$CO_2$-Alkyl, —$(CR_{9a}R_{9b})_m$O-Alkyl, —$(CR_{9a}R_{9b})_m$OPO$_3$Na$_2$, —$(CR_{9a}R_{9b})_m$O(CR$_{9a}R_{9b})_n$O-Alkyl, —$(CR_{9a}R_{9b})_m$O(C=O)-Alkyl, —$(CR_{9a}R_{9b})_m$O(CR$_{9a}R_{9b})_n$O(C=O)-Alkyl, —(C═O)CH═CH$_2$, —SO$_2$R$_{C8'}$; or is taken with one of R$_{C4}$, R$_{C5}$ or R$_{C6}$ to form the moiety

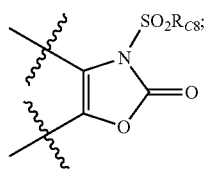

R$_{C8}$ is a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

R$_{C8'}$ is a linear or branched C1-C6 alkyl, a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

Each R$_{9a}$ and R$_{9b}$, where present, is independently hydrogen or C1-C6 linear or branched alkyl;

R10 and R11 are independently hydrogen, —SO$_2$R$_{C8'}$, C1-C6 linear or branched alkyl, C2-C6 linear or branched alkenyl, C3-C6 cycloalkyl, or C3-C6 cycloalkenyl; or are taken together with the N to which they are attached to form a C3-C6 heterocycle, pyrrolidinone, piperidinone, oxazolidinone, oxazinanone, imidazolidinone, tetrahydropyrimidin-2(1H)-one, a 1λ$^6$,2-thiazolidine-1,1-dione, a 1,2λ$^6$,3-oxathiazolidine-2,2-dione, or a 1λ$^6$,2,5-thiadiazolidine-1,1-dione;

X is a heteroatom selected from S, O; or NR$_B$ wherein R$_B$ is hydrogen, a C1-C6 linear or branched alkyl, or a C3-C6 cycloalkyl; and Each m and n is 1, 2 or 3.

2. The compound of claim 1, wherein compound is of formulae (IIa):

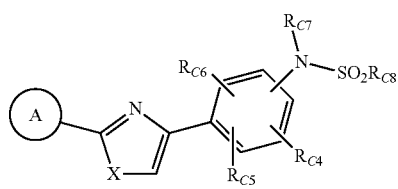

(IIa)

or a pharmaceutically acceptable salt thereof, wherein:
A is a moiety selected from the group consisting of:

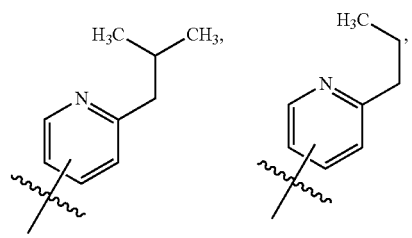

-continued

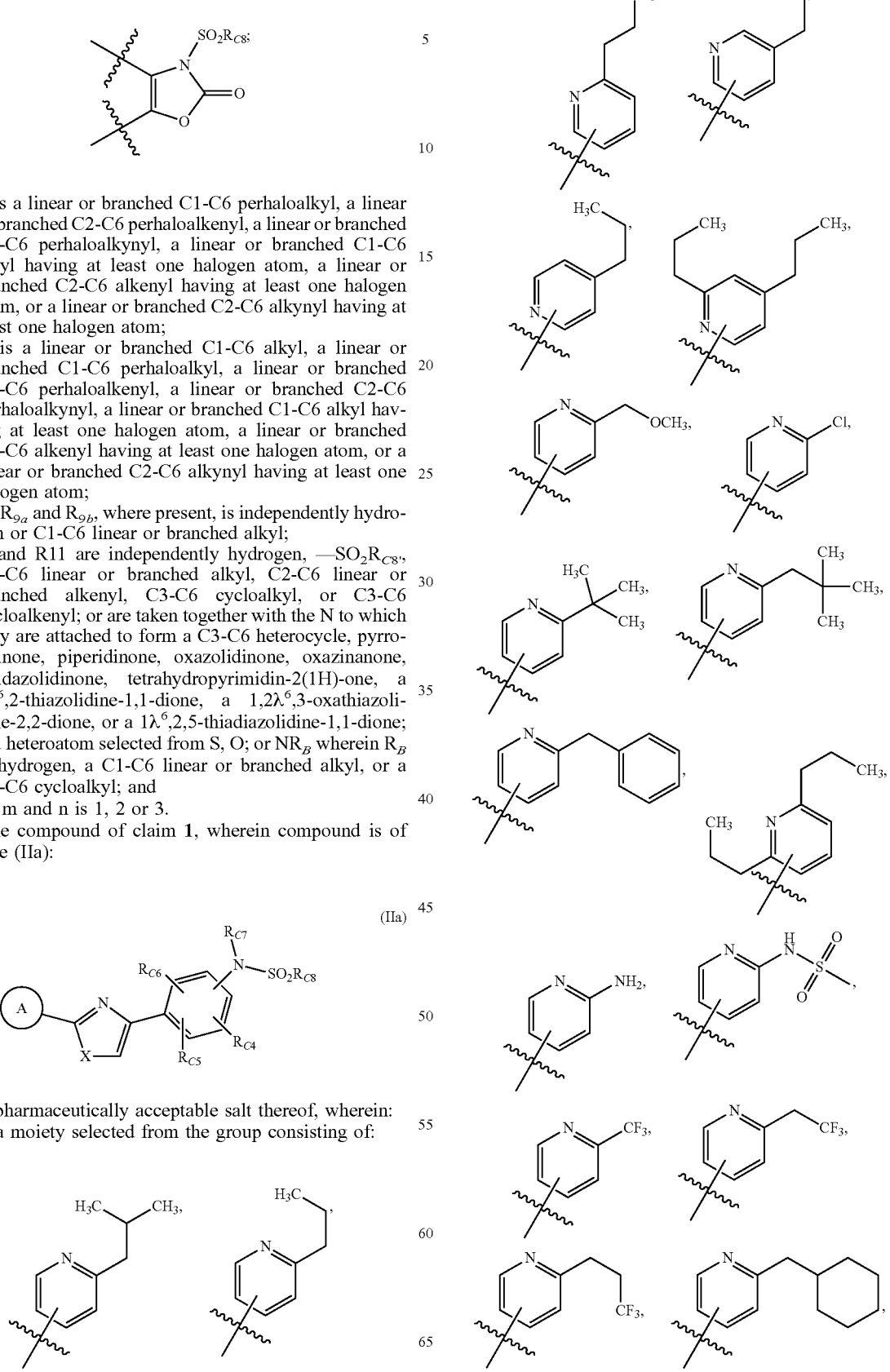

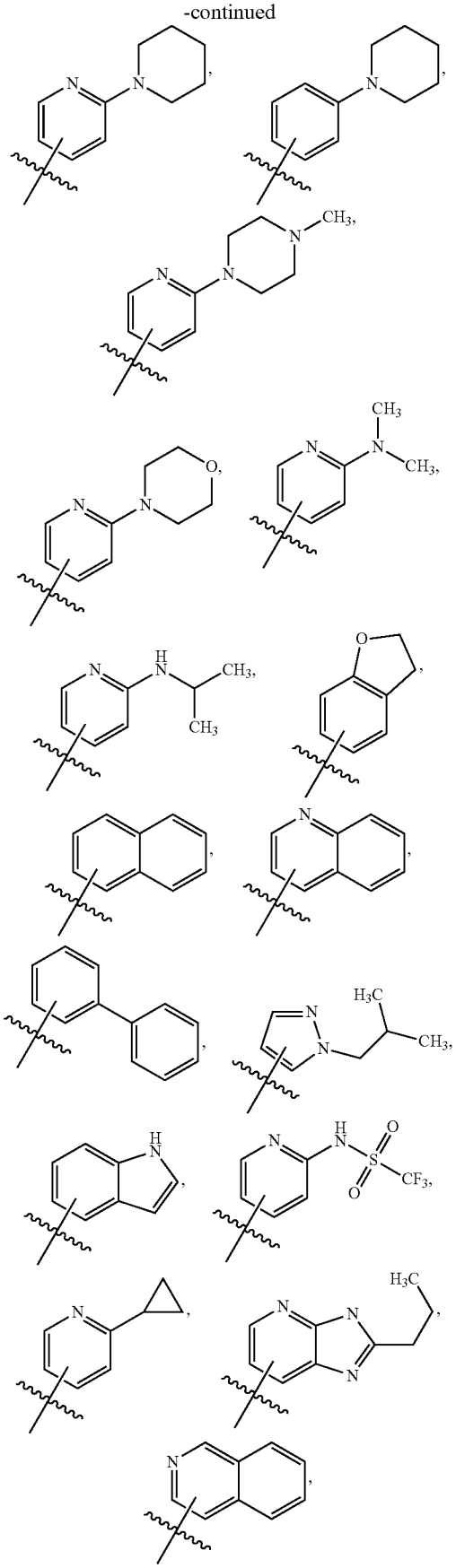
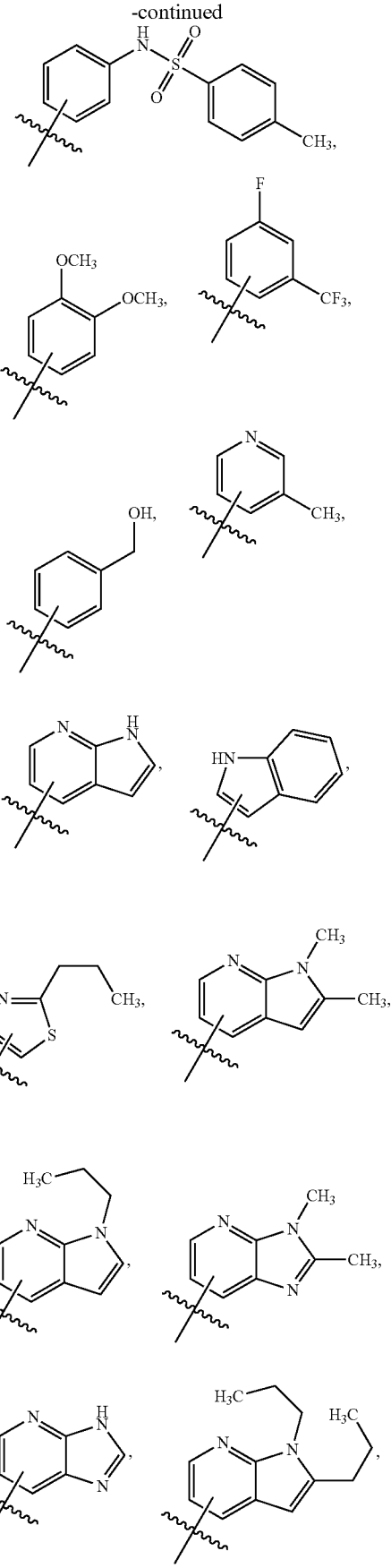

149
-continued

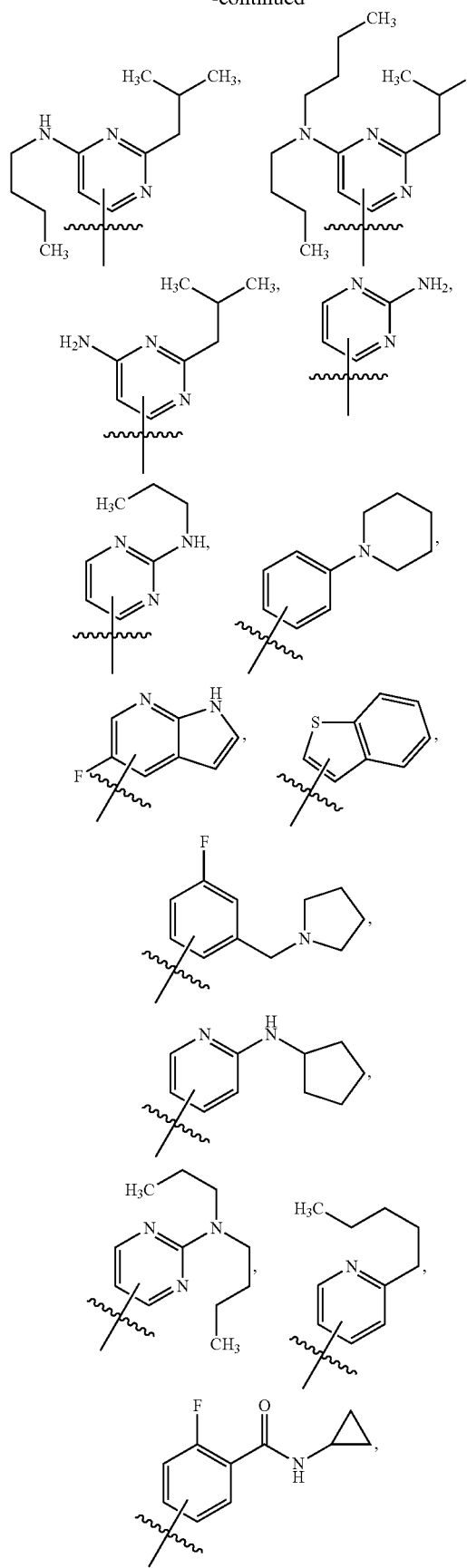

150
-continued

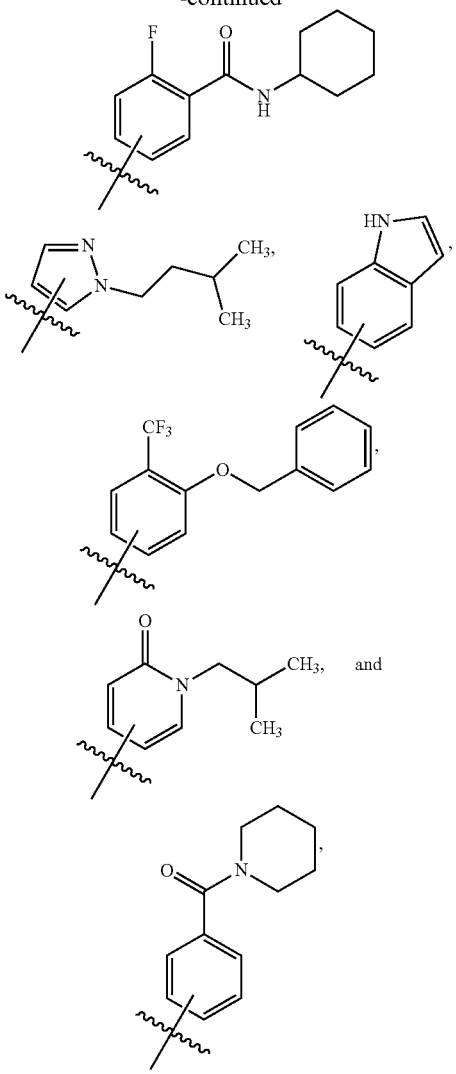

wherein the ring containing X is linked to ring A at any available position on ring A;

Each $R_{C4}$, $R_{C5}$, and $R_{C6}$, is independently hydrogen, halogen, CN, $CF_3$, OH, C1-C3 linear or branched alkyl, C2-C3 alkenyl, C2-C3 alkynyl, C3-C6 cycloalkyl, C3-C6 cycloalkenyl, C1-C3 linear or branched alkoxy, —$CO_2H$, —CONR10R11, or —$NHCONH_2$;

or is taken with $R_{C7}$ to form the moiety

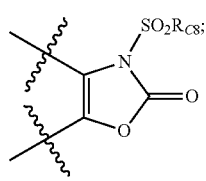

$R_{C7}$ is hydrogen, C1-C6 linear or branched alkyl, C1-C6 linear or branched hydroxyalkyl, —$(CR_{9a}R_{9b})_m NR10R11$, —$(CR_{9a}R_{9b})_m O$-Alkyl, —$(CR_{9a}R_{9b})_m OPO_3Na_2$, —$(CR_{9a}R_{9b})_m O(CR_{9a}R_{9b})_n O$-Alkyl, —$(CR_{9a}R_{9b})_m O(C=O)$-Alkyl, —$(CR_{9a}R_{9b})_m O$ $(CR_{9a}R_{9b})_nO(C=O)$-Alkyl, $-(C=O)CH=CH_2$, $-SO_2R_{C8'}$; or is taken with one of $R_{C4}$, $R_{C5}$ or $R_{C6}$ to form the moiety

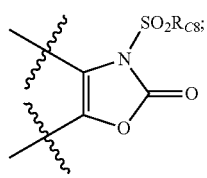

$R_{C8}$ is a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

$R_{C8'}$ is a linear or branched C1-C6 alkyl, a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

Each $R_{9a}$ and $R_{9b}$, where present, is independently hydrogen or C1-C6 linear or branched alkyl;

R10 and R11 are independently hydrogen, $-SO_2R_{C8'}$, C1-C6 linear or branched alkyl, C2-C6 linear or branched alkenyl, C3-C6 cycloalkyl, or C3-C6 cycloalkenyl; or are taken together with the N to which they are attached to form a C3-C6 heterocycle, pyrrolidinone, piperidinone, oxazolidinone, oxazinanone, imidazolidinone, tetrahydropyrimidin-2(1H)-one, a $1\lambda^6,2$-thiazolidine-1,1-dione, a $1,2\lambda^6,3$-oxathiazolidine-2,2-dione, or a $1\lambda^6,2,5$-thiadiazolidine-1,1-dione;

X is a heteroatom selected from S, O; or $NR_B$ wherein $R_B$ is hydrogen, a C1-C6 linear or branched alkyl, or a C3-C6 cycloalkyl; and Each m and n is 1, 2 or 3.

3. The compound of claim 2, wherein A is a moiety selected from the group consisting of:

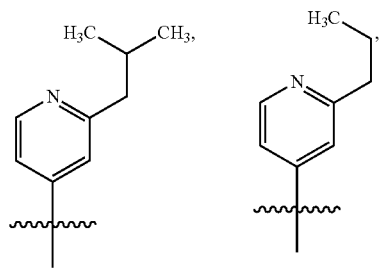

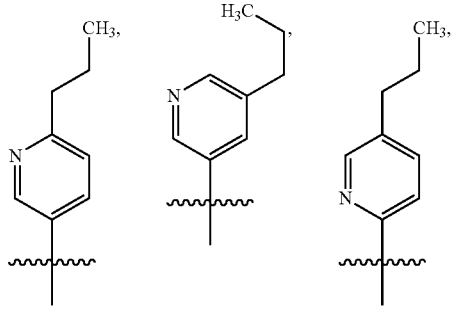

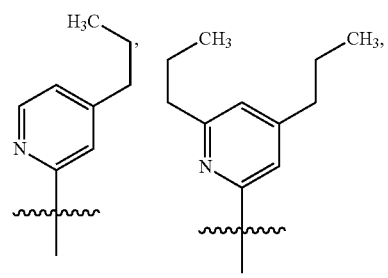

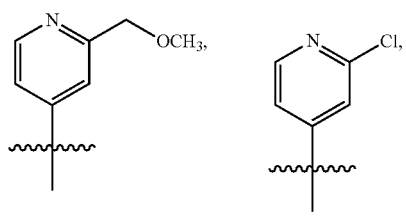

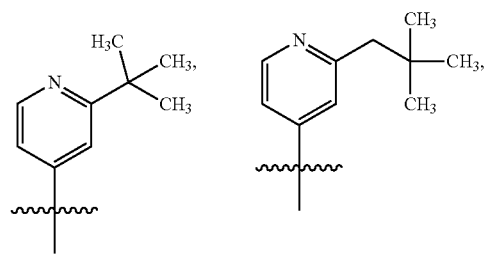

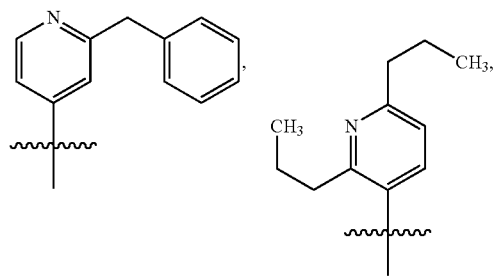

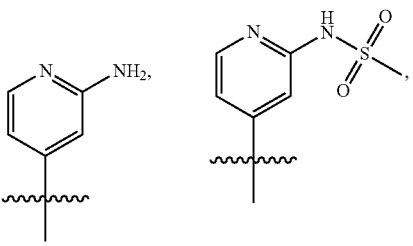

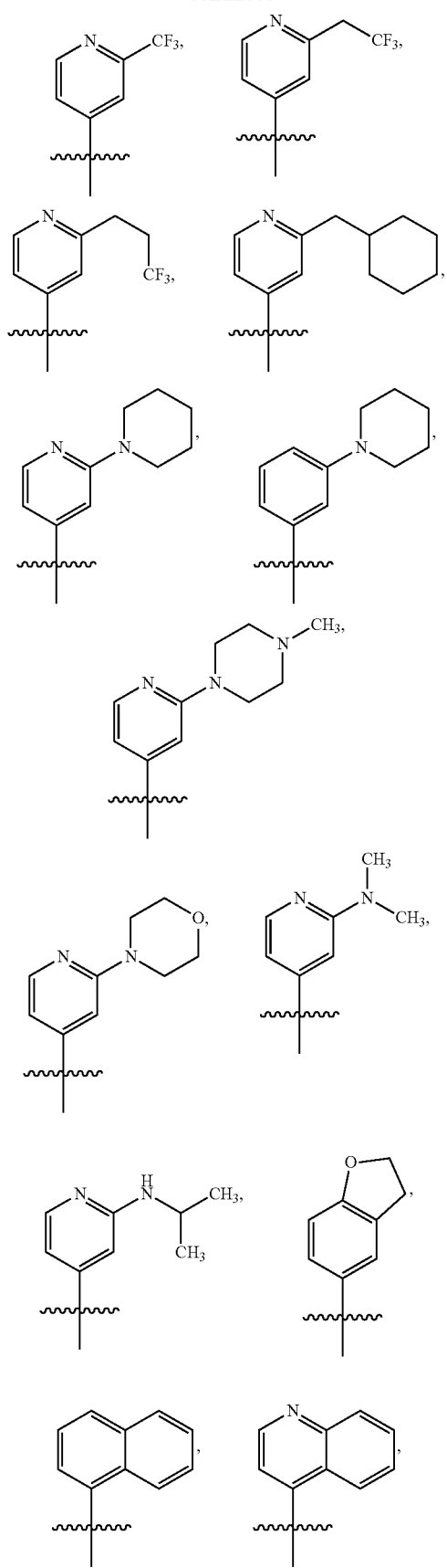
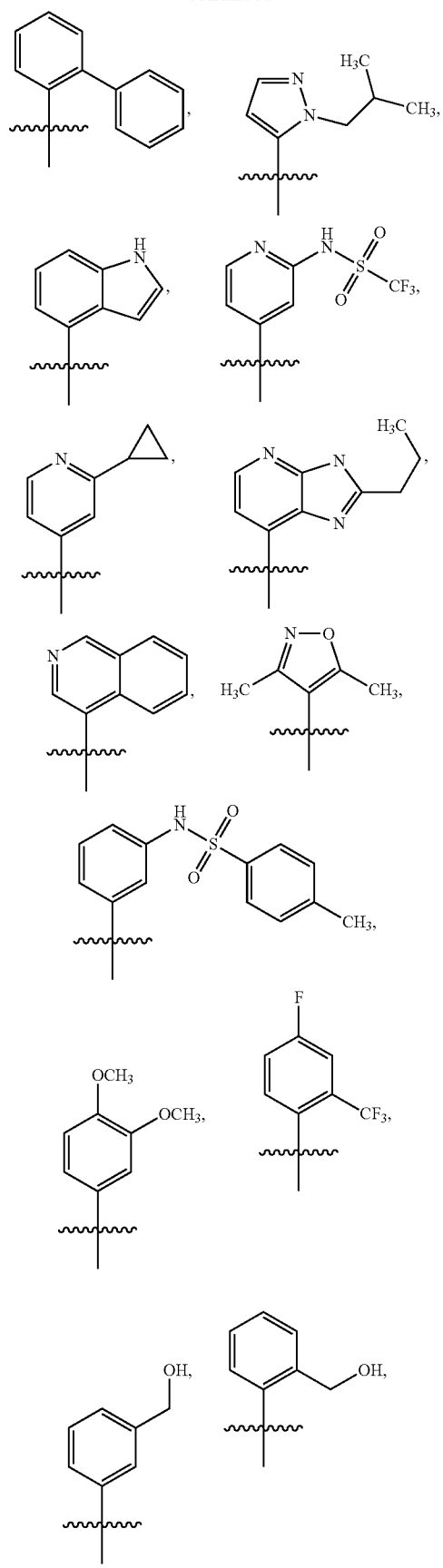

155
-continued
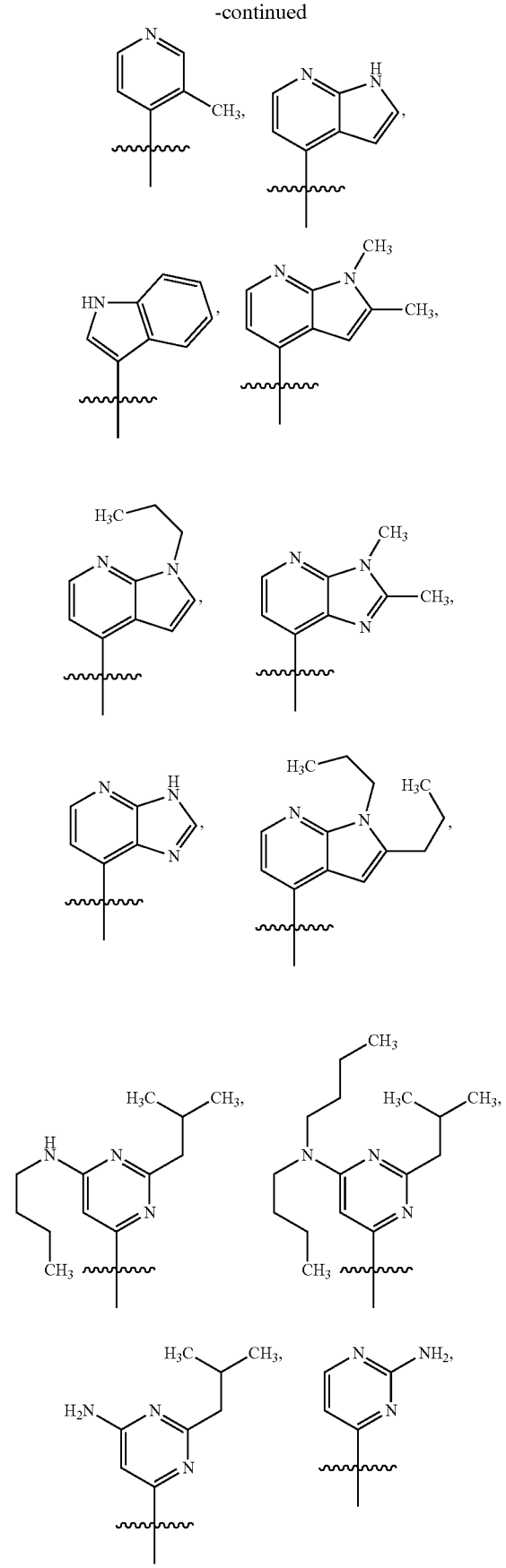
156
-continued
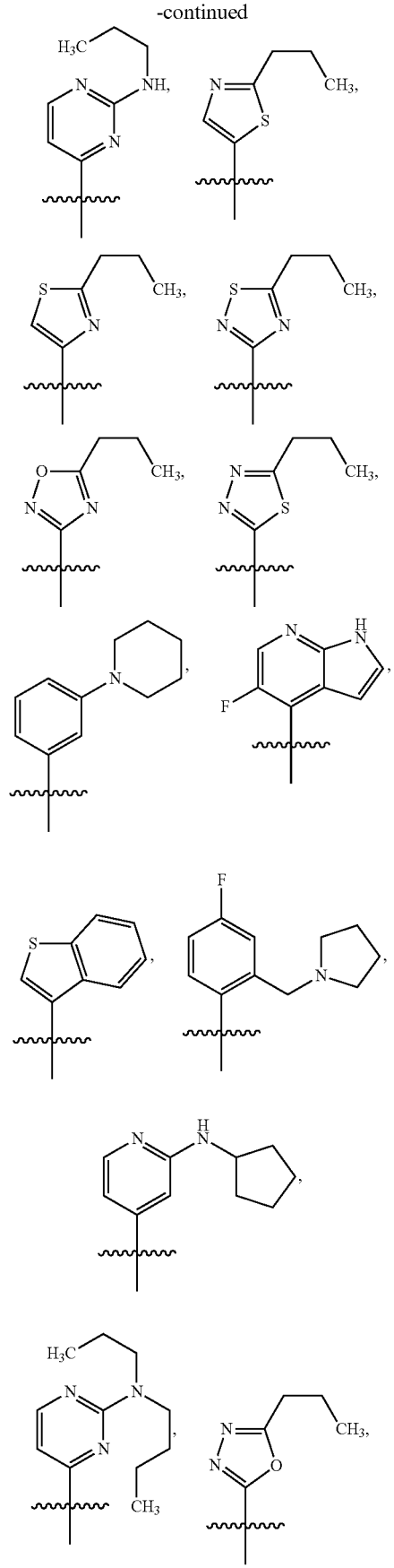

-continued
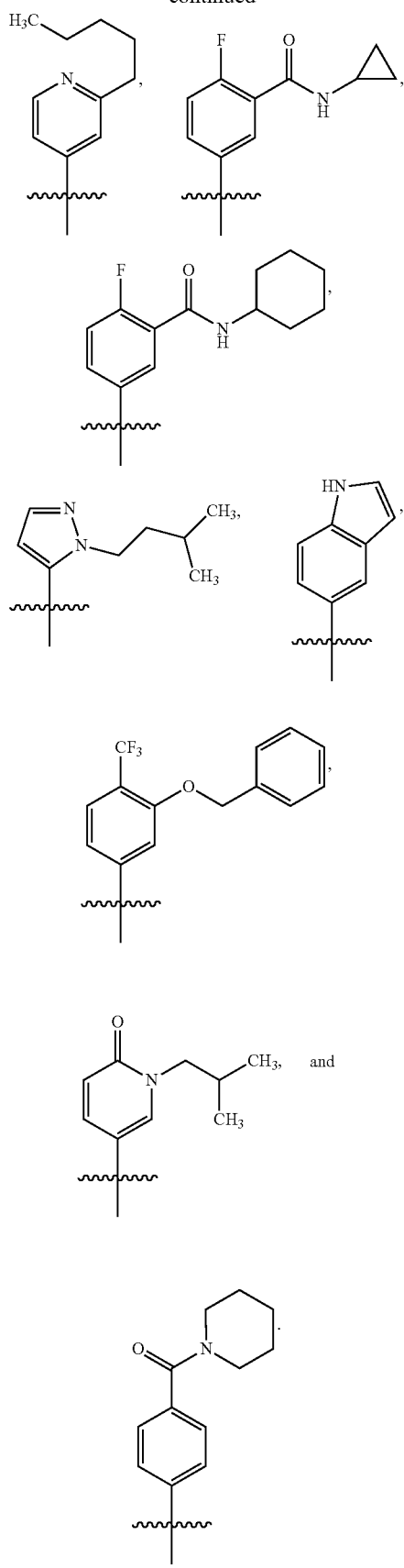
4. The compound of claim 3, wherein A is a moiety selected from the group consisting of:
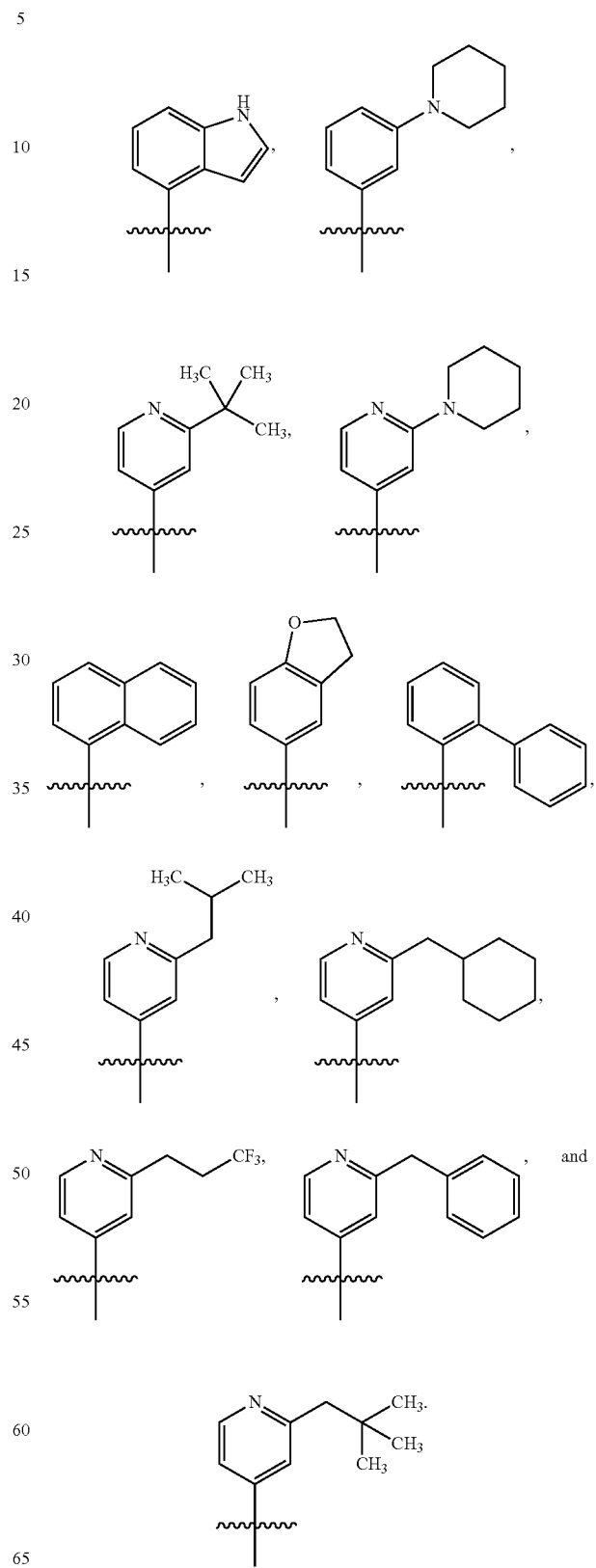

5. The compound of claim 4, wherein A is a moiety selected from the group consisting of:

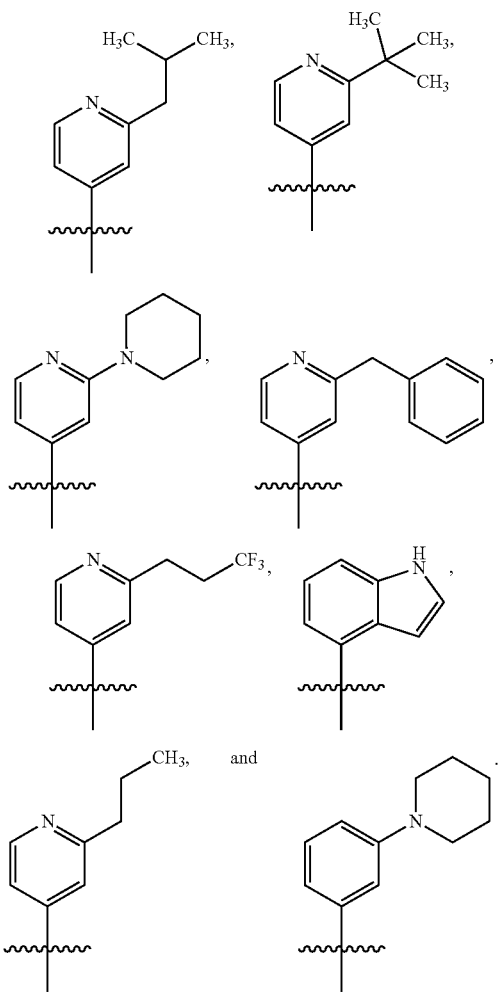

6. The compound of claim 1, wherein X is S.

7. The compound of claim 1, wherein X is NR$_B$, wherein R$_B$ is a linear or branched C1-C6 alkyl.

8. The compound of claim 7, wherein R$_B$ is a linear C1-C6 alkyl selected from methyl, ethyl, n-propyl, n-butyl, n-pentyl or n-hexyl.

9. The compound of claim 7, wherein R$_B$ is a branched C1-C6 alkyl selected from iso-propyl, iso-pentyl, and tert-butyl.

10. The compound of claim 1, wherein the phenyl ring containing the groups R$_{C4}$, R$_{C5}$, R$_{C6}$, and —NR$_{C7}$SO$_2$R$_{C8}$, is a moiety selected from:

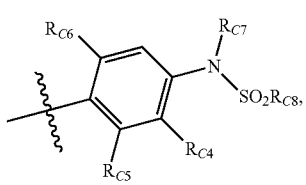

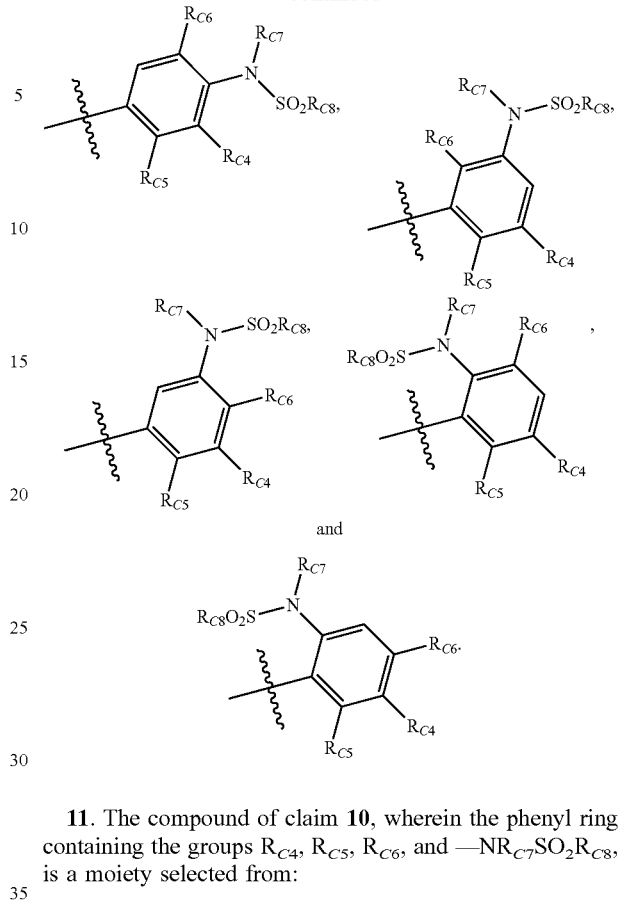

11. The compound of claim 10, wherein the phenyl ring containing the groups R$_{C4}$, R$_{C5}$, R$_{C6}$, and —NR$_{C7}$SO$_2$R$_{C8}$, is a moiety selected from:

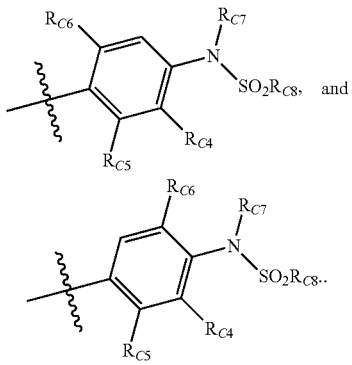

12. The compound of claim 1, wherein at least one of R$_{C4}$, R$_{C5}$ and R$_{C6}$ is hydrogen.

13. The compound of claim 12, wherein two of R$_{C4}$, R$_{C5}$ and R$_{C6}$ are hydrogen.

14. The compound of claim 12, wherein each R$_{C4}$, R$_{C5}$ and R$_{C6}$ is hydrogen.

15. The compound of claim 1, wherein at least one of R$_{C4}$, R$_{C5}$ and R$_{C6}$ is halogen.

16. The compound of claim 15, wherein two of R$_{C4}$, R$_{C5}$ and R$_{C6}$ are halogen.

17. The compound of claim 15, wherein each R$_{C4}$, R$_{C5}$ and R$_{C6}$ is halogen.

18. The compound of claim 1, wherein one of R$_{C4}$, R$_{C5}$ and R$_{C6}$ is hydrogen, and the remaining two of R$_{C4}$, R$_{C5}$ and R$_{C6}$ are halogen.

19. The compound of claim 1, wherein two of $R_{C4}$, $R_{C5}$ and $R_{C6}$ are hydrogen, and the remaining one of $R_{C4}$, $R_{C5}$ and $R_{C6}$ is halogen.
20. The compound of claim 1, wherein:
A is a moiety selected from
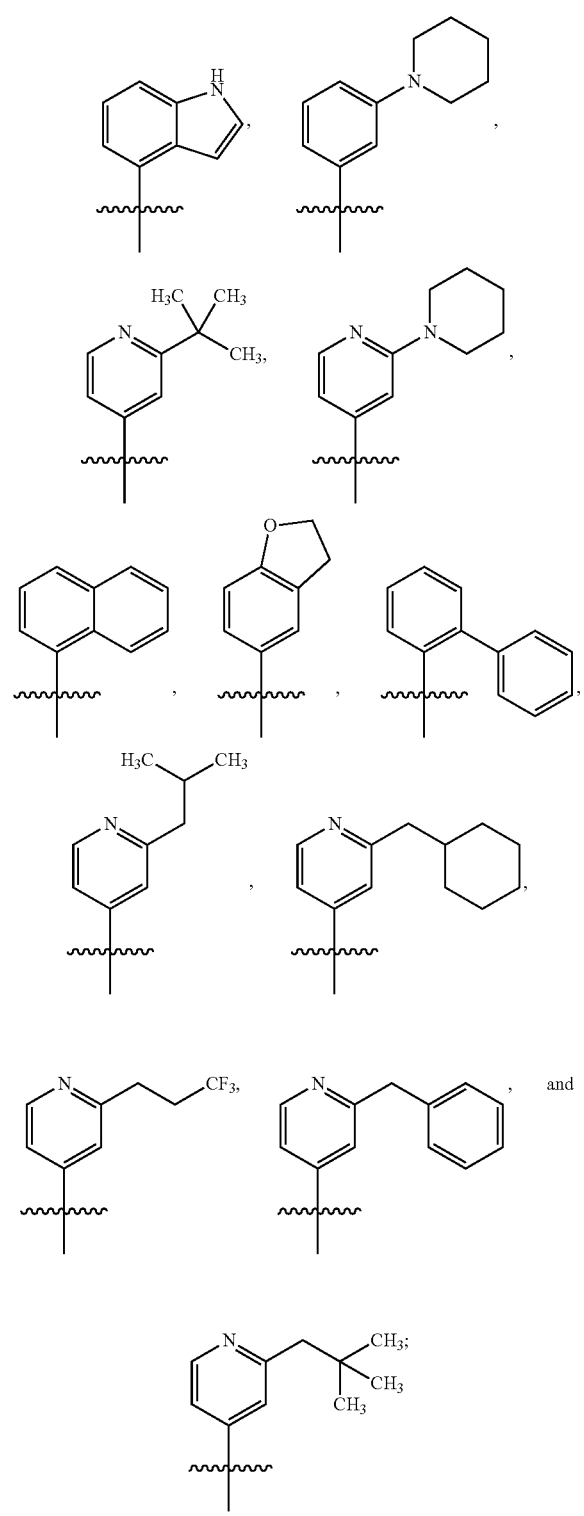
X is S, and
the phenyl ring containing the groups $R_{C4}$, $R_{C5}$, $R_{C6}$, and $-NR_{C7}SO_2R_{C8}$, is a moiety selected from:
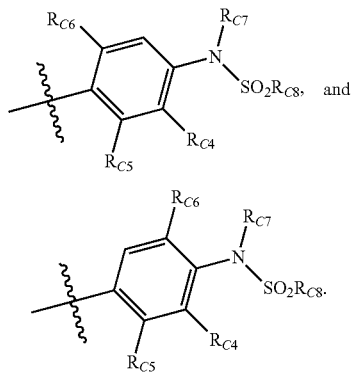
21. The compound of claim 1, wherein:
A is a moiety selected from
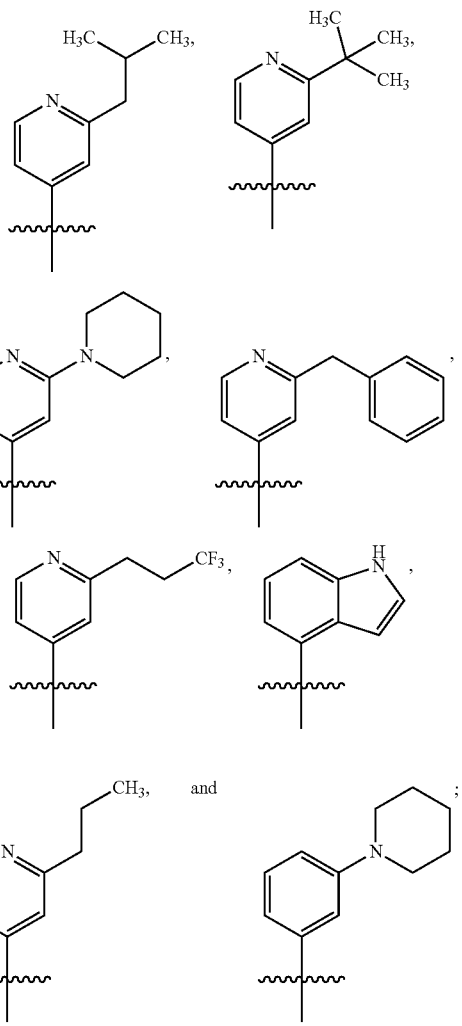

X is S, and the phenyl ring containing the groups $R_{C4}$, $R_{C5}$, $R_{C6}$ and —$NR_{C7}SO_2R_{C8}$, is a moiety selected from

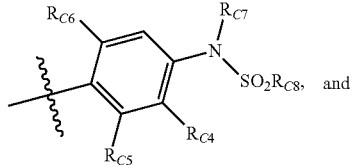

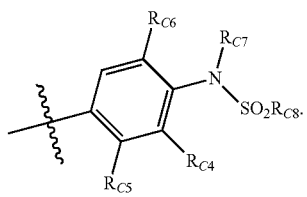

22. The compound of claim 1, wherein:
A is

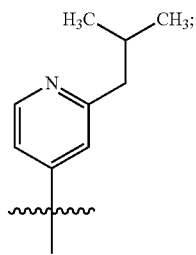

X is S, and the phenyl ring containing the groups $R_{C4}$, $R_{C5}$, $R_{C6}$, and —$NR_{C7}SO_2R_{C8}$, is selected from

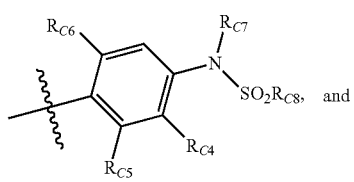

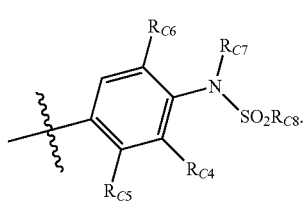

23. The compound of claim 2, wherein:
A is

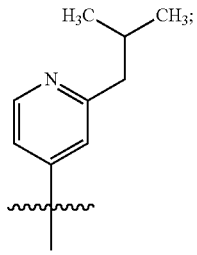 [SMILES: *c1ccnc(CC(C)C)c1]

X is S;

the phenyl ring containing the groups $R_{C4}$, $R_{C5}$, $R_{C6}$, and —$NR_{C7}SO_2R_{C8}$, is selected from

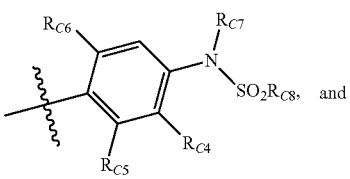

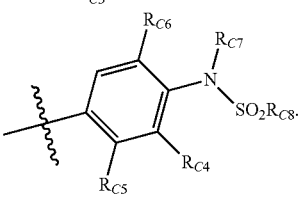

24. A compound selected from the group consisting of:
1,1,1-trifluoro-N-(4-(2-(2-propylpyridin-4-yl)thiazol-4-yl)phenyl)methanesulfonamide;
1,1,1-trifluoro-N-(3-(2-(2-propylpyridin-4-yl)thiazol-4-yl)phenyl)methanesulfonamide;
N-(3-chloro-4-(2-(1-isobutyl-1H-pyrazol-)thiazol-4-yl)phenyl)-1,1,1-trifluoromethanesulfonamide;
N-(3-chloro-4-(2-(2-propylpyridin-4-yl)thiazol-4-yl)phenyl)-1,1,1-trifluoromethanesulfonamide;
N-(4-(2-(2-tert-butylpyridin-4-yl)thiazol-4-yl)-3-chlorophenyl)-1,1,1-trifluoromethanesulfonamide;
N-(3-chloro-4-(2-(1,2-dimethyl-1H-pyrrolo[2,3-b]pyridin-4-yl)thiazol-4-yl)phenyl)-1,1,1-trifluoromethanesulfonamide;
N-(3-chloro-4-(2-(1-propyl-1H-pyrrolo[2,3-b]pyridin-4-yl)thiazol-4-yl)phenyl)-1,1,1-trifluoromethanesulfonamide;
N-(3-chloro-4-(2-(2,3-dimethyl-3H-imidazo[4,5-b]pyridin-7-yl)thiazol-4-yl)phenyl)-1,1,1-trifluoromethanesulfonamide;
N-(3-chloro-4-(2-(3-propyl-3H-imidazo[4,5-b]pyridin-7-yl)thiazol-4-yl)phenyl)-1,1,1-trifluoromethanesulfonamide;
N-(4-(2-(3H-imidazo[4,5-b]pyridin-7-yl)thiazol-4-yl)-3-chlorophenyl)-1,1,1-trifluoromethanesulfonamide;
N-(3-chloro-4-(2-(1,2-dipropyl-1H-pyrrolo[2,3-b]pyridin-4-yl)thiazol-4-yl)phenyl)-1,1,1-trifluoromethanesulfonamide;
N-(4-(2-(6-(butylamino)-2-isobutylpyrimidin-4-yl)thiazol-4-yl)-3-chlorophenyl)-1,1,1-trifluoromethanesulfonamide;

N-(3-chloro-4-(2-(6-(dibutylamino)-2-isobutylpyrimidin-4-yl)thiazol-4-yl)phenyl)-1,1,1-trifluoromethanesulfonamide;
N-(4-(2-(6-amino-2-isobutylpyrimidin-4-yl)thiazol-4-yl)-3-chlorophenyl)-1,1,1-trifluoromethanesulfonamide;
N-(4-(2-(2-aminopyrimidin-4-yl)thiazol-4-yl)-3-chlorophenyl)-1,1,1-trifluoromethanesulfonamide;
N-(3-chloro-4-(2-(2-(propylamino)pyrimidin-4-yl)thiazol-4-yl)phenyl)-1,1,1-trifluoromethanesulfonamide;
N-(3-chloro-4-(2-(2-(dibutylamino)pyrimidin-4-yl)thiazol-4-yl)phenyl)-1,1,1-trifluoromethanesulfonamide;
N-(3-chloro-4-(2'-propyl-2,4'-bithiazol-4-yl)phenyl)-1,1,1-trifluoromethanesulfonamide;
N-(3-chloro-4-(2-(5-propyl-1,2,4-thiadiazol-3-yl)thiazol-4-yl)phenyl)-1,1,1-trifluoromethanesulfonamide;
N-(3-chloro-4-(2-(5-propyl-1,2,4-oxadiazol-3-yl)thiazol-4-yl)phenyl)-1,1,1-trifluoromethanesulfonamide;
N-(3-chloro-4-(2'-propyl-2,5'-bithiazol-4-yl)phenyl)-1,1,1-trifluoromethanesulfonamide;
N-(3-chloro-4-(2-(5-propyl-1,3,4-thiadiazol-2-yl)thiazol-4-yl)phenyl)-1,1,1-trifluoromethanesulfonamide;
N-(3-chloro-4-(2-(5-propyl-1,3,4-oxadiazol-2-yl)thiazol-4-yl)phenyl)-1,1,1-trifluoromethanesulfonamide;
N-(3-chloro-4-(2-(1-isobutyl-6-oxo-1,6-dihydropyridin-3-yl)thiazol-4-yl)phenyl)-1,1,1-trifluoromethanesulfonamide;
N-(3-chloro-4-(2-(4-fluoro-3-isobutylphenyl)thiazol-4-yl)phenyl)-1,1,1-trifluoromethanesulfonamide;
N-(2-bromo-3-chloro-4-(2-(2-isobutylpyridin-4-yl)thiazol-4-yl)phenyl)-1,1,1-trifluoromethanesulfonamide;
N-(3,5-dichloro-4-(2-(2-isobutylpyridin-4-yl)thiazol-4-yl)phenyl)-1,1,1-trifluoromethanesulfonamide;
1,1,1-trifluoro-N-(4-(2-(2-isobutylpyridin-4-yl)thiazol-4-yl)-2-(trifluoromethyl)phenyl)methanesulfonamide;
N-(2-cyclopropyl-4-(2-(2-isobutylpyridin-4-yl)thiazol-4-yl)phenyl)-1,1,1-trifluoromethanesulfonamide;
1,1,1-trifluoro-N-(4-(2-(2-isobutylpyridin-4-yl)thiazol-4-yl)-2-methylphenyl)methanesulfonamide;
1,1,1-trifluoro-N-(4-(2-(2-isobutylpyridin-4-yl)thiazol-4-yl)-2-isopropylphenyl)methanesulfonamide;
N-(2-ethynyl-4-(2-(2-isobutylpyridin-4-yl)thiazol-4-yl)phenyl)-1,1,1-trifluoromethanesulfonamide;
N-(2-bromo-3-ethynyl-4-(2-(2-isobutylpyridin-4-yl)thiazol-4-yl)phenyl)-1,1,1-trifluoromethanesulfonamide;
N-(2-bromo-6-chloro-4-(2-(2-isobutylpyridin-4-yl)thiazol-4-yl)phenyl)-1,1,1-trifluoromethanesulfonamide;
N-(2-chloro-4-(2-(2-isobutylpyridin-4-yl)thiazol-4-yl)-6-methylphenyl)-1,1,1-trifluoromethanesulfonamide;
N-(4-(4-(2-tert-butylpyridin-4-yl)-1-methyl-1H-imidazol-2-yl)-3-chlorophenyl)-1,1,1-trifluoromethanesulfonamide;
N-(3-chloro-4-(2-(2-isobutylpyridin-4-yl)thiazol-4-yl)phenyl)-1,1,1-trifluoromethanesulfonamide;
N-(2-bromo-4-(1-methyl-2-(2-propylpyridin-4-yl)-1H-imidazol-4-yl)phenyl)-1,1,1-trifluoromethanesulfonamide;
N-(2-bromo-3-chloro-4-(2-(2-propylpyridin-4-yl)-1H-imidazol-4-yl)phenyl)-1,1,1-trifluoromethanesulfonamide;
N-(2-bromo-5-chloro-4-(1-methyl-2-(2-propylpyridin-4-yl)-1H-imidazol-4-yl)phenyl)-1,1,1-trifluoromethanesulfonamide;
N-(4-(4-(2-tert-butylpyridin-4-yl)oxazol-2-yl)-3-chlorophenyl)-1,1,1-trifluoromethanesulfonamide;
N-(4-(2-(2-tert-butylpyridin-4-yl)oxazol-4-yl)-3-chlorophenyl)-1,1,1-trifluoromethanesulfonamide;
N-(3-chloro-4-(2-(2-(dimethylamino)pyridin-4-yl)thiazol-4-yl)phenyl)-1,1,1-trifluoromethanesulfonamide;
N-(3-chloro-4-(2-(2-propylpyridin-4-yl)thiazol-4-yl)phenyl)-N-(trifluoromethylsulfonyl)acrylamide;
N-(3-chloro-4-(2-(2-(methylsulfonamido)pyridin-4-yl)thiazol-4-yl)phenyl)-1,1,1-trifluoromethanesulfonamide;
N-(3-chloro-4-(2-(2-(3,3,3-trifluoropropyl)pyridin-4-yl)thiazol-4-yl)phenyl)-1,1,1-trifluoromethanesulfonamide;
1,1,1-trifluoro-N-(2-hydroxy-4-(2-(2-isobutylpyridin-4-yl)thiazol-4-yl)phenyl)methanesulfonamide;
1,1,1-trifluoro-N-(2-hydroxy-4-(2-(2-propylpyridin-4-yl)thiazol-4-yl)phenyl)methanesulfonamide;
N-(4-(2-(2-tert-butylpyridin-4-yl)thiazol-4-yl)-2-hydroxyphenyl)-1,1,1-trifluoromethanesulfonamide;
1,1,1-trifluoro-N-(2-methoxy-4-(2-(2-propylpyridin-4-yl)thiazol-4-yl)phenyl)methanesulfonamide;
1,1,1-trifluoro-N-(4-(2-(2-isobutylpyridin-4-yl)thiazol-4-yl)-2-methoxyphenyl)methanesulfonamide;
N-(4-(2-(2-tert-butylpyridin-4-yl)thiazol-4-yl)-2-methoxyphenyl)-1,1,1-trifluoromethanesulfonamide;
1,1,1-trifluoro-N-(4-(2-(2-isobutylpyridin-4-yl)thiazol-4-yl)-3-(trifluoromethyl)phenyl)methanesulfonamide;
N-(3-chloro-4-(2-(2-neopentylpyridin-4-yl)thiazol-4-yl)phenyl)-1,1,1-trifluoromethanesulfonamide;
6-(2-(2-isobutylpyridin-4-yl)thiazol-4-yl)-3-(trifluoromethyl sulfonyl)benzo[d]oxazol-2(3H)-one;
N-(3-chloro-4-(2-(2-isobutylpyridin-4-yl)thiazol-4-yl)phenyl)-1,1,2,2,2-pentafluoroethanesulfonamide;
1,1,1-trifluoro-N-(2-methoxy-4-{2-[2-(2-methylpropyl)pyridin-4-yl]-1,3-thiazol-4-yl}phenyl)methanesulfonamide;
1,1,1-trifluoro-N-{2-methoxy-4-[2-(2-propylpyridin-4-yl)-1,3-thiazol-4-yl]phenyl}methanesulfonamide;
N-{4-[2-(2-tert-butylpyridin-4-yl)-1,3-thiazol-4-yl]-2-methoxyphenyl}-1,1,1-trifluoromethanesulfonamide;
N-{4-[2-(2-benzylpyridin-4-yl)-1,3-thiazol-4-yl]-3-chlorophenyl}-1,1,1-trifluoromethanesulfonamide;
N-{4-[2-(2-aminopyridin-4-yl)-1,3-thiazol-4-yl]-3-chlorophenyl}-1,1,1-trifluoromethanesulfonamide;
N-{3-chloro-4-[2-(2-methanesulfonamidopyridin-4-yl)-1,3-thiazol-4-yl]phenyl}-1,1,1-trifluoromethanesulfonamide;
1,1,1-trifluoro-N-{2-hydroxy-4-[2-(2-propylpyridin-4-yl)-1,3-thiazol-4-yl]phenyl}methanesulfonamide;
N-(3-chloro-4-{2-[2-(3,3,3-trifluoropropyl)pyridin-4-yl]-1,3-thiazol-4-yl}phenyl)-1,1,1-trifluoromethanesulfonamide;
N-(4-{2-[2-(2,2-dimethylpropyl)pyridin-4-yl]-1,3-thiazol-4-yl}-2-methoxyphenyl)-1,1,1-trifluoromethanesulfonamide;
N-{3-chloro-4-[2-(2-trifluoromethanesulfonamidopyridin-4-yl)-1,3-thiazol-4-yl]phenyl}-1,1,1-trifluoromethanesulfonamide;
N-(3-chloro-4-(2-(4-(piperidine-1-carbonyl)phenyl)thiazol-4-yl)phenyl)-1,1,1-trifluoromethanesulfonamide;
N-(3-chloro-4-{2-[1-(3-methylbutyl)-1H-pyrazol-5-yl]-1,3-thiazol-4-yl}phenyl)-1,1,1-trifluoromethanesulfonamide;
N-{4-[5-(2-tert-butylpyridin-4-yl)thiophen-3-yl]-3-chlorophenyl}methanesulfonamide;
N-(3-chloro-4-{2-[2-(cyclohexylmethyl)pyridin-4-yl]-1,3-thiazol-4-yl}phenyl)-1,1,1-trifluoromethanesulfonamide;
N-{3-chloro-4-[2-(naphthalen-1-yl)-1,3-thiazol-4-yl]phenyl}-1,1,1-trifluoromethanesulfonamide;

N-{3-chloro-4-[2-(1H-indol-6-yl)-1,3-thiazol-4-yl]phenyl}-1,1,1-trifluoromethanesulfonamide;
N-(4-{2-[3-(benzyloxy)-4-(trifluoromethyl)phenyl]-1,3-thiazol-4-yl}-3-chlorophenyl)-1,1,1-trifluoromethanesulfonamide;
N-{3-chloro-4-[2-(2-phenylphenyl)-1,3-thiazol-4-yl]phenyl}-1,1,1-trifluoromethanesulfonamide;
N-{3-chloro-4-[2-(isoquinolin-4-yl)-1,3-thiazol-4-yl]phenyl}-1,1,1-trifluoromethanesulfonamide;
N-(3-chloro-4-{2-[2-(4-methylpiperazin-1-yl)pyridin-4-yl]-1,3-thiazol-4-yl}phenyl)-1,1,1-trifluoromethanesulfonamide;
N-{3-chloro-4-[2-(dimethyl-1,2-oxazol-4-yl)-1,3-thiazol-4-yl]phenyl}-1,1,1-trifluoromethanesulfonamide;
N-{3-[4-(2-chloro-4-trifluoromethanesulfonamidophenyl)-1,3-thiazol-2-yl]phenyl}-4-methylbenzene-1-sulfonamide;
N-{3-chloro-4-[2-(3,4-dimethoxyphenyl)-1,3-thiazol-4-yl]phenyl}-1,1,1-trifluoromethanesulfonamide;
N-{3-chloro-4-[2-(1H-indol-4-yl)-1,3-thiazol-4-yl]phenyl}-1,1,1-trifluoromethanesulfonamide;
N-(3-chloro-4-{2-[4-fluoro-2-(trifluoromethyl)phenyl]-1,3-thiazol-4-yl}phenyl)-1,1,1-trifluoromethanesulfonamide;
N-{3-chloro-4-[2-(2,3-dihydro-1-benzofuran-5-yl)-1,3-thiazol-4-yl]phenyl}-1,1,1-trifluoromethanesulfonamide;
N-(3-chloro-4-{2-[3-(hydroxymethyl)phenyl]-1,3-thiazol-4-yl}phenyl)-1,1,1-trifluoromethanesulfonamide;
N-(3-chloro-4-{2-[2-(hydroxymethyl)phenyl]-1,3-thiazol-4-yl}phenyl)-1,1,1-trifluoromethanesulfonamide;
N-(3-chloro-4-{2-[2-(piperidin-1-yl)pyridin-4-yl]-1,3-thiazol-4-yl}phenyl)-1,1,1-trifluoromethanesulfonamide;
N-{3-chloro-4-[2-(3-methylpyridin-4-yl)-1,3-thiazol-4-yl]phenyl}-1,1,1-trifluoromethanesulfonamide;
N-[3-chloro-4-(2-{1H-pyrrolo[2,3-b]pyridin-4-yl}-1,3-thiazol-4-yl)phenyl]-1,1,1-trifluoromethanesulfonamide;
N-(3-chloro-4-{2-[3-(piperidin-1-yl)phenyl]-1,3-thiazol-4-yl}phenyl)-1,1,1-trifluoromethanesulfonamide;
N-[3-chloro-4-(2-{5-fluoro-1H-pyrrolo[2,3-b]pyridin-4-yl}-1,3-thiazol-4-yl)phenyl]-1,1,1-trifluoromethanesulfonamide;
N-{4-[2-(1-benzothiophen-3-yl)-1,3-thiazol-4-yl]-3-chlorophenyl}-1,1,1-trifluoromethanesulfonamide;
N-(3-chloro-4-{2-[4-fluoro-2-(pyrrolidin-1-ylmethyl)phenyl]-1,3-thiazol-4-yl}phenyl)-1,1,1-trifluoromethanesulfonamide;
N-(3-chloro-4-{2-[2-(cyclopentylamino)pyridin-4-yl]-1,3-thiazol-4-yl}phenyl)-1,1,1-trifluoromethanesulfonamide;
N-{3-chloro-4-[2-(1H-indol-3-yl)-1,3-thiazol-4-yl]phenyl}-1,1,1-trifluoromethanesulfonamide;
N-(3-chloro-4-(2-(quinolin-4-yl)thiazol-4-yl)phenyl)-1,1,1-trifluoromethanesulfonamide;
N-(3-chloro-4-(2-(2-chloropyridin-4-yl)thiazol-4-yl)phenyl)-1,1,1-trifluoromethanesulfonamide;
N-(2-bromo-4-(2-(2-tert-butylpyridin-4-yl)thiazol-4-yl)-3-chlorophenyl)-1,1,1-trifluoromethanesulfonamide;
N-(2-bromo-4-(2-(2-propylpyridin-4-yl)-1H-imidazol-4-yl)phenyl)-1,1,1-trifluoromethanesulfonamide;
N-(2-bromo-4-(2-(2-tert-butylpyridin-4-yl)thiazol-4-yl)-3-chlorophenyl)-1,1,1-trifluoro-N-(2-hydroxyethyl)methanesulfonamide;
N-(4-(2-(2-tert-butylpyridin-4-yl)thiazol-4-yl)-3-chlorophenyl)-1,1,1-trifluoro-N-(2-(2-oxopyrrolidin-1-yl)ethyl)methanesulfonamide;
N-(4-(2-(2-tert-butylpyridin-4-yl)thiazol-4-yl)-3-chlorophenyl)-1,1,1-trifluoro-N-(2-(2-oxooxazolidin-3-yl)ethyl)methanesulfonamide;
N-(4-(2-(2-tert-butylpyridin-4-yl)thiazol-4-yl)-3-chlorophenyl)-1,1,1-trifluoro-N-(2-(2-oxoimidazolidin-1-yl)ethyl)methanesulfonamide;
N-(2-bromo-4-(2-(2-(piperidin-1-yl)pyridin-4-yl)-1H-imidazol-4-yl)phenyl)-1,1,1-trifluoromethanesulfonamide;
2-(N-(4-(2-(2-tert-butylpyridin-4-yl)thiazol-4-yl)-3-chlorophenyl)-1,1,1-trifluoromethyl sulfonamido)ethyl acetate;
(2-(N-(4-(2-(2-tert-butylpyridin-4-yl)thiazol-4-yl)-3-chlorophenyl)-1,1,1-trifluoromethyl sulfonamido)ethoxy)methyl acetate;
N-{4-[2-(2-tert-butylpyridin-4-yl)-1,3-thiazol-4-yl]-3-chlorophenyl}-N-(2-{[4-(3-chlorophenyl)-2-oxo-1,3,2λ$^5$-dioxaphosphinan-2-yl]oxy}ethyl)-1,1,1-trifluoromethanesulfonamide;
(N-(4-(2-(2-tert-butylpyridin-4-yl)thiazol-4-yl)-3-chlorophenyl)-1,1,1-trifluoromethyl sulfonamido)methyl acetate;
N-(4-(2-(2-tert-butylpyridin-4-yl)thiazol-4-yl)-3-chlorophenyl)-1,1,1-trifluoro-N-(methoxymethyl)methanesulfonamide;
N-{4-[2-(2-tert-butylpyridin-4-yl)-1,3-thiazol-4-yl]-3-chlorophenyl}-N-({[4-(3-chlorophenyl)-2-oxo-1,3,2λ$^5$-dioxaphosphinan-2-yl]oxy}methyl)-1,1,1-trifluoromethanesulfonamide;
methyl 4-(2-(2-tert-butylpyridin-4-yl)thiazol-4-yl)-3-chlorophenyl(trifluoromethylsulfonyl)carbamate;
sodium (N-(4-(2-(2-tert-butylpyridin-4-yl)thiazol-4-yl)-3-chlorophenyl)-1,1,1-trifluoromethylsulfonamido) methyl phosphate;
1-(N-(3-chloro-4-(2-(2-isobutylpyridin-4-yl)thiazol-4-yl)phenyl)-1,1,1-trifluoromethylsulfonamido)ethyl isobutyrate;
N-(3-chloro-4-(2-(2-isobutylpyridin-4-yl)thiazol-4-yl)phenyl)-1,1,1-trifluoro-N-(2-(2-oxooxazolidin-3-yl)ethyl)methanesulfonamide;
N-(4-(2-(2-tert-butylpyridin-4-yl)thiazol-4-yl)-3-chlorophenyl)-1,1,1-trifluoro-N-(2-hydroxyethyl)methanesulfonamide;
N-(3-chloro-4-(2-(2-isobutylpyridin-4-yl)thiazol-4-yl)phenyl)-1,1,1-trifluoro-N-(2-(pyrrolidin-1-yl)ethyl)methanesulfonamide;
N-(3-chloro-4-(2-(2-isobutylpyridin-4-yl)thiazol-4-yl)phenyl)-N-(2-(diethylamino)ethyl)-1,1,1-trifluoromethanesulfonamide;
N-(3-chloro-4-(2-(2-isobutylpyridin-4-yl)thiazol-4-yl)phenyl)-N-(2-(dimethylamino)ethyl)-1,1,1-trifluoromethanesulfonamide;
1,1,1-trifluoro-N-(3-fluoro-4-(2-(2-propylpyridin-4-yl)thiazol-4-yl)phenyl)methanesulfonamide;
N-(3-chloro-4-(2-(2-isobutylpyridin-4-yl)-1H-imidazol-4-yl)phenyl)-1,1,1-trifluoromethanesulfonamide;
N-(3-chloro-4-(2-(2-isobutylpyridin-4-yl)thiazol-4-yl)phenyl)-1,1,1-trifluoro-N-(2-hydroxyethyl)methanesulfonamide;
N-(3-chloro-4-(2-(2-propylpyridin-4-yl)thiazol-4-yl)phenyl)-1,1,1-trifluoro-N-methylmethanesulfonamide;
1,1,1-trifluoro-N-(3-(2-(2-isobutylpyridin-4-yl)thiazol-4-yl)phenyl)methanesulfonamide;

N-(2-bromo-4-(2-(2-isobutylpyridin-4-yl)thiazol-4-yl)phenyl)-1,1,1-trifluoromethanesulfonamide;
1,1,1-trifluoro-N-methyl-N-(4-(2-(2-propylpyridin-4-yl)thiazol-4-yl)phenyl)methanesulfonamide;
N-(4-(2-(2-butylpyridin-4-yl)thiazol-4-yl)phenyl)-1,1,1-trifluoromethanesulfonamide
1,1,1-trifluoro-N-(4-(2-(2-(methoxymethyl)pyridin-4-yl)thiazol-4-yl)phenyl)methanesulfonamide;
N-(4-(2-(4,6-dipropylpyridin-2-yl)thiazol-4-yl)phenyl)-1,1,1-trifluoromethanesulfonamide;
1,1,1-trifluoro-N-(4-(2-(4-propylpyridin-2-yl)thiazol-4-yl)phenyl)methanesulfonamide;
N-(4-(2-(2,6-dipropylpyridin-3-yl)thiazol-4-yl)phenyl)-1,1,1-trifluoromethanesulfonamide;
N-(4-(2-(2-(cyclohexylmethyl)pyridin-4-yl)thiazol-4-yl)phenyl)-1,1,1-trifluoromethanesulfonamide;
1,1,1-trifluoro-N-(4-(2-(2-isobutylpyridin-4-yl)thiazol-4-yl)-3-methoxyphenyl)methanesulfonamide;
N-(3-chloro-4-(2-(2-((trifluoromethylsulfonyl)methyl)pyridin-4-yl)thiazol-4-yl)phenyl)-1,1,1-trifluoromethanesulfonamide;
N-(4-(2-(1H-pyrrolo[2,3-b]pyridin-4-yl)thiazol-4-yl)-3-chlorophenyl)-1,1,1-trifluoromethanesulfonamide;
N-(3-chloro-4-(2-(2-propyl-3H-imidazo[4,5-b]pyridin-7-yl)thiazol-4-yl)phenyl)-1,1,1-trifluoromethanesulfonamide;
5-(4-(2-chloro-4-(trifluoromethylsulfonamido)phenyl)thiazol-2-yl)-N-cyclopropyl-2-fluorobenzamide;
5-(4-(2-chloro-4-(trifluoromethylsulfonamido)phenyl)thiazol-2-yl)-N-cyclohexyl-2-fluorobenzamide;
N-(4-(2-(1H-indol-4-yl)thiazol-4-yl)-3-chlorophenyl)-1,1,1-trifluoromethanesulfonamide;
N-(3-chloro-4-(2-(3-(piperidin-1-yl)phenyl)thiazol-4-yl)phenyl)-1,1,1-trifluoromethanesulfonamide;
N-(3-chloro-4-(2-(2-(piperidin-1-yl)pyridin-4-yl)thiazol-4-yl)phenyl)-1,1,1-trifluoromethanesulfonamide;
N-(2-bromo-4-(2-(2-tert-butylpyridin-4-yl)-1H-imidazol-4-yl)phenyl)-1,1,1-trifluoromethanesulfonamide;
N-(2-chloro-4-(2-(2-propylpyridin-4-yl)-1H-imidazol-4-yl)phenyl)-1,1,1-trifluoromethanesulfonamide;
N-(2-bromo-5-chloro-4-(2-(2-propylpyridin-4-yl)-1H-imidazol-4-yl)phenyl)-1,1,1-trifluoromethanesulfonamide; and
N-(2-bromo-4-(2-(2-propylpyridin-4-yl)thiazol-4-yl)phenyl)-1,1,1-trifluoromethanesulfonamide.

25. The compound of claim 24, wherein the compound is selected from the group consisting of:
1,1,1-trifluoro-N-(4-(2-(2-propylpyridin-4-yl)thiazol-4-yl)phenyl)methanesulfonamide;
1,1,1-trifluoro-N-(3-(2-(2-propylpyridin-4-yl)thiazol-4-yl)phenyl)methanesulfonamide;
N-(3-chloro-4-(2-(1-isobutyl-1H-pyrazol-)thiazol-4-yl)phenyl)-1,1,1-trifluoromethanesulfonamide;
N-(3-chloro-4-(2-(2-propylpyridin-4-yl)thiazol-4-yl)phenyl)-1,1,1-trifluoromethanesulfonamide;
N-(4-(2-(2-tert-butylpyridin-4-yl)thiazol-4-yl)-3-chlorophenyl)-1,1,1-trifluoromethanesulfonamide;
N-(3-chloro-4-(2-(2-isobutylpyridin-4-yl)thiazol-4-yl)phenyl)-1,1,1-trifluoromethanesulfonamide;
1,1,1-trifluoro-N-(2-methoxy-4-{2-[2-(2-methylpropyl)pyridin-4-yl]-1,3-thiazol-4-yl}phenyl)methanesulfonamide;
1,1,1-trifluoro-N-{2-methoxy-4-[2-(2-propylpyridin-4-yl)-1,3-thiazol-4-yl]phenyl}methanesulfonamide;
N-{4-[2-(2-tert-butylpyridin-4-yl)-1,3-thiazol-4-yl]-2-methoxyphenyl}-1,1,1-trifluoromethanesulfonamide;
N-{4-[2-(2-benzylpyridin-4-yl)-1,3-thiazol-4-yl]-3-chlorophenyl}-1,1,1-trifluoromethanesulfonamide;
N-{4-[2-(2-aminopyridin-4-yl)-1,3-thiazol-4-yl]-3-chlorophenyl}-1,1,1-trifluoromethanesulfonamide;
N-{3-chloro-4-[2-(2-methanesulfonamidopyridin-4-yl)-1,3-thiazol-4-yl]phenyl}-1,1,1-trifluoromethanesulfonamide;
1,1,1-trifluoro-N-{2-hydroxy-4-[2-(2-propylpyridin-4-yl)-1,3-thiazol-4-yl]phenyl}methanesulfonamide;
N-(3-chloro-4-{2-[2-(3,3,3-trifluoropropyl)pyridin-4-yl]-1,3-thiazol-4-yl}phenyl)-1,1,1-trifluoromethanesulfonamide;
N-(4-{2-[2-(2,2-dimethylpropyl)pyridin-4-yl]-1,3-thiazol-4-yl}-2-methoxyphenyl)-1,1,1-trifluoromethanesulfonamide;
N-{3-chloro-4-[2-(2-trifluoromethanesulfonamidopyridin-4-yl)-1,3-thiazol-4-yl]phenyl}-1,1,1-trifluoromethanesulfonamide;
N-(3-chloro-4-(2-(4-(piperidine-1-carbonyl)phenyl)thiazol-4-yl)phenyl)-1,1,1-trifluoromethanesulfonamide;
N-(3-chloro-4-{2-[1-(3-methylbutyl)-1H-pyrazol-5-yl]-1,3-thiazol-4-yl}phenyl)-1,1,1-trifluoromethanesulfonamide;
N-{4-[5-(2-tert-butylpyridin-4-yl)thiophen-3-yl]-3-chlorophenyl}methanesulfonamide;
N-(3-chloro-4-{2-[2-(cyclohexylmethyl)pyridin-4-yl]-1,3-thiazol-4-yl}phenyl)-1,1,1-trifluoromethanesulfonamide;
N-{3-chloro-4-[2-(naphthalen-1-yl)-1,3-thiazol-4-yl]phenyl}-1,1,1-trifluoromethanesulfonamide;
N-{3-chloro-4-[2-(1H-indol-6-yl)-1,3-thiazol-4-yl]phenyl}-1,1,1-trifluoromethanesulfonamide;
N-(4-{2-[3-(benzyloxy)-4-(trifluoromethyl)phenyl]-1,3-thiazol-4-yl}-3-chlorophenyl)-1,1,1-trifluoromethanesulfonamide;
N-{3-chloro-4-[2-(2-phenylphenyl)-1,3-thiazol-4-yl]phenyl}-1,1,1-trifluoromethanesulfonamide;
N-{3-chloro-4-[2-(isoquinolin-4-yl)-1,3-thiazol-4-yl]phenyl}-1,1,1-trifluoromethanesulfonamide;
N-(3-chloro-4-{2-[2-(4-methylpiperazin-1-yl)pyridin-4-yl]-1,3-thiazol-4-yl}phenyl)-1,1,1-trifluoromethanesulfonamide;
N-{3-chloro-4-[2-(dimethyl-1,2-oxazol-4-yl)-1,3-thiazol-4-yl]phenyl}-1,1,1-trifluoromethanesulfonamide;
N-{3-[4-(2-chloro-4-trifluoromethanesulfonamidophenyl)-1,3-thiazol-2-yl]phenyl}-4-methylbenzene-1-sulfonamide;
N-{3-chloro-4-[2-(3,4-dimethoxyphenyl)-1,3-thiazol-4-yl]phenyl}-1,1,1-trifluoromethanesulfonamide;
N-{3-chloro-4-[2-(1H-indol-4-yl)-1,3-thiazol-4-yl]phenyl}-1,1,1-trifluoromethanesulfonamide;
N-(3-chloro-4-{2-[4-fluoro-2-(trifluoromethyl)phenyl]-1,3-thiazol-4-yl}phenyl)-1,1,1-trifluoromethanesulfonamide;
N-{3-chloro-4-[2-(2,3-dihydro-1-benzofuran-5-yl)-1,3-thiazol-4-yl]phenyl}-1,1,1-trifluoromethanesulfonamide;
N-(3-chloro-4-{2-[3-(hydroxymethyl)phenyl]-1,3-thiazol-4-yl}phenyl)-1,1,1-trifluoromethanesulfonamide;
N-(3-chloro-4-{2-[2-(hydroxymethyl)phenyl]-1,3-thiazol-4-yl}phenyl)-1,1,1-trifluoromethanesulfonamide;
N-(3-chloro-4-{2-[2-(piperidin-1-yl)pyridin-4-yl]-1,3-thiazol-4-yl}phenyl)-1,1,1-trifluoromethanesulfonamide;
N-{3-chloro-4-[2-(3-methylpyridin-4-yl)-1,3-thiazol-4-yl]phenyl}-1,1,1-trifluoromethanesulfonamide;

N-[3-chloro-4-(2-{1H-pyrrolo[2,3-b]pyridin-4-yl}-1,3-thiazol-4-yl)phenyl]-1,1,1-trifluoromethanesulfonamide;

N-(3-chloro-4-{2-[3-(piperidin-1-yl)phenyl]-1,3-thiazol-4-yl}phenyl)-1,1,1-trifluoromethanesulfonamide;

N-[3-chloro-4-(2-{5-fluoro-1H-pyrrolo[2,3-b]pyridin-4-yl}-1,3-thiazol-4-yl)phenyl]-1,1,1-trifluoromethanesulfonamide;

N-{4-[2-(1-benzothiophen-3-yl)-1,3-thiazol-4-yl]-3-chlorophenyl}-1,1,1-trifluoromethanesulfonamide;

N-(3-chloro-4-{2-[4-fluoro-2-(pyrrolidin-1-ylmethyl)phenyl]-1,3-thiazol-4-yl}phenyl)-1,1,1-trifluoromethanesulfonamide;

N-(3-chloro-4-{2-[2-(cyclopentylamino)pyridin-4-yl]-1,3-thiazol-4-yl}phenyl)-1,1,1-trifluoromethanesulfonamide;

N-{3-chloro-4-[2-(1H-indol-3-yl)-1,3-thiazol-4-yl]phenyl}-1,1,1-trifluoromethanesulfonamide; and N-(3-chloro-4-(2-(quinolin-4-yl)thiazol-4-yl)phenyl)-1,1,1-trifluoromethanesulfonamide.

26. The compound of claim 25, wherein the compound is selected from the group consisting of:

N-(3-chloro-4-(2-(2-propylpyridin-4-yl)thiazol-4-yl)phenyl)-1,1,1-trifluoromethanesulfonamide;

N-(4-(2-(2-tert-butylpyridin-4-yl)thiazol-4-yl)-3-chlorophenyl)-1,1,1-trifluoromethanesulfonamide;

N-(3-chloro-4-(2-(2-isobutylpyridin-4-yl)thiazol-4-yl)phenyl)-1,1,1-trifluoromethanesulfonamide;

N-{4-[2-(2-benzylpyridin-4-yl)-1,3-thiazol-4-yl]-3-chlorophenyl}-1,1,1-trifluoromethanesulfonamide;

N-(3-chloro-4-{2-[2-(3,3,3-trifluoropropyl)pyridin-4-yl]-1,3-thiazol-4-yl}phenyl)-1,1,1-trifluoromethanesulfonamide;

N-{3-chloro-4-[2-(1H-indol-4-yl)-1,3-thiazol-4-yl]phenyl}-1,1,1-trifluoromethanesulfonamide;

N-(3-chloro-4-{2-[2-(piperidin-1-yl)pyridin-4-yl]-1,3-thiazol-4-yl}phenyl)-1,1,1-trifluoromethanesulfonamide; and N-(3-chloro-4-{2-[3-(piperidin-1-yl)phenyl]-1,3-thiazol-4-yl}phenyl)-1,1,1-trifluoromethanesulfonamide.

27. A compound N-(3-chloro-4-(2-(2-isobutylpyridin-4-yl)thiazol-4-yl)phenyl)-1,1,1-trifluoromethanesulfonamide.

28. A pharmaceutical composition comprising a compound of claim 1 and a pharmaceutically acceptable vehicle.

29. A method of treating a cancer selected from the group consisting of breast cancer, prostate cancer, and liver cancer, comprising administering to an individual in need thereof a therapeutically effective amount of a compound of claim 1.

30. The method of claim 29, wherein the cancer is breast cancer.

31. The method of claim 29, wherein the cancer is prostate cancer.

32. The method of claim 29, wherein the cancer is liver cancer.

33. The pharmaceutical composition of claim 28, wherein the compound is compound N-(3-chloro-4-(2-(2-isobutylpyridin-4-yl)thiazol-4-yl)phenyl)-1,1,1-trifluoromethanesulfonamide.

34. The method of claim 30, wherein the compound is compound N-(3-chloro-4-(2-(2-isobutylpyridin-4-yl)thiazol-4-yl)phenyl)-1,1,1-trifluoromethanesulfonamide.

35. The method of claim 31, wherein the compound is compound N-(3-chloro-4-(2-(2-isobutylpyridin-4-yl)thiazol-4-yl)phenyl)-1,1,1-trifluoromethanesulfonamide.

36. The method of claim 32, wherein the compound is compound N-(3-chloro-4-(2-(2-isobutylpyridin-4-yl)thiazol-4-yl)phenyl)-1,1,1-trifluoromethanesulfonamide.

* * * * *